(12) United States Patent
Morris et al.

(10) Patent No.: US 11,939,575 B2
(45) Date of Patent: Mar. 26, 2024

(54) MODIFIED TRACRRNAS GRNAS, AND USES THEREOF

(71) Applicant: CITY OF HOPE, Duarte, CA (US)

(72) Inventors: Kevin V. Morris, Duarte, CA (US); Tristan Scott, Duarte, CA (US)

(73) Assignee: City of Hope, Duarte, CA (US)

( * ) Notice: Subject to any disclaimer, the term of this patent is extended or adjusted under 35 U.S.C. 154(b) by 431 days.

(21) Appl. No.: 16/955,293

(22) PCT Filed: Dec. 17, 2018

(86) PCT No.: PCT/US2018/066005
§ 371 (c)(1),
(2) Date: Jun. 18, 2020

(87) PCT Pub. No.: WO2019/126037
PCT Pub. Date: Jun. 27, 2019

(65) Prior Publication Data
US 2021/0017518 A1   Jan. 21, 2021

Related U.S. Application Data

(60) Provisional application No. 62/659,037, filed on Apr. 17, 2018, provisional application No. 62/658,944, (Continued)

(51) Int. Cl.
*C12N 9/22* (2006.01)
*C12N 15/11* (2006.01)
(Continued)

(52) U.S. Cl.
CPC ............... *C12N 15/11* (2013.01); *C12N 9/22* (2013.01); *C12N 15/115* (2013.01);
(Continued)

(58) Field of Classification Search
CPC ..... C12N 15/11; C12N 15/113; C12N 15/115; C12N 2310/16; C12N 2310/20; C12N 2310/321; C12N 2310/322
See application file for complete search history.

(56) References Cited

U.S. PATENT DOCUMENTS

| 4,861,760 | A | 8/1989 | Mazuel et al. |
| 4,911,920 | A | 3/1990 | Jani et al. |
(Continued)

FOREIGN PATENT DOCUMENTS

| WO | WO-96/17958 A1 | 6/1996 |
| WO | WO-2016/170484 A1 | 10/2016 |
(Continued)

OTHER PUBLICATIONS

Scott et al. (Sci Rep. 2019; 9: 16104. Published online Nov. 6, 2019).*
(Continued)

*Primary Examiner* — Terra C Gibbs
(74) *Attorney, Agent, or Firm* — Mintz, Levin, Cohn, Ferris, Glovsky and Popeo, P.C.

(57) ABSTRACT

Provided are compositions and methods for altering gene expression in cells. The compositions and methods may utilize a nucleic acid sequence that has a genetically modified trans-activating crRNA (tracrRNA) sequence, where at least one uracil nucleotide of the tracrRNA sequence is replaced with a nucleotide other than uracil, and/or a nucleic acid sequence that has a guide RNA (gRNA) sequence wherein one or more cytosine nucleotides and/or one or more uracil nucleotides of said gRNA sequence are modified nucleotides. Also provided are methods of treating a disorder in a subject in need of the treatment. The method may
(Continued)

involve administering to the subject the nucleic acid or a vector thereof in combination with an RNA-guided DNA endonuclease enzyme.

16 Claims, 42 Drawing Sheets

Specification includes a Sequence Listing.

Related U.S. Application Data filed on Apr. 17, 2018, provisional application No. 62/607,838, filed on Dec. 19, 2017.

(51) Int. Cl.
| | |
|---|---|
| C12N 15/115 | (2010.01) |
| C12N 15/90 | (2006.01) |
| A61K 38/00 | (2006.01) |

(52) U.S. Cl.
CPC .......... *C12N 15/907* (2013.01); *A61K 38/00* (2013.01); *C12N 2310/16* (2013.01); *C12N 2310/20* (2017.05); *C12N 2310/321* (2013.01); *C12N 2310/322* (2013.01); *C12N 2310/3519* (2013.01); *C12N 2800/80* (2013.01)

(56) References Cited

U.S. PATENT DOCUMENTS

| | | | |
|---|---|---|---|
| 5,034,506 | A | 7/1991 | Summerton et al. |
| 5,143,854 | A | 9/1992 | Pirrung et al. |
| 5,212,162 | A | 5/1993 | Missel et al. |
| 5,235,033 | A | 8/1993 | Summerton et al. |
| 5,403,841 | A | 4/1995 | Lang et al. |
| 8,906,616 | B2 | 12/2014 | Zhang et al. |
| 2016/0355795 | A1 | 12/2016 | Ran et al. |
| 2017/0044535 | A1 | 2/2017 | Collingwood et al. |
| 2017/0327820 | A1 | 11/2017 | May et al. |
| 2017/0349894 | A1 | 12/2017 | Dahlman et al. |

FOREIGN PATENT DOCUMENTS

| | | | | |
|---|---|---|---|---|
| WO | WO-2017/004279 | A2 | 1/2017 | |
| WO | WO-2017/004279 | A3 | 1/2017 | |
| WO | WO-2017044776 | A1 * | 3/2017 | ........... C12N 15/111 |
| WO | WO-2017093969 | A1 * | 6/2017 | ......... A61K 31/7088 |
| WO | WO-2017/136794 | A1 | 8/2017 | |

OTHER PUBLICATIONS

Scott et al. (Molecular Therapy: Nucleic Acids vol. Mar. 19, 2020).*
Al-Muhammed, J. et al. (May-Jun. 1996). "In-vivo studies on dexamethasone sodium phosphate liposomes," *J Microencapsul* 13(3):293-306.
Chen, J. et al. (Jul. 10, 2015, e-published Jun. 25, 2015). "HIV-1 Envelope. Effect of the cytoplasmic domain on antigenic characteristics of HIV-1 envelope glycoprotein," *Science* 349(6244):191-195.
Chonn, A. et al. (Dec. 1995). "Recent advances in liposomal drug-delivery systems," *Curr Opin Biotechnol* 6(6):698-708.
Chylinski, K. e al. (May 2013, e-published Apr. 5, 2013). "The tracrRNA and Cas9 families of type II CRISPR-Cas immunity systems," *RNA Biol* 10(5):726-737.
Eyles, J.E. et al. (Jul. 1997). "Oral delivery and fate of poly(lactic acid) microsphere-encapsulated interferon in rats," *J. Pharm. Pharmacol.* 49(7):669-674.
Findlay, S.D. et al. (Apr. 18, 2016). "A Digital PCR-Based Method for Efficient and Highly Specific Screening of Genome Edited Cells," *PLoS One* 11(4):e0153901.
Fodor, S.P. et al. (Feb. 15, 1991). "Light-directed, spatially addressable parallel chemical synthesis," *Science* (251):4995:767-773.
Ford, K.G. et al. (Jan. 2001). "Protein transduction: an alternative to genetic intervention?" *Gene Ther* 8(1):1-4.
Gao, Z.H. et al. (Jun. 1995). "Controlled release of a contraceptive steroid from biodegradable and injectable gel formulations: in vitro evaluation," *Pharm. Res* 12(6):857-863.
Howell, D.N. et al. (Feb. 1985). "Natural killing target antigens as inducers of interferon: studies with an immunoselected, natural killing-resistant human T lymphoblastoid cell line," *J Immunol* 134(2):971-976.
International Search Report dated May 30, 2019, for PCT Application No. PCT/US2018/066005, filed Dec. 17, 2018, 6 pages.
Johnston, M. (Feb. 26, 1998). "Gene chips: array of hope for understanding gene regulation," *Curr Biol* 8(5):R171-174.
Kelley, M.L. et al. (Sep. 10, 2016, e-published Jun. 30, 2016). "Versatility of chemically synthesized guide RNAs for CRISPR-Cas9 genome editing,"*J Biotechnol* 233:74-83.
Kern, S. et al. (Jul. 1997). "Direct hybridization of large-insert genomic clones on high-density gridded cDNA filter arrays," *Biotechniques* 23(1):120-124.
Lee, K. et al. (May 2, 2017). "Synthetically modified guide RNA and donor DNA are a versatile platform for CRISPR-Cas9 engineering," *eLife* 6:e25312.
Lyerly, H.K. et al. (1987). "Anti-GP 120 antibodies from HIV seropositive individuals mediate broadly reactive anti-HIV ADCC," 3(4):409-422.
Miyakawa, S. et al. (Jun. 2008, e-published Apr. 25, 2008). "Structural and molecular basis for hyperspecificity of RNA aptamer to human immunoglobulin G," *RNA* 14(6): 1154-1163.
Nishimasu, H. et al. (Feb. 27, 2014, e-published Feb. 13, 2014). "Crystal structure of Cas9 in complex with guide RNA and target DNA," *Cell* 156(5):935-949.
Nozari, A. et al. (Mar. 17, 2017, e-published Dec. 10, 2016). "Aptamers for CD Antigens: From Cell Profiling to Activity Modulation," *Mol Ther Nucleic Acids* 6:29-44.
Ostro, M.J. et al. (Aug. 1989). "Use of liposomes as injectable-drug delivery systems," *Am J Hosp Pharm* 46(8):1576-1587.
Prochiantz, A. (Feb. 2007). "For protein transduction, chemistry can win over biology," *Nat Methods* 4(2):119-120.
Rao. K.P. (1995). "Recent developments of collagen-based materials for medical applications and drug delivery systems," *J. Biomater Sci. Polym. Ed.* 7(7):623-645.
Saayman, S.M. et al. (Mar. 2016, e-published Nov. 19, 2015). "Potent and Targeted Activation of Latent HIV-1 Using the CRISPR/dCas9 Activator Complex," *Mol Ther* 24(3):488-498.
Schummer, M. et al. (Dec. 1997). "Inexpensive handheld device for the construction of high-density nucleic acid arrays," *Biotechniques* 23(6):1087-1092.
Scott, T. et al. (Aug. 7, 2017). "ssAAVs containing cassettes encoding SaCas9 and guides targeting hepatitis B virus inactivate replication of the virus in cultured cells," *Sci Rep* 7(1):7401.
Shao, S. et al. (May 19, 2016, e-published Feb. 4, 2016). "Long-term dual-color tracking of genomic loci by modified sgRNAs of the CRISPR/Cas9 system," *Nucleic Acids Res* 44(9):e86.
Shmakov, S. et al. (Mar. 2017, e-published Jan. 23, 2017). "Diversity and evolution of class 2 CRISPR-Cas systems," *Nat Rev Microbiol* 15(3):169-182.
Trkola, A. et al. (Nov. 1999). "A cell line-based neutralization assay for primary human immunodeficiency virus type 1 isolates that use either the CCR5 or the CXCR4 coreceptor," *J Virol* 73(11):8966-8974.
Wang, S. et al. (May 27, 2016). "An RNA-aptamer-based two-color CRISPR labeling system," *Sci Rep* 6:26857.
Written Opinion dated May 30, 2019, for PCT Application No. PCT/US2018/066005, filed Dec. 17, 2018, 9 pages.
Zhen, S. et al. (Feb. 7, 2017). "Targeted delivery of CRISPR/Cas9 to prostate cancer by modified gRNA using a flexible aptamer-cationic liposome," *Oncotarget* 8(6):9375-9387.

\* cited by examiner

SEQ ID NO: 157

SEQ ID NO: 158

Table: Possible substitutions for U-replaced gRNAs

| Nucleotide position | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 | 43 | 44 | 45 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| gRNA sequence (SEQ ID NO: 267) | G | U | U | U | U | A | G | A | G | C | U | A | U | G | C | U | G | g | a | a | a | C | A | G | C | A | U | A | G | C | A | A | G | U | U | A | A | A | A | U | A | A | G | G | C |
| U-Replacements | U | | | A | U | | | | | | U | | | | | | | | | | | | | A | | | | | A | A | U | | | A | | | | | | | |
| | C | | | C | C | | | | | | C | | | | | | | | | | | | | G | | | | | C | G | G | | | G | | | | | | | |
| | G | | | | | | | | | | | | | | | | | | | | | | | | | | | | | | | | | | | | | | | | | | | | |
| U-replacement Consensus | B | | | M | Y | | | | | | Y | | | | | | | | | | | | | R | | | | | M | R | K | | | V | | | | | | | | | | | |

| Nucleotide position | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 | 85 | 86 | 87 | 88 | 89 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| gRNA sequence (SEQ ID NO: 267) | U | A | G | U | C | C | G | U | U | A | U | C | A | A | C | U | U | G | A | A | A | A | A | G | U | G | G | C | A | C | C | G | A | G | U | C | G | G | U | G | C | U | U | U |
| U-Replacements | A | A | A | A | A | G | U | A | A | A | G | C | G | C | C | G | | | | | | | | | | | | C | G | A | | A | | | C | A | A | G | C | | G | U | A | A |
| | G | G | G | G | G | | | C | | C | | | C | G | G | | | | | | | | | | | | | | | | | | | | | | | | | | C | | G | G |
| U-replacement Consensus | R | R | R | R | R | S | Y | W | W | M | S | Y | S | S | S | S | | | | | | | | | | | | Y | V | W | | V | | | S | M | R | V | S | | S | Y | W | W |

The crRNA is highlighted in bold.
The tetraloop is in lower case.
The tracrRNA is underlined.

| Nucleotide position | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| gRNA sequence (SEQ ID NO: 267) | G | U | U | U | U | A | G | A | G | C | U | A | U | G | C | U | G | g | a | a |
| U-Replacements | | | | | A | U | | | | | | U | | | | | | | | |
| | C | | | | C | C | | | | | | C | | | | | | | | |
| | G | | | | | | | | | | | | | | | | | | | |

| Nucleotide position | 21 | 22 | 23 | 24 | 25 | 26 | 27 | 28 | 29 | 30 | 31 | 32 | 33 | 34 | 35 | 36 | 37 | 38 | 39 | 40 |
|---|---|---|---|---|---|---|---|---|---|---|---|---|---|---|---|---|---|---|---|---|
| gRNA sequence (SEQ ID NO: 267) | a | C | A | G | C | A | U | A | G | C | A | A | G | U | U | A | A | A | A | U |
| U-Replacements | | | | | | | U | | | | | | | U | U | | | | | A |
| | | | | | | | A | | | | | | | A | A | | | | | |
| | | | | | | | G | | | | | | | C | G | | | | | |

| Nucleotide position | 41 | 42 | 43 | 44 | 45 | 46 | 47 | 48 | 49 | 50 | 51 | 52 | 53 | 54 | 55 | 56 | 57 | 58 | 59 | 60 |
|---|---|---|---|---|---|---|---|---|---|---|---|---|---|---|---|---|---|---|---|---|
| gRNA sequence (SEQ ID NO: 267) | A | C | G | A | C | U | A | G | U | C | C | G | U | U | A | U | C | A | A | C |
| U-Replacements | | | | | | U | A | A | | | | | U | U | U | A | | A | A | |
| | | | | | | A | G | C | A | | | | A | A | | G | | A | C | |
| | | | | | | G | | G | G | | | | G | G | G | C | | | G | |

| Nucleotide position | 61 | 62 | 63 | 64 | 65 | 66 | 67 | 68 | 69 | 70 | 71 | 72 | 73 | 74 | 75 | 76 | 77 | 78 | 79 | 80 |
|---|---|---|---|---|---|---|---|---|---|---|---|---|---|---|---|---|---|---|---|---|
| gRNA sequence (SEQ ID NO: 267) | U | U | G | U | A | A | A | C | G | U | G | G | C | A | C | C | G | A | A | U |
| U-Replacements | | | | | | | A | C | A | G | C | | C | A | C | C | G | A | A | G |
| | G | G | | | | | G | C | G | C | | | | C | | | | A | C | A |
| | C | C | | | | | C | | C | | | | | G | | | | | G | C |

| Nucleotide position | 81 | 82 | 83 | 84 | 85 | 86 | 87 | 88 | 89 |
|---|---|---|---|---|---|---|---|---|---|
| gRNA sequence (SEQ ID NO: 267) | C | G | G | U | G | C | U | U | U |
| U-Replacements | | | | G | | | A | A | A |
| | | | | C | | | G | G | G |
| | | | | | | | C | C | C |

Tar3
GGUUAGACCAGAUCUGAGCC
(SEQ ID NO: 233)

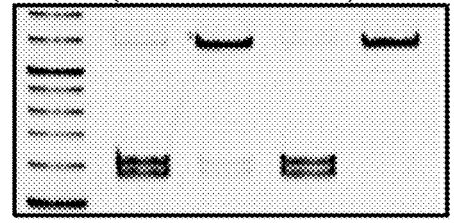

2'F base:   -   U   C   CU
FIG. 17B

Tar7
UAGUUAGCCAGAGAGCUCCC
(SEQ ID NO: 284)

2'F base:   -   U   C   CU
FIG. 17C

Tar4
GGGAGCUCUCUGGCUAAC
(SEQ ID NO: 234)

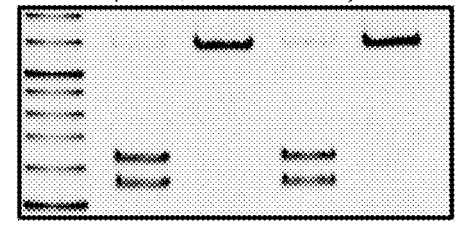

2'F base:   -   U   C   CU
FIG. 17D

Tar8
UUUAUUGAGGCUUAAGCAGU
(SEQ ID NO: 285)

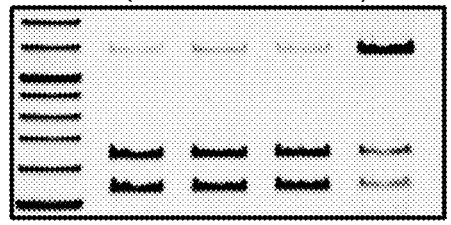

2'F base:   -   U   C   CU
FIG. 17E

Tar5
UAACCAGAGAGACCCAGUAC
(SEQ ID NO: 286)

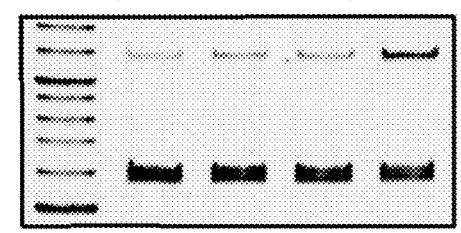

2'F base:   -   U   C   CU
FIG. 17F

Tar9
AUCUGAGCCUGGGAGCUCUC
(SEQ ID NO: 287)

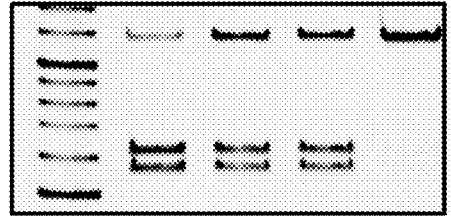

2'F base:   -   U   C   CU
FIG. 17G

Tar6
AGAGCUCCCAGGCUCAGAUC
(SEQ ID NO: 288)

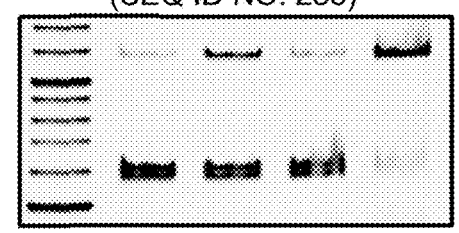

2'F base:   -   U   C   CU
FIG. 17H

Tar10
GGGAGCUCUCUGGCUAACUA
(SEQ ID NO: 289)

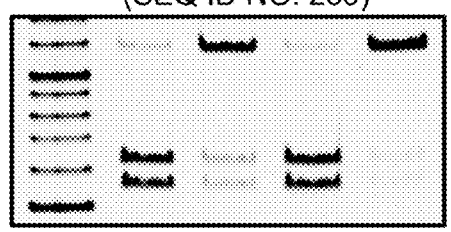

2'F base:   -   U   C   CU
FIG. 17I

20 nt guide
5'- NNNNNNNNNNNNNNNNNNNNGUUAAGA- -GCUAUGCUGG
                                 •||||•• ||||||||||  A
                             UC-GGAAUAAAUUUGAACGAUACGACA  A
Modified RNA              A GUCCGUUAUCAACUUG            A
Scaffold                     |||||               A
(MT)                      AGCCACGGUGAAA
                          G |||||||
                          UCGGUGCUUU - 3' (SEQ ID NO: 162)

FIG. 20B

Anti-HIV (20 nt) guide                                Fc Apatmer
5'- NNNNNNNNNNNNNNNNNNNNGUUAAGA- -GCUAUGCUGGGCCAG   G U G C    G
                                •||||•• ||||||||||||||     U C C  A
                             UC-GGAAUAAAUUUGAACGAUACGACCCGGUC  A  A G G  A
Modified RNA              A GUCCGUUAUCAACUUG           A
Scaffold                     |||||               A
Aptamer-Fc-V1             AGCCACGGUGAAA
                          G |||||||
                          UCGGUGCUUU - 3' (SEQ ID NO: 163)

FIG. 20C

Anti-HIV (20 nt) guide
5'- NNNNNNNNNNNNNNNNNNNNGUUAAGA- -GCUAUGCUGG
                                •||||•• ||||||||||  A
                             UC-GGAAUAAAUUUGAACGAUACGACA   G U G C    G
Modified RNA              A GUCCGUUAUCAACUUGGCCAG           U C C  A
Scaffold                     |||||||||||              A G G  A
Aptamer-Fc-V2             AGCCACGGUGAACCGGUC       A
                          G |||||||
                          UCGGUGCUUU - 3' (SEQ ID NO: 164)

FIG. 20D

20 nt guide
5'- NNNNNNNNNNNNNNNNNNNNGUUAAGA- -GCUAUGCUGGGCCAG   G U G C    G
                                •||||•• ||||||||||||||     U C C  A
                             UC-GGAAUAAAUUUGAACGAUACGACCCGGUC  A  A G G  A
Modified RNA              A GUCCGUUAUCAACUUGGCCAG    G U G C    G
Scaffold                     |||||||||||              U C C  A
Aptamer-Fc-V3             AGCCACGGUGAACCGGUC    A  A G G  A
                          G |||||||
                          UCGGUGCUUU - 3' (SEQ ID NO: 165)

FIG. 20E

MODIFIED TRACRRNAS GRNAS, AND USES THEREOF

CROSS-REFERENCE

This application is a national stage entry, filed under 35 U.S.C. § 371, of International Application No. PCT/US2018/066005, filed Dec. 17, 2018, which claims the benefit of priority to U.S. Provisional Application No. 62/607,838, filed Dec. 19, 2017, U.S. Provisional Application No. 62/658,944, filed Apr. 17, 2018, and U.S. Provisional Application No. 62/659,037, filed Apr. 17, 2018, which are hereby incorporated by reference in their entitles for all purposes.

STATEMENT AS TO RIGHTS TO INVENTIONS MADE UNDER FEDERALLY SPONSORED RESEARCH AND DEVELOPMENT

This invention was made with government support under MH113407, AI099783, AI111139, and DK104681 awarded by the National Institutes of Health. The government has certain rights in the invention.

SEQUENCE LISTING

The Sequence Listing written in file 048440-659NO1US_Sequence_Listing_ST25.txt, created on Feb. 17, 2023, 98 kilobytes, machine format IBM-PC, MS-Windows operating system, is hereby incorporated by reference.

BACKGROUND OF THE DISCLOSURE

The development of efficient and reliable ways to make precise, targeted changes to the genome of living cells is a long-standing goal in the field of life science. Recently, a new tool based on a CRISPR-associated genome edition system has been developed for targeted genome edition (or modification). While this system has been shown to be an effective tool to cause permanent gene and genome edition, it may still benefit from improvements.

BRIEF SUMMARY OF THE DISCLOSURE

Provided herein are solutions to these and other needs in the art. Provided herein, inter alia, is a nucleic acid including a genetically modified trans-activating crRNA (tracrRNA) sequence, wherein (a) at least one nucleotide of the modified tracrRNA sequence corresponding to a uracil of SEQ ID NO: 1 is a nucleotide other than uracil, and (b) the modified tracrRNA sequence is not a naturally occurring tracrRNA sequence. In embodiments, the modified tracrRNA sequence is at least 80% identical to SEQ ID NO: 1 or a tracrRNA sequence selected from any of Tables 1-10. In embodiments, the tracrRNA sequence does not comprise a tracrRNA sequence of Table 9 or Table 10. In embodiments, the modified tracrRNA sequence increases activity of a CRISPR complex relative to SEQ ID NO: 1. In embodiments, the modified tracrRNA sequence further includes one or more modified nucleotides. In embodiments, the nucleic acid further includes a guide RNA (gRNA) sequence, wherein one or more cytosine nucleotides and/or one or more uracil nucleotides of said gRNA sequence are modified nucleotides. In embodiments, the modified tracrRNA sequence is further modified with an insertion of an aptamer nucleic acid sequence at a loop region of said modified tracrRNA sequence. In embodiments, the gRNA sequence is further modified with an insertion of an aptamer nucleic acid sequence at a loop region of said gRNA sequence.

In one aspect, provided herein is a nucleic acid having a guide RNA (gRNA) sequence, wherein all cytosine nucleotides of the gRNA sequence are modified nucleotides and wherein the gRNA sequence is further modified with an insertion of an aptamer nucleic acid sequence at a loop region of the gRNA sequence.

In one aspect, provided herein is a nucleic acid having a guide RNA (gRNA) sequence, wherein all cytosine nucleotides of the gRNA sequence are modified nucleotides.

In one aspect, provided herein is a composition that includes (a) a first nucleic acid comprising a genetically modified trans-activating crRNA (tracrRNA) sequence, wherein (i) at least one nucleotide of the modified tracrRNA sequence corresponding to a uracil of SEQ ID NO: 1 is a nucleotide other than uracil, and (ii) the modified tracrRNA sequence is not a naturally occurring tracrRNA sequence; and (b) a second nucleic acid comprising a guide RNA (gRNA) sequence, wherein one or more cytosine nucleotides and/or one or more uracil nucleotides of said gRNA sequence are modified nucleotides.

In one aspect, provided herein is a vector including or encoding one or more of the nucleic acids of the disclosure.

In one aspect, provided herein is a pharmaceutical composition including any of the nucleic acids of the disclosure, any of the compositions of the disclosure, or any of the vectors of the disclosure, and a pharmaceutically acceptable excipient.

In one aspect, provided herein is a method of altering gene expression in a cell. The method may include introducing into the cell any of the nucleic acids of the disclosure, any of the compositions of the disclosure, any of the vectors of the disclosure, or any of the pharmaceutical compositions of the disclosure.

In another aspect, provided herein is a method of treating a disorder in a subject in need thereof. The method may include administering to the subject any of the nucleic acid of the disclosure, any of the vector of the disclosure, or any of the pharmaceutical composition of the disclosure, in combination with an RNA-guided DNA endonuclease enzyme.

BRIEF DESCRIPTION OF THE DRAWINGS

FIG. 5A is a bar graph depicting results of sequences gRNA sequences V3.0-1, V3.0-3, and V4.0-1 through V4.0-31. FIG. 5B is a bar graph depicting results of sequences gRNA sequences V4.0-32 through V4.0-46.

FIG. 8A is a bar graph showing TZM-BL cells transfected with a Cas9 expression vector with a wild-type or U-replaced gRNAs. Levels of luciferase were measured and KD was made relative to wild-type gRNA set at 100%. FIG. 8B is a bar graph depicting results for in vitro transcribed U-replaced tracrRNAs annealed with an anti-HIV crRNA and transfected into LTR-GFP-Cas9 cell line, and 48-hr post-transfection the levels of GFP were determined by FACS.

FIG. 9A is a bar graph depicting measurement of GFP of U-depleted gRNA-1. FIG. 9B is a bar graph depicting measurement of GFP of U-depleted gRNA-1 and U-depleted gRNA-2. FIG. 9C is a bar graph depicting measurement of GFP of U-depleted gRNA-2 and U-depleted gRNA-3. FIG. 9D is a bar graph depicting measurement of GFP of U-depleted gRNA-3 and Near-pan depleted gRNA. FIG. 9E is a schematic depicting the sequences of the U-depleted tracrRNAs.

FIG. 10A is a bar graph depicting GFP levels in unmodified U-depleted tracrRNAs. The levels of LTR-GFP knockdown was assessed for a gRNA that had Cas9-interacting uridines replaced with G's or A (U-depleted gRNA-V1) and compared to a wild-type gRNA. FIG. 10B is a bar graph depicting GFP levels in 2'F modified U-depleted modifications. A U-depleted tracrRNA was in vitro transcribed with 2'F-bases and annealed with a unmodified crRNA. The RNA was transfected into a HEK-LTR-GFP-Cas9 cells and levels of GFP were assessed by FACS. FIG. 10C is a schematic depicting the sequences of the U-depleted tracrRNAs. A gRNA was developed with further U-depletions in the internal loop region and the levels of activity were assessed.

FIG. 11 is a table depicting example substitutions for U-replaced gRNAs. The crRNA is highlighted in bold; the tetraloop is in lower case, and the tracrRNA is underlined.

FIG. 12 is a table depicting example substitutions with respect to a reference sequence, including substitutions in the tracrRNA sequence. The crRNA is highlighted in bold; the tetraloop is in lower case; and the tracrRNA is underlined.

FIGS. 17A-17I present results showing in vitro cleavage activity of chemically modified gRNAs.

FIGS. 20A-20E show schematics of modified gRNAs with an Fc aptamer.

FIG. 26A is a schematic showing the nucleotide sequence. FIG. 26B is a graph showing the relative LTR activity at increasing concentration. FIG. 26C is an image of a blot. FIG. 26D is a bar graph showing pMO-C6-spCas9. FIG. 26E is a bar graph showing RNP+gRNA-CCR5 at 700 nM.

FIGS. 31A-33B provide bar graphs illustrating U-replaced tracrRNA activity with Cas9 RNPs. FIG. 33B) A series of sequence modifications were made to tracrRNA-9 to generate U-replaced tracrRNAs 10-19.

FIG. 32 is a bar graph illustrating that U-replaced tracrRNAs can improve activity of Cas9 RNPs. A WT-tracrRNA and a series of U-replaced tracrRNAs were in vitro transcribed with unmodified bases and annealed to a crRNA that targets the TAR element of HIV (TAR6). The crRNA:tracrRNAs were incubated with a Cas9 RNP and then transfected into a LTR-GFP cell line. At 48-hr post-transfection the levels of GFP were determined by FACS. Errors bars were obtained by transfections performed in duplicate. Significance was determined using a one-way Anova. *p<0.05, ***p<0.001.

FIGS. 33A-33B are bar graphs illustrating that U-replaced tracrRNA-26 improves activity with Cas9 RNPs. A WT-tracrRNA and U-replaced tracrRNA-26 were in vitro transcribed with unmodified bases and annealed to a crRNA that targets the TAR element of HIV (TAR6). The crRNA:tracrRNAs were incubated with a Cas9 RNP and serially diluted amounts were then transfected into a LTR-GFP cell line. At 48-hr post-transfection the levels of GFP (FIG. 33A) or NHEJ (FIG. 33B) were determined by FACS and drop-off assay, respectively. Errors bars were obtained by transfections performed in duplicate.

FIG. 34A: A WT-tracrRNA and a series of U-replaced tracrRNAs were in vitro transcribed with unmodified bases and annealed to a crRNA that targets the TAR element of HIV (TAR6). The crRNA:tracrRNAs were incubated with a Cas9 RNP and either undiluted or a 1:2 dilution was transfected into a LTR-GFP cell line. At 48-hr post-transfection the levels of GFP was determined by FACS. FIG. 34B: Drop-off assays were performed on samples transfected with the tracrRNA-26 and 36, and compared to a WT control, either undiluted or at a 1:2 dilution. FIG. 34C: A WT-tracrRNA or U-replaced tracrRNA-26 and 36 were electroporated into a LTR-GFP cell line either undiluted or at a 1:2 dilution, and the levels of indels were quantified by drop-off assay. Error bars were obtained by transfections performed in duplicate. Significance was determined using a one-way Anova, *p<0.05, **p<0.01.

FIG. 35A: A WT-tracrRNA and U-replaced tracrRNA-26 and 36 were in vitro transcribed with unmodified bases and annealed to a crRNA that targets the TAR element of HIV (TAR3,4 and 5). The crRNA:tracrRNAs were incubated with a Cas9 RNP and transfected into a LTR-GFP cell line. At 48-hr post-transfection the levels of GFP (FIG. 35A) or % NHEJ (FIG. 35B) were determined by FACS and drop-off assay, respectively. Errors bars were obtained by transfections performed in duplicate. Significance was determined using a one-way Anova, *p<0.05, p<0.01, *<0.001.

FIG. 36A: A WT tracrRNA and U-replaced tracrRNA-26 and 36 were in vitro transcribed with unmodified bases and annealed to one of two crRNAs targeted to CCR5, CCR5-1 crRNA (FIG. 36A) and CCR5-2 crRNA (FIG. 36B). The crRNA:tracrRNAs were incubated with a Cas9 RNP and electroporated into CEM.CCR5 cell line. At 72-hr post-transfection the levels of CCR5 and amount of NHEJ were determined by FACS and drop-off assay, respectively. Errors bars were obtained by transfections performed in triplicate. Significance was determined using a one-way Anova, p<0.01, *<0.001.

FIG. 37A: A WT-tracrRNA or U-replaced tracrRNA-26 and 36 were in vitro transcribed with unmodified bases and annealed to one of two crRNAs, CCR5-1 (FIG. 37A) and CCR5-2 (FIG. 37B), which target CCR5. The crRNA:tracrRNAs were incubated with a Cas9 RNP and electroporated into purified CD4+ primary T-cells. At 72-hr post-transfection, the % NHEJ was determined by drop-off assay. Errors bars were obtained by transfections performed in triplicate. Significance was determined using a one-way Anova, *p<0.01, ***<0.001.

DETAILED DESCRIPTION OF THE DISCLOSURE

Figure 1A:
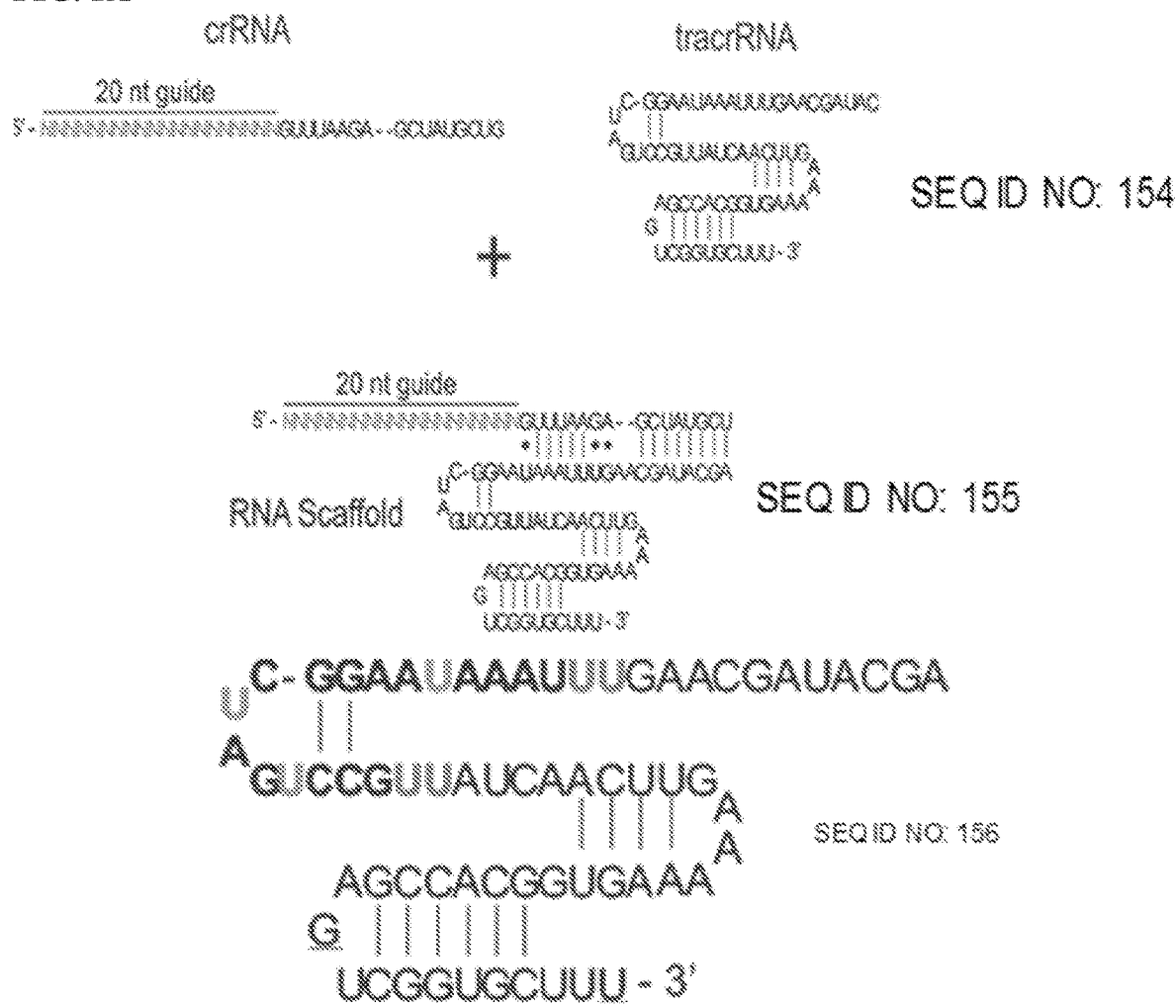
FIG. 1A is a schematic depicting an example tracrRNA with selected regions synthesized with 2'F-Us: internal loop region (bold), the external region (underlined), and internal uridines that interact with Cas9 (boxed) and internal non-interacting uridines (circled).

Disclosed herein are, inter alia, compositions and methods for altering gene expression in a cell. In one aspect, the compositions and methods utilize a CRISPR-associated system which includes a guide RNA (gRNA) sequence and a tracrRNA sequence. The tracrRNA sequence may be separate from, or form a part of the gRNA. In embodiments, the tracrRNA sequence is a genetically modified tracrRNA sequence. In embodiments, at least one nucleotide of the modified tracrRNA sequence corresponding to a uracil of SEQ ID NO: 1 is a nucleotide other than uracil, and the modified tracrRNA sequence is not a naturally occurring tracrRNA sequence. In embodiments, the tracrRNA sequence does not comprise a tracrRNA sequence of Table 9 or Table 10. In embodiments, the sgRNA, the modified tracrRNA, or both include one or more modified nucleotides, such as one or more (or all) modified cytosines and/or one or more (or all) modified uracils. Also disclosed herein are, inter alia, methods of treating a disorder in a subject in need thereof. The method may include administering the compositions described herein or applying the methods described herein to the subject.

Definitions

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY 2nd ed., J. Wiley & Sons (New York, NY 1994); Sambrook et al., MOLECULAR CLONING, A LABORATORY MANUAL, Cold Springs Harbor Press (Cold Springs Harbor, NY 1989). Any methods, devices and materials similar or equivalent to those described herein can be used in the practice of this disclosure. The following definitions are provided to facilitate understanding of certain terms used frequently herein and are not meant to limit the scope of the present disclosure.

The use of a singular indefinite or definite article (e.g., "a," "an," "the," etc.) in this disclosure and in the following claims means "at least one" unless in a particular instance it is clear from context that the term is intended in that particular instance to mean specifically one and only one. Likewise, the term "comprising" is open ended, not excluding additional items, features, components, etc. References identified herein are expressly incorporated herein by reference in their entireties unless otherwise indicated.

The terms "comprise," "include," and "have," and the derivatives thereof, are used herein interchangeably as comprehensive, open-ended terms. For example, use of "comprising," "including," or "having" means that whatever element is comprised, had, or included, is not the only element encompassed by the subject of the clause that contains the verb.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and 0-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "polypeptide," "peptide" and "protein" are used interchangeably herein to refer to a polymer of amino acid residues, wherein the polymer may in embodiments be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. A "fusion protein" refers to a chimeric protein encoding two or more separate protein sequences that are recombinantly expressed as a single moiety.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, Proteins (1984)).

As may be used herein, the terms "nucleic acid," "nucleic acid molecule," "nucleic acid oligomer," "oligonucleotide," "nucleic acid sequence," "nucleic acid fragment" and "polynucleotide" are used interchangeably and are intended to include, but are not limited to, a polymeric form of nucleotides covalently linked together that may have various lengths, either deoxyribonucleotides or ribonucleotides, or analogs, derivatives or modifications thereof. Different polynucleotides may have different three-dimensional structures, and may perform various functions, known or unknown. Non-limiting examples of polynucleotides include a gene, a gene fragment, an exon, an intron, intergenic DNA (including, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, a nucleic acid probe, and a primer. Polynucleotides useful in the methods of the invention may comprise natural nucleic acid sequences and variants thereof, artificial nucleic acid sequences, or a combination of such sequences.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

"Nucleic acid" refers to deoxyribonucleotides or ribonucleotides and polymers thereof in either single-, double- or multiple-stranded form, or complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA (including siRNA), and hybrid molecules having mixtures of single and double stranded DNA and RNA. Nucleic acids can be linear or branched. For example, nucleic acids can be a linear chain of nucleotides or the nucleic acids can be branched, e.g., such that the nucleic acids comprise one or more arms or branches of nucleotides. Optionally, the branched nucleic acids are repetitively branched to form higher ordered structures such as dendrimers and the like.

Nucleic acids, including nucleic acids with a phosphothioate backbone can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amino acid on a protein or polypeptide through a covalent, non-covalent or other interaction.

The terms also encompass nucleic acids containing known nucleotide analogues or modified backbone residues or linkages, which are synthetic, naturally occurring, and non-naturally occurring, which have similar binding properties as the reference nucleic acid, and which are metabolized in a manner similar to the reference nucleotides. In other words, the term "nucleotide analog" as used herein generally refers to a purine or pyrimidine nucleotide that differs structurally from A, T, G, C, or U, but is sufficiently similar to substitute for such "normal" nucleotides in a nucleic acid molecule. As used herein, the term "nucleotide analog" encompasses altered bases, different (or unusual) sugars, altered phosphate backbones, or any combination of these alterations. Examples of such analogues include, without limitation, phosphodiester derivatives including, e.g., phosphoramidate, phosphorodiamidate, phosphorothioate (also known as phosphothioate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see Eckstein, Oligonucleotides and Analogues: A Practical Approach, Oxford University Press); and peptide nucleic acid backbones and linkages. Other analogue nucleic acids include those with positive backbones; non-ionic backbones, modified sugars, and non-ribose backbones (e.g. phosphorodiamidate morpholino oligos or locked nucleic acids (LNA)), including those described in U.S. Pat. Nos. 5,235,033 and 5,034,506, and Chapters 6 and 7, ASC Symposium Series 580, *Carbohydrate Modifications in Antisense Research*, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Nucleotide analogues used herein also include nucleotides having modified 2' position of the ribose ring. For example, the 2' position of the ribose ring is substituted by O-methyl, O-alkyl, 0-allyl, S-alkyl, S-allyl, or halo group. Mixtures of naturally occurring nucleic acids and analogues can be made; alternatively, mixtures of different nucleic acid analogues, and mixtures of naturally occurring nucleic acids and analogues may be made. In embodiments, the internucleotide linkages in DNA are phosphodiester, phosphodiester derivatives, or a combination of both.

"Conservatively modified variants" applies to both amino acid and nucleic acid sequences. With respect to particular nucleic acid sequences, "conservatively modified variants" refers to those nucleic acids that encode identical or essentially identical amino acid sequences. Because of the degeneracy of the genetic code, a number of nucleic acid sequences will encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As used herein, the term "conjugate" refers to the association between atoms or molecules. The association can be direct or indirect. For example, a conjugate between a first moiety (e.g., nucleic acid moiety) and a second moiety (peptide moiety) provided herein can be direct, e.g., by covalent bond, or indirect, e.g., by non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). In embodiments, conjugates are formed using conjugate chemistry including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the first moiety (e.g., polyamine moiety) is non-covalently attached to the second moiety (peptide moiety) through a non-covalent chemical reaction between a component of the first moiety (e.g., polyamine moiety) and a component of the second moiety (peptide moiety). In other embodiments, the first moiety (e.g., polyamine moiety) includes one or more reactive moieties, e.g., a covalent reactive moiety, as described herein (e.g., alkyne, azide, maleimide or thiol reactive moiety). In other embodiments, the first moiety (e.g., polyamine moiety) includes a linker with one or more reactive moieties, e.g., a covalent reactive moiety, as described herein (e.g., alkyne, azide, maleimide or thiol reactive moiety). In other embodiments, the second moiety (peptide moiety) includes one or more reactive moieties, e.g., a covalent reactive moiety, as described herein (e.g., alkyne, azide, maleimide or thiol reactive moiety). In other embodiments, the second moiety (peptide moiety) includes a linker with one or more reactive moieties, e.g., a covalent reactive moiety, as described herein (e.g., alkyne, azide, maleimide or thiol reactive moiety).

A "labeled nucleic acid or oligonucleotide" is one that is bound, either covalently, through a linker or a chemical bond, or noncovalently, through ionic, van der Waals, electrostatic, or hydrogen bonds to a label such that the presence of the nucleic acid may be detected by detecting the presence of the detectable label bound to the nucleic acid. Alternatively, a method using high affinity interactions may achieve the same results where one of a pair of binding partners binds to the other, e.g., biotin, streptavidin. In embodiments, the phosphorothioate nucleic acid or phosphorothioate polymer backbone includes a detectable label, as disclosed herein and generally known in the art.

A "label" or a "detectable moiety" is a composition detectable by spectroscopic, photochemical, biochemical, immunochemical, chemical, or other physical means. For example, useful labels include $^{32}$P, fluorescent dyes, electron-dense reagents, enzymes (e.g., as commonly used in an ELISA), biotin, digoxigenin, or haptens and proteins or other entities which can be made detectable, e.g., by incorporating a radiolabel into a peptide or antibody specifically reactive with a target peptide. Any appropriate method known in the art for conjugating an antibody to the label may be employed, e.g., using methods described in Hermanson, Bioconjugate Techniques 1996, Academic Press, Inc., San Diego.

The term "probe" or "primer", as used herein, is defined to be one or more nucleic acid fragments whose specific hybridization to a sample can be detected. A probe or primer can be of any length depending on the particular technique it will be used for. For example, PCR primers are generally between 10 and 40 nucleotides in length, while nucleic acid probes for, e.g., a Southern blot, can be more than a hundred nucleotides in length. The probe may be unlabeled or labeled as described below so that its binding to the target or sample can be detected. The probe can be produced from a source of nucleic acids from one or more particular (preselected) portions of a chromosome, e.g., one or more clones, an isolated whole chromosome or chromosome fragment, or a collection of polymerase chain reaction (PCR) amplification products. The length and complexity of the nucleic acid fixed onto the target element is not critical to the invention. One of skill can adjust these factors to provide optimum hybridization and signal production for a given hybridization procedure, and to provide the required resolution among different genes or genomic locations.

The probe may also be isolated nucleic acids immobilized on a solid surface (e.g., nitrocellulose, glass, quartz, fused silica slides), as in an array. In some embodiments, the probe may be a member of an array of nucleic acids as described, for instance, in WO 96/17958. Techniques capable of producing high density arrays can also be used for this purpose (see, e.g., Fodor (1991) Science 767-773; Johnston (1998) Curr. Biol. 8: R171-R174; Schummer (1997) Biotechniques 23: 1087-1092; Kern (1997) Biotechniques 23: 120-124; U.S. Pat. No. 5,143,854).

The term "isolated", when applied to a nucleic acid or protein, denotes that the nucleic acid or protein is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified.

The term "complementary" or "complementarity" refers to the ability of a nucleic acid to form hydrogen bond(s) with another nucleic acid sequence by either traditional Watson-Crick or other non-traditional types. For example, the sequence A-G-T is complementary to the sequence T-C-A. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%. 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques In Biochemistry And Molecular Biology-Hybridization With Nucleic Acid Probes Part 1, Second Chapter "Overview of principles of hybridization and the strategy of nucleic acid probe assay", Elsevier, N.Y.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence.

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions of the reference sequence in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, optionally 65%, 70%, 75%, 80%, 85%, 90%, 95%, 98%, or 99% identity over a specified region of a reference sequence, e.g., of an entire polynucleotide sequence described herein or individual domains of a a polynucleotide sequence described herein), when compared and aligned for maximum correspondence over a comparison window, or designated region as measured using a sequence comparison algorithm or by manual alignment and visual inspection. In embodiments, two sequences are said to be "substantially identical" when they are at least about 90%, 95%, 98%, or 99% identical. This definition also refers to the complement of a test sequence. Optionally, the identity exists over a region that is at least about 25, 50, or more nucleotides in length, or more preferably over a region that is about or at least about 67, 75, 89, 116, or more nucleotides in length. In embodiments, the identity exists over a region that is about 67 nucleotides in length, such as nucleotides 2-68 of SEQ ID NO: 1.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that must be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence. Whether a nucleotide corresponds to a particular position in a reference sequence (e.g., a uracil in SEQ ID NO: 1), optionally at a different position, can be determined by sequence alignment. In general, an alignment showing identity of one or more nucleotides flanking the indicated position of the reference sequence will allow the corresponding position of the query sequence to be positioned locally with respect to the reference sequence to confirm the presence of a genetic modification of the corresponding nucleotide, optionally at a shifted numerical position in the query sequence. In embodiments, a region comprising at least three to fifteen nucleotides, including the substituted position, will locally align with the corresponding reference sequence with a relatively high percent identity, except for the position of the substituted nucleotide along the query sequence (e.g. at least about 90%, 95%, or 100% identity). In embodiments, a nucleotide of a query tracrRNA sequence corresponds to a particular position of a reference sequence if the nucleotide of the query sequence aligns to the particular position of the reference sequence when the two sequences are optimally aligned using a BLASTN alignment algorithm with default parameters.

Percent sequence identity, percent complementarity, and the location of a position corresponding to a reference position in a reference sequence (e.g., a uracil in SEQ ID NO: 1) may be determined by any suitable alignment algorithm, including but not limited to the Needleman-Wunsch algorithm (see e.g. the EMBOSS Needle aligner available at www.ebi.ac.uk/Tools/psa/emboss needle/nucleotide.html, optionally with default settings), the BLAST algorithm (see e.g. the BLAST alignment tool available at blast.ncbi.nlm.nih.gov/Blast.cgi, optionally with default settings), or the Smith-Waterman algorithm (see e.g. the EMBOSS Water aligner available at www.ebi.ac.uk/Tools/psa/emboss water/nucleotide.html, optionally with default settings). Optimal alignment may be assessed using any suitable parameters of a chosen algorithm, preferably default parameters.

The term "gene" means the segment of DNA involved in producing a protein; it includes regions preceding and following the coding region (leader and trailer) as well as intervening sequences (introns) between individual coding segments (exons). The leader, the trailer as well as the introns include regulatory elements that are necessary during the transcription and the translation of a gene. Further, a "protein gene product" is a protein expressed from a particular gene.

The word "expression" or "expressed" as used herein in reference to a gene means the transcriptional and/or translational product of that gene. The level of expression of a DNA molecule in a cell may be determined on the basis of either the amount of corresponding mRNA that is present within the cell or the amount of protein encoded by that DNA produced by the cell. The level of expression of non-coding nucleic acid molecules (e.g., sgRNA) may be detected by standard PCR or Northern blot methods well known in the art. See, Sambrook et al., 1989 *Molecular Cloning: A Laboratory Manual*, 18.1-18.88.

The term "CRISPR," "Clustered Regularly Interspaced Short Palindromic Repeats," "CRISPR system," "CRISPR/Cas system" or "CRISPR-associated system" used herein refers to a molecular system that can perform genome edition, and modified versions thereof (e.g., systems incorporating dCas9). In embodiments, the CRISPR-associated system refers to a general term that applies to three types of systems, and system sub-types. Three types of CRISPR systems (see below Table 1) have been identified, each with differing features.

TABLE 1

CRISPR System Types Overview

| System | Features | Examples |
|---|---|---|
| Type I | Multiple proteins (5-7 proteins typical), crRNA. DNA Cleavage is catalyzed by Cas3. | *Staphylococcus epidermidis* (Type IA) |
| Type II | 3-4 proteins (one protein (Cas9) has nuclease activity) two RNAs. Target DNA cleavage catalyzed by Cas9 and RNA components. | *Streptococcus pyogenes* CRISPR/Cas9, *Francisella novicida* U112 Cpf1 |
| Type III | Five or six proteins required for cutting, number of required RNAs unknown but expected to be 1. Type IIIB systems have the ability to target RNA. | *S. epidermidis* (Type IIIA); *P. furiosus* (Type IIIB). |

In embodiments, the CRISPR-associated system of the disclosure refers to a molecular system that can alter gene expression, e.g. transcription and/or translation. The term "alter," "altering," "alteration of" or "altered" gene expression used herein refers to any action or process that is capable of modulating (interchangeably used with "altering," "regulating," "modifying," "controlling" and"changing") transcription and/or translation of a sequence of interest (e.g. a gene). Therefore, in one example, the alteration of gene expression includes any transcriptional regulation such as transcriptional activation (interchangeably used with "promotion," "enhancement," "increase" or "upregulation" of transcription) and transcriptional repression (interchangeably used with "reduction," "decrease," "inhibition" or "suppression" of transcription). In another example, the alteration of gene expression includes translational activation (interchangeably used with "promotion," "enhancement," "increase" or "upregulation" of transcription) and translational repression (interchangeably used with "reduction," "decrease," "inhibition" or "suppression" of transcription). In embodiments, the alteration of gene expression includes edition of nucleic acid sequence in genomic DNA. Thus, in embodiments the edition of nucleic acid sequence includes genome edition. In embodiments, the edition of nucleic acid sequence includes editing the sequence of non-genomic DNA or RNA (e.g. mRNA). In embodiments, the edition of nucleic acid sequence is done by mutating and/or deleting one or more nucleic acids from the sequence of interest (e.g. a genomic DNA sequence, non-genomic DNA sequence or RNA sequence), or inserting additional nucleic acid(s) into the sequence of interest.

The term "genome edition" or "editing genome" used herein refers to alteration of DNA sequence in a genome. The alternation of genome can be done by deletion of part of genomic DNA sequence, insertion of an additional DNA sequence into the genome and/or replacement of part of genome with a different DNA sequence. In embodiments, the edition of genome is permanent such that a daughter cell dived from the original cell that has the edited genome will have the same, altered (or modified) genome.

The term "gene replacement" used herein refers to replacing (or substituting) at least part of a sequence of interest with another sequence that is not present in the endogenous sequence of the target. In embodiments, a coding or non-coding sequence from a genome of a cell is replaced with a sequence that is different from the original, endogenous sequence of the genome. In embodiments, at least part of non-genomic DNA or RNA can be replaced with a sequence that is different from the original, endogenous sequence. The gene replacement can be done by inserting a new sequence into a target sequence, with or without deleting any part of the target sequence. In embodiments, the gene replacement can be done by deleting at least part of the target sequence and inserting a new sequence into the target sequence.

In embodiments, CRISPR protein also refers to a protein that can form a complex that binds a first nucleic acid molecule. Thus, one CRISPR protein may bind to, for example, a guide RNA and another protein may have endonuclease activity. These are all considered to be CRISPR proteins because they function as part of a complex that performs the same functions as a single protein, such as Cas9 or CPF1.

The term "dCas9" as provided herein refers to a nuclease inactivated Cas9. In embodiments, the DNA-binding modulation-enhancing agent may be a guide RNA bound to a dCas9 domain. In other embodiments, the modulation complex is a dCas9 domain bound to a gRNA, wherein the modulation complex further includes one or more additional peptides that is capable of altering gene expression (e.g. VP16 transcriptional activation domain, viral protein R(VPR), p65 transactivating subunit of NF-kappa B, heat-shock factor 1 (HSF) activation domain, VP64 (tetramer of VP16) activation domain, synergistic activation mediator (SAM), acetyltransferase, KRAB transcriptional repressor domain, DNA methyltransferase(e.g. DNA methyltransferase 3 alpha or DNMT3A, and APOBEC3A DNA deaminase domain) that is operably linked to the dCas9 domain. Such a system could be used to induce expression of, for example, an endogenous gene in a mammalian cell. A person of ordinary skill in the art will immediately recognize that the types of DNA-binding modulation-enhancing agents used will vary depending on the cell type and specific application.

CRISPR systems that may be used vary greatly. These systems will generally have the functional activities of a being able to form complex having a protein and a gRNA sequence where the complex recognizes a second nucleic acid. CRISPR systems can be a type I, a type II, or a type III system. Non-limiting examples of suitable CRISPR proteins include Cas3, Cas4, Cas5, Cas5e (or CasD), Cas6, Cas6e, Cas6f, Cas7, Cas8a1, Cas8a2, Cas8b, Cas8c, Cas9, Cas10, Cas1 Od, CasF, CasG, CasH, Csy1, Csy2, Csy3, Cse1 (or CasA), Cse2 (or CasB), Cse3 (or CasE), Cse4 (or CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3,Csx17, Csx14, Csx10, Csx16, CsaX, Csx3, Csz1, Csx15, Csf1, Csf2, Csf3, Csf4, and Cu1966.

In embodiments, the CRISPR protein (e.g., Cas9) is derived from a type II CRISPR system. In some embodiments, the CRISPR system is designed to act as an oligonucleotide (e.g., DNA or RNA) guided endonuclease derived from a Cas9 protein. The Cas9 protein for this and other functions set out herein can be from *Streptococcus pyogenes, Streptococcus thermophilus, Streptococcus sp., Nocardiopsis dassonvillei, Streptomyces pristinaespiralis, Streptomyces viridochromogenes, Streptomyces viridochromogenes, Streptosporangium roseum, Alicyclobacillus acidocaldarius, Bacillus pseudomycoides, Bacillus selenitireducens, Exiguobacterium sibiricum, Lactobacillus delbrueckii, Lactobacillus salivarius, Microscilla marina,* Burkholderiales *bacterium, Polaromonas naphthalenivorans, Polaromonas sp., Crocosphaera watsonii,* Cyanothece *sp., Microcystis aeruginosa, Synechococcus sp., Acetohalobium arabaticum, Ammonifex degensii,* Caldicelulosiruptor becscii, *Candidatus* Desulforudis, *Clostridium botulinum, Clostridium difficile, Finegoldia magna, Natranaerobius thermophilus,* Pelotomaculumthermopropionicum, *Acidithiobacillus caldus,* Acidithiobacillus *ferrooxidans, Allochromatium vinosum, Marinobacter sp.,* Nitrosococcus *halophilus, Nitrosococcus watsoni, Pseudoalteromonas haloplanktis, Ktedonobacter racemifer, Methanohalobium evestigatum, Anabaena variabilis, Nodularia spumigena, Nostoc sp., Arthrospira maxima, Arthrospira platensis, Arthrospira sp., Lyngbya sp., Microcoleus chthonoplastes, Oscillatoria sp., Petrotoga mobilis, Thermosipho africanus,* or Acaryochloris *marina.*

For specific proteins described herein (e.g., Cas9, Cpf1, and the like), the named protein includes any of the protein's naturally occurring forms, or variants or homologs that maintain the protein's activity (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In other embodiments, the protein is the protein as identified by its NCBI sequence reference. In other embodiments, the protein is the protein as identified by its NCBI sequence reference or functional fragment or homolog thereof.

A "guide RNA" or "gRNA" as provided herein refers to a ribonucleotide sequence capable of binding a nucleoprotein, thereby forming ribonucleoprotein complex. Likewise a "guide DNA" or "gDNA" as provided herein refers to a deoxyribonucleotide sequence capable of binding a nucleoprotein, thereby forming deoxyribonucleoprotein complex. In embodiments, the guide RNA includes one or more RNA molecules. In embodiments, the guide DNA includes one or more DNA molecules. In embodiments, the gRNA includes a nucleotide sequence complementary to a target site (e.g., a modulator binding sequence). In embodiments, the gDNA includes a nucleotide sequence complementary to a target site (e.g., a modulator binding sequence). The complementary nucleotide sequence may mediate binding of the ribonucleoprotein complex or the deoxyribonucleoprotein complex to the target site thereby providing the sequence specificity of the ribonucleoprotein complex or the deoxyribonucleoprotein complex. Thus, in embodiments, the guide RNA or the guide DNA includes a sequence that is complementary to a target nucleic acid (e.g., a modulator binding sequence). In embodiments, the guide RNA binds a target nucleic acid sequence (e.g., a modulator binding sequence). In embodiments, the guide DNA binds a target nucleic acid sequence (e.g., a modulator binding sequence). In embodiments, the guide RNA is complementary to a CRISPR nucleic acid sequence. In embodiments, the complement of the guide RNA or guide DNA includes a sequence having a sequence identity of about 50%, 55%, 60%, 65%, 70%, 75%, 80%, 85%, 90%, 95%, 96%, 97%, 98% or 99% to a target nucleic acid (e.g., a modulator binding sequence). In embodiments, a target nucleic acid sequence is a nucleic acid sequence expressed by a cell. In embodiments, the target nucleic acid sequence is an exogenous nucleic acid sequence. In embodiments, the target nucleic acid sequence is an endogenous nucleic acid sequence. In embodiments, the target nucleic acid sequence (e.g., a modulator binding sequence) forms part of a cellular gene. Thus, in embodiments, the guide RNA or guide DNA is complementary to a cellular gene or fragment thereof. In embodiments, the guide RNA or guide DNA includes a sequence having sequence identity of about 50%, 55%, 60%, 65%, 70%, 75%, 80%, 85%, 90%, 95%, 96%, 97%, 98% or 99% to the target nucleic acid sequence (e.g., a modulator binding sequence). In embodiments, the guide RNA or guide DNA includes a sequence that is about 50%, 55%, 60%, 65%, 70%, 75%, 80%, 85%, 90%, 95%, 96%, 97%, 98% or 99% complementary to the sequence of a cellular gene. In embodiments, the guide RNA or the guide DNA binds a cellular gene sequence. In embodiments, the guide RNA or guide DNA, or complement thereof, includes a sequence having a sequence identity of at least about 90%, 95%, or 100% to a target nucleic acid. In embodiments, the target nucleic acid is about or at least about 10, 20, 25, or more nucleotides in length.

In embodiments, the guide RNA is a single-stranded ribonucleic acid. In embodiments, the guide RNA or guide DNA is about 10, 20, 30, 40, 50, 60, 70, 80, 90, 100 or more nucleic acid residues in length. In embodiments, the guide RNA or guide DNA is from about 10 to about 30 nucleic acid residues in length. In embodiments, the guide RNA or guide DNA is about 20 nucleic acid residues in length. In embodiments, the length of the guide RNA or the guide DNA can be at least about 5, 6, 7, 8, 9, 10, 11, 12, 13, 14, 15, 16, 17, 18, 19, 20, 21, 22, 23, 24, 25, 26, 27, 28, 29, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more nucleic acid residues or sugar residues in length. In embodiments, the guide RNA or guide DNA is from 5 to 10 to 50, 15 to 50, 20 to 50, 25 to 50, 30 to 50, 35 to 50, 40 to 50, 45 to 50, 5 to 75, 10 to 75, 15 to 75, 20 to 75, 25 to 75, 30 to 75, 35 to 75, 40 to 75, 45 to 75, 50 to 75, 55 to 75, 60 to 75, 65 to 75, 75, 5 to 100, 10 to 100, 15 to 100, 20 to 100, 25 to 100, 30 to 100, 35 to 100, 40 to 100, 45 to 100, 50 to 100, 55 to 100, 60 to 100, 65 to 100, 70 to 100, 75 to 100, 80 to 100, 85 to 100, 90 to 100, 95 to 100, or more residues in length. In embodiments, the guide RNA or guide DNA is from to 15, 10 to 20, 10 to 30, 10 to 40, or 10 to 50 residues in length.

Thus, a "CRISPR associated protein 9," "Cas9," "Csn1" or "Cas9 protein" as referred to herein includes any of the recombinant or naturally-occurring forms of the Cas9 endonuclease or variants or homologs thereof that maintain Cas9 endonuclease enzyme activity (e.g. within at least 50%, 80%, 90%, 95%, 96%, 97%, 98%, 99% or 100% activity compared to Cas9). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring Cas9 protein. In embodiments, the Cas9 protein is substantially identical to the protein identified by the UniProt reference number Q99ZW2 or a variant or homolog having substantial identity thereto. Cas9 refers to the protein also known in the art as "nickase". In embodiments, Cas9 is an RNA-guided DNA endonuclease enzyme that binds a CRISPR (clustered regularly interspaced short palindromic repeats) nucleic acid sequence. In embodiments, the CRISPR nucleic acid sequence is a prokaryotic nucleic acid sequence. In embodiments, the Cas9 nuclease from *Streptococcus pyogenes* is targeted to genomic DNA by a synthetic guide RNA consisting of a 20-nt guide sequence and a scaffold. The guide sequence base-pairs with the DNA target, directly upstream of a requisite 5'-NGG protospacer adjacent motif (PAM), and Cas9 mediates a double-stranded break (DSB) about 3-base pair upstream of the PAM. In embodiments, the CRISPR nuclease from *Streptococcus aureus* is targeted to genomic DNA by a synthetic guide RNA consisting of a 21-23-nt guide sequence and a scaffold. The guide sequence base-pairs with the DNA target, directly upstream of a requisite 5'-NNGRRT protospacer adjacent motif (PAM), and Cas9 mediates a double-stranded break (DSB) about 3-base pair upstream of the PAM.

The term "Cas9 variant" refers to proteins that have at least 80%, 85%, 90%, 95%, 96%, 97%, 98%, 99% or 100% amino acid sequence identity across the whole sequence or a functional portion of the sequence (e.g. a 50, 100, 150 or 200 continuous amino acid portion) compared to wild-type Cas9 protein and have one or more mutations that increase its binding specificity to PAM compared to wild-type Cas9 protein. In embodiments, the Cas9 variant has at least 90%, 95%, or more amino acid sequence identity across the whole sequence compared to a wild-type Cas9 protein.

A "Cpf1" or "Cpf1 protein" as referred to herein includes any of the recombinant or naturally-occurring forms of the Cpf1(Clustered Regularly Interspaced Short Palindromic Repeats from *Prevotella* and *Francisella* 1 or CRISPR/Cpf1) endonuclease or variants or homologs thereof that maintain Cpf1 endonuclease enzyme activity (e.g. within at least 50%, 80%, 90%, 95%, 96%, 97%, 98%, 99% or 100% activity compared to Cpf1). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring Cpf1 protein. In embodiments, the variant or homolog has at least 90%, 95%, or more amino acid sequence identity across the whole sequence compared wild-type Cpf1.

The term "Class II CRISPR endonuclease" refers to endonucleases that have similar endonuclease activity as Cas9 and participate in a Class II CRISPR system. An example Class II CRISPR system is the type II CRISPR locus from *Streptococcus pyogenes* SF370, which contains a cluster of four genes Cas9, Cas1, Cas2, and Csn1, as well as two non-coding RNA elements, a tracrRNA and a characteristic array of repetitive sequences (direct repeats) interspaced by short stretches of non-repetitive sequences (spacers, about 30 bp each). In this system, targeted DNA double-strand break (DSB) may be generated in four sequential steps. First, two non-coding RNAs, the pre-crRNA array and tracrRNA, may be transcribed from the CRISPR locus. Second, tracrRNA may hybridize to the direct repeats of pre-crRNA, which is then processed into mature crRNAs containing individual spacer sequences. Third, the mature crRNA:tracrRNA complex may direct Cas9 to the DNA target consisting of the protospacer and the corresponding PAM via heteroduplex formation between the spacer region of the crRNA and the protospacer DNA. Finally, Cas9 may mediate cleavage of target DNA upstream of PAM to create a DSB within the protospacer.

The term "RNA-guided DNA endonuclease" and the like refer, in the usual and customary sense, to an enzyme that cleaves a phosphodiester bond within a DNA polynucleotide chain, wherein the recognition of the phosphodiester bond is facilitated by a separate RNA sequence (for example, a single guide RNA).

The terms "single guide RNA," "single guide RNA sequence," "chimeric RNA," "chimeric guide RNA," "guide RNA", and "synthetic guide RNA" are used interchangeably and refer to the polynucleotide sequence including the crRNA sequence and optionally the tracrRNA sequence. The crRNA sequence includes a guide sequence (i.e., "guide" or "spacer") and a tracr mate sequence (i.e., direct repeat(s)"). The term "guide sequence" refers to the sequence that specifies the target site. In embodiments, a first nucleic acid includes a tracrRNA sequence, and a separate second nucleic acid includes a gRNA sequence lacking a tracrRNA sequence. In embodiments, the first nucleic acid including the tracrRNA sequence and the second nucleic acid including the gRNA sequence interact with one another, and optionally are included in a CRISPR complex.

In general, a guide sequence (i.e., a DNA-targeting sequence) is any polynucleotide sequence having sufficient complementarity with a target polynucleotide sequence to hybridize with the target sequence (e.g., a genomic or mitochondrial DNA target sequence) and direct sequence-specific binding of a CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. In some embodiments, the degree of complementarity between a guide sequence and its corresponding target sequence, when optimally aligned using a suitable alignment algorithm, is at least about 80%, 85%, 90%, 95%, or 100%. In embodiments, the degree of complementarity is at least 90%. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies, ELAND (Illumina, San Diego, Calif), SOAP (available at soap.genomics.org.cn), and Maq (available at maq.sourceforge.net). In embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 50, 75, or more nucleotides in length. In embodiments, a guide sequence is about 10 to about about 15 to about 30, or about 20 to about 25 nucleotides in length. In embodiments, a guide sequence is less than about 75, 50, 45, 40, 35, 30, 25, 20, 15, 12, or fewer nucleotides in length. In embodiments, the guide sequence is about or more than about 20 nucleotides in length. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay known in the art. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art.

In general, a tracr mate sequence includes any sequence that has sufficient complementarity with a tracrRNA sequence to promote one or more of: (1) excision of a guide sequence flanked by tracr mate sequences in a cell containing the corresponding tracr sequence; and (2) formation of a CRISPR complex at a target sequence, wherein the CRISPR complex comprises the tracr mate sequence hybridized to the tracr sequence. In general, degree of complementarity is with reference to the optimal alignment of the tracr mate sequence and tracrRNA sequence, along the length of the shorter of the two sequences. Optimal alignment may be determined by any suitable alignment algorithm, and may further account for secondary structures, such as self-complementarity within either the tracrRNA sequence or tracr mate sequence. In some embodiments, the degree of complementarity between the tracrRNA sequence and tracr mate sequence along the length of the shorter of the two when optimally aligned is about or more than about 25%, 30%, 40%, 50%, 60%, 70%, 80%, 90%, 95%, 97.5%, 99%, or higher. In embodiments, the degree of complementarity is about or at least about 80%, 90%, 95%, or 100%. In some embodiments, the tracrRNA sequence is about or more than about 5, 6, 7, 8, 9, 10, 11, 12, 13, 14, 16, 17, 18, 19, 20, 25, 30, 40, 50, or more nucleotides in length. In some embodiments, the tracrRNA sequence and tracr mate sequence are contained within a single transcript, such that hybridization between the two produces a transcript having a secondary structure, such as a hairpin.

Without wishing to be bound by theory, the tracrRNA sequence, which may comprise or consist of all or a portion of a wild-type tracrRNA sequence (e.g. about or more than about 20, 26, 32, 45, 48, 54, 63, 67, 85, or more nucleotides of a wild-type tracrRNA sequence), may also form part of a CRISPR complex, such as by hybridization along at least a portion of the tracrRNA sequence to all or a portion of a tracr mate sequence that is operably linked to the guide sequence. In some embodiments, the tracrRNA sequence has sufficient complementarity to a tracr mate sequence to hybridize and participate in formation of a CRISPR complex. As with the target sequence, it is believed that complete complementarity is not needed, provided there is sufficient complementarity to be functional. In some embodiments, the tracrRNA sequence has at least 50%, 60%, 70%, 80%, 90%, 95% or 99% of sequence complementarity along the length of the tracr mate sequence when optimally aligned. In embodiments, the degree of sequence complementarity is about or at least about 80%, 90%, 95%, or 100%. Where the tracrRNA sequence is less than 100 (99 or less) nucleotides in length, the sequence is one of 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, or 20 nucleotides in length.

In embodiments, the wild type tracrRNA sequence for *S. pyogenes* is: 5'-CAGCAUAGCAAGUUAAAAUAAGG-GUAGUCCGUUAUCAACUUGAAAAGUGGCACC GAGUCGGUGCUUU-3' (SEQ ID NO: 1). In embodiments, the tracrRNA sequence may have 80%, 85%, 90%, 91%, 92%, 93%, 94%, 95%, 96%, 97%, 98%, 99% or 100% sequence identity to SEQ ID NO: 1. In embodiments, the tracrRNA sequence has about 80% to about 99%, 85% to about 95%, or less than about 95% sequence identity to SEQ ID NO: 1. In embodiments, the tracrRNA sequence is less than 90% identity to SEQ ID NO: 1.

In embodiments, the tracrRNA sequence may have 80%, 85%, 90%, 91%, 92%, 93%, 94%, 95%, 96%, 97%, 98%, 99% or 100% sequence identity to the whole sequence or a portion (e.g. a 10, 20, 30, 40, 50, or 67 continuous nucleotide portion) of SEQ ID NO: 1 or any of the tracrRNA sequences listed in Tables 2-10. In Tables 2-10, the letter "N" in the sequences represents any nucleotides, followed by a digital number (e.g., 20-23) that indicates the total number of N nucleotides.

In embodiments, the tracrRNA sequence is not a naturally occurring tracrRNA sequence. In general, a tracrRNA sequence is "naturally occurring" if it occurs in nature without human intervention. Examples of human intervention include, without limitation, synthesis of a tracrRNA sequence with one or more deliberate sequence changes relative to a naturally occurring tracrRNA sequence to produce a non-naturally occurring tracrRNA sequence, and mutagenesis and screening to identify mutant tracrRNA sequences with a desired activity.

TABLE 2

| | Version 1 sequences |
|---|---|
| Version 1 | Sequence of gRNA (5'-3') |
| U-replaced gRNA V1.0-1 | (N20) GTTTAAGAGCTATGCTGGAAACAGCATAGCA AGaTTAAATAAGGCTAGTCCGTTATCAACTT GAAAAAGTGGCACCGAGTCGGTGCTTT (SEQ ID NO: 3) |
| U-replaced gRNA V1.0-2 | (N20) GTTTAAGAGCTATGCTGGAAACAGCATAGCA AGTgTAAATAAGGCTAGTCCGTTATCAACTT GAAAAAGTGGCACCGAGTCGGTGCTTT (SEQ ID NO: 4) |
| U-replaced gRNA V1.0-3 | (N20) GTTTAtGAGCTATGCTGGAAACAGCATAGCA AGTaTAAATAAGGCTAGTCCGTTATCAACTT GAAAAAGTGGCACCGAGTCGGTGCTTT (SEQ ID NO: 5) |
| U-replaced gRNA V1.0-4 | (N20) GTTTAtGAGCTATGCTGGAAACAGCATAGCA AGTgTAAATAAGGCTAGTCCGTTATCAACTT GAAAAAGTGGCACCGAGTCGGTGCTTT (SEQ ID NO: 6) |

TABLE 2-continued

Version 1 sequences

| Version 1 | Sequence of gRNA (5'-3') |
|---|---|
| U-replaced gRNA V1.0-5 | (N20) GTTTAAGAGCTATGCTGGAAACAGCATAGCAAGTTTAAATAAGGCTAGTCCGaaATCAACTTGAAAAAGTGGCACCGAGTCGGTGCTTT (SEQ ID NO: 7) |
| U-replaced gRNA V1.0-6 | (N20) GTTTAAGAGCTATGCTGGAAACAGCATAGCAAGTTTAAATAAGGCTAGTCCGggATCAACTTGAAAAAGTGGCACCGAGTCGGTGCTTT (SEQ ID NO: 8) |
| U-replaced gRNA V1.0-7 | (N20) GTTTAAGAGCTATGCTGGAAACAGCATAGCAAGTTTAAAgAAGGCTAGTCCGTTATCAACTTGAAAAAGTGGCACCGAGTCGGTGCTTT (SEQ ID NO: 9) |
| U-replaced gRNA V1.0-8 | (N20) GTTTAAGAGCTATGCTGGAAACAGCATAGCAAAGTTTAATAAGGCAGTCCGTTATCAACTTGAAAAAGTGGCACCGAGTCGGTGCTTT (SEQ ID NO: 10) |
| U-replaced gRNA V1.0-9 | (N20) GTTTAAGAGCTATGCTGGAAACAGCATAGCAAGTTTAAATAAGGCaAGTCCGTTATCAACTTGAAAAAGTGGCACCGAGTCGGTGCTTT (SEQ ID NO: 11) |
| U-replaced gRNA V1.0-10 | (N20) GTTTAAGAGCTATGCTGGAAACAGCATAGCAAAGTTTAATAAGGCgAGTCCGTTATCAACTTGAAAAAGTGGCACCGAGTCGGTGCTTT (SEQ ID NO: 12) |
| U-replaced gRNA V1.0-11 | (N20) GTTTAAGAGCTATGCTGGAAACAGCATAGCAAGTTTAAATAAGGCTAGaCCGTTATCAACTTGAAAAAGTGGCACCGAGTCGGTGCTTT (SEQ ID NO: 13) |

TABLE 3

Version 2 sequences

| Version 2 | Sequence of gRNA (5'-3') |
|---|---|
| U-replaced gRNA V2.0-1 | (N20) GTTTAtGAGCTATGCTGGAAACAGCATAGCAAGaaTAAATAAGGCTAGTCCGggATCAACTTGAAAAAGTGGCACCGAGTCGGTGCTTT (SEQ ID NO: 14) |
| U-replaced gRNA V2.0-2 | (N20) GTTTAtGAGCTATGCTGGAAACAGCATAGCAAGTaTAAATAAGGCTAGTCCGggATCAACTTGAAAAAGTGGCACCGAGTCGGTGCTTT (SEQ ID NO: 15) |
| U-replaced gRNA V2.0-3 | (N20) GTTTAtGAGCTATGCTGGAAACAGCATAGCAAGagTAAATAAGGCTAGTCCGggATCAACTTGAAAAAGTGGCACCGAGTCGGTGCTTT (SEQ ID NO: 16) |
| U-replaced gRNA V2.0-4 | (N20) GTTTAtGAGCTATGCTGGAAACAGCATAGCAAGaaTAAATAAGGCTAGTCCGaaATCAACTTGAAAAAGTGGCACCGAGTCGGTGCTTT (SEQ ID NO: 17) |

TABLE 3-continued

Version 2 sequences

| Version 2 | Sequence of gRNA (5'-3') |
|---|---|
| U-replaced gRNA V2.0-5 | (N20) GTTTAtGAGCTATGCTGGAAACAGCATAGCAAGagTAAATAAGGCTAGTCCGaaATCAACTTGAAAAAGTGGCACCGAGTCGGTGCTTT (SEQ ID NO: 18) |
| U-replaced gRNA V2.0-6 | TAATACGACTCACTATAGGAGCATAGCAAGTaTAAATAAGGCTAGaCCGggATCAACTTGAAAAAGTGGCACCGAGTCGGTGCTTT (SEQ ID NO: 19) |

TABLE 4

Version 3 sequences

| Version 3 | Sequence of gRNA (5'-3') |
|---|---|
| U-replaced gRNA V3.0-1 | (N20) GTTTAtGAGCTATGCTGGAAACAGCATAGCAAGTaTAAATAAGGCTAGTCCGggATCAACTTGAAAAAGTGGCACCGAGTCGGTGCTTT (SEQ ID NO: 20) |
| U-replaced gRNA V3.0-2 | (N20) GTTTAtGAGCTATGCTGGAAACAGCATAGCAAGTaTAAAtAAGGCGaGaCCGggATCAACTTGAAAAAGTGGCACCGAGTCGGTGCTTT (SEQ ID NO: 21) |
| U-replaced gRNA V3.0-3 | (N20) GTTTAtGAGCTATGCTGGAAACAGCATAGCAAGTaTAAATAAGGCaAGaCCGggATCAACTTGAAAAAGTGGCACCGAGTCGGTGCTTT (SEQ ID NO: 22) |
| U-replaced gRNA V3.0-4 | (N20) GTTTAtGAGCTATGCTGGAAACAGCATAGCAAGTaTAAATAAGGCAGaCCGggATCAACTTGAAAAAGTGGCACCGAGTCGGTGCTTT (SEQ ID NO: 23) |
| U-replaced gRNA V3.0-5 | (N20) GTTTAtGAGCTATGCTGGAAACAGCATAGCAAGTaTAAAgAAGGCGaGaCCGggATCAACTTGAAAAAGTGGCACCGAGTCGGTGCTTT (SEQ ID NO: 24) |
| U-replaced gRNA V3.0-6 | (N20) GTTTAtGAGCTATGCTGGAAACAGCATAGCAAGTaTAAAgAAGGCaAGaCCGggATCAACTTGAAAAAGTGGCACCGAGTCGGTGCTTT (SEQ ID NO: 25) |
| U-replaced gRNA V3.0-7 | (N20) GTTTAtGAGCTATGCTGGAAACAGCATAGCAAGTaTAAAgAAGGCAGaCCGggATCAACTTGAAAAAGTGGCACCGAGTCGGTGCTTT (SEQ ID NO: 26) |
| U-replaced gRNA V3.0-8 | (N20) tTTTAtGAGCTATGCTGGAAACAGCATAGCAAGTaTAAAgAAGGCGaGaCCGggATCAACTTGAAAAAGTGGCACCGAGTCGGTGCTTT (SEQ ID NO: 27) |
| U-replaced gRNA V3.0-9 | (N20) tTTTAtGAGCTATGCTGGAAACAGCATAGCAAGTaTAAAgAAGGCaAGaCCGggATCAACTTGAAAAAGTGGCACCGAGTCGGTGCTTT (SEQ ID NO: 28) |

TABLE 4-continued

Version 3 sequences

| Version 3 | Sequence of gRNA (5'-3') |
|---|---|
| U-replaced gRNA V3.0-10 | (N20) tTTTAtGAGCTATGCTGGAAACAGCATAGCAAG TaTAAAaAAGGCgAGaCCGggATCAACTTGAAAA AGTGGCACCGAGTCGGTGCTTT (SEQ ID NO: 29) |
| U-replaced gRNA V3.0-11 | (N20) tTTTAtGAGCTATGCTGGAAACAGCATAGCAAG TaTAAAaAAGGCaAGaCCGggATCAACTTGAAAA AGTGGCACCGAGTCGGTGCTTT (SEQ ID NO: 30) |
| U-replaced gRNA V3.0-12 | (N20) cTTAtGAGCTATGCTGGAAACAGCATAGCAAGT aTAAAgAAGGCgAGaCCGggATCAACTTGAAAA AGTGGCACCGAGTCGGTGCTTT (SEQ ID NO: 31) |
| U-replaced gRNA V3.0-13 | (N20) cTTAtGAGCTATGCTGGAAACAGCATAGCAAGT aTAAAgAAGGCaAGaCCGggATCAACTTGAAAA AGTGGCACCGAGTCGGTGCTTT (SEQ ID NO: 32) |

TABLE 5

Version 4 sequences

| Version 4 | Sequence of gRNA (5'-3') |
|---|---|
| U-replaced gRNA V4.0-1 | (N20) GTTTAtGAGCRTGCTGGAAACAGCAaAGCAAGT aTAAATAAGGCaAGaCCGggATCAACTTGAAAA AGTGGCACCGAGTCGGTGCTTT (SEQ ID NO: 33) |
| U-replaced gRNA V4.0-2 | (N20) GTTTAtGAGCRTGCTGGAAACAGCAaAGCAAGT aTAAATAAGGCaAGaCCGggAaCAACTTGAAAA AGTGGCACCGAGTCGGTGCTTT (SEQ ID NO: 34) |
| U-replaced gRNA V4.0-3 | (N20) GTTTAtGAGCRTGCTGGAAACAGCAaAGCAAGT aTAAATAAGGCaAGaCCGggAaCAACTTGAAAA AGTGGCACCGAGaCGGTGCTTT (SEQ ID NO: 35) |
| U-replaced gRNA V4.0-4 | (N20) GTTTAtGAGCRTGCTGGAAACAGCAaAGCAAGT aTAAATAAGGCaAGaCCGggAaCAACTTGAAAA AGTGGCACCGAGaCGGaGCTTT (SEQ ID NO: 36) |
| U-replaced gRNA V4.0-5 | (N20) GTTTAtGAGCRTGCTGGAAACAGCAaAGCAAGT aTAAATAAGGCaAGaCCGggAaCAACTTGAAAA AGTGGCACCGAGgCGGTGCTTT (SEQ ID NO: 37) |
| U-replaced gRNA V4.0-6 | (N20) GTTTAtGAGCRTGCTGGAAACAGCAaAGCAAGT aTAAATAAGGCaAGaCCGggAaCAACTTGAAAA AGTGGCACCGAGgCGGaGCTTT (SEQ ID NO: 38) |
| U-replaced gRNA V4.0-7 | (N20) GTTTAtGAGCRTGCTGGAAACAGCAaAGCAAGT aTAAATAAGGCaAGaCCGggAgCAACTTGAAAA AGTGGCACCGAGTCGGTGCTTT (SEQ ID NO: 39) |

TABLE 5-continued

Version 4 sequences

| Version 4 | Sequence of gRNA (5'-3') |
|---|---|
| U-replaced gRNA V4.0-8 | (N20) GTTTAtGAGCRTGCTGGAAACAGCAaAGCAAGT aTAAATAAGGCaAGaCCGggAgCAACTTGAAAA AGTGGCACCGAGaCGGTGCTTT (SEQ ID NO: 40) |
| U-replaced gRNA V4.0-9 | (N20) GTTTAtGAGCRTGCTGGAAACAGCAaAGCAAGT aTAAATAAGGCaAGaCCGggAgCAACTTGAAAA AGTGGCACCGAGaCGGaGCTTT (SEQ ID NO: 41) |
| U-replaced gRNA V4.0-10 | (N20) GTTTAtGAGCTtTGCTGGAAACAGCAaAGCAAG TaTAAATAAGGCaAGaCCGggAgCAACTTGAAAA AGTGGCACCGAGgCGGTGCTTT (SEQ ID NO: 42) |
| U-replaced gRNA V4.0-11 | (N20) GTTTAtGAGCTtTGCTGGAAACAGCAaAGCAAG TaTAAATAAGGCaAGaCCGggAgCAACTTGAAAA AGTGGCACCGAGgCGGaGCTTT (SEQ ID NO: 43) |
| U-replaced gRNA V4.0-12 | (N20) GTTTAtGAGCTtTGCTGGAAACAGCAaAGCAAG TaTAAATAAGGCaAGaCCGggATCAACTTGAAAA AGTGGCACCGAGTCGGaGCTTT (SEQ ID NO: 44) |
| U-replaced gRNA V4.0-13 | (N20) GTTTAtGAGCTATGCTGGAAACAGCATAGCAAG TaTAAATAAGGCaAGaCCGggAaCAACTTGAAAA AGTGGCACCGAGTCGGTGCTTT (SEQ ID NO: 45) |
| U-replaced gRNA V4.0-14 | (N20) GTTTAtGAGCTATGCTGGAAACAGCATAGCAAG TaTAAATAAGGCaAGaCCGggAgCAACTTGAAAA AGTGGCACCGAGTCGGTGCTTT (SEQ ID NO: 46) |
| U-replaced gRNA V4.0-15 | (N20) GTTTAtGAGCTATGCTGGAAACAGCATAGCAAG TaTAAAcAAGGCaAGaCCGggATCAACTTGAAAA AGTGGCACCGAGTCGGTGCTTT (SEQ ID NO: 47) |
| U-replaced gRNA V4.0-16 | (N20) GTTTAAGAGCTATGCTGGAAACAGCATAGCAAG TTTAAAcAAGGCTAGTCCGTTATCAACTTGAAAA AGTGGCACCGAGTCGGTGCTTT (SEQ ID NO: 48) |
| U-replaced gRNA V4.0-17 | (N20) GTTTAtGAGCTATGCTGGAAACAGCATAGCAAG TaTAAATAAGGCaAGaCCGggATCAACTTGAAAA AGTGGCACCGAGaCGGTGCTTT (SEQ ID NO: 49) |
| U-replaced gRNA V4.0-18 | (N20) GTTTAtGAGCTATGCTGGAAACAGCATAGCAAG TaTAAATAAGGCaAGaCCGggATCAACTTGAAAA AGTGGCACCGAGgCGGTGCTTT (SEQ ID NO: 50) |
| U-replaced gRNA V4.0-19 | (N20) GTTTAtGAGCTATGCTGGAAACAGCATAGCAAG TaTAAATAAGGCaAGaCCGggATCAACTTGAAAA AGTGGCACCGAGTCGGaGCTTT (SEQ ID NO: 51) |

TABLE 5-continued

Version 4 sequences

| Version 4 | Sequence of gRNA (5'-3') |
|---|---|
| U-replaced gRNA (N20) V4.0-20 | GTTTAtGAGCTtTGCTGGAAACAGCAaAGCAAG TaTAAATAAGGCaAGaCCGggCAACaTGAAA AAGTGGCACCGAGgCGGTGCTTT (SEQ ID NO: 52) |
| U-replaced gRNA (N20) V4.0-21 | GTTTAtGAGCTtTGCTGGAAACAGCAaAGCAAG TaTAAATAAGGCaAGaCCGggAgCAACacGAAA gAGTGGCACCGAGgCGGTGCTTT (SEQ ID NO: 53) |
| U-replaced gRNA (N20) V4.0-22 | GTTTAtGAGCTtTGCTGGAAACAGCAaAGCAAG TaTAAATAAGGCaAGaCCGggAgCAgCacGAAA gAGcGGCACCGAGgCGGTGCTTT (SEQ ID NO: 54) |
| U-replaced gRNA (N20) V4.0-23 | GTTTAtGAGCTtTGCTGGAAACAGCAaAGCAAG TaTAAATAAGGCaAGaCCGggAgCAgCacGAAA gAGcGGCACCGAGgCGGaGCTTT (SEQ ID NO: 55) |
| U-replaced gRNA (N20) V4.0-24 | GTTTAtGAGCRTGCTGGAAACAGCAaAGCAAGT aTAAATAAGGCaAGaCCGggAgCAcCacGAAAg AGgGGCACCGAGgCGGTGCTTT (SEQ ID NO: 56) |
| U-replaced gRNA (N20) V4.0-25 | GTTTAtGAGCRTGCTGGAAACAGCAaAGCAAGT aTAAATAAGGCaAGaCCGggAgCAcCacGAAAg AGgGGCACCGAGgCGGaGCTTT (SEQ ID NO: 57) |
| U-replaced gRNA (N20) V4.0-26 | GTTTAtGAGCRTGCTGGAAACAGCAaAGCAAGT aTAAATAAGGCaAGaCCGggAgCAACcTGAAAA gGTGGCACCGAGgCGGTGCTTT (SEQ ID NO: 58) |
| U-replaced gRNA (N20) V4.0-27 | GTTTAtGAGCRTGCTGGAAACAGCAaAGCAAGT aTAAATAAGGCaAGaCCGggAgCAACccGAAAg gGTGGCACCGAGgCGGTGCTTT (SEQ ID NO: 59) |
| U-replaced gRNA (N20) V4.0-28 | GTTTAtGAGCRTGCTGGAAACAGCAaAGCAAGT aTAAATAAGGCaAGaCCGggAgCAgCccGAAAg gGcGGCACCGAGgCGGTGCTTT (SEQ ID NO: 60) |
| U-replaced gRNA (N20) V4.0-29 | GTTTAtGAGCRTGCTGGAAACAGCAaAGCAAGT aTAAATAAGGCaAGaCCGggAgCAgCccGAAAg gGcGGCACCGAGgCGGaGCTTT (SEQ ID NO: 61) |
| U-replaced gRNA (N20) V4.0-30 | GTTTAtGAGCRTGCTGGAAACAGCAaAGCAAGT aTAAATAAGGCaAGaCCGggAgCAcCccGAAAg gGgGGCACCGAGgCGGTGCTTT (SEQ ID NO: 62) |
| U-replaced gRNA (N20) V4.0-31 | GTTTAtGAGCRTGCTGGAAACAGCAaAGCAAGT aTAAATAAGGCaAGaCCGggAgCAcCccGAAAg gGgGGCACCGAGgCGGaGCTTT (SEQ ID NO: 63) |
| U-replaced gRNA (N20) V4.0-32 | GTTTAAGAGCTATGCTGGAAACAGCATAGCAAG TTTAAATAAGGCTAGTCCGTTATCAACTTGAAA AAGTGGCACCGAGTCGGTGCaaa (SEQ ID NO: 64) |
| U-replaced gRNA (N20) V4.0-33 | GTTTAAGAGCTATGCTGGAAACAGCATAGCAAG TTTAAATAAGGCTAGTCCGTTATCAACTTGAAA AAGTGGCACCGAGTCGGTGCaTT (SEQ ID NO: 65) |
| U-replaced gRNA (N20) V4.0-34 | GTTTAAGAGCTATGCTGGAAACAGCATAGCAAG TTTAAATAAGGCTAGTCCGTTATCAACTTGAAA AAGTGGCACCGAGTCGGTGCaaT (SEQ ID NO: 66) |
| U-replaced gRNA (N20) V4.0-35 | GTTTAAGAGCTATGCTGGAAACAGCATAGCAAG TTTAAATAAGGCTAGTCCGTTATCAACTTGAAA AAGTGGCACCGAGTCGGTGCaTa (SEQ ID NO: 67) |
| U-replaced gRNA (N20) V4.0-36 | GTTTAAGAGCTATGCTGGAAACAGCATAGCAAG TTTAAATAAGGCTAGTCCGTTATCAACTTGAAA AAGTGGCACCGAGTCGGTGCTaT (SEQ ID NO: 68) |
| U-replaced gRNA (N20) V4.0-37 | GTTTAAGAGCTATGCTGGAAACAGCATAGCAAG TTTAAATAAGGCTAGTCCGTTATCAACTTGAAA AAGTGGCACCGAGTCGGTGCTaa (SEQ ID NO: 69) |
| U-replaced gRNA (N20) V4.0-38 | GTTTAAGAGCTATGCTGGAAACAGCATAGCAAG TTTAAATAAGGCTAGTCCGTTATCAACTTGAAA AAGTGGCACCGAGTCGGTGCTTa (SEQ ID NO: 70) |
| U-replaced gRNA (N20) V4.0-39 | GTTTAAGAGCTATGCTGGAAACAGCATAGCAAG TTTAAATAAGGCTAGTCCGTTATCAACTTGAAA AAGTGGCACCGAGTCGGTGCggg (SEQ ID NO: 7) |
| U-replaced gRNA (N20) V4.0-40 | GTTTAAGAGCTATGCTGGAAACAGCATAGCAAG TTTAAATAAGGCTAGTCCGTTATCAACTTGAAA AAGTGGCACCGAGTCGGTGCggT (SEQ ID NO: 72) |
| U-replaced gRNA (N20) V4.0-41 | GTTTAAGAGCTATGCTGGAAACAGCATAGCAAG TTTAAATAAGGCTAGTCCGTTATCAACTTGAAA AAGTGGCACCGAGTCGGTGCgTg (SEQ ID NO: 73) |
| U-replaced gRNA (N20) V4.0-42 | GTTTAAGAGCTATGCTGGAAACAGCATAGCAAG TTTAAATAAGGCTAGTCCGTTATCAACTTGAAA AAGTGGCACCGAGTCGGTGCgTT (SEQ ID NO: 74) |
| U-replaced gRNA (N20) V4.0-43 | GTTTAAGAGCTATGCTGGAAACAGCATAGCAAG TTTAAATAAGGCTAGTCCGTTATCAACTTGAAA AAGTGGCACCGAGTCGGTGCTgT (SEQ ID NO: 75) |

TABLE 5-continued

Version 4 sequences

| Version 4 | Sequence of gRNA (5'-3') |
|---|---|
| U-replaced gRNA (N20) V4.0-44 | GTTTAAGAGCTATGCTGGAAACAGCATAGCAAG TTTAAATAAGGCTAGTCCGTTATCAACTTGAAA AAGTGGCACCGAGTCGGTGCTgg (SEQ ID NO: 76) |
| U-replaced gRNA (N20) V4.0-45 | GTTTAAGAGCTATGCTGGAAACAGCATAGCAAG TTTAAATAAGGCTAGTCCGTTATCAACTTGAAA AAGTGGCACCGAGTCGGTGCTTg (SEQ ID NO: 77) |
| U-replaced gRNA (N20) V4.0-46 | GTTTAAGAGCTATGCTGGAAACAGCATAGCAAG TTTAAATAAGGCTAGTCCGTTATCAACTTGAAA AAGTGGCACCGAGTCGGTGCccc (SEQ ID NO: 78) |

TABLE 6

Version 5 sequences

| Version 5 | Sequence of gRNA (5'-3') |
|---|---|
| U-replaced gRNA (N20) V4.0-3 | GTTTAtGAGCTtTGCTGGAAACAGCAaAGCAAG TaTAAATAAGGCaAGaCCGggAaCAACTTGAAA AAGTGGCACCGAGaCGGTGCTTT (SEQ ID NO: 35) |
| U-replaced gRNA (N20) V5.0-1 | GTTTAtGAGCTtTGCTGGAAACAGCAaAGCAAG TaTAAATAAGGCaAGaCCGggAaCAACTTGAAA AAGTGGCACCGAGaCGGTGCaaa (SEQ ID NO: 79) |
| U-replaced gRNA (N20) V4.0-5 | GTTTAtGAGCTtTGCTGGAAACAGCAaAGCAAG TaTAAATAAGGCaAGaCCGggAaCAACTTGAAA AAGTGGCACCGAGgCGGTGCTTT (SEQ ID NO: 80) |
| U-replaced gRNA (N20) V5.0-2 | GTTTAtGAGCTtTGCTGGAAACAGCAaAGCAAG TaTAAATAAGGCaAGaCCGggAaCAACTTGAAA AAGTGGCACCGAGgCGGTGCaaa (SEQ ID NO: 81) |
| U-replaced gRNA (N20) V5.0-3 | GTTTAtGAGCTtTGCTGGAAACAGCAaAGCAAG aaTAAATAAGGCaAGaCCGggAaCAACTTGAAA AAGTGGCACCGAGaCGGTGCTTT (SEQ ID NO: 82) |
| U-replaced gRNA (N20) V5.0-4 | GTTTAtGAGCTtTGCTGGAAACAGCAaAGCAAG aaTAAATAAGGCaAGaCCGggAaCAACTTGAAA AAGTGGCACCGAGgCGGTGCTTT (SEQ ID NO: 3) |
| U-replaced gRNA (N20) V5.0-5 | GTTTAtGAGCTtTGCTGGAAACAGCAaAGCAAG aaTAAATAAGGCaAGaCCGggAaCAACTTGAAA AAGTGGCACCGAGaCGGTGCaaa (SEQ ID NO: 83) |
| U-replaced gRNA (N20) V5.0-6 | GTTTAtGAGCTtTGCTGGAAACAGCAaAGCAAG aaTAAATAAGGCaAGaCCGggAaCAACTTGAAA AAGTGGCACCGAGgCGGTGCaaa (SEQ ID NO: 84) |

TABLE 6-continued

Version 5 sequences

| Version 5 | Sequence of gRNA (5'-3') |
|---|---|
| U-replaced gRNA (N20) V5.0-7 | GTTTAtGAGCTtTGCTGGAAACAGCAaAGCAAG aaTAAATAAGGCaAGaCCGggAaCAACCcGAAA ggGTGGCACCGAGaCGGTGCTTT (SEQ ID NO: 85) |
| U-replaced gRNA (N20) V5.0-8 | GTTTAtGAGCTtTGCTGGAAACAGCAaAGCAAG aaTAAATAAGGCaAGaCCGggAaCAACCcGAAA ggGTGGCACCGAGgCGGTGCTTT (SEQ ID NO: 86) |
| U-replaced gRNA (N20) V5.0-9 | GTTTAtGAGCTtTGCTGGAAACAGCAaAGCAAG aaTAAATAAGGCaAGaCCGggAaCAACCcGAAA ggGTGGCACCGAGaCGGTGCaaa (SEQ ID NO: 87) |
| U-replaced gRNA (N20) V5.0-10 | GTTTAtGAGCTtTGCTGGAAACAGCAaAGCAAG aaTAAATAAGGCaAGaCCGggAaCAACCcGAAA ggGTGGCACCGAGgCGGTGCaaa (SEQ ID NO: 88) |
| U-replaced gRNA (N20) V5.0-11 | GTTTAtGAGCTtTGCTGGAAACAGCAaAGCAAG TaTAAATAAGGCaAGaCCGggAaCAACCcGAAA ggGTGGCACCGAGaCGGTGCTTT (SEQ ID NO: 89) |
| U-replaced gRNA (N20) V5.0-12 | GTTTAtGAGCTtTGCTGGAAACAGCAaAGCAAG TaTAAATAAGGCaAGaCCGggAaCAACCcGAAA ggGTGGCACCGAGgCGGTGCTTT (SEQ ID NO: 90) |
| U-replaced gRNA (N20) V5.0-13 | GTTTAtGAGCTtTGCTGGAAACAGCAaAGCAAG TaTAAATAAGGCaAGaCCGggAaCAgCccGAAA ggGcGGCACCGAGaCGGTGCTTT (SEQ ID NO: 91) |
| U-replaced gRNA (N20) V5.0-14 | GTTTAtGAGCTtTGCTGGAAACAGCAaAGCAAG TaTAAATAAGGCaAGaCCGggAaCAgCccGAAA ggGcGGCACCGAGgCGGTGCTTT (SEQ ID NO: 92) |
| U-replaced gRNA (N20) V5.0-15 | GTTTAtGAGCTtTGCTGGAAACAGCAaAGCAAG TaTAAATAAGGCaAGaCCGggAaCAgCccGAAA ggGcGGCcCCGAGaCGGgGCTTT (SEQ ID NO: 93) |
| U-replaced gRNA (N20) V5.0-16 | GTTTAtGAGCTtTGCTGGAAACAGCAaAGCAAG TaTAAATAAGGCaAGaCCGggAaCAgCccGAAA ggGcGGCcCCGAGgCGGgGCTTT (SEQ ID NO: 94) |
| U-replaced gRNA (N20) V5.0-17 | GTTTAtGAGCTtTGCTGGAAACAGCAaAGCAAG TaTAAATAAGGCaAGaCCGggAaCAgCccGAAA ggGcGGCgCCGAGaCGGcGCTTT (SEQ ID NO: 95) |
| U-replaced gRNA (N20) V5.0-18 | GTTTAtGAGCTtTGCTGGAAACAGCAaAGCAAG TaTAAATAAGGCaAGaCCGggAaCAgCccGAAA ggGcGGCgCCGAGgCGGcGCTTT (SEQ ID NO: 96) |

TABLE 6-continued

Version 5 sequences

| Version 5 | Sequence of gRNA (5'-3') |
|---|---|
| U-replaced gRNA (N20) V5.0-19 | GTTTAtGAGCTtTGCTGGAAACAGCAaAGCAAG TaTAAATAAGGCaAGaCCGggAaCAcCccGAAA ggGgGGCACCGAGaCGGTGCTTT (SEQ ID NO: 97) |
| U-replaced gRNA (N20) V5.0-20 | GTTTAtGAGCTtTGCTGGAAACAGCAaAGCAAG TaTAAATAAGGCaAGaCCGggAaCAcCccGAAA ggGgGGCACCGAGgCGGTGCTTT (SEQ ID NO: 3) |
| U-replaced gRNA (N20) V5.0-21 | GTTTAtGAGCTtTGCTGGAAACAGCAaAGCAAG TaTAAATAAGGCaAGaCCGggAaCAcCccGAAA ggGgGGCcCCGAGaCGGgCTTT (SEQ ID NO: 98) |
| U-replaced gRNA (N20) V5.0-22 | GTTTAtGAGCTtTGCTGGAAACAGCAaAGCAAG TaTAAATAAGGCaAGaCCGggAaCAcCccGAAA ggGgGGCcCCGAGgCGGgCTTT (SEQ ID NO: 99) |
| U-replaced gRNA (N20) V5.0-23 | GTTTAtGAGCTtTGCTGGAAACAGCAaAGCAAG TaTAAATAAGGCaAGaCCGggAaCAcCccGAAA ggGgGGCgCCGAGaCGGcGCTTT (SEQ ID NO: 100) |
| U-replaced gRNA (N20) V5.0-24 | GTTTAtGAGCTtTGCTGGAAACAGCAaAGCAAG TaTAAATAAGGCaAGaCCGggAaCAcCccGAAA ggGgGGCgCCGAGgCGGcGCTTT (SEQ ID NO: 101) |

TABLE 7

Version 6 sequences

| Version 6 | Sequence of gRNA (5'-3') |
|---|---|
| U-replaced gRNA (N20) V6.0-1 | GTTTAtGAGCTtTGCTGGAAACAGCAaAGCAAG TaTAAATAAGGCaAGaCCGggAaCAgCccGAAA ggGcGGCgCCGAGaCGGcGCccc (SEQ ID NO: 102) |
| U-replaced gRNA (N20) V6.0-2 | GTTTctGAGCTtTGCTGGAAACAGCAaAGCAAG TagAAATAAGGCaAGaCCGggAaCAgCccGAAA ggGcGGCgCCGAGaCGGcGCTTT (SEQ ID NO: 103) |
| U-replaced gRNA (N20) V6.0-3 | GTTTctGAGCTtTGCTGGAAACAGCAaAGCAAG TagAAATAAGGCaAGaCCGggAaCAgCccGAAA ggGcGGCgCCGAGaCGGcGCccc (SEQ ID NO: 104) |
| U-replaced gRNA (N20) V6.0-4 | GTTTctGAGCTATGCTGGAAACAGCATAGCAAG TagAAATAAGGCaAGaCCGggATCAACTTGAAA AAGTGGCACCGAGTCGGTGCTTT (SEQ ID NO: 105) |
| U-replaced gRNA (N20) V6.0-5 | GTTTctGAGCRTGCTGGAAACAGCAaAGCAAGT agAAATAAGGCaAGaCCGggATCAACTTGAAAA AGTGGCACCGAGTCGGTGCTTT (SEQ ID NO: 106) |

TABLE 7-continued

Version 6 sequences

| Version 6 | Sequence of gRNA (5'-3') |
|---|---|
| U-replaced gRNA (N20) V6.0-6 | GTTTctGAGCRTGCTGGAAACAGCAaAGCAAGT agAAATAAGGCaAGaCCGggAaCAACTTGAAAA AGTGGCACCGAGgCGGTGCTTT (SEQ ID NO: 107) |
| U-replaced gRNA (N20) V6.0-7 | GTTTctGAGCRTGCTGGAAACAGCAaAGCAAGT agAAATAAGGCaAGaCCGggAaCAACTTGAAAA AGTGGCACCGAGaCGGTGCTTT (SEQ ID NO: 108) |
| U-replaced gRNA (N20) V6.0-8 | GTTTTtGAGCRTGCTGGAAACAGCAaAGCAAGT aAAAATAAGGCaAGaCCGggAaCAgCccGAAAg gGcGGCgCCGAGaCGGcGCTTT (SEQ ID NO: 109) |
| U-replaced gRNA (N20) V6.0-9 | GTTTTtGAGCRTGCTGGAAACAGCAaAGCAAGT aAAAATAAGGCaAGaCCGggAaCAgCccGAAAg gGcGGCgCCGAGaCGGcGCccc (SEQ ID NO: 110) |
| U-replaced gRNA (N20) V6.0-10 | GTTTTtGAGCTATGCTGGAAACAGCATAGCAAG TaAAAATAAGGCaAGaCCGggATCAACTTGAAA AAGTGGCACCGAGTCGGTGCTTT (SEQ ID NO: 111) |
| U-replaced gRNA (N20) V6.0-11 | GTTTTtGAGCRTGCTGGAAACAGCAaAGCAAGT aAAAATAAGGCaAGaCCGggATCAACTTGAAAA AGTGGCACCGAGTCGGTGCTTT (SEQ ID NO: 112) |
| U-replaced gRNA (N20) V6.0-12 | GTTTTtGAGCRTGCTGGAAACAGCAaAGCAAGT aAAAATAAGGCaAGaCCGggAaCAACTTGAAAA AGTGGCACCGAGgCGGTGCTTT (SEQ ID NO: 113) |
| U-replaced gRNA (N20) V6.0-13 | GTTTTtGAGCRTGCTGGAAACAGCAaAGCAAGT aAAAATAAGGCaAGaCCGggAaCAACTTGAAAA AGTGGCACCGAGaCGGTGCTTT (SEQ ID NO: 114) |
| U-replaced gRNA (N20) V6.0-14 | GTTTTtGAGCTATGCTGGAAACAGCATAGCAAG TaAAAATAAGGCTAGTCCGggATCAACTTGAAA AAGTGGCACCGAGTCGGTGCTTT (SEQ ID NO: 115) |
| U-replaced gRNA (N20) V6.0-15 | GTTTcAGAGCTATGCTGAAAAGCATAGCAAGTT gAAATAAGGCTAGTCCGTTATCAACTTGAAAAA GTGGCACCGAGTCGGTGCTTTTT (SEQ ID NO: 116) |
| U-replaced gRNA (N20) V6.0-16 | GTTTctGAGCRTGCTGAAAAGCAaAGCAAGtag AAATAAGGCaAGaCCGggAaCAgCccGAAAggG cGGCgCCGAGaCGGcGCTTT (SEQ ID NO: 117) |
| U-replaced gRNA (N20) V6.0-17 | GTTTctGAGCRTGCTGAAAAGCAaAGCAAGTag AAATAAGGCaAGaCCGggAaCAgCccGAAAggG cGGCgCCGAGaCGGcGCccc (SEQ ID NO: 118) |

TABLE 7-continued

Version 6 sequences

| Version 6 | Sequence of gRNA (5'-3') |
|---|---|
| U-replaced gRNA V6.0-18 | (N20) GTTTctGAGCTATGCTGAAAAGCATAGCAAGTagAAATAAGGCaAGaCCGggATCAACTTGAAAAAGTGGCACCGAGTCGGTGCTTT (SEQ ID NO: 119) |
| U-replaced gRNA V6.0-19 | (N20) GTTTctGAGCTLTGCTGAAAAGCAaAGCAAGTagAAATAAGGCaAGaCCGggATCAACTTGAAAAAGTGGCACCGAGTCGGTGCTTT (SEQ ID NO: 120) |
| U-replaced gRNA V6.0-20 | (N20) GTTTctGAGCTLTGCTGAAAAGCAaAGCAAGTagAAATAAGGCaAGaCCGggAaCAACTTGAAAAAGTGGCACCGAGgCGGTGCTTT (SEQ ID NO: 121) |
| U-replaced gRNA V6.0-21 | (N20) GTTTctGAGCTLTGCTGAAAAGCAaAGCAAGTagAAATAAGGCaAGaCCGggAaCAACTTGAAAAAGTGGCACCGAGaCGGTGCTTT (SEQ ID NO: 122) |
| U-replaced gRNA V6.0-22 | (N20) GTTTTtGAGCRTGCTGAAAAGCAaAGCAAGTaAAAATAAGGCaAGaCCGggAaCAgCccGAAAggGcGGCgCCGAGaCGGcGCTTT (SEQ ID NO: 123) |
| U-replaced gRNA V6.0-23 | (N20) GTTTTtGAGCRTGCTGAAAAGCAaAGCAAGTaAAAATAAGGCaAGaCCGggAaCAgCccGAAAggGcGGCgCCGAGaCGGcGCccc (SEQ ID NO: 124) |

TABLE 8

Sequences of U-replaced tracrRNAs

| dddd | Complementary crRNA tracrRNA sequence (5'-3') | crRNA (5'-3') |
|---|---|---|
| Wild-type with A to T change (aka AU Flip) | AGCAUAGCAAGUUUAAAUAAGGCUAWT-crRNA GUCCGUUAUCAACUUGAAAAAGUGG CACCGAGUCGGUGCUUU (SEQ ID NO: 125) | N(20) GUUUAAGAGCUAUGCU (SEQ ID NO: 126) |
| U-replaced tracrRNA-1 | AGCAUAGCAAGUaUAAAUAAGGCUAcrRNA-1 GCUUGggAUCAACUUGAAAAAGUGG CACCGAGUCGGUGCUUU (SEQ ID NO: 127) | N(20) GUUUAUGAGCUAUGCU (SEQ ID NO: 128) |
| U-replaced tracrRNA-2 | AGCAaAGCAAGUagAAAUAAGGCaAcrRNA-2 GaCCGggAaCAACUUGAAAAAGUGG CACCGAGgCGGUGCUUU (SEQ ID NO: 129) | N(20) GUUUcUGAGCUUUGCU (SEQ ID NO: 130) |
| U-replaced tracrRNA-3 | AGCAaAGCAAGUagAAAUAAGGCaAcrRNA-2 GaCCGggAaCAACccGAAAggGUGG CACCGAGgCGGUGCUUU (SEQ ID NO: 131) | N(20) GUUUcUGAGCUUUGCU (SEQ ID NO: 132) |
| U-replaced tracrRNA-4 | AGCAaAGCAAGUagAAAUAAGGCaAcrRNA-2 GaCCGggAaCAgCccGAAAggGcGG CgCCGAGgCGGcGCaaa (SEQ ID NO: 133) | N(20) GUUUcUGAGCUUUGCU (SEQ ID NO: 134) |
| U-replaced tracrRNA-5 | AGCAUAGCAAGUaUAAAUAAGGCUAcrRNA-1 GaCCGggAUCAACUUGAAAAAGUGG CACCGAGUCGGUGCUUU (SEQ ID NO: 135) | N(20) GUUUAUGAGCUAUGCU (SEQ ID NO: 136) |
| U-replaced tracrRNA-6 | AGCAUAGCAAGUUUAAAUAAGGCUAWT-crRNA GaCCGUUAUCAACUUGAAAAAGUGG CACCGAGUCGGUGCUUU (SEQ ID NO: 137) | N(20) GUUUAAGAGCUAUGCU (SEQ ID NO: 138) |
| U-replaced tracrRNA-7 | AGCAUAGCAAGUaUAAAUAAGGCaAcrRNA-1 GaCCGggAUCAACUUGAAAAAGUGG CACCGAGUCGGUGCUUU (SEQ ID NO: 167) | N(20) GUUUAUGAGCUAUGCU (SEQ ID NO: 168) |
| U-replaced tracrRNA-8 | AGCAUAGCAAGUaUAAAUAAGGCaAcrRNA-1 GaCCGggAaCAACUUGAAAAAGUGG CACCGAGgCGGUGCUUU (SEQ ID NO: 169) | N(20) GUUUAUGAGCUAUGCU (SEQ ID NO: 170) |

TABLE 8-continued

Sequences of U-replaced tracrRNAs

| dddd | Complementary tracrRNA sequence (5'-3') | crRNA | crRNA (5'-3') |
|---|---|---|---|
| U-replaced tracrRNA-9 | AGCAUAGCAAGUaUAAAUAAGGCaA GaCCGggAaCAgCccGAAAggGcGG CgCCGAGgCGGcGCccc (SEQ ID NO: 171) | crRNA-1 | N(20) GUUUAUGAGCUAUGCU (SEQ ID NO: 172) |
| U-replaced tracrRNA-10 | AGCAUAGCAAGUaUAAAUAAGGCUA GUCCGggAUCAgCccGAAAggGcGG CgCCGAGUCGGcGCccc (SEQ ID NO: 173) | crRNA-1 | N(20) GUUUAUGAGCUAUGCU (SEQ ID NO: 174) |
| U-replaced tracrRNA-11 | AGCAUAGCAAGUaUAAAUAAGGCaA GUCCGggAaCAgCccGAAAggGcGG CgCCGAGgCGGcGCccc (SEQ ID NO: 175) | crRNA-1 | N(20) GUUUAUGAGCUAUGCU (SEQ ID NO: 176) |
| U-replaced tracrRNA-12 | AGCAUAGCAAGUaUAAAUAAGGCUA GaCCGggAaCAgCccGAAAggGcGG CgCCGAGgCGGcGCccc (SEQ ID NO: 177) | crRNA-1 | N(20) GUUUAUGAGCUAUGCU (SEQ ID NO: 178) |
| U-replaced tracrRNA-13 | AGCAUAGCAAGUaUAAAUAAGGCaA GaCCGggAUCAgCccGAAAggGcGG CgCCGAGgCGGcGCccc (SEQ ID NO: 179) | crRNA-1 | N(20) GUUUAUGAGCUAUGCU (SEQ ID NO: 180) |
| U-replaced tracrRNA-14 | AGCAUAGCAAGUaUAAAUAAGGCaA GaCCGggAaCAgCccGAAAggGcGG CgCCGAGUCGGcGCccc (SEQ ID NO: 181) | crRNA-1 | N(20) GUUUAUGAGCUAUGCU (SEQ ID NO: 182) |
| U-replaced tracrRNA-15 | AGCAUAGCAAGUaUAAAUAAGGCUA GUCCGggAaCAgCccGAAAggGcGG CgCCGAGgCGGcGCccc (SEQ ID NO: 183) | crRNA-1 | N(20) GUUUAUGAGCUAUGCU (SEQ ID NO: 184) |
| U-replaced tracrRNA-16 | AGCAUAGCAAGUaUAAAUAAGGCaA GUCCGggAaCAgCccGAAAggGcGG CgCCGAGUCGGcGCccc (SEQ ID NO: 185) | crRNA-1 | N(20) GUUUAUGAGCUAUGCU (SEQ ID NO: 186) |
| U-replaced tracrRNA-17 | AGCAUAGCAAGUaUAAAUAAGGCUA GUCCGggAaCAgCccGAAAggGcGG CgCCGAGUCGGcGCccc (SEQ ID NO: 187) | crRNA-1 | N(20) GUUUAUGAGCUAUGCU (SEQ ID NO: 188) |
| U-replaced tracrRNA-18 | AGCAUAGCAAGUaUAAAUAAGGCaA GaCCGggAaCAgCccGAAAggGcGG CACCGAGUCGGUGCccc (SEQ ID NO: 189) | crRNA-1 | N(20) GUUUAUGAGCUAUGCU (SEQ ID NO: 190) |
| U-replaced tracrRNA-19 | AGCAUAGCAAGUaUAAAUAAGGCaA GaCCGggAaCAgCccGAAAggGcGG CACCGAGUCGGUGCUUU (SEQ ID NO: 191) | crRNA-1 | N(20) GUUUAUGAGCUAUGCU (SEQ ID NO: 192) |
| U-replaced tracrRNA-1 | AGCAUAGCAAGUaUAAAUAAGGCUA GUCCGUUAUCAACUUGAAAAAGUGG CACCGAGUCGGUGCUUU (SEQ ID NO: 193) | crRNA-1 | N(20) GUUUAUGAGCUAUGCU (SEQ ID NO: 194) |
| U-replaced tracrRNA-22 | AGCAaGCAAGUaUAAAUAAGGCaAG aCCGggAUCAACUUGAAAAAGUGGC ACCGAGUCGGUGCUUU (SEQ ID NO: 195) | crRNA-3 | N(20) GUUUaUGAGCUUUGCU (SEQ ID NO: 196) |
| U-replaced tracrRNA-23 | AGCAaGCAAGUaUAAAUAAGGCaA GaCCGggAaCAACUUGAAAAAGUGG CACCGAGUCGGUGCUUU (SEQ ID NO: 197) | crRNA-1 | N(20) GUUUaUGAGCUUUGCU (SEQ ID NO: 198) |
| U-replaced tracrRNA-24 | AGCAaAGCAAGUUUAAAUAAGGCUA GUCCGUUAUCAACUUGAAAAAGUGG CACCGAGUCGGUGCUUU (SEQ ID NO: 199) | crRNA-1 | N(20) GUUUaAGAGCUUUGCU (SEQ ID NO: 200) |

TABLE 8-continued

Sequences of U-replaced tracrRNAs

| dddd | tracrRNA sequence (5'-3') | Complementary crRNA | crRNA (5'-3') |
|---|---|---|---|
| U-replaced tracrRNA-25 | AGCAUAGCAAGUaUAAAUAAGGCaAc GaCCGggAaCAACUUGAAAAAGUGG CACCGAGUCGGUGCUUU (SEQ ID NO: 201) | crRNA-1 | N(20) GUUUAUGAGCUAUGCU (SEQ ID NO: 202) |
| U-replaced tracrRNA-26 | AGCAUAGCAAGUUUAAAUAAGGCUAW GUCCGUUAaCAACUUGAAAAAGUGG CACCGAGUCGGUGCUUU (SEQ ID NO: 203) | T-crRNA | N(20) GUUUAAGAGCUAUGCU (SEQ ID NO: 204) |
| U-replaced tracrRNA-27 | AGCAUAGCAAGUaUAAAUAAGGCaAc GaCCGggAUCAACUUGAAAAAGUGG CACCGAGUCGGUGCUUU (SEQ ID NO: 205) | crRNA-1 | N(20) GUUUAUGAGCUAUGCU (SEQ ID NO: 206) |
| U-replaced tracrRNA-28 | AGCAUAGCAAGUUUAAAUAAGGCaAW GUCCGUUAUCAACUUGAAAAAGUGG CACCGAGUCGGUGCUUU (SEQ ID NO: 207) | T-crRNA | N(20) GUUUAAGAGCUAUGCU (SEQ ID NO: 208) |
| U-replaced tracrRNA-29 | AGCAUAGCAAGUUUAAAUAAGGCUAW GUCCGggAUCAACUUGAAAAAGUGG CACCGAGUCGGUGCUUU (SEQ ID NO: 209) | T-crRNA | N(20) GUUUAAGAGCUAUGCU (SEQ ID NO: 210) |
| U-replaced tracrRNA-30 | AGCAUAGCAAGUaUAAAUAAGGCaAc GaCCGggAUCAACUUGAAAAAGUGG CACCGAGaCGGUGCUUU (SEQ ID NO: 211) | crRNA-1 | N(20) GUUUAUGAGCUAUGCU (SEQ ID NO: 212) |
| U-replaced tracrRNA-31 | AGCAUAGCAAGUaUAAAUAAGGCaAc GaCCGggAUCAACUUGAAAAAGUGG CACCGAGgCGGUGCUUU (SEQ ID NO: 213) | crRNA-1 | N(20) GUUUAUGAGCUAUGCU (SEQ ID NO: 214) |
| U-replaced tracrRNA-32 | AGCAUAGCAAGUUUAAAUAAGGCUAW GUCCGgUAUCAACUUGAAAAAGUGG CACCGAGUCGGUGCUUU (SEQ ID NO: 215) | T-crRNA | N(20) GUUUAAGAGCUAUGCU (SEQ ID NO: 216) |
| U-replaced tracrRNA-33 | AGCAUAGCAAGUUUAAAUAAGGCUAW GUCCGUgAUCAACUUGAAAAAGUGG CACCGAGUCGGUGCUUU (SEQ ID NO: 217) | T-crRNA | N(20) GUUUAAGAGCUAUGCU (SEQ ID NO: 218) |
| U-replaced tracrRNA-34 | AGCAUAGCAAGUUUAAAUAAGGCAGW UCCGUUAUCAACUUGAAAAAGUGGC ACCGAGUCGGUGCUUU (SEQ ID NO: 219) | T-crRNA | N(20) GUUUAAGAGCUAUGCU (SEQ ID NO: 220) |
| U-replaced tracrRNA-35 | AGCAUAGCAAGUaUAAAUAAGGCUAc GUCCGUUAaCAACUUGAAAAAGUGG CACCGAGUCGGUGCUUU (SEQ ID NO: 221) | crRNA-1 | N(20) GUUUAUGAGCUAUGCU (SEQ ID NO: 222) |
| U-replaced tracrRNA-36 | AGCAUAGCAAGUUUAAAUAAGGCUAW GUCCGUUAaCAACggGAAAccGUGG CACCGAGUCGGUGCUUU (SEQ ID NO: 223) | T-crRNA | N(20) GUUUAAGAGCUAUGCU (SEQ ID NO: 224) |
| U-replaced tracrRNA-37 | AGCAUAGCAAGUaUAAAUAAGGCUAc GUCCGUgAaCAcCggGAAAccGgGG CACCGAGUCGGUGCUUU (SEQ ID NO: 225) | crRNA-1 | N(20) GUUUAUGAGCUAUGCU (SEQ ID NO: 226) |
| U-replaced tracrRNA-38 | AGCAUAGCAAGUUUAAAUAAGGCUAW GUCCGUgAaCAcCggGAAAccGgGG CACCGAGUCGGUGCUUU (SEQ ID NO: 227) | T-crRNA | N(20) GUUUAAGAGCUAUGCU (SEQ ID NO: 228) |
| U-replaced tracrRNA-39 | AGCAUAGCAAGUUUAAAUAAGGCUAW GUCCGUUAaCAcCggGAAAccGgGG CACCGAGUCGGUGCUUU (SEQ ID NO: 229) | T-crRNA | N(20) GUUUAAGAGCUAUGCU (SEQ ID NO: 230) |

TABLE 8-continued

Sequences of U-replaced tracrRNAs

| dddd | Complementary tracrRNA sequence (5'-3') crRNA | crRNA (5'-3') |
|---|---|---|
| U-replaced tracrRNA-40 | AGCAUAGCAAGUUUAAAUAAGGCUAWT-crRNA GUCCGUgAaCAACUUGAAAAAGUGG CACCGAGUCGGUGCUUU (SEQ ID NO: 231) | N(20) GUUUAAGAGCUAUGCU (SEQ ID NO: 232) |
| U-replaced tracrRNA-9-CCR5 | AGCAUAGCAAGUaUAAAUAAGGCaAcrRNA-1 GaCCGggAaCAgCccUCGGGAGGAC GAUGCGGGCCUUCGUUUGUUUCGUC CACAGACGACUCGCCCGAggGcGGC gCCGAGgCGGcGCccc (SEQ ID NO: 255) | N(20) GUUUAUGAGCUAUGCU (SEQ ID NO: 256) |

TABLE 9

Cas9 Orthologues tracrRNA

| Type | | 5'-3' SEQUENCE sgRNA |
|---|---|---|
| II | spCas9 | (N20-23) GUUUUAGAGCUAUGCUGgaaaCAGCAUAGCAAGUUA AAAUAAGGCUAGUCCGUUAUCAACUUGAAAAAGUGG CACCGAGUCGGUGCUUU (SEQ ID NO: 139) |
| | nmCas9 | (N20-23) GUUGUAGCUCCCUUUCUCAUUUCGgaaaCGAAAUGA GAACCGUUGCUACAAUAAGGCCGUCUGAAAAGAUGU GCCGCAACGCUCUGCCCCUUAAAGCUUCUGCUUUAA GGGGCAUCGUUUA (SEQ ID NO: 140) |
| | saCas9 | (N20-23) GUUUUAGUACUCUGUAAUUUgaaaAAAUUACAGAAU CUACUAAAACAAGGCAAAAUGCCGUGUUUAUCUCGU CAACUUGUUGGCGAGAUUU (SEQ ID NO: 141) |
| | st1Cas9 | (N20-23) GUUUUUGUACUCUCAAGAUUcaauAAUCUUGCAGAA GCUACAAAGAUAAGGCUUCAUGCCGAAAUCAACACC CUGUCAUUUUAUGGCAGGGUGUUU (SEQ ID NO: 142) |
| | st3Cas9 | (N20-23) GUUUUAGAGCUGUGUUGUUUgttaAAACAACACAGC GAGUUAAAAUAAGGCUUAGUCCGUACUCAACUUGAA AAGGUGGCACCGAUUCGGUGUUU (SEQ ID NO: 143) |
| | cjCas9 | (N20-23) GUUUUAGUCCCUgaaaAGGGACUAAAAUAAAGAGUU UGCGGGACUCUGCGGGGUUACAAUCCCCUAAAACCG CUUU (SEQ ID NO: 144) |
| | GeoCas9 | (N20-23) GUCAUAGUUCCCCUGAgaaaUCAGGGUUACUAUGAU AAGGCUUUCUGCCUAAGGCAGACUGACCCGCGGCG UUGGGGAUCGCCUGUCGCCCGCUUUUGGCGGGCAUU CCCCAUCCUU (SEQ ID NO: 145) |
| | FnCas9 | (N20-23) GUUUUCAGUUGCGCCgaaaGGCGCUCUGUAAUCAUUU AAAAGUAUUUUGAACGGACCUCUGUUUGACACGUCU G (SEQ ID NO: 146) | crRNA (bold), tetraloop (lowercase), tracrRNA (underlined)

TABLE 10

| Type | | 5' handle |
|---|---|---|
| V | fnCas12a | UAAUUUCUACUGUUGUAGAU (N20-23) (SEQ ID NO: 147) |
| | AsCas12a | UAAUUUCUACUCUUGUAGAU (N20-23) (SEQ ID NO: 148) |
| | Lb2Cas12a | UAAUUUCUACUAUUGUAGAU (N20-23) (SEQ ID NO: 149) |
| | CMtCas12a | UAAUUUCUACUCUUUGUAGAU (N20-23) (SEQ ID NO: 150) |
| | EeCas12a | UAAUUUCUACUUUGUAGAU (N20-23) (SEQ ID NO: 151) |
| | MbCas12a | UAAUUUCUACUGUUUGUAGAU (N20-23) (SEQ ID NO: 152) |
| | PdCas12a | UAAUUUCUACUUCGGUAGAU (N20-23) (SEQ ID NO: 153) |
| | AacCas12b | GGUCUAGAGGACAGAAUUUUUCAACGGGUG UGCCAAUGGCCACUUUCCAGGUGGCAAAGC CCGUUGAGCUUCUCAAAUCUGAGAAGUGGC AC (N20-23) (SEQ ID NO: 154) |
| VI | LshCas13a | GGCCACCCCAAUAUCGAAGGGGACUAAAAC (N20-23) (SEQ ID NO: 155) |
| | AaCas13b | AAUUCUACUCUUGUAGAU (N20-23) (SEQ ID NO: 156) |
| | PspCas13b | (N20-23) GUUGUGGAAGGUCCAGUUUUGGGGCUAUU ACAACA (SEQ ID NO: 157) |

The term "aptamer(s)" or "aptamer(s) sequence" as used herein refers to an oligonucleotide or peptide molecule(s) that can bind to a specific target molecule (e.g. a specific nucleic acid sequence or peptide sequence). In embodiments, the aptamer(s) used herein refer to nucleic acid aptamers (DNA or RNA aptamers). In embodiments, aptamers can be selected and engineered through in vitro selection, such as SELEX (systematic evolution of ligands by exponential enrichment) to bind to various molecular targets such as small molecules, proteins, nucleic acids, and even cells, tissues and organisms. In embodiments, aptamers can be covalently or non-covalently associated with other molecules. Therefore, in embodiments, one or more aptamers can be bound to another nucleic acid sequence (e.g. a tracrRNA sequence or a gRNA sequence), forming a recombinant nucleic acid sequence useful for altering gene expression.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include but are not limited to yeast cells and cells derived from plants and animals, for example mammalian, insect (e.g., *spodoptera*) and human cells.

As used herein, the term "vector" refers to a nucleic acid molecule capable of transporting another nucleic acid to which it has been linked. One type of vector is a "plasmid", which refers to a linear or circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions. Additionally, some viral vectors are capable of targeting a particular cell type either specifically or non-specifically. Replication-incompetent viral vectors or replication-defective viral vectors refer to viral vectors that are capable of infecting their target cells and delivering their viral payload, but then fail to continue the typical lytic pathway that leads to cell lysis and death.

The term "expression" or "expressed" as used herein in reference to a gene means the transcriptional and/or translational product of that gene. The level of expression of a DNA molecule in a cell may be determined on the basis of either the amount of corresponding mRNA that is present within the cell or the amount of protein encoded by that DNA produced by the cell (Sambrook et al., 1989, Molecular Cloning: A Laboratory Manual, 18.1-18.88).

Expression of a transfected gene can occur transiently or stably in a cell. During "transient expression" the transfected gene is not transferred to the daughter cell during cell division. Since its expression is restricted to the transfected cell, expression of the gene is lost over time. In contrast, stable expression of a transfected gene can occur when the gene is co-transfected with another gene that confers a selection advantage to the transfected cell. Such a selection advantage may be a resistance towards a certain toxin that is presented to the cell.

The terms "transfection," "transduction," "transfecting" or "transducing" can be used interchangeably and are defined as a process of introducing a nucleic acid molecule and/or a protein to a cell. Nucleic acids may be introduced to a cell using various methods. The nucleic acid molecule can be a sequence encoding complete proteins or functional portions thereof. Typically, a nucleic acid vector comprises the elements necessary for protein expression (e.g., a promoter, transcription start site, etc.). Exemplary transfection methods include calcium phosphate transfection, liposomal transfection, nucleofection, sonoporation, transfection through heat shock, magnetifection and electroporation. The terms "transfection" or "transduction" also refer to introducing proteins into a cell from the external environment. Typically, transduction or transfection of a protein relies on attachment of a peptide or protein capable of crossing the cell membrane to the protein of interest. See, e.g., Ford et al. (2001) Gene Therapy 8:1-4 and Prochiantz (2007) Nat. Methods 4:119-20.

As used herein, the terms "specific binding" "specifically bind" or "specifically binds" refer to two molecules (e.g., DNA-binding domain and its specific binding (or targeting) nucleic acid sequence) that bind to each other with a higher affinity and specificity than a binding between random (e.g. non-target) molecules.

The terms "target," "targeting" or "targeted," in the context of altering a specific locus, site or gene, refer to a locus or site in the genome or gene that is intended to be altered in their expression, e.g. transcription and/or translation. In embodiments, the specific locus, site or gene targeted for alteration, i.e. a target sequence, target site or target gene is modulated in its transcription such that, for example, the transcription of the target locus, site or gene can be activated (or increased or promoted) or repressed (or reduced or inhibited). In embodiments, the target sequence, site or gene can be modified in their DNA or RNA sequences. Thus, in one example, the target sequence, site or gene in the genome is altered, e.g. mutated, deleted or inserted. In another example, RNA sequences that are transcribed from the genomic sequences of the target sequence, site or gene can be altered, e.g. via mutation, deletion or insertion. As used herein, the phrase "recognition sequence," "recognition site," "target sequence" or "target site" refers to a particular sequence which a system capable of altering the expression of a target sequence recognizes and binds. A recognition sequence or target sequence may refer to a nucleic acid sequence, DNA or RNA that is recognized and bound by a CRISPR-associated system with specificity.

A "pharmaceutical composition" is a formulation containing the nucleic acids described herein in a form suitable for administration to a subject. In embodiments, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed nucleic acid) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this invention include powders, sprays, ointments, pastes, creams, lotions, gels, solutions, patches and inhalants. In embodiments, the active nucleic acid is mixed under sterile conditions with a pharmaceutically acceptable carrier, and with any preservatives, buffers, or propellants that are required.

As used herein, the phrase "pharmaceutically acceptable" refers to those compounds, anions, cations, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used in the specification and claims includes both one and more than one such excipient. A thorough discussion of pharmaceutically acceptable excipients is available in REMINGTON'S PHARMACEUTICAL SCIENCES (Mack Pub. Co., N.J. 1991). Pharmaceutically acceptable excipients in therapeutic compositions may contain liquids such as water, saline, glycerol and ethanol. Additionally, auxiliary substances, such as wetting or emulsifying agents, pH buffering substances, and the like, may be present in such vehicles.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), and transmucosal administration.

Formulations suitable for oral administration include, without limitation, (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

A pharmaceutical composition of the present disclosure can be administered to a subject in many of the well-known methods currently used for chemotherapeutic treatment. For example, for treatment of cancers, a composition of the present disclosure may be injected directly into tumors, injected into the blood stream or body cavities or taken orally or applied through the skin with patches. The dose chosen should be sufficient to constitute effective treatment but not so high as to cause unacceptable side effects. The state of the disease condition (e.g., cancer, pre-cancer, and the like) and the health of the patient should preferably be closely monitored during and for a reasonable period after treatment.

The terms "subject," "individual," and "patient" are used interchangeably herein to refer to a vertebrate, preferably a mammal, more preferably a human. The mammal can be e.g., a human or appropriate non-human mammal, such as primate, mouse, rat, dog, cat, cow, horse, goat, camel, sheep or a pig. The subject can also be a bird or fowl. Tissues, cells and their progeny of a biological entity obtained in vivo or cultured in vitro are also encompassed. As used herein, a "subject in need thereof" or "a patient" may be a subject having a disease, such as a mitochondrial disease.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

By "co-administer" it is meant that a composition described herein is administered at the same time, just prior to, or just after the administration of one or more additional therapies. The compound of the disclosure can be administered alone or can be co-administered to the patient. Co-administration is meant to include simultaneous or sequential administration of the compound individually or in combination (more than one compound or agent).

As used herein, "treatment" or "treating," or "palliating" or "ameliorating" are used interchangeably herein. These terms refer to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made. Treatment includes preventing the disease, that is, causing the clinical symptoms of the disease not to develop by administration of a protective composition prior to the induction of the disease; suppressing the disease, that is, causing the clinical symptoms of the disease not to develop by administration of a protective composition after the inductive event but prior to the clinical appearance or reappearance of the disease; inhibiting the disease, that is, arresting the development of clinical symptoms by administration of a protective composition after their initial appearance; preventing re-occurring of the disease and/or relieving the disease, that is, causing the regression of clinical symptoms by administration of a protective composition after their initial appearance.

The terms "prevent," "preventing," or "prevention," and other grammatical equivalents as used herein, include to keep from developing, occur, hinder or avert a disease or condition symptoms as well as to decrease the occurrence of symptoms. The prevention may be complete (i.e., no detectable symptoms) or partial, so that fewer symptoms are observed than would likely occur absent treatment. The terms further include a prophylactic benefit. For a disease or condition to be prevented, the compositions may be administered to a patient at risk of developing a particular disease, or to a patient reporting one or more of the physiological symptoms of a disease, even though a diagnosis of this disease may not have been made.

An "effective amount" is an amount sufficient to accomplish a stated purpose (e.g. achieve the effect for which it is administered, treat a disease, reduce enzyme activity, reduce one or more symptoms of a disease or condition, or reduce viral replication in a cell). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme or protein relative to the absence of the antagonist. A "function disrupting amount," as used herein, refers to the amount of antagonist required to disrupt the function of an enzyme or protein relative to the absence of the antagonist. Guidance can be found in the literature for appropriate dosages for given classes of pharmaceutical products. For example, for the given parameter, an effective amount will show an increase or decrease of at least 5%, 10%, 15%, 20%, 25%, 40%, 50%, 60%, 75%, 80%, 90%, or at least 100%. Efficacy can also be expressed as "-fold" increase or decrease. For example, a therapeutically effective amount can have at least a 1.2-fold, 1.5-fold, 2-fold, 5-fold, or more effect over a control. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated, however, that the resulting reaction product can be produced directly from a reaction between the added reagents or from an intermediate from one or more of the added reagents which can be produced in the reaction mixture.

A "control" sample or value refers to a sample that serves as a reference, usually a known reference, for comparison to a test sample. For example, a test sample can be taken from a test condition, e.g., in the presence of a test compound, and compared to samples from known conditions, e.g., in the absence of the test compound (negative control), or in the presence of a known compound (positive control). A control can also represent an average value gathered from a number of tests or results. One of skill in the art will recognize that controls can be designed for assessment of any number of parameters. For example, a control can be devised to compare therapeutic benefit based on pharmacological data (e.g., half-life) or therapeutic measures (e.g., comparison of side effects). One of skill in the art will understand which standard controls are most appropriate in a given situation and be able to analyze data based on comparisons to standard control values. Standard controls are also valuable for determining the significance (e.g. statistical significance) of data. For example, if values for a given parameter are widely variant in standard controls, variation in test samples will not be considered as significant.

As used herein, the term "about" means a range of values including the specified value, which a person of ordinary skill in the art would consider reasonably similar to the specified value. In embodiments, the term "about" means within a standard deviation using measurements generally acceptable in the art. In embodiments, about means a range extending to +/−10% of the specified value. In embodiments, about means the specified value.

In one aspect, the disclosure provides compositions, kits and methods of altering gene expression in a cell. In embodiments, the compositions, kits and methods utilize a cell-targeting CRISPR-associated system. In another aspect, the disclosure provides methods of treating a disease in a subject in need of such treatment using any of the compositions, kits and/or methods of the disclosure.

Compositions

In one aspect, the present disclosure provides a composition for altering gene expression in a cell. In embodiments, the composition has a nucleic acid sequence having a genetically modified tracrRNA sequence. In embodiments, the composition has a nucleic acid sequence having a gRNA sequence. A gRNA sequence and a tracrRNA sequence can be provided on separate nucleic acids, or as parts of a single nucleic acid. In embodiments, the composition has a RNA-guided DNA endonuclease enzyme.

In embodiments, the composition of the disclosure has a CRISPR-associated system or any components thereof. In embodiments where the CRISPR-associated system is used, the RNA-guided DNA endonuclease enzyme can be a Cas protein or any derivative or variant thereof, including modified Cas proteins, e.g. dCas protein.

In embodiments, the composition of the disclosure includes a CRISPR-associated system for genome edition. In embodiments, the composition of the disclosure includes a CRISPR-associated system for transcriptional regulation. In embodiments, the composition of the disclosure includes a CRISPR-associated system for translational regulation. In embodiments, the composition of the disclosure includes a CRISPR-associated system for gene replacement.

In embodiments, the CRISPR-associated system of the disclosure contains a plasmid or vector to transfect target cells. For example, one or more crRNAs and a tracrRNA can be packaged together to form a single-guide RNA (sgRNA) which is made into a plasmid or vector in order to be transfected into cells. In embodiments, an expression vector that includes a sequence encoding a Cas protein or any derivative or variant thereof can be used as part of or in combination with the CRISPR-associated system.

In embodiments, crRNA contains a guide RNA (gRNA) sequence and is present as a separate molecule from tracrRNA. In such embodiments, the composition of the disclosure can contain one or more of the following: (1) a Cas protein or a nucleic acid encoding a Cas protein, (2) crRNA (or gRNA) and (3) tracrRNA, where the tracrRNA is genetically modified and optionally the crRNA is genetically modified in order to maintain the complementary pairing. In embodiments, crRNA and tracrRNA are covalently bound, forming a single molecule, i.e. a single guide RNA (sgRNA) sequence. Thus, in embodiments, the composition of the disclosure can contain one or more of the following: (1) a Cas protein or a nucleic acid encoding a Cas protein and (2) sgRNA sequence, where the tracrRNA portion of the sgRNA is genetically modified and optionally the crRNA portion of the sgRNA is also genetically modified in order to maintain the complementary pairing. In embodiments, the composition can further include one or more additional components, e.g. a DNA repair template (or donor template) if an insertion of a foreign gene into a target sequence is desired. In embodiments, any of the nucleic acid sequences used in the composition and method of the disclosure can be in the form of a vector, e.g. an expression vector.

In embodiments, the composition of the disclosure contains a nucleic acid that has a guide RNA (gRNA) sequence. In embodiments, the gRNA sequence of the composition has modified nucleotides in the sequence. In embodiments, the modification includes modification of one or more cytosine nucleotides present in the gRNA sequence. In embodiments, all cytosine nucleotides in the gRNA sequence are modified. In embodiments, one or more or all cytosine nucleotides in the gRNA are modified without modifying any uracil nucleotide that is present in the same gRNA, if any. In embodiments, one or more uracil nucleotides present in the gRNA sequence are modified. In embodiments, all of uracil nucleotides present in the gRNA sequence are modified. In embodiments, one or more or all uracil nucleotides in the gRNA are modified without modifying any cytosine nucleotide that is present in the same gRNA, if any. In embodiments, all cytosine nucleotides and all uracil nucleotides in the gRNA sequence are modified.

In embodiments, the composition of the disclosure contains a genetically modified trans-activating crRNA (tracrRNA) sequence, where at least one (e.g., 1, 2, 3, 4, 5, 6, 7, 8, 9, 10, 11, 12, 13, 14, 15 or more) uracil nucleotides of the tracrRNA sequence is replaced with a nucleotide other than uracil. In embodiments, at least one nucleotide of the modified tracrRNA sequence corresponding to a uracil of SEQ ID NO: 1 is a nucleotide other than uracil, and the modified tracrRNA sequence is not a naturally occurring tracrRNA sequence. In embodiments, the modified tracrRNA sequence is at least 80% identical (e.g., at least 85%, 90%, 95%, 98%, 99%, or 100% identical) to SEQ ID NO: 1 or a tracrRNA sequence selected from any of Tables 1-10. In embodiments, the nucleotide other than uracil is guanine (G). In embodiments, the nucleotide other than uracil is adenine (A). In embodiments, the nucleotide other than uracil is cytosine (C). In embodiments, the tracrRNA sequence has about 80% to about 99%, 85% to about 95%, or less than about 95% sequence identity to SEQ ID NO: 1. In embodiments, the tracrRNA sequence is less than 90% identity to SEQ ID NO: 1.

In embodiments, the genetically modified tracrRNA sequence contains 1, 2, 3, 4, 5, 6, 7, 8, 9, 10, 11, 12, 13, 14, 15 or more uracil nucleotides replaced with either G or A or C (i.e., U-replaced with G or A or C). Described herein, the term "U-replaced" and the term "U-depleted" are equivalent and interchangeable. In embodiments, about 1-15, about 3-12, or about 5-10 uracils are replaced. In embodiments, at least 5 uracils are replaced. In embodiments, at least 10 uracils are replaced.

In embodiments, the genetically modified tracrRNA sequence contains 1, 2, 3, 4, 5, 6, 7, 8, 9, 10, 11, 12, 13, 14, 15 or more uracil nucleotides replaced with either G or A (i.e., U-replaced with G or A). In embodiments, about 1-15, about 3-12, or about 5-10 uracils are replaced. In embodiments, at least 5 uracils are replaced. In embodiments, at least 10 uracils are replaced.

In embodiments, at least or at most about 10%, about 20%, about 30%, about 40%, about 50%, about 60%, about 70%, about 80%, about 90% or about 100% of uracil nucleotides present in a reference tracrRNA sequence (e.g., a tracrRNA sequence of SEQ ID NO: 1) are replaced with a nucleotide other than uracil. In embodiments, about 50% to about 90% of uracil nucleotides are replaced. In embodiments, about 10%, about 20%, about 30%, about 40%, about 50%, about 60%, about 70%, about 80%, about 90% or about 100% of uracil nucleotides present in a reference tracrRNA sequence are replaced with a nucleotide other than uracil. In embodiments, about 10% to about 95%, about 20% to about 80%, 30% to about 70%, 40% to about 60%, or at least about 50% of the uracils are replaced.

In embodiments, at least or at most about 10%, about 20%, about 30%, about 40%, about 50%, about 60%, about 70%, about 80%, about 90% or about 100% of uracil nucleotides present in a reference tracrRNA sequence are replaced with G or A. In embodiments, about 50% to about 90% of uracil nucleotides are replaced. In embodiments, about 10%, about 20%, about 30%, about 40%, about 50%, about 60%, about 70%, about 80%, about 90% or about 100% of uracil nucleotides present in a reference tracrRNA sequence are replaced with G or A. In embodiments, about 10%, about 20%, about 30%, about 40%, about 50%, about 60%, about 70%, about 80%, about 90% or about 100% of uracil nucleotides present in a reference tracrRNA sequence are replaced with a nucleotide other than uracil. In embodiments, about 10% to about 95%, about 20% to about 80%, 30% to about 70%, 40% to about 60%, or at least about 50% of the uracils are replaced.

In embodiments, one or more (e.g., 1, 2, 3, 4, 5, 6, 7, 8, 9, 10, 11, 12, 13, 14, 15, 16, 17 or 18) of the following positions of the tracrRNA sequence shown in FIG. 12 are replaced: 22, 27, 34, 35, 40, 46, 49, 53, 54, 56, 61, 62, 70, 80, 84, 87, 88, and 89, with G or A or C. In embodiments, about 1-15, about 3-12, or about 5-10 of the positions are replaced. In embodiments, at least 5 of the positions are replaced. In embodiments, at least 10 of the positions are replaced.

In embodiments, a uracil nucleotide of the tracrRNA sequence that is essential for binding to an RNA-guided DNA endonuclease enzyme (e.g., Cas9) is not replaced or depleted. A uracil nucleotide of the tracrRNA sequence that is essential for binding to an RNA-guided DNA endonuclease enzyme (e.g., Cas9) refers to a uracil nucleotide within the tracrRNA sequence that is absolutely required for the binding of the tracrRNA sequence (as the scaffold) to the RNA-guided DNA endonuclease enzyme (e.g., Cas9). In embodiments, the U nucleotide at position 34 of the tracrRNA sequence shown in FIG. 12 cannot be replaced or depleted. In embodiments, the U nucleotide at position 34 of the tracrRNA sequence shown in FIG. 12 cannot be replaced or depleted without additional U replacements. In embodiments, a gRNA sequence and/or a tracrRNA sequence comprises one or more (e.g., 2, 3, 4, 5, 6, 7, 8, 19, 10, 15, or more) of the substitutions indicated in FIG. 12. In embodiments, a gRNA sequence and/or a tracrRNA sequence comprises at least 5 or at least 10 of the substitutions indicated in FIG. 12.

In embodiments, the mutation, substitution or deletion of such essential uracil nucleotide will lead to at least 1-fold, 2-fold, 3-fold, 4-fold, 5-fold, 6-fold, 7-fold, 8-fold, 9-fold, 10-fold or greater reduction of the binding affinity (e.g., Kd).

In embodiments, the mutation, substitution or deletion of such essential uracil nucleotide will lead to no measurable binding. The binding of a tracrRNA to an RNA-guided DNA endonuclease enzyme (e.g., Cas9) can be measured by any method known in the art, for example, an electrophoretic mobility shift assay (EMSA) or Fluorescence Resonance Energy Transfer (FRET). In embodiments, the Surveyor nuclease assay may be used as a functional assay for the degree of tracrRNA binding and/or of CRISPR complex activity.

In embodiments, the mutation, substitution or deletion of such essential uracil nucleotide will lead to at least 1-fold, 2-fold, 3-fold, 4-fold, 5-fold, 6-fold, 7-fold, 8-fold, 9-fold, 10-fold or greater reduction of the functionality of the RNA-guided DNA endonuclease enzyme (e.g., Cas9), such as gene editing capability. The gene editing functionality of the RNA-guided DNA endonuclease enzyme (e.g., Cas9) can be measured by any method known in the art, for example, the Surveyor nuclease assay, drop-off assay, deep sequencing, knockdown assays, in vitro cleavage assay or an assay described in the examples of the present disclosure.

In embodiments, the genetically modified tracrRNA sequence described herein has a tracrRNA sequence described in Tables 2-8. In embodiments, the genetically modified tracrRNA sequence may have 80%, 85%, 90%, 91%, 92%, 93%, 94%, 95%, 96%, 97%, 98%, 99% or 100% sequence identity to the whole sequence or a portion (e.g. a 10, 20, 30, 40, or 50 continuous amino acids portion) of any of the U-replaced tracrRNA sequences listed in Tables 2-8. In embodiments, the genetically modified tracrRNA sequences has about or at least about 90% or 95% sequence identity to a tracrRNA sequence in any of Tables 2-8.

In embodiments, the genetically modified tracrRNA sequence described herein is derived from one of the wild type tracrRNA sequences disclosed in Tables 9-10. In embodiments, one or more of the U nucleotides in the wild type tracrRNA sequence described in Tables 9-10 (SEQ ID Nos 139-157) are replaced with G or A or C. In embodiments, about 1-15, about 3-12, or about 5-uracils are replaced. In embodiments, at least 5 uracils are replaced. In embodiments, at least 10 uracils are replaced.

In embodiments, the wild type tracrRNA sequence can be determined by any method known in the art. Exemplary wild type tracrRNA sequences include, but are not limited to, those in Tables 9-10 and those described in references Shmakov et al., Nat Rev Microbiol 15 (3), 169-182, 2017 and Chylinski et al., RNA Biology, 10:5, 726-737, 2015, the contents of each of which are incorporated herein by reference.

In embodiments, the genetically modified tracrRNA sequence described herein increases an activity of a CRISPR complex or component thereof (e.g., an RNA-guided DNA endonuclease, such as Cas9) compared to a corresponding wild-type or other reference tracrRNA sequence in the absence of such genetic modification (e.g., SEQ ID NO: 1). In embodiments, the increased activity is gene editing functionality or other activity of the associated RNA-guided DNA endonuclease enzyme (e.g., Cas9), such as target sequence binding, target sequence cleavage, mutation induction (e.g., at a target sequence), and knockdown of target gene expression (e.g., a gene target in an activity assay, such as GFP). In embodiments, increased activity is increased mutation induction at a target site, such as that measured in a drop-off assay. In embodiments, the increased activity is increased knockdown of target gene expression (e.g., knockdown in expression of a target polynucleotide encoding GFP). In embodiments, the genetically modified tracrRNA sequence described herein increases an activity of a CRISPR complex or component thereof by at least 5%, 10%, 15%, 20%, 50%, 75%, 100%, 200%, or more, compared to a corresponding wild-type or other reference tracrRNA sequence in the absence of such genetic modification (e.g., SEQ ID NO: 1). In embodiments, the CRISPR complex activity is increased by at least about 50%. In embodiments, CRISPR complex activity is increased at least about 2-fold. Gene editing functionality of the RNA-guided DNA endonuclease enzyme (e.g., Cas9) can be measured by any method known in the art, for example, the Surveyor nuclease assay or the assay described in the examples. Other non-limiting examples of assays for measuring CRISPR complex activity include the drop-off assay, deep sequencing, knockdown assays, in vitro cleavage assays, and assays described in the examples of the present disclosure. In embodiments, CRISPR complex activity is measured in an assay for GFP-knockdown in HEK293-LTR-GFP-spCas9 cells in which GFP expression is measured by FACS analysis 48 hours after transfection with the tracrRNA (genetically modified or reference) and a gRNA targeting the TAR element of HIV (e.g., gRNA including the sequence of Tar4 (SEQ ID NO: 234)). In embodiments, CRISPR complex activity is measured by a drop-off assay in HEK293-LTR-GFP cells 48 hours after transfection with a Cas9 RNP comprising a gRNA targeting the TAR element of HIV (e.g., gRNA including the sequence of Tar6 (SEQ ID NO: 236)). An example drop-off assay is described in Findlay et al., PLOS ONE 11, e0153901, 2016.

In embodiments, replacement of uracil nucleotides occur in crRNA sequence and/or the genetically modified tracrRNA sequence. In embodiments, the replacement of uracil nucleotides occur only in a tracrRNA sequence but not in crRNA sequence. In embodiments, the replacement of uracil nucleotides occur both in crRNA sequence and tracrRNA sequence. In embodiments, the replacement of uracil nucleotides occur in a sgRNA sequence that is a combined molecule of crRNA and tracrRNA. In embodiments, only the tracrRNA portion of the sgRNA contains replacement of uracil. In embodiments, both the crRNA and tracrRNA portions of the sgRNA contain replacement of uracil. In embodiments, replacement is with respect to a wild-type or other reference sequence (e.g., SEQ ID NO: 1). In embodiments, one or more nucleotide replacements in a tracrRNA sequence occur at one or more positions corresponding to a uracil of SEQ ID NO: 1. In embodiments, one or more nucleotide replacements in a crRNA sequence occur at one or more positions corresponding to a uracil of SEQ ID NO: 126.

In embodiments, the genetically modified tracrRNA sequence of the composition includes further modified nucleotides in the sequence. In embodiments, the modification includes modification of one or more cytosine nucleotides present in the genetically modified tracrRNA sequence. In embodiments, all cytosine nucleotides in the genetically modified tracrRNA sequence are modified. In embodiments, one or more or all cytosine nucleotides in the genetically modified tracrRNA are modified without modifying any remaining uracil nucleotide that is present in the same genetically modified tracrRNA, if any. In embodiments, one or more remaining uracil nucleotides present in the genetically modified tracrRNA sequence are modified. In embodiments, all of remaining uracil nucleotides present in the genetically modified tracrRNA sequence are modified. In embodiments, one or more or all remaining uracil nucleotides in the genetically modified tracrRNA are modified without modifying any cytosine nucleotide that is present in the same genetically modified tracrRNA, if any. In embodiments, all cytosine nucleotides and all remaining uracil nucleotides in the genetically modified tracrRNA sequence are modified.

In embodiments, the modifications of cytosine and/or uracil nucleotides occur in crRNA sequence and/or tracrRNA sequence. In embodiments, the modifications of cytosine and/or uracil nucleotides occur only in a crRNA sequence but not in a tracrRNA sequence. In embodiments, the modifications of cytosine and/or uracil nucleotides occur only in a tracrRNA sequence but not in a crRNA sequence. In embodiments, the modifications of cytosine and/or uracil nucleotides occur both in a crRNA sequence and a tracrRNA sequence. In embodiments, the modifications of cytosine and/or uracil nucleotides occur in a sgRNA sequence that is a combined molecule of a crRNA sequence and a tracrRNA sequence. In embodiments, cytosine and/or uracil in only the crRNA portion of the sgRNA are modified. In embodiments, cytosine and/or uracil in only the tracrRNA portion of the sgRNA are modified. In embodiments, cytosine and/or uracil in both the crRNA and tracrRNA portions of the sgRNA are modified.

In embodiments, the modified nucleotide in the gRNA sequence of the disclosure includes 2'-modified nucleotides. For example, the 2'-modified nucleotides may include 2'-amine modified nucleotides, 2'-fluoro modified nucleotides, 2'-O-methyl modified nucleotides or any combination thereof.

In embodiments, the gRNA sequence and/or the tracrRNA sequence of the disclosure contains one or more cytosine nucleotides that are modified. In embodiments, the modified cytosine nucleotide is 2'-modified cytosine nucleotides. In embodiments, the modified cytosine nucleotide is 2'-fluroro cytosine nucleotides. In embodiments, all cytosine nucleotides present in a single gRNA sequence are modified. In embodiments, not all but only part of the cytosine nucleotides present in a single gRNA sequence are modified.

In embodiments, at least or at most about 10%, about 20%, about 30%, about 40%, about 50%, about 60%, about 70%, about 80%, about 90% or about 100% of cytosine nucleotides present in a gRNA sequence and/or a tracrRNA sequence are modified. In embodiments, at least about or at most about 50% to about 90% of cytosine nucleotides present in a gRNA sequence and/or a tracrRNA sequence are modified. In embodiments, about 10%, about 20%, about 30%, about 40%, about 50%, about 60%, about 70%, about 80%, about 90% or about 100% of cytosine nucleotides present in a gRNA sequence and/or a tracrRNA sequence are modified. In embodiments, about 20% to about 90%, about 30% to about 80%, about 40% to about 70%, or about 50% to about 60% of cytosine nucleotides present in a gRNA sequence and/or a tracrRNA sequence are modified.

Figure 3:
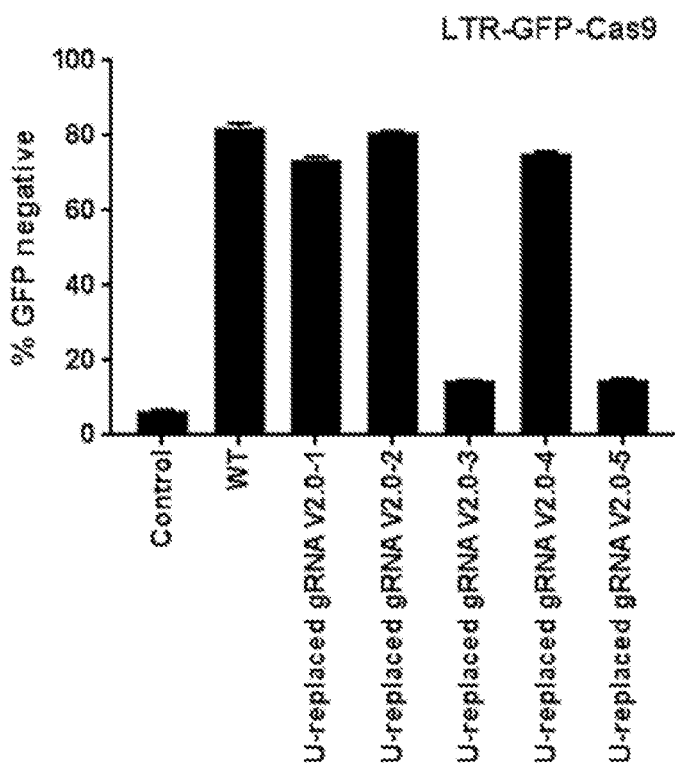
FIG. 3 is a bar graph depicting example results for U-replaced gRNA sequences V2.0 (sequences shown in Table 3). gBLOCKs containing a U6 Pol III promoter driving the expression of gRNA or U-replaced gRNAs were transfected into an LTR-GFP-Cas9 expression cell line. The levels of GFP were measured 48-hrs later. A WT gRNA was included as a positive control. A gRNA not targeted to HIV was included as a negative control.
Figure 4:
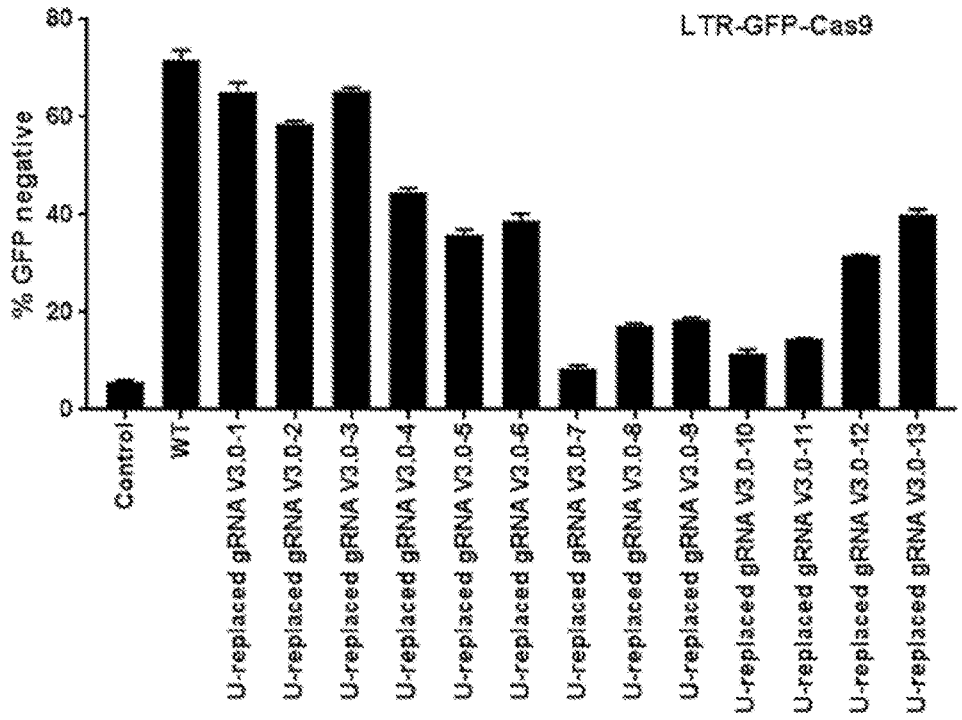
FIG. 4 is a bar graph depicting example results for U-replaced gRNA sequences V3.0 (sequences shown in Table 4). gBLOCKs containing a U6 Pol III promoter driving the expression of U-replaced gRNAs were transfected into an LTR-GFP-Cas9 expression cell line. The levels of GFP were measured 48-hrs later. A WT gRNA was included as a positive control. A gRNA not targeted to HIV was included as a negative control.

In embodiments, the gRNA sequence and/or a tracrRNA sequence of the disclosure contains one or more uracil nucleotides that are modified. In embodiments, the modified uracil nucleotide is 2'-modified uracil nucleotides. In embodiments, the modified uracil nucleotide is 2'-fluroro uracil nucleotides as seen in FIGS. 3 and 4. In embodiments, all of uracil nucleotides present in a single gRNA sequence are modified. In embodiments, not all but only part of the uracil nucleotides present in a single gRNA sequence are modified.

In embodiments, at least or at most about 10%, about 20%, about 30%, about 40%, about 50%, about 60%, about 70%, about 80%, about 90% or about 100% of uracil nucleotides present in a gRNA sequence and/or a tracrRNA sequence are modified. In embodiments, at least about or at most about 50% to about 90% of uracil nucleotides present in a gRNA sequence and/or a tracrRNA sequence are modified. In embodiments, about 10%, about 20%, about 30%, about 40%, about 50%, about 60%, about 70%, about 80%, about 90% or about 100% of uracil nucleotides present in a gRNA sequence and/or a tracrRNA sequence are modified. In embodiments, about 20% to about 90%, about 30% to about 80%, about 40% to about 70%, or about 50% to about 60% of uracil nucleotides present in a gRNA sequence and/or a tracrRNA sequence are modified.

In embodiments, the gRNA sequence of the disclosure is further modified with a functional RNA sequence, such as an RNA sequence having a biological activity in vitro or in vivo (e.g., an RNA sequence capable of specifically binding to a target biomolecule or altering the activity of a biomolecule). In embodiments, the modification includes an insertion of a functional RNA sequence, such as an aptamer nucleic acid sequence, into the gRNA sequence. In embodiments, the insertion of an aptamer is done in a loop region of the gRNA sequence. In embodiments where the gRNA has more than one loop, e.g. loop 1 and 2, the insertion can be done in a single loop (e.g. loop 1 or loop 2) or in both loops.

In embodiments, the gRNA sequence or tracrRNA sequence of the disclosure has one or more loops in the sequence. The loop (or loop region) used herein is according to its plain and ordinary meaning in the art and refers to a stem-loop intramolecular base pairing that can occur in a single-stranded nucleic acid, e.g. DNA and RNA. The loop can occur when two regions of the same strand, usually at least partially complementary in nucleotide sequence, base-pair to form a double helix. The term "loop" or "loop region" can also refer to a series unpaired nucleotides at the end of a stem-loop structure. In embodiments, at least part of the sequence in a loop of a gRNA can be modified or replaced with an alternative sequence such as 8-2 aptamer (Apt8-2) to provide additional functionality to the gRNA or tracrRNA. The term "tetraloop" is according to its plain and ordinary meaning in the art and refers to a 4 nucleotide sequence (GAAA) in a gRNA sequence that can be used to link a crRNA to a tracrRNA to allow for expression of a single guide RNA. In embodiments, the tetraloop can be modified or replaced likewise with other functional RNAs. Thus, in embodiments a tetraloop and loop 2 of a gRNA can be modified, e.g. by including an aptamer sequence.

In embodiments, the aptamer used in the disclosure is a nucleic acid aptamer that is capable of binding to (or recognizing) a specific target molecule or sequence. The aptamer of the disclosure, in particular a nucleic acid aptamer can contain one or more modified nucleotides, e.g. 2'-modified nucleotides.

In embodiments, the aptamer used in the disclosure is any nucleic acid sequence that can bind to (or recognize) a target molecule or sequence of interest. In embodiments, the aptamer of the disclosure binds to (or recognizes) a specific nucleic acid sequence (e.g. DNA or RNA sequence). In embodiments the aptamer of the disclosure binds to (or recognizes) a specific peptide sequence.

In embodiments the aptamer of the disclosure binds to (or recognizes) an antibody or part (or fragment) thereof. In embodiments, the aptamer is capable of binding to (or recognizing) an Fc antibody region. Therefore, when such an aptamer is used with its specific antibody, the aptamer can be recruited (or targeted) to the antigen of the antibody or to the cells having such an antigen.

For example, if the target molecule of interest is an antibody, the aptamer sequence can include the sequence of SEQ ID NO: 2 or a derivative thereof that has sequence identity of at least about 50%, about 60%, about 70%, about 80%, about 90%, about 95%, about 96%, about 97%, about 98%, about 99% or about 100% to SEQ ID NO: 2. In embodiments, the derivative has at least 90% or 95% identity to SEQ ID NO: 2. The sequence of SEQ ID NO: 2 is Aptamer 8-2 that is known to bind to (or recognize) the Fc region of human IgG. Therefore, in embodiments one or more aptamers having the sequence of SEQ ID NO: 2 or a derivative thereof can be included in the gRNA sequence or tracrRNA sequence of the disclosure. This gRNA sequence or tracrRNA sequence can be targeted to the cells having the antigen of human IgG via the binding (or recognition) of the 8-2 aptamer and the Fc region of human IgG.

In embodiments, the aptamer of the disclosure binds to (or recognizes) a cellular receptor or part (or fragment) thereof. In embodiments, a cellular receptor includes any biomolecules including a peptide, lipid and carbohydrate molecule that is present either on the surface of a cell membrane or embedded, at least in part, in the cellular membrane. Therefore, binding (or recognition) of such a biomolecule by the aptamer may allow targeting only the cells having the biomolecule with specificity over non-target cells that do not have the biomolecule.

For example, if the target molecule of interest is a cellular receptor, the aptamer sequence can include a nucleic acid sequence that can bind to (or recognize) the target cellular receptor. In embodiments, the target cellular receptor includes, but is not limited to, CD34, CD4, CD32a, CCR5, IL4, VEGFA and any part (or fragment) thereof. Any nucleic acid sequence that can bind to (or recognize) such a target cellular receptor can be used. In embodiments, any nucleic sequences known in the art as being capable of binding to (or recognizing) the target cellular receptor can be used. In embodiments, suitable aptamers can be synthesized using techniques available in the field. For example, it is within the knowledge of a person skilled in the art that aptamers can be selected and engineered through one or more rounds of in vitro selection techniques such as SELEX (systematic evolution of ligands by exponential enrichment) to bind to (or recognize) various molecular targets such as small molecules, proteins, nucleic acids and even cells, tissues and organisms. In embodiments, this aspect of aptamers can provide particular benefits as they can be engineered via a test tube and readily produced by chemical synthesis processes, exhibit desirable storage properties, and elicit little or no immunogenicity in therapeutic applications. Therefore, synthesis of any suitable (or desired) aptamer sequences that are in accordance with a variety of intended target molecules or sequences and uses thereof in a gRNA sequence or tracrRNA sequence is still within the scope of the present disclosure.

For example, if the target molecule of interest is CCR5, the aptamer sequence can include the sequence of SEQ ID NO: 257 or a derivative thereof that has sequence identity of at least about 50%, about 60%, about 70%, about 80%, about 90%, about 95%, about 96%, about 97%, about 98%, about 99% or about 100% to SEQ ID NO: 257. In embodiments, the derivative has at least 90% or 95% identity to SEQ ID NO: 257. The sequence of SEQ ID NO: 257 binds CCR5. In embodiments, one or more aptamers having the sequence of SEQ ID NO: 257 or a derivative thereof can be included in the gRNA sequence or tracrRNA sequence of the disclosure. This gRNA sequence or tracrRNA sequence can be targeted to the cells having CCR5 on their surface via the binding (or recognition) of the CCR5.

In embodiments, the gRNA sequence or tracrRNA sequence of the disclosure that has one or more aptamers forms a complex with a Cas protein, i.e. a ribonucleoprotein complex. Therefore, in embodiments the ribonucleoprotein complex is targeted (or recruited) to a specific target cell via the binding (or recognition) of the aptamer of the gRNA sequence or tracrRNA sequence to its target molecule. In one example where the gRNA or tracrRNA sequence has the aptamer 8-2 that can bind to (or recognize) the Fc region of human IgG, the gRNA can form a complex with a Cas protein such as Cas9 protein. When this gRNA-Cas9 protein complex is provided, in the presence of human IgG, to a mixture of various types of cells (e.g. in vitro administration) or an organism (e.g. in vivo administration to a subject), the ribonucleoprotein complex is targeted (or recruited) to the cell having the antigen of the human IgG. This targeting is achieved via the dual binding of the human IgG to the aptamer in the gRNA sequence and its antigen molecule that is present in the certain target cell. Therefore, the target cells can be targeted by the gRNA (or tracrRNA sequence) and Cas 9 protein of the disclosure with specificity, as compared to a random or non-target cell that does not have the antigen of human IgG. In another example, the gRNA sequence or tracrRNA sequence can have one or more aptamers that can specifically bind to (or recognize) CD34 protein. In embodiments, this gRNA sequence can form a complex with a Cas protein, e.g. Cas 9 protein and be recruited (or targeted) together to the target cell that expresses CD34 on their surface. Therefore, the composition of the disclosure can be delivered to a certain target cell with specificity and accuracy. In embodiments, the gRNA sequence of the disclosure forms a complex with a Cas protein that is sufficient to cause alteration in gene expression. Therefore, in embodiments the present disclosure delivers a fully functional CRISPR-associated system to its target cell with high efficiency. In embodiments, this can also result in avoiding transfection or vector-based delivery of the various CRISPR or dCas complexes. In alternative embodiments, the CRISPR-associated system of the disclosure utilizes transfection or vector-based delivery.

In embodiments, the aptamer sequence that is inserted into the gRNA or tracrRNA of the disclosure can increase or promote internalization of the gRNA, tracrRNA, and/or Cas protein into cells, relative to the absence of the aptamer sequence. In one example, the gRNA having the aptamer 8-2 sequence can form a ribonucleoprotein complex with Cas9 protein, e.g. the Cas9-GFP:gRNA-8-2 complex. This complex can be bound to the antibody 2G12 which can bind to the GP160 protein that can enhance internalization of the Cas9-GFP:gRNA-8-2 complex and release thereof into the cells.

In embodiments, the CRISPR-associated system of the disclosure can perform any of a variety of desired gene modification functions. In embodiments, the CRISPR-associated system of the disclosure includes any form of CRISPR, e.g. genome excision (CRISPR), genome edition (e.g. dCas-APOBEC3A fusion) and transcriptional activation (e.g. dCas-VPR fusion) or repression (e.g. dCas-KRAB fusion). Any CRISPR-associated system that is suitable or desired in accordance with a specific purpose can be targeted either ex vivo or in vivo to specific cells by their particular receptors which can be bound (or recognized) by an aptamer used in embodiments of the system.

In embodiments, the Cas protein used in the CRISPR-associated system of the disclosure can be a wild-type Cas protein or modified Cas protein. In embodiments, a wild-type Cas protein such as Cas 9 isolated from various sources (e.g. bacterial or mammal sources) or synthesized in view of the wild-type sequences can be used. In embodiments, a modified Cas protein in which some of properties or functionalities of a wild-type Cas protein has been modulated is used. In embodiments, a dCas9 in which a nuclease function is inactivated in Cas9 can be used. In embodiments, a modified or mutated Cas protein such as a nickase Cas 9 (D10a) can be used. In embodiments, a mutated nickase version of the Cas9 enzyme generates a single-strand DNA break (or nick) at a specific location based on a co-expressed gRNA-defined target sequence, rather than a double-strand DNA break (or cut) produced by the wild type enzyme.

In embodiments, one or more additional components such as additional peptides can be associated with Cas 9 protein. In embodiments, a Cas protein includes not only a wild-type Cas protein, e.g. Cas 9 protein, and a modified Cas protein, e.g. dCas9 protein, but also a conjugate thereof. In embodiments, a Cas 9 protein, e.g. Cas 9 or dCas 9 protein, is associated with the one or more peptides to form a recombinant peptide or conjugate. The conjugate can be formed, for example, via a chemical linkage such as a covalent bond or a non-chemical linkage such as ionic binding. In embodiments, the Cas 9 protein and the additional peptide can be covalently linked to each other, e.g. by forming a fusion protein with or without a sequence linking the two.

In some embodiment, the additional peptide that forms a conjugate with a Cas protein is a peptide capable of transcriptional regulation, e.g. activation or repression. In embodiments, the additional peptide that forms a conjugate with a Cas protein is a transcriptional factor. In embodiments, the peptide capable of transcriptional activation is a transcriptional activator. In embodiments, a transcriptional activator is a protein that increases the transcription of a gene or set of genes. In some cases, transcriptional activators, when recruited to a DNA site, e.g. a promoter of a target sequence for activation, make or enhance protein-protein interactions with the general transcription machinery (e.g. RNA polymerase and general transcription factors), thereby facilitating the binding of the general transcription machinery to the promoter. In embodiments, the peptide capable of transcriptional repression is a transcriptional repressor (or inhibitor). In embodiments, a transcriptional repressor is a protein that reduces or inhibits gene transcription of a gene or set of genes. In some cases, transcriptional repressors, when recruited to a DNA site, e.g. a promoter of a target sequence for activation, inhibits, dissociates or prevents protein-protein interactions with the general transcription machinery (e.g. RNA polymerase and general transcription factors), thereby reducing or inhibiting the binding of the general transcription machinery to the promoter.

Any peptide that is capable of transcription modulation or regulation can be used in the composition of the disclosures. In embodiments, the transcriptional activators used in the present disclosure include, but not limited to, viral protein R (VPR), p65 transactivating subunit of NF-kappa B, heat-shock factor 1 (HSF) activation domain, VP64 (tetramer of VP16) activation domain, synergistic activation mediator (SAM), acetyltransferase and any derivatives thereof. In embodiments, the transcriptional repressor used in the present disclosure includes, but is not limited to, KRAB, DNA methyltransferase (e.g. DNA methyltransferase 3 alpha or DNMT3A) and any derivatives thereof. Each of the foregoing transcriptional factors or domains thereof are according to its plain and ordinary meaning in the art. Each of the foregoing gene edition peptides are according to its plain and ordinary meaning in the art.

In embodiments, the additional peptide that forms a conjugate with a Cas protein is a peptide capable of gene edition. One example of such peptides for gene edition is an APOBEC3A, which is a cytidine deaminase, causing edition of C to T (in DNA) or U (in RNA). Another example of peptides for gene edition is an Adenine deaminase which can make A-G changes. Additional examples of the peptides of gene edition also include, but are not limited to, Activation-induced cytidine deaminase (AID), APOBEC3G and lamprey CDA1. Any peptide that is capable of gene edition can be used in the composition of the disclosures. Each of the foregoing gene edition peptides are according to its plain and ordinary meaning in the art.

In embodiments, the additional peptide that forms a conjugate with a Cas protein is a cell-penetrating peptide (e.g. a TAT peptide or a derivative thereof). In embodiments, cell-penetrating peptides (CPPs) are short peptides that can facilitate cellular intake/uptake of various molecular equipment (e.g. a recombinant peptide). Any peptide that is a CPP or has cell-penetrating activity can be used in the compositions of the disclosure. In embodiments, the trans-activating transcriptional activator (TAT) or a derivative of TAT is used as a CPP, thereby enhancing the intake/uptake of the recombinant peptide into the cells. In addition to enhancing the transfer to the nucleus of the cell, the TAT peptide can also facilitate crossing the blood brain barrier, which can further enhance the delivery of the recombinant protein to the cells. Each of the foregoing gene edition peptides are according to its plain and ordinary meaning in the art.

In embodiments, a Cas protein can form a conjugate with any labeling peptide, which can enhance visual detection or monitoring of the conjugate. Any peptide that is capable of labeling and visualizing the conjugate directly or indirectly can be used in the compositions of the disclosure. In embodiments, a fluorescent protein such as green fluorescent protein (GFP) or mCherry protein can be used. Each of the foregoing gene edition peptides are according to its plain and ordinary meaning in the art.

In embodiments, a Cas protein or any conjugate thereof as described herein can be used as a protein or peptide form. In embodiments, instead of a protein or peptide sequence, a nucleic acid sequence encoding the Cas protein or any conjugate thereof can be used, e.g. as a component of a CRISPR-associated system of the disclosure. In embodiments, a vector such as an expression vector having a nucleic acid sequence encoding the Cas protein or any conjugate thereof can be used.

In one aspect, provided is a vector that has a guide RNA (gRNA) sequence. In embodiments, the vector is transfected into cells (e.g. eukaryotic cells such as mammalian cells or human cell lines) to alter the expression of a gene of interest or edit the genome.

In embodiments, the vector of the disclosure is capable of directing the expression (or transcription) of nucleic acids to which they are operatively linked. The term "operably linked" means that the nucleotide sequence of interest is linked to regulatory sequence(s) in a manner that allows for expression (or transcription) of the nucleotide sequence. The regulatory sequence may include, for example, promoters, enhancers and other expression control elements (e.g., polyadenylation signals). Such regulatory sequences are well known in the art and are described, for example, in Goeddel; Gene Expression Technology: Methods in Enzymology 185, Academic Press, San Diego, CA (1990). Regulatory sequences include those that direct constitutive expression (or transcription) of a nucleotide sequence in many types of host cells, and those that direct expression (or transcription) of the nucleotide sequence only in certain host cells (e.g., tissue-specific regulatory sequences). It will be appreciated by those skilled in the art that the design of the vector can depend on such factors as the choice of the target cell, the level of expression (or transcription) desired, and the like.

The vectors contemplated include, but are not limited to, viral vectors based on various viral sequences as well as those contemplated for eukaryotic target cells or prokaryotic target cells. The "target cells" may refer to the cells where the expression vector is transfected and the nucleotide sequence having gRNA sequence is expressed or transcribed. Upon expression or transcription of the gRNA sequence in the target cells, a desired gene edition can occur if other component(s) of CRISPR-associated system necessary for alteration of gene expression or genome edition, e.g. a Cas protein, is also present in the target cells. Any vectors can be used so long as they are compatible with the desired or intended target cell. The skilled person in the art can use any suitable vectors known and available in the art depending on their system, e.g. the target cell or the process of culturing the cell and purifying the recombinant peptides.

In some examples, a vector has one or more transcription control elements. Depending on the target/vector system utilized, any of a number of suitable transcription control elements, including constitutive and inducible promoters, transcription enhancer elements, transcription terminators, etc. can be used in the vector.

Non-limiting examples of suitable eukaryotic promoters (i.e., promoters functional in a eukaryotic cell) include those from cytomegalovirus (CMV) immediate early, H1, herpes simplex virus (HSV) thymidine kinase, early and late SV40, long terminal repeats (LTRs) from retrovirus, human elongation factor-1 promoter (EF1), a hybrid construct having the cytomegalovirus (CMV) enhancer fused to the chicken beta-actin promoter (CAG), murine stem cell virus promoter (MSCV), phosphoglycerate kinase-1 locus promoter (PGK), and mouse metallothionein-I. The promoter can be a constitutive promoter (e.g., CMV promoter, UBC promoter). In some cases, the promoter can be a spatially restricted and/or temporally restricted promoter (e.g., a tissue specific promoter, a cell type specific promoter, etc.).

In embodiments, the composition of the disclosure includes any of the nucleotide sequences described herein. In embodiments, the nucleotide sequence of the composition has a sgRNA sequence that has a tracrRNA (such as a genetically modified tracrRNA, as described herein) and one or more crRNA in a single molecule. In embodiments, the composition further includes a Cas protein. In embodiments, the composition contains a wild-type Cas 9 protein and/or conjugate thereof. In embodiments, the composition contains a dCas 9 protein and/or conjugate thereof.

In embodiments, the composition of the disclosure includes any vector that has or encodes a nucleotide sequence described herein. In embodiments, the vector encodes a sgRNA sequence that will be transcribed into a single molecule having a tracrRNA and one or more crRNA. In embodiments, the vector encodes crRNA and/or tracrRNA, both of which will be transcribed into separate molecules. In embodiments, the composition further includes a Cas protein, e.g. a wild-type Cas 9 protein, dCas 9 protein or a conjugate thereof.

In embodiments, the composition of the disclosure allows alteration of gene expression in a modular manner. The composition of the disclosure has a number of ways to change or adjust the specificity and target of the alteration. The process of altering gene expression can vary at least in terms of (i) a target locus or gene (ii) a target cell and/or (iii) an intended gene regulation mode. As to the target locus or gene, each process can target a different locus or gene in the genome for modulation. The specificity of the target locus (or gene) can be determined or adjusted by gRNA sequences. The gRNA sequence has a sequence homologous to the target locus (or gene) and guides the machinery of a CRISPR-associated system to the target locus (or gene). Therefore, by using various tools available in the art to search and select gRNA sequences, one skilled in the art can design gRNA sequences that can target the intended target locus (or gene) with specificity. There are also a number of tools available in the art to select gRNA sequences with a low or no off-target property. Thus, by designing and using different gRNA sequences, one can determine and adjust the specificity to the intended target locus (or gene). In addition, the composition of the disclosure provides a variety of ways to target specific cells. In embodiments, such a targeting to a certain type of cells can be achieved by utilizing one or more aptamers in the gRNA sequence or tracrRNA sequence as described above. The aptamer sequences can directly bind to (or recognized) a molecule, e.g. a cellular receptor present on the surface of target cells. In embodiments, the aptamers can bind to (or recognize) an antibody that can bring the aptamers (and any other molecules that are associated with the aptamers) to the antigen of the antibody. The antigen may present in certain target cells, resulting in targeting the gRNA (and other machinery of the CRISPR-associated system such as a Cas protein) to the target cells. Thus, by selecting and utilizing different aptamers in the gRNA sequence or tracrRNA sequence, one can determine and adjust the specificity to certain cell types. Also, the CRISPR-associated system of the disclosure provides multiple gene regulation modes. In embodiments, the CRISPR-associated system of the disclosure can cause transcriptional regulation, e.g. transcriptional activation or repression, or gene edition such as mutation, deletion and/or insertion. These regulation modes can be achieved, e.g. by utilizing a Cas protein or conjugate thereof that is suitable for the intended mode. For example, one can use a Cas 9 that can perform genome excision (CRISPR), a dCas-APOBEC3A fusion that can perform gene edition, a dCas-VPR fusion that can activate transcription or a dCas-KRAB fusion that can repress transcription. Accordingly by selecting and utilizing different Cas proteins, one can determine and adjust the desired mode of gene regulation. As such, the CRISPR-associated system of the disclosure provides a highly versatile and modular system that allows targeting different target loci (or genes) and different cell types as well as different modes of regulation.

Methods

In one aspect, provided is a method of altering gene expression in a cell. In embodiments, the method includes introducing into the cell any of the nucleic acid sequences, any of the compositions, any of the vectors, or any of the pharmaceutical compositions of the disclosure. The pharmaceutical composition of the disclosure may contain any of the nucleic acids, any of the compositions, or any of the vectors of the disclosure, and a pharmaceutically acceptable excipient.

In embodiments, the method of the disclosure of altering gene expression in a cell further includes introducing to the cell an RNA-guided DNA endonuclease enzyme. In embodiments, the RNA-guided DNA endonuclease enzyme is a Cas protein. The Cas protein used in the method can be any Cas protein described herein. Thus, in embodiments, the method of the disclosure utilizes any of a variety of forms of Cas proteins that include a wild-type Cas protein, e.g. Cas 9, a modified Cas protein, e.g. dCas 9 protein, as well as any conjugate thereof. Accordingly, in embodiments, the method of the disclosure utilizes a Cas 9 that can perform genome excision (CRISPR). In embodiments, the method of the disclosure utilizes a dCas-APOBEC3A fusion that can perform gene edition. In embodiments, the method of the disclosure utilizes a dCas-VPR fusion that can activate transcription. In embodiments, the method of the disclosure utilizes a dCas-KRAB fusion that can repress transcription.

In embodiments, the cell is a cell in which gene expression is desired to be altered. For this purpose, any of the nucleic acids, any of the compositions, any of the vectors, any of the pharmaceutical compositions and/or any of Cas proteins of the disclosure can be introduced (or provided or delivered) to the cell. This provision (or delivery) to the cell can be done by using various techniques available in the art, which include, but are not limited to, calcium phosphate transfection, liposomal transfection, nucleofection, sonoporation, transfection through heat shock, magnetifection and electroporation.

In embodiments, the composition and method of the disclosure can be used for a therapeutic purpose, e.g. treatment of a disorder in a subject, e.g. a patient in need of such a treatment. The treatment performed in accordance with the present disclosure includes ex vivo and in vivo approaches.

In embodiments, the ex vivo approach for treating a disorder includes alteration of gene expression in cells in vitro (i.e. outside of a patient) and introduction of such cells into the patient. The method of altering gene expression in a cell can be used to produce therapeutically effective cells in which gene expression is altered. In embodiments, the cells are autologous that were obtained from the patient. In embodiments the cells are allogenic that were obtained from a donor, who is not the patient but acceptable by the patient. After a desired gene expression is altered in the autologous or allogenic cells, these cells can be introduced to the patient for treatment.

In embodiments, the in vivo approach for treating a disorder includes alteration of gene expression in cells that are present in a subject in need of the treatment, e.g. a patient. Thus, in one aspect, provided is a method of treating a disorder in a subject in need thereof. In embodiments, the method includes administering to the subject any of the nucleic acids, and of the compositions, any of the vectors or any of the pharmaceutical compositions of the disclosure, in combination with an RNA-guided DNA endonuclease enzyme.

In embodiments, the RNA-guided DNA endonuclease enzyme used in the in vivo method of the disclosure is a Cas protein. The Cas protein used in this method can be any Cas protein described herein. Thus, for example, a wild-type Cas protein (e.g. Cas 9), a modified Cas protein (e.g. dCas 9 protein) and any conjugate thereof (e.g. dCas-APOBEC3A, dCas-VPR and dCas-KRAB fusion proteins) can be used in the methods.

In embodiments, any disorder that can be treated at least partially or substantially completely via alteration of gene expression can be targeted by the treatment method of the disclosure. In embodiments, the disorder targeted by a treatment method of the disclosure includes, but is not limited to, HIV, cancer, Chronic obstructive pulmonary disease (COPD), Cystic Fibrosis, heart conditions/repair, and diabetes.

As used herein, the term "cancer" refers to all types of cancer, neoplasm or malignant tumors found in mammals (e.g. humans), including leukemias, lymphomas, carcinomas and sarcomas. Exemplary cancers that may be treated with a compound or method provided herein include brain cancer, glioma, glioblastoma, neuroblastoma, prostate cancer, colorectal cancer, pancreatic cancer, Medulloblastoma, melanoma, cervical cancer, gastric cancer, ovarian cancer, lung cancer, cancer of the head, Hodgkin's Disease, and Non-Hodgkin's Lymphomas. Exemplary cancers that may be treated with a compound or method provided herein include cancer of the thyroid, endocrine system, brain, breast, cervix, colon, head & neck, liver, kidney, lung, ovary, pancreas, rectum, stomach, and uterus. Additional examples include, thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma, non-small cell lung carcinoma, mesothelioma, multiple myeloma, neuroblastoma, glioma, glioblastoma multiforme, ovarian cancer, rhabdomyosarcoma, primary thrombocytosis, primary macroglobulinemia, primary brain tumors, malignant pancreatic insulanoma, malignant carcinoid, urinary bladder cancer, premalignant skin lesions, testicular cancer, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

The term "heart condition" or "heart disease" refers to any disorder that affects the heart. Sometimes the term "heart disease" is used narrowly and incorrectly as a synonym for coronary artery disease. Heart disease is synonymous with cardiac disease but not with cardiovascular disease which is any disease of the heart or blood vessels. Among the many types of heart disease, see, for example: Angina; Arrhythmia; Congenital heart disease; Coronary artery disease (CAD); Dilated cardiomyopathy; Heart attack (myocardial infarction); Heart failure; Hypertrophic cardiomyopathy; Mitral regurgitation; Mitral valve prolapse; and Pulmonary stenosis.

In embodiments, the method of treating a disorder in accordance with the disclosure includes administering any of the compositions or pharmaceutical compositions described herein to a subject in need of the treatment. In embodiments, the composition or pharmaceutical composition for treating a disorder has one or more compounds of the disclosure (e.g. a nucleic acid sequence having a gRNA sequence or a tracrRNA sequence, or a vector having or encoding the nucleic acid sequence). In embodiments, the method further includes administering a Cas protein.

In embodiments, the pharmaceutical composition has one or more compounds of the disclosure and one or more pharmaceutically acceptable excipients. In embodiments, in the pharmaceutical compositions, the compound or pharmaceutically acceptable salt thereof is included in a therapeutically effective amount.

The pharmaceutical composition of the disclosure can be prepared and administered in a wide variety of dosage formulations. Compounds described can be administered orally, rectally, or by injection (e.g. intravenously, intramuscularly, intracutaneously, subcutaneously, intraduodenally, or intraperitoneally). For example, the compositions disclosed herein can be delivered transdermally, by a topical route, formulated as applicator sticks, solutions, suspensions, emulsions, gels, creams, ointments, pastes, jellies, paints, powders, and aerosols. Oral preparations include tablets, pills, powder, dragées, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present disclosure can additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions disclosed herein can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., *Gao Pharm. Res.* 12:857-863, 1995); or, as microspheres for oral administration (see, e.g., Eyles, *J. Pharm. Pharmacol.* 49:669-674, 1997). In another embodiment, the formulations of the compositions of the present disclosure can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present disclosure into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions can also be delivered as nanoparticles.

Pharmaceutical compositions can include compositions wherein the active ingredient (e.g. compounds described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., altering a target gene expression and/or treatment of a target disorder in a subject who was treated with the composition.

In embodiments, the effective amount of the composition in accordance with the disclosure or active ingredient thereof, e.g. the nucleic acid having a gRNA sequence and/or tracrRNA sequence, the vector having the nucleic acid sequence or the pharmaceutical composition having the nucleic acid or the vector, is administered to a subject in need thereof, e.g. an in vivo approach. In embodiments of in vivo treatment, the effective amount of the composition or active ingredient to be administered to the subject in one application is about 1 ng/kg of subject body weight, about 10 ng/kg of subject body weight, about 50 ng/kg of subject body weight, about 100 ng/kg of subject body weight, about 500 ng/kg of subject body weight, about 1 µg/kg of subject body weight, about 10 µg/kg of subject body weight, about 50 µg/kg of subject body weight, about 100 µg/kg of subject body weight, about 150 µg/kg of subject body weight, about 200 µg/kg of subject body weight, about 250 µg/kg of subject body weight, about 300 µg/kg of subject body weight, about 350 µg/kg of subject body weight, about 375 µg/kg of subject body weight, about 400 µg/kg of subject body weight, about 450 µg/kg of subject body weight, about 500 µg/kg of subject body weight, about 550 µg/kg of subject body weight, about 600 µg/kg of subject body weight, about 650 µg/kg of subject body weight, about 700 µg/kg of subject body weight, about 750 µg/kg of subject body weight, about 800 µg/kg of subject body weight, about 850 µg/kg of subject body weight, about 900 µg/kg of subject body weight, about 1 mg/kg of subject body weight, about 10 mg/kg of subject body weight, about 50 mg/kg of subject body weight, about 100 mg/kg of subject body weight, about 500 mg/kg of subject body weight, about 1 g/kg of subject body weight or more or any intervening ranges of the of the foregoing. In embodiments, the effective amount of the composition or active ingredient thereof to be administered to the subject in one application is about 0.5 µg, about 1.0 µg, about 1.5 µg, about 2.0 µg, about 2.5 µg, about 3.0 µg, about 3.5 µg, about 4.0 µg, about 4.5 µg about 5.0 µg, about 5.5 µg, about 6.0 µg, about 6.5 µg, about 7.0 µg, about 7.5 µg, about 8.0 µg, about 8.5 µg, about 9.0 µg, about 9.5 µg, about 1.0 mg, about 1.5 mg, about 2.0 mg, about 2.5 mg, about 3.0 mg, about 3.5 mg, about 4.0 mg, about 4.5 mg about 5.0 mg, about 5.5 mg, about 6.0 mg, about 6.5 mg, about 7.0 mg, about 7.5 mg, about 8.0 mg, about 8.5 mg, about 9.0 mg, about 9.5 mg, about 1 g or more or any intervening ranges of the foregoing. In embodiments, one or more than one applications of the composition containing the active ingredient can be administered to the subject over a period of time, e.g. several hours, several days, several weeks or several months.

In embodiments, therapeutic cells that were previously modified to alter expression of target gene are introduced to a subject to treat a disorder, e.g. an ex vivo approach. In embodiment of ex vivo treatment, an effective amount of therapeutic cells is at least $10^2$ cells, at least $5 \times 10^2$ cells, at least $10^3$ cells, at least $5 \times 10^3$ cells, at least $10^4$ cells, at least $5 \times 10^4$ cells, at least $10^5$ cells, at least $2 \times 10^5$ cells, at least $3 \times 10^5$ cells, at least $4 \times 10^5$ cells, at least $5 \times 10^5$ cells, at least $6 \times 10^5$ cells, at least $7 \times 10^5$ cells, at least $8 \times 10^5$ cells, at least $9 \times 10^5$ cells, at least $1 \times 10^6$ cells, at least $2 \times 10^6$ cells, at least $3 \times 10^6$ cells, at least $4 \times 10^6$ cells, at least $5 \times 10^6$ cells, at least $6 \times 10^6$ cells, at least $7 \times 10^6$ cells, at least $8 \times 10^6$ cells, at least $9 \times 10^6$ cells, at least $1 \times 10^7$ cells, at least $2 \times 10^7$ cells, at least $3 \times 10^7$ cells, at least $4 \times 10^7$ cells, at least $5 \times 10^7$ cells, at least $6 \times 10^7$ cells, at least $7 \times 10^7$ cells, at least $8 \times 10^7$ cells, at least $9 \times 10^7$ cells, at least $1 \times 10^8$ cells, at least $2 \times 10^8$ cells, at least $3 \times 10^8$ cells, at least $4 \times 10^8$ cells, at least $5 \times 10^8$ cells, at least $6 \times 10^8$ cells, at least $7 \times 10^8$ cells, at least $8 \times 10^8$ cells, at least $9 \times 10^8$ cells, at least $1 \times 10^9$ cells, at least $2 \times 10^9$ cells, at least $3 \times 10^9$ cells, at least $4 \times 10^9$ cells, at least $5 \times 10^9$ cells, at least $6 \times 10^9$ cells, at least $7 \times 10^9$ cells, at least $8 \times 10^9$ cells, at least $9 \times 10^9$ cells, or multiples thereof. In embodiments, the therapeutic cells can be expanded in culture prior to administration to the subject in need thereof.

The dosage and frequency (single or multiple doses) administered to a subject can vary depending upon a variety of factors, for example, whether the subject suffers from another disease, and its route of administration; size, age, sex, health, body weight, body mass index, and diet of the recipient; nature and extent of symptoms of the disease being treated, kind of concurrent treatment, complications from the disease being treated or other health-related problems. Adjustment and manipulation of established dosages (e.g., frequency and duration) are well within the ability of those skilled in the art.

In embodiments, the compound or composition described herein can be used as a sole active ingredient(s). In embodiments, the compound or composition can be used in combination with one another, or with other active compounds or drugs known to be useful in treating a target disorder or with adjunctive agents that may not be effective alone, but may contribute to the efficacy of the active agent.

For preparing pharmaceutical compositions from compounds described herein, pharmaceutically acceptable carriers can be either solid or liquid. Solid form preparations include powders, tablets, pills, capsules, cachets, suppositories, and dispersible granules. A solid carrier may be one or more substances that may also act as diluents, flavoring agents, binders, preservatives, tablet disintegrating agents, or an encapsulating material.

Utilizing the teachings provided herein, an effective therapeutic treatment regimen can be planned that does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration, and the toxicity profile of the selected agent.

Kits

In one aspect, provided herein is a kit for, in part, altering gene expression in cells and treatment of a disorder. As part of the kit, materials and instruction are provided for altering gene expression in cells that are cultured in vitro or present in a subject(e.g. a patient) and the preparation of reaction mixtures for storage and use of kit components.

In embodiments, the kit can contain one or more of the following components:
1. any of the nucleic acids of the disclosure that has a gRNA, wherein all cytosine nucleotides and/or all uracil nucleotides of the gRNA sequence are modified nucleotides,
2. any of the nucleic acids of the disclosure that has a genetically modified tracrRNA sequence as disclosed herein,
3. any of the vectors of the disclosure that has or encodes a nucleic acid sequence disclosed herein,
4. any of the RNA-guided DNA endonuclease enzymes of the disclosure, and
5. instructions for how to use the kit components.

In embodiments, the composition, pharmaceutical composition and method of the disclosure has a variety of utilities. For example, human cells can be modified ex vivo (or in vitro) and implanted into an autologous patient. In embodiments, CD34 cells are removed from an HIV patient and CCR5 (the receptor for HIV) are deleted using a CRISPR complex that targets a specific cell (i.e. the cell targeting CRISPR complex), rendering these cells and their descendants resistant to HIV. These modified cells can then be implanted back into the patient. In another example, the cell targeting CRISPR complexes can also target specific repair of a mutation. In embodiments, the cell targeting CRISPR complex can enter into the cell and direct cytosine to thymine mutations (C-T) or cut a gene and insert the corrected DNA. In another example, the cell targeting CRISPR complex can be used as a recombinant complex to turn on or off any gene in the body. Thus, in embodiments the cell targeting CRISPR complex can be used to activate CFTR in Cystic Fibrosis patients and repair the 4508 mutation driving the disease. The compositions and methods described herein can be applied in a very wide range of utilities without limitation. As discussed previously, the CRISPR-associated system of the disclosure is modular in that by designing and utilizing different gRNA sequences and different cell targeting molecules (e.g. aptamers), the system can target any genes and any types of cells without limitation. Also by utilizing different RNA-guided DNA endonuclease enzymes (e.g. any Cas protein and any derivatives or conjugates thereof) various modes of altering gene expression can be achieved. Therefore, the compositions and methods of the disclosure provide a highly effective and powerful tool to alter gene expression in cells or in a subject for a number of purposes, e.g. therapeutic treatment of many different disorders.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entireties for all purposes.

EXAMPLES

Figure 27:
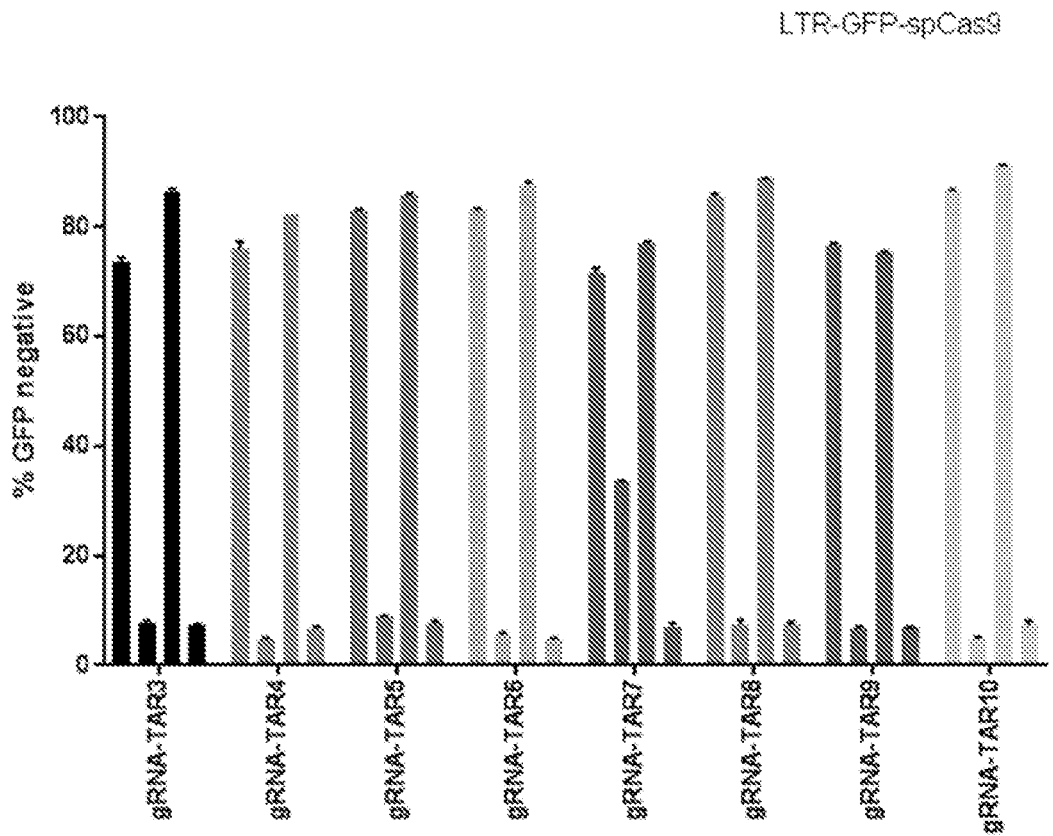
FIG. 27 is a bar graph illustrating 2'F-C are tolerated in example CRISPR/Cas gRNAs, and that 2'F-U may decrease activity. gRNAs that target the TAR element of HIV were in vitro transcribed with unmodified, 2'F-U, 2'F-C and 2'F-CU bases (from left to right in each group of bars). The gRNAs were transfected into a LTR-GFP-spCas9 cell line. At 48-hr post-transfection the levels of GFP were determined by FACS. Errors bars were obtained by transfections performed in duplicate.
Figure 28:
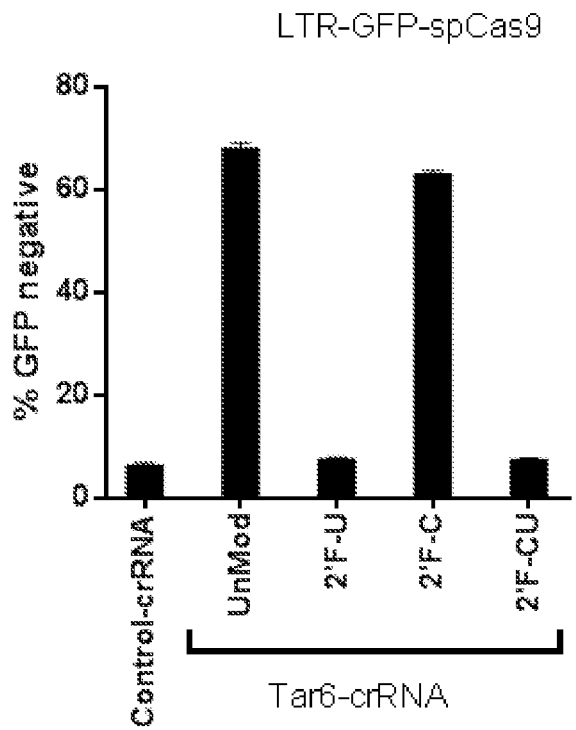
FIG. 28 is a bar graph illustrating that 2'F-C are tolerated in example CRISPR/Cas tracrRNA, and that 2'F-U may decrease activity. TracrRNAs were in vitro transcribed with unmodified, 2'F-U, 2'F-C and 2'F-CU bases. The tracrRNAs were annealed to a crRNA that targets the TAR element of HIV (TAR6) and then transfected into a LTR-GFP-spCas9 cell line. At 48-hr post-transfection the levels of GFP were determined by FACS. Errors bars were obtained by transfections performed in duplicate.
Figure 29:
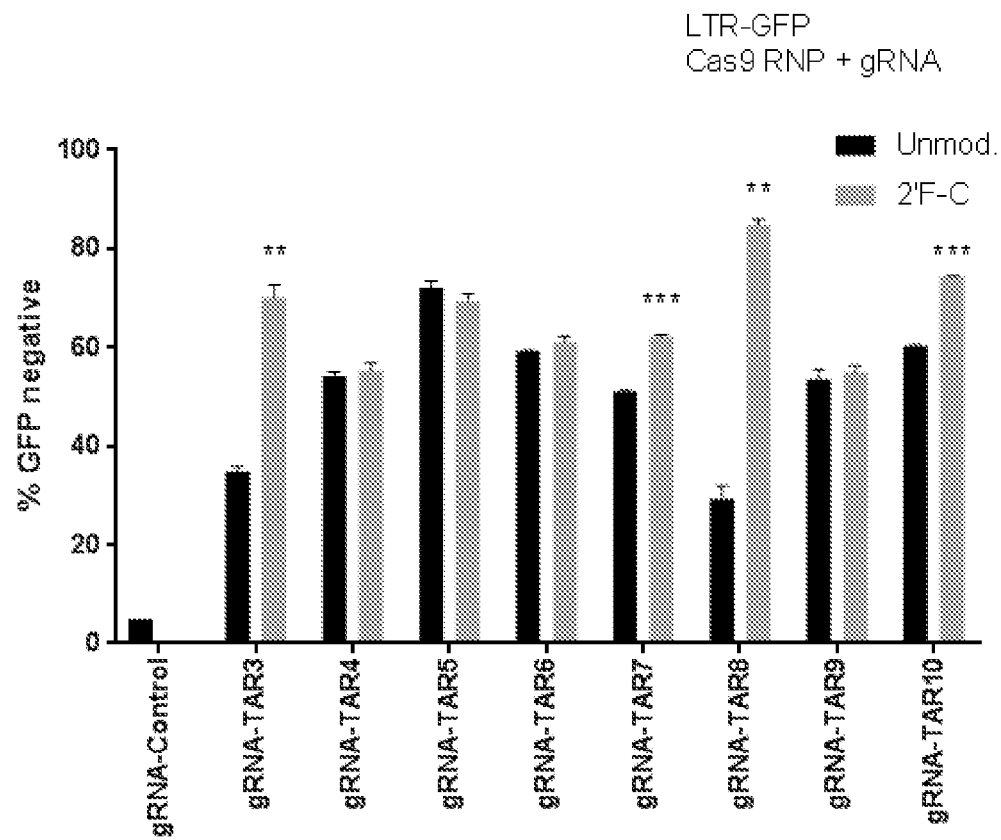
FIG. 29 is a bar graph illustrating that 2'F-C modifications in gRNAs can improve CRISPR/Cas RNP activity. gRNAs that target the TAR element of HIV (TAR3-10) were in vitro transcribed with unmodified or 2'F-C bases. The gRNAs were pre-incubated with a Cas9 RNP and then transfected into a LTR-GFP cell line. At 48-hr post-transfection the levels of GFP were determined by FACS. Errors bars were obtained by transfections performed in duplicate. Significance was determined using an unpaired t test., p<0.01, *p<0.001.

Example 1: Functionality of tracrRNAs with 2'F bases sgRNAs and tracrRNAs that were synthesized with 2'F-uridines completely lost activity (see, e.g., FIGS. 27 and 28). However, 2'F-Cs were well tolerated when incorporated into gRNAs or tracrRNA in cell lines stably expressing Cas9 (see, e.g., FIGS. 27 and 28), as well as when the 2'F-C gRNAs were transfected preloaded into a Cas9 RNP complex (see, e.g., FIG. 29). Interestingly, several gRNAs (TAR3, 6, 7 and 10) also showed improved activity when synthesized with 2'F-C, suggesting 2'F-C may be useful to improve CRISPR/Cas activity (see, e.g., FIG. 29, and Table 11).

Example 2: Functionality of U-Replaced tracrRNAs with 2'F Bases

Figure 1B:
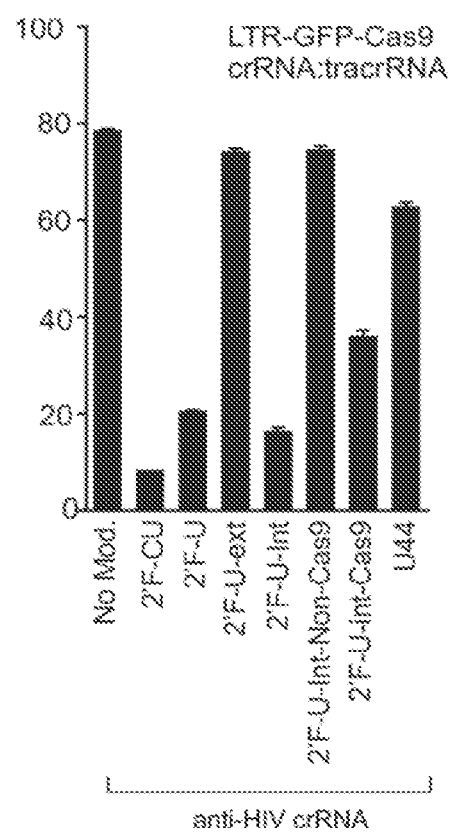
FIG. 1B is a bar graph depicting tracrRNAs synthesized with 2'F-U at specific sites and annealed with its corresponding anti-HIV crRNA and transfected in a LTR-GFP-Cas9 cell line, and 48-hr post-transfection the levels of GFP were determined by FACS. The activity of the 2'F tracrRNAs were made relative to the unmodified control.

Next, it was sought to determine the uridines responsible for the loss of activity with 2'F modifications. Guided by the crystal structure of spCas9 (Nishimasu, H., et al, 2014. Crystal Structure of Cas9 in Complex with Guide RNA and Target DNA. Cell 156, 935-949), it was found that the internal loop had several uridines that interact with Cas9, and a series of tracrRNAs were synthesized with 2'F-Us in various positions in the tracrRNA (FIG. 1A). These Cas9-interacting uridines were largely, although not completely, responsible for the loss of activity (FIG. 1B). Interestingly, although 2'F modification of non-interacting Cas9 uridines only had a slight loss of activity compared to a wild-type tracrRNA, when combined with the Cas9-interacting uridines, resulted in a significant decrease in reporter knockdown, suggesting modification of non-interacting Cas9 internal uridines also effected CRISPR/Cas9 function. 2'F-U in the regions outside of the internal loop (external uridines), also had a similar slight loss of activity compared to non-interacting uridines. These data indicated that 2'F modification of uridines within the internal loops was largely responsible for compromising CRISPR/Cas9 activity, but modification of other uridines within the tracrRNA may affect function too.

Figure 2:
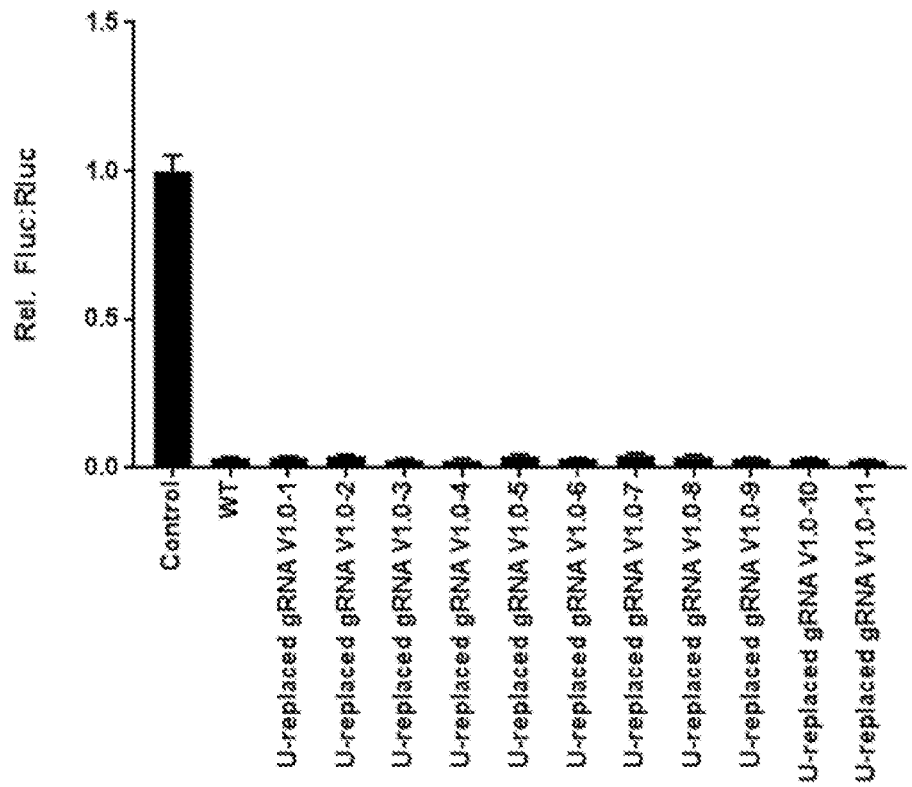
FIG. 2 is a bar graph depicting example results for U-replaced gRNA sequences V1.0 (sequences shown in Table 2). TZM-BL cells were transfected with a Cas9 expression vector and panel of U-replaced gRNAs and 48-hrs later the levels of luciferase was measured. The gRNAs were made relative to a control gRNA set at 100%. The wild-type (WT) gRNA was included as a positive control.

Next, a "version 1" gRNA that replaced single uridines within the internal loop was developed, which showed that U6-Pol III expressed gRNAs with a Cas9 expression vector maintained knockdown activity compared to a wild-type expressed gRNA (FIG. 2). An optimized replacement of combinations of internal uridines that interact with Cas9 (FIG. 3) and non-Cas9 interactions (FIG. 4) was determined.

Figure 5A:
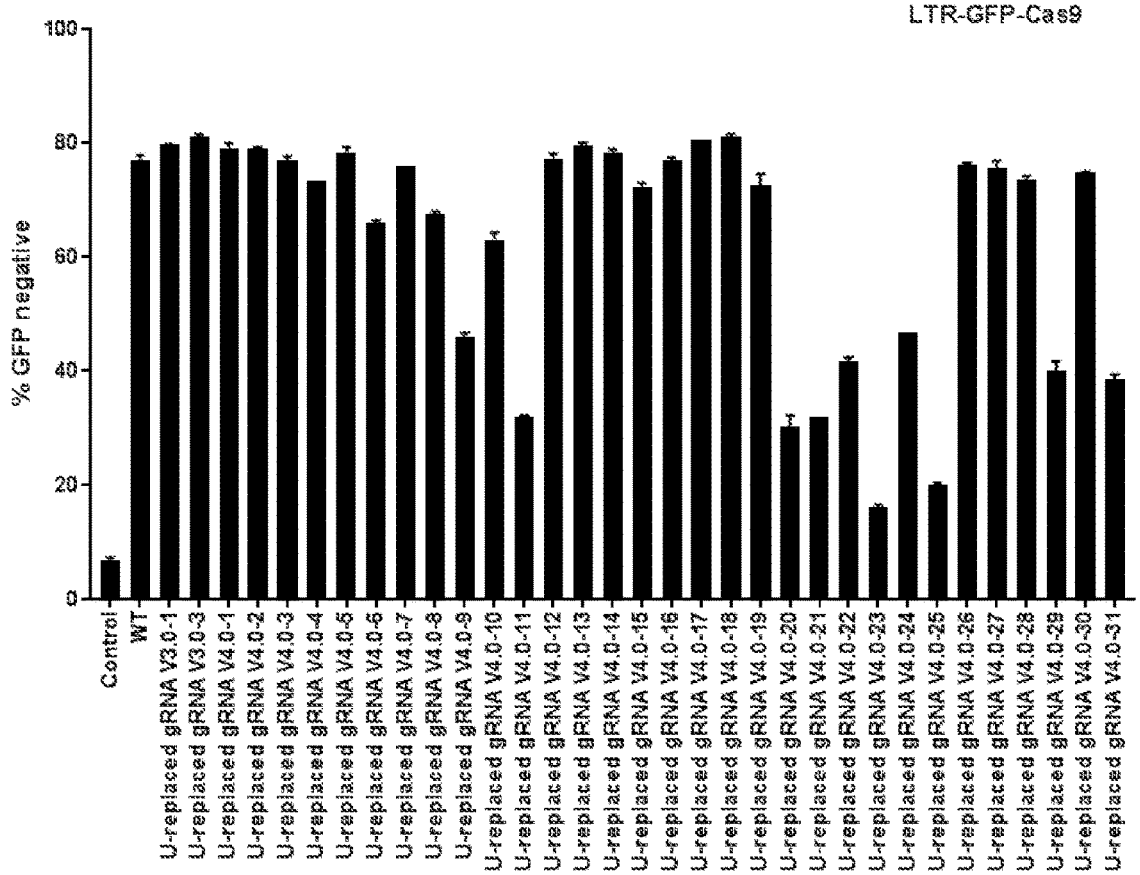
FIGS. 5A-5B are bar graphs depicting example results for U-replaced gRNA sequences V4.0 (sequences shown in Table 5). gBLOCKs containing a U6 Pol III promoter driving the expression of U-replaced gRNAs were transfected into an LTR-GFP-Cas9 expression cell line. The levels of GFP were measured 48-hrs later. A WT gRNA was included as a positive control. A gRNA not targeted to HIV was included as a negative control.
Figure 5B:
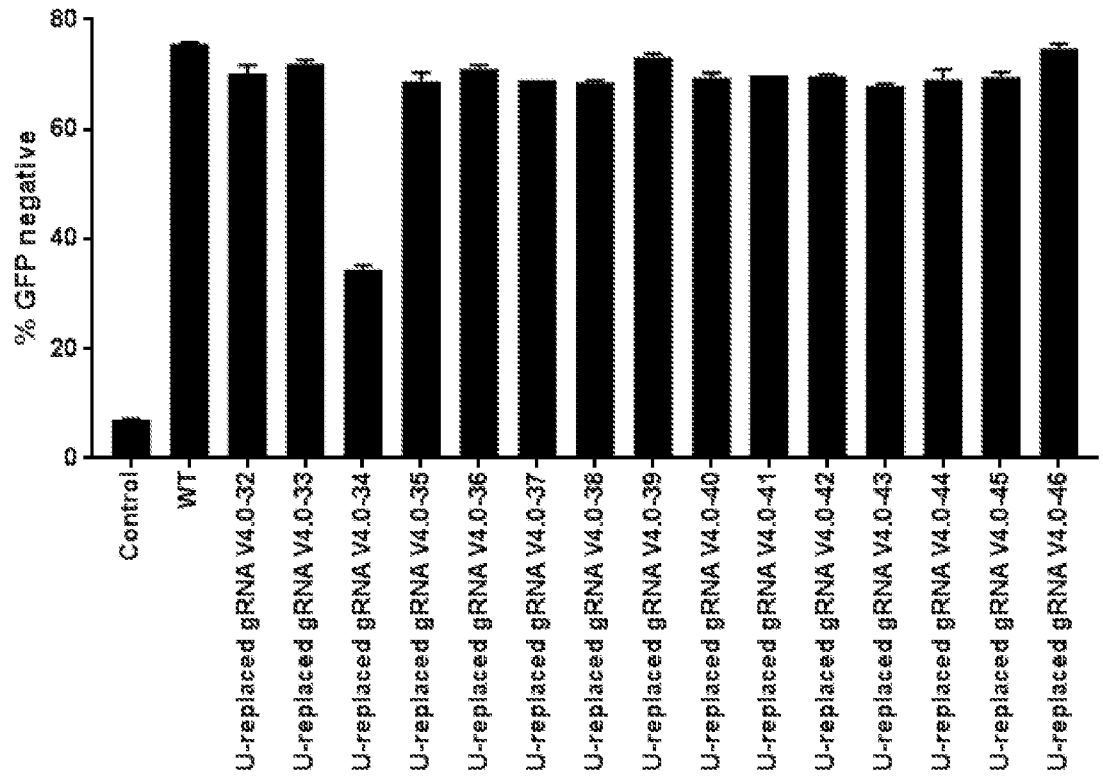
Figure 6:
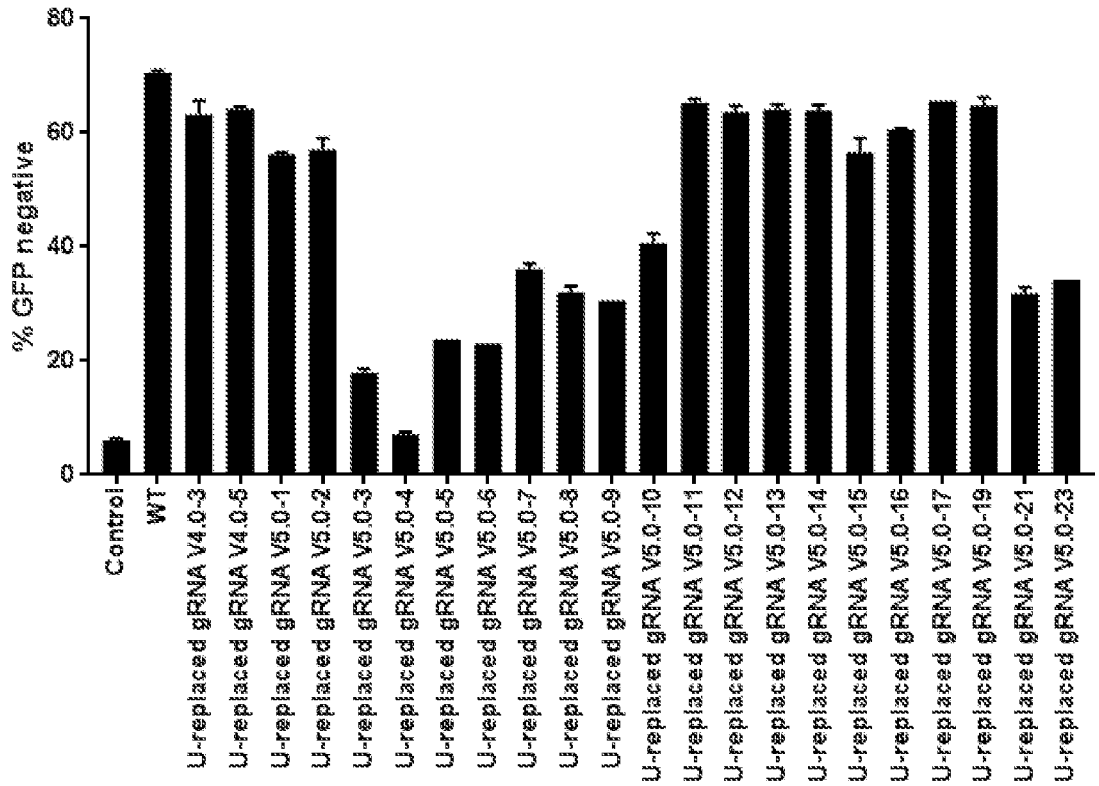
FIG. 6 is a bar graph depicting example results for gRNA sequences V5.0 (sequences shown in Table 6). gBLOCKs containing a U6 Pol III promoter driving the expression of U-replaced gRNAs were transfected into an LTR-GFP-Cas9 expressing cell line. The levels of GFP were measured 48-hrs later. A WT gRNA was included as a positive control. A gRNA not targeted to HIV was included as a negative control.

External uridines were replaced with combinations of the internal changes and developed tracrRNAs that had near-pan replacement of uridines (FIGS. 5A, 5B and 6). Overall, these data indicated that gRNAs with significant U-replacement functioned comparably to a wild-type sequence.

Figure 7:
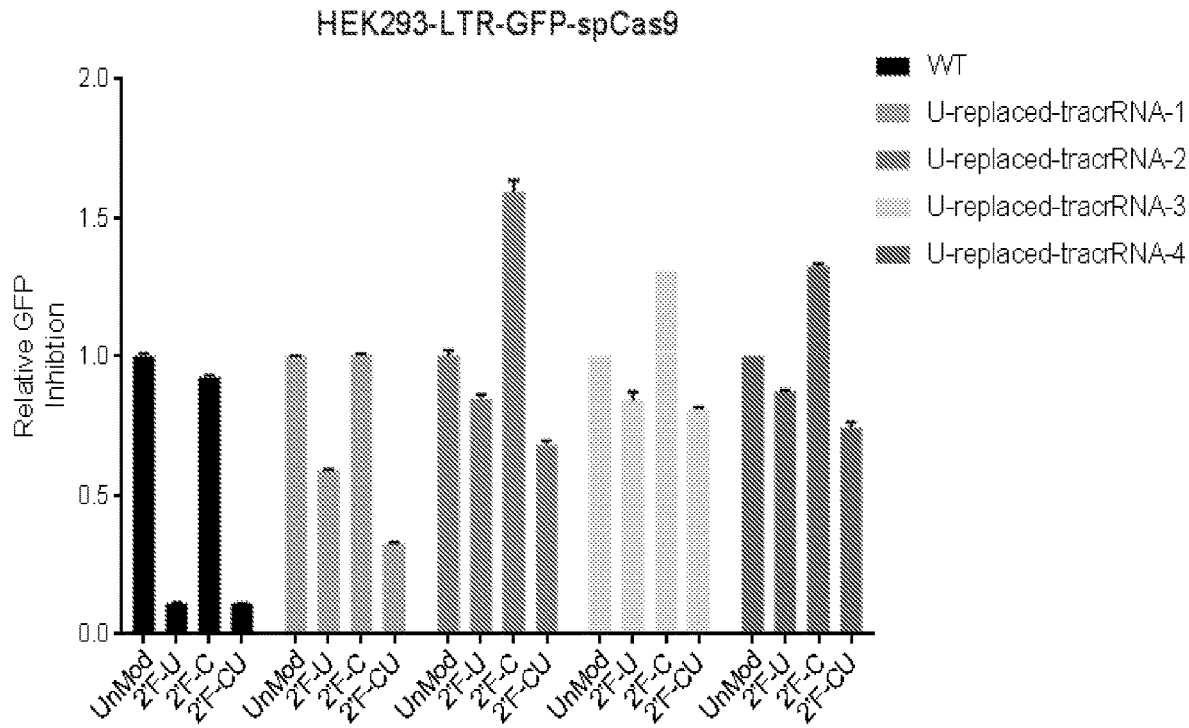
FIG. 7 is a bar graph depicting example results for 2'F-tolerant tracrRNA. U-replaced tracrRNAs improved activity when synthesized with 2'F-pyrimadines (U and C). In vitro transcribed U-replaced tracrRNAs were annealed with an anti-HIV crRNA and transfected in LTR-GFP-Cas9 cell line, and 48-hr post-transfection the levels of GFP were determined by FACS. The activity of the 2'F tracrRNAs were made relative to the unmodified control.
Figure 30:
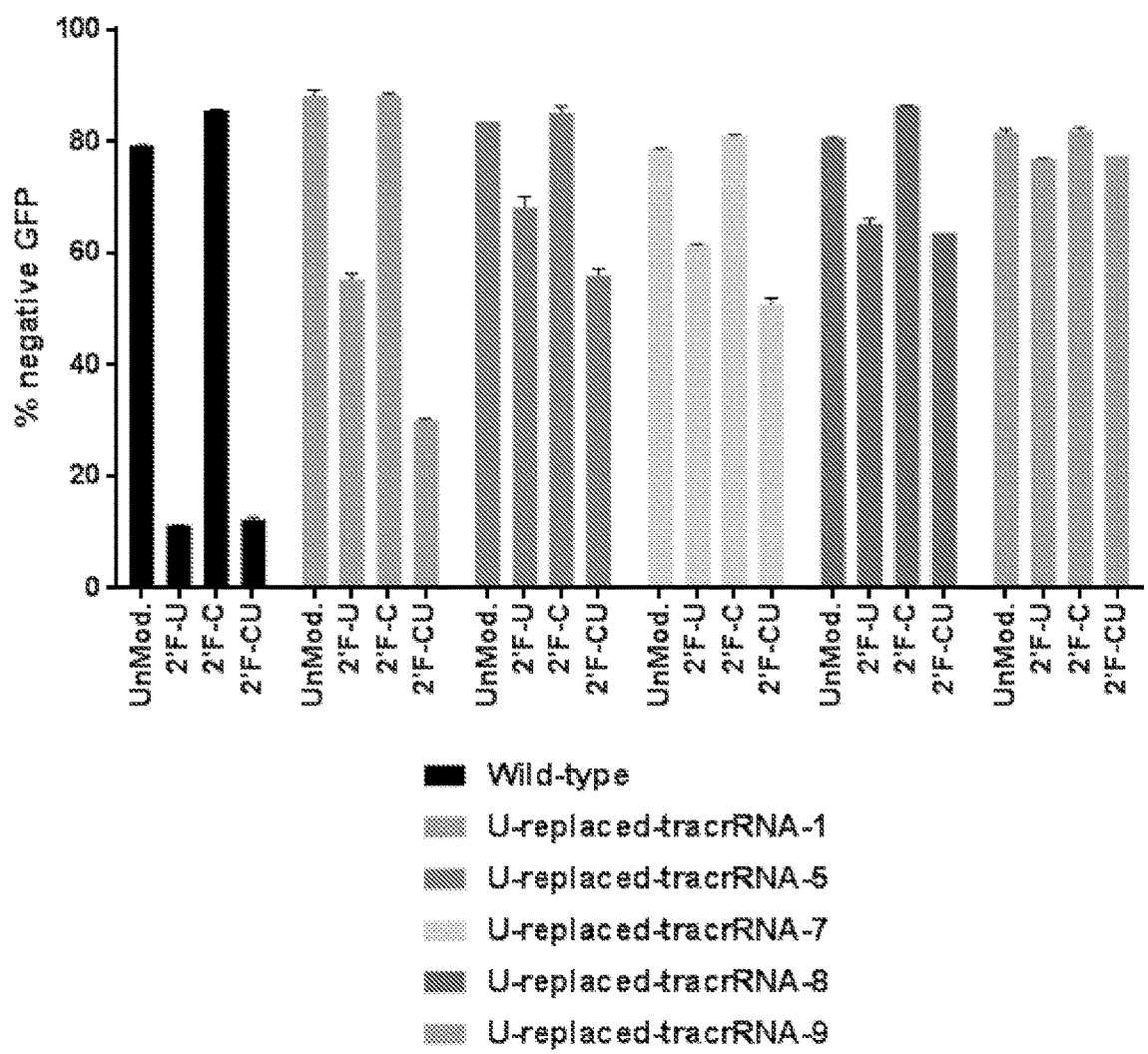
FIG. 30 is a bar graph illustrating that U-replaced tracrRNAs improve activity when synthesized with 2'F-pyrimidines (U and C). In vitro transcribed U-replaced tracrRNAs were annealed with an anti-HIV crRNA and transfected in LTR-GFP-spCas9, and 48-hr post-transfection the levels of GFP were determined by FACS. Errors bars were obtained by transfections performed in duplicate. The tracrRNAs identified in the legend from top to bottom correspond to the 4-bar groupings in the graph from left to right, respectively.
Figure 31A:
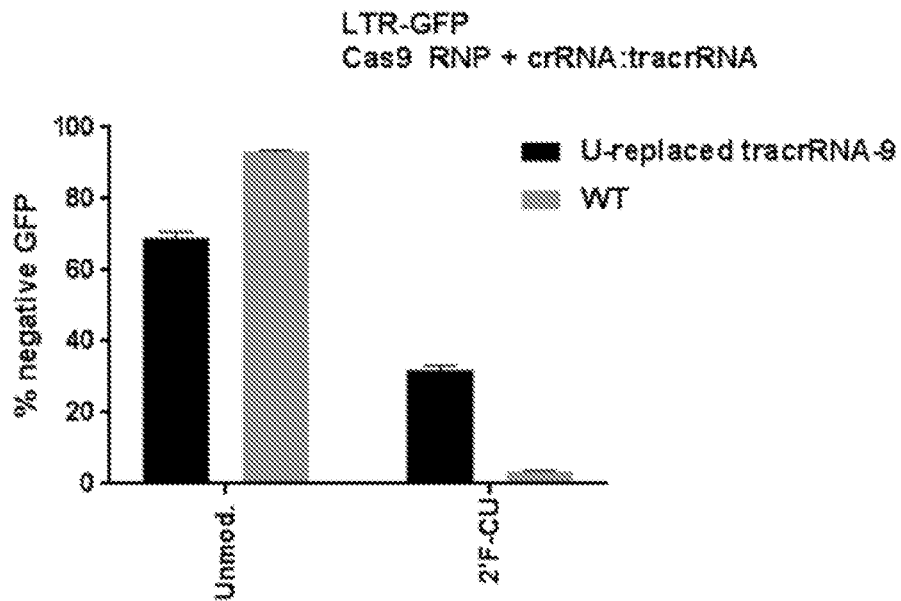
Figure 31B:
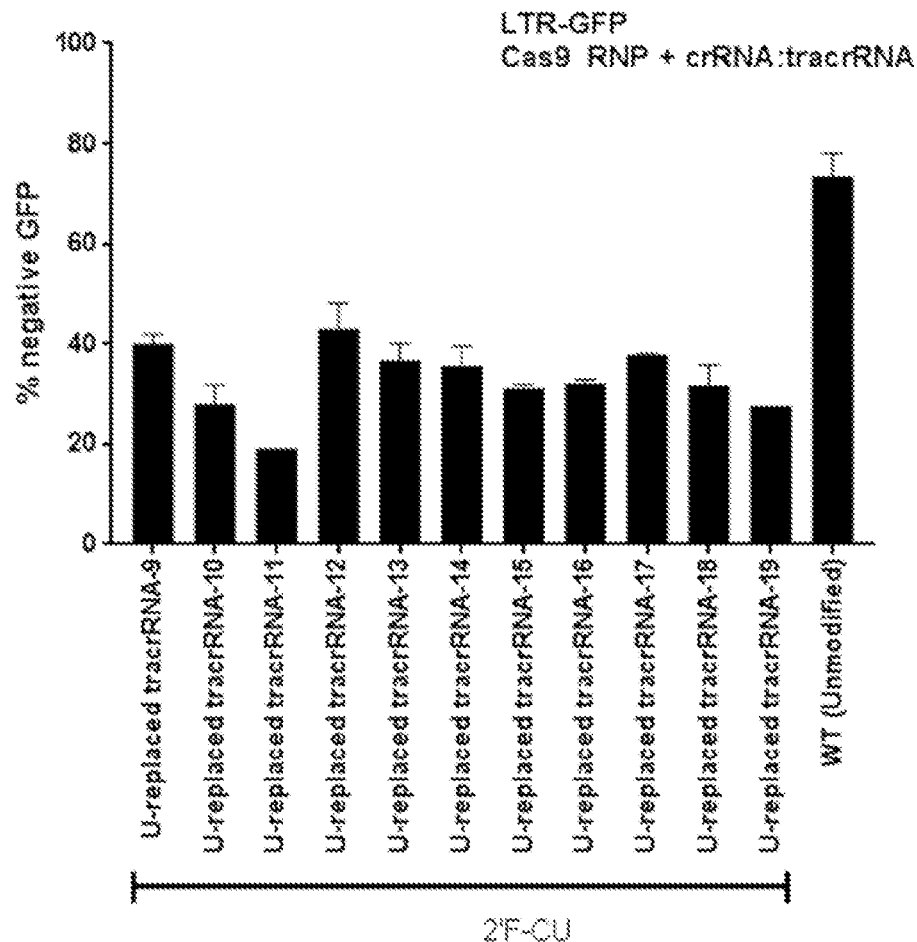

Several versions of U-replaced tracrRNAs were then selected to be synthesized with 2'F bases. These U-replaced tracrRNAs were able to function similar to an U-replaced unmodified tracrRNA (FIG. 7). It also appeared that the level of U-replacement within the tracrRNA corresponded with a gain of activity with 2'F bases. Importantly, there was a significant increase in activity compared to wild-type tracrRNA synthesized with 2'F-Us and CUs. Further modifications were made to tracrRNA with a new series of U-replaced tracrRNA, which resulted in knockdown activities comparable to a WT-tracrRNA when a 2'F-CU modified U-replaced tracrRNA was transfected into stable Cas9 expressing cell lines (FIG. 30). The U-replaced tracrRNA-9 showed the best overall activity in stable Cas9 expressing cell lines (FIG. 30, right-most group of bars). Next, it was determined how the U-replaced tracrRNA-9 would function when pre-loaded into a Cas9 RNP complex. The U-replaced tracrRNA-9 was electroporated into a LTR-GFP cell lines and showed a significant improvement in activity with 2'F-CU bases compared to a WT-tracrRNA (FIG. 31A). However, the activity of U-replaced tracrRNA with 2'F-CU or unmodified was lower than WT-tracrRNA without modifications. A series of sequence changes were made to determine if the activity of U-replaced tracrRNA-9 could be improved. This series of U-replaced tracrRNAs (10-19) were synthesized with 2'F-CUs and compared to a WT-tracrRNA without modification, and the levels of activity were not improved over the U-replaced tracrRNA-9 activity (FIG. 31B).

Figure 8A:
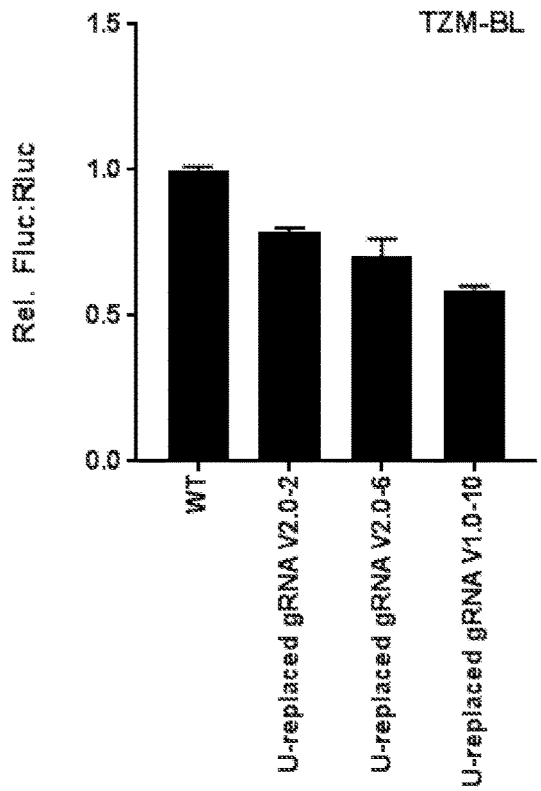
FIGS. 8A-8B are bar graphs depicting that enhanced tracrRNA U-replaced gRNAs may improve CRISPR-Cas activity.
Figure 8B:
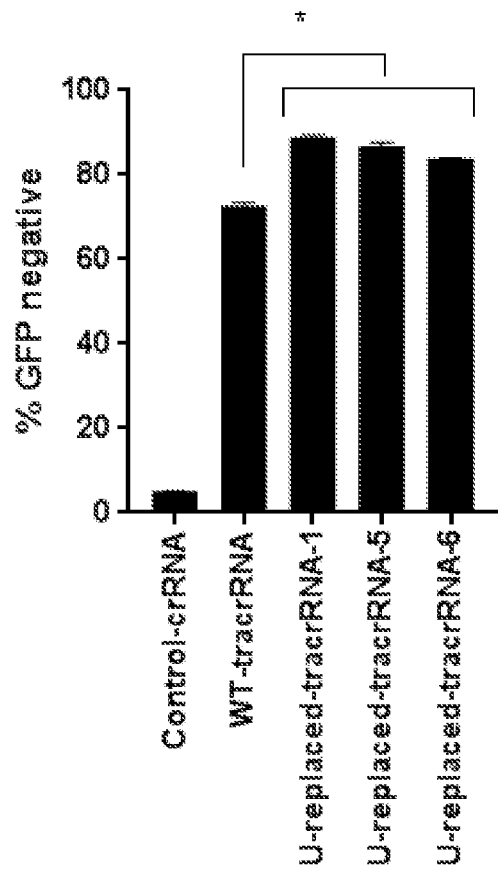
Figure 9A:
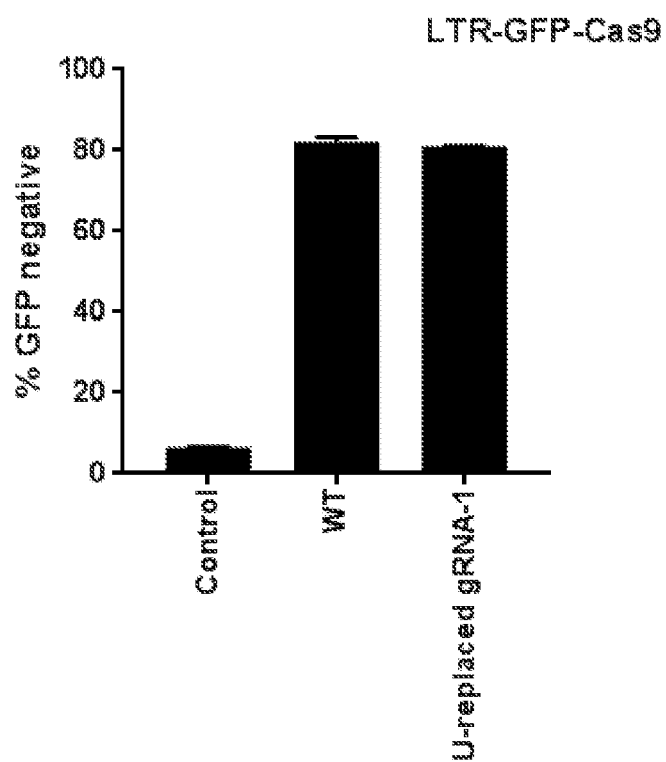
FIGS. 9A-9E are bar graphs depicting that U-depleted tracrRNAs maintained activity compared to a wild-type in vivo (LTR-GFP-Cas9 expressing system). gBLOCKs containing a U6 Pol III promoter driving the expression of gRNA or U-depleted gRNAs were transfected into an LTR-GFP-Cas9 expression cell line. The levels of GFP were measured 48-hrs later.
Figure 9B:
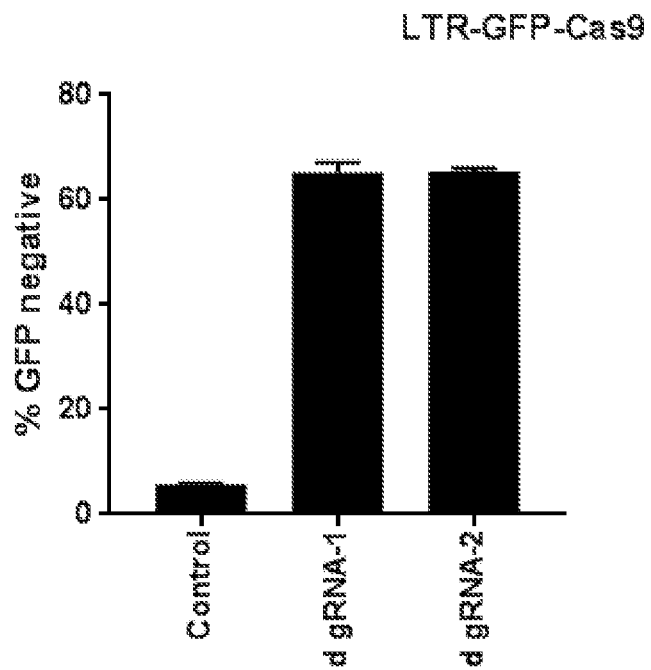
Figure 9C:
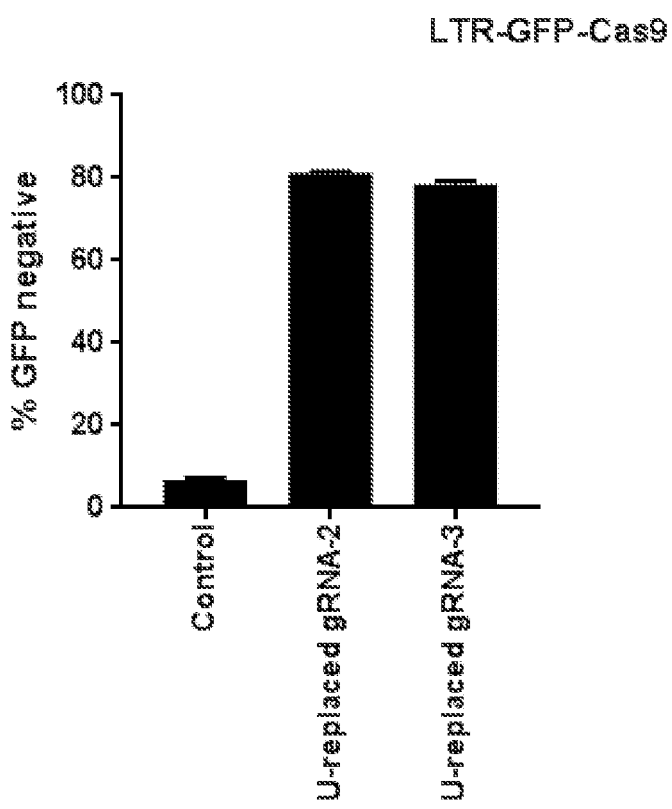
Figure 9D:
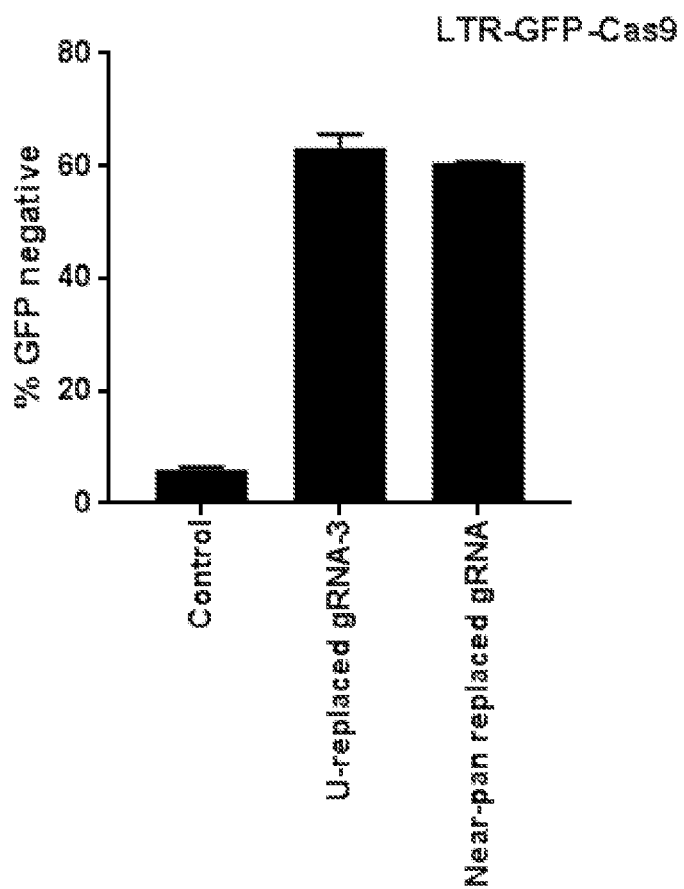
Figure 9E:
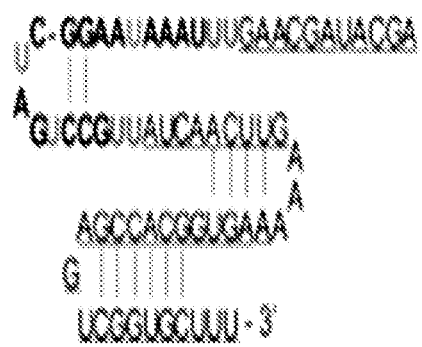
Figure 10A:
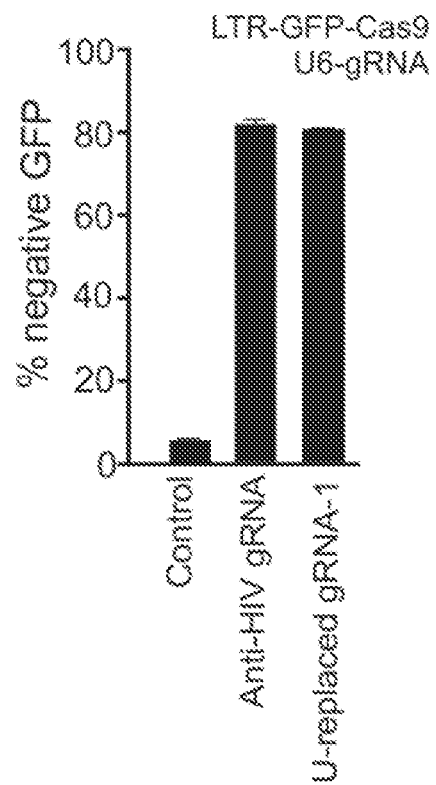
FIGS. 10A-10C provide bar graphs depicting that U-depleted tracrRNAs lacked function when 2'F modifications were incorporated in vivo (LTR-GFP-Cas9 cells), and an example schematic U-depleted tracrRNA.
Figure 10B:
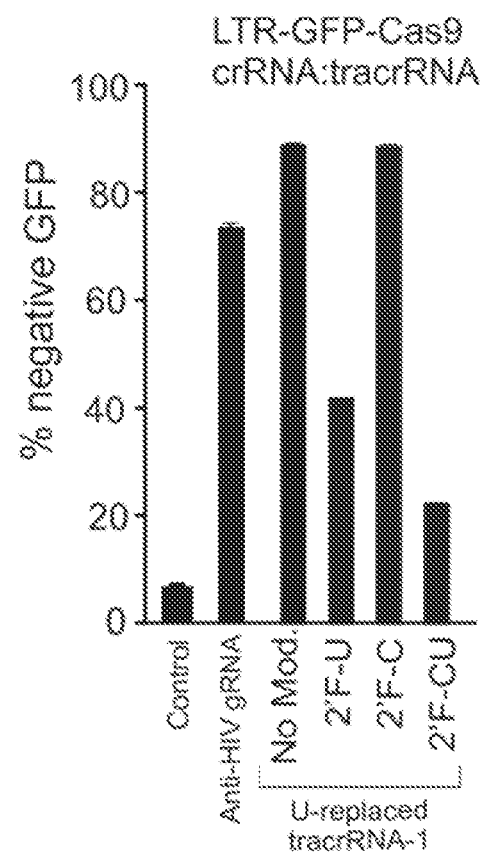
Figure 10C:
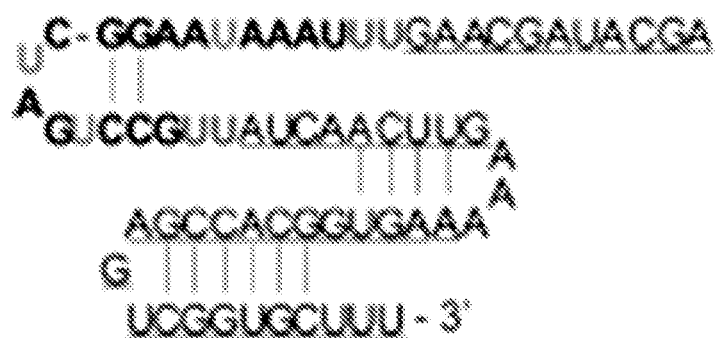
Figure 13A:
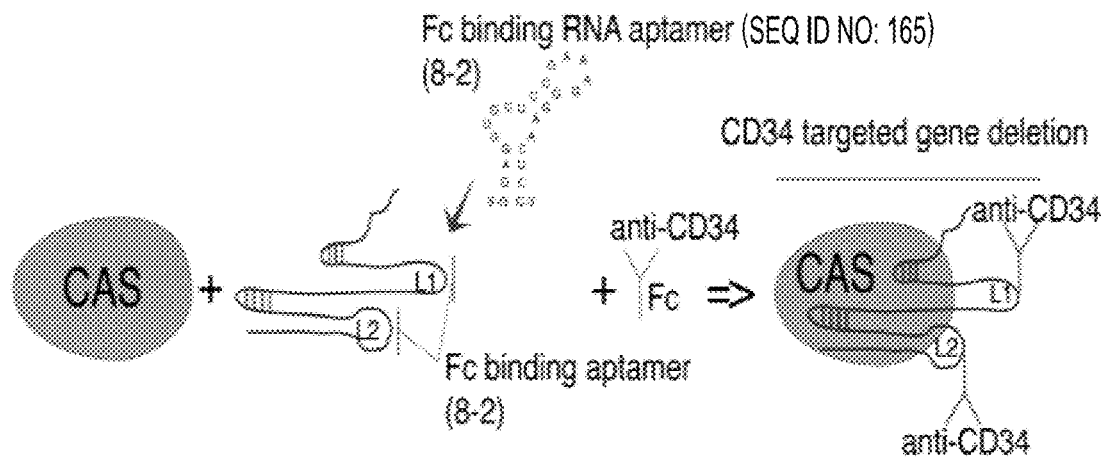
FIGS. 13A-13F show some non-limiting examples of cell specific targeting modes of a CRISPR-associated system of the disclosure. In these schematic illustrations, the CRISPR guide RNA sequence having aptamers on either loop 1 (L1) or loop 2 (L2) are presented. (13A) The 8-2 Aptamer is an RNA aptamer that can bind to the Fc of humanized antibodies. A schematic is shown for how this aptamer can engage the Fc of any humanized antibody and direct the CRISPR complex, which has a gRNA and Cas protein, to cells bearing receptors targeted by the antibody loaded onto the complex. (13B) A schematic is shown whereby the gRNA containing the 8-2 aptamer can direct the dCas-APOBEC3a complex to induce cytosine to thymine (C->T) mutations in the genome. (13C-13D) A schematic is shown for how other receptor targeted aptamers, e.g. CD34, can be embedded into the gRNA and (13C) guide cutting of target loci or (13D)C->T mutations at targeted loci. (13E-13F) A schematic is shown depicting the embedding of a DNA binding aptamer. In embodiments, an RNA aptamer is developed to a particular piece of donor DNA, and the targeted complex loop 1 is used to direct the complex in an aptamer or aptamer-Fc (8-2) antibody dependent manner while loop 2 can provide the donor DNA for targeted repair of a mutation.
Figure 13B:
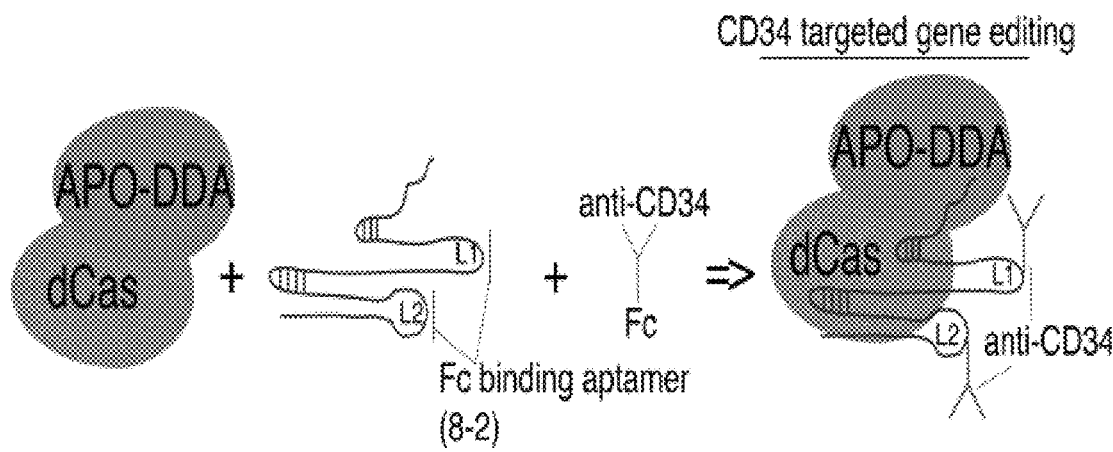
Figure 13C:
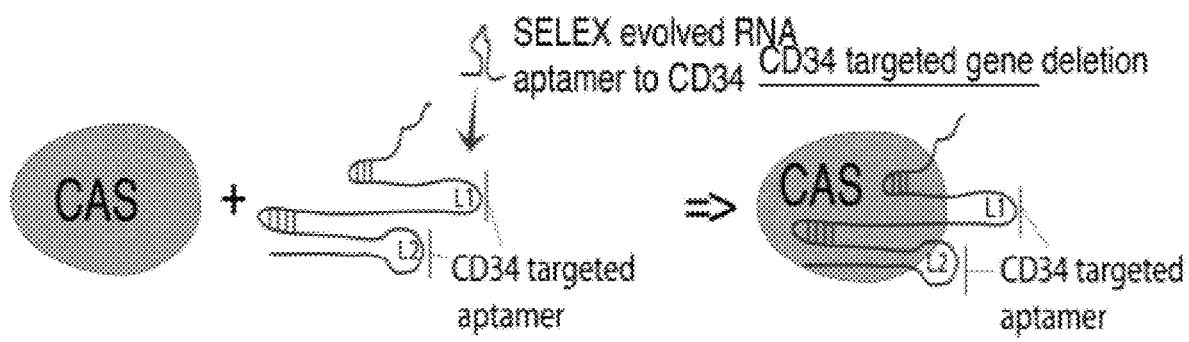
Figure 13D:
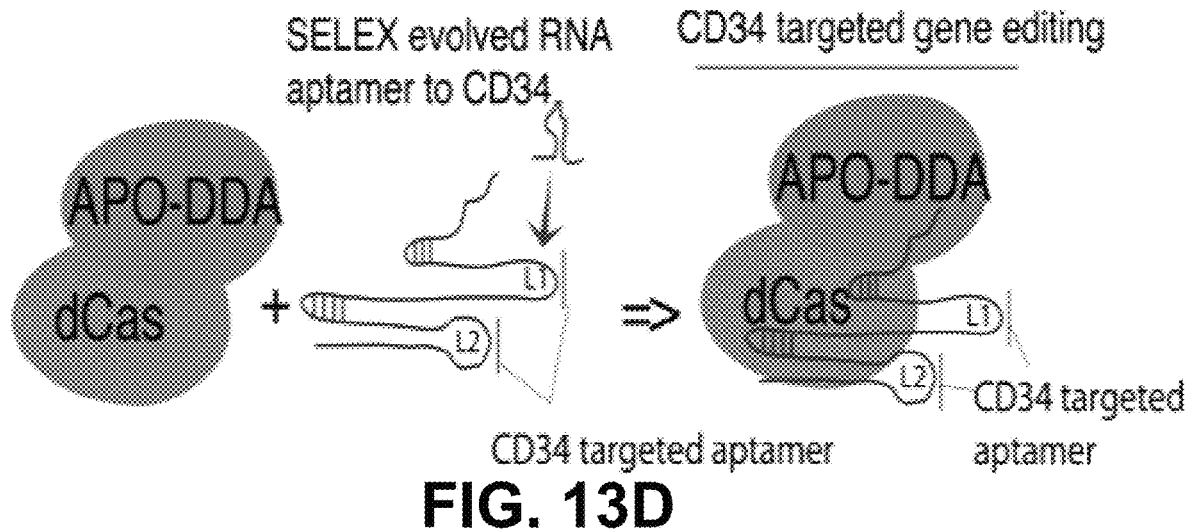
Figure 13E:
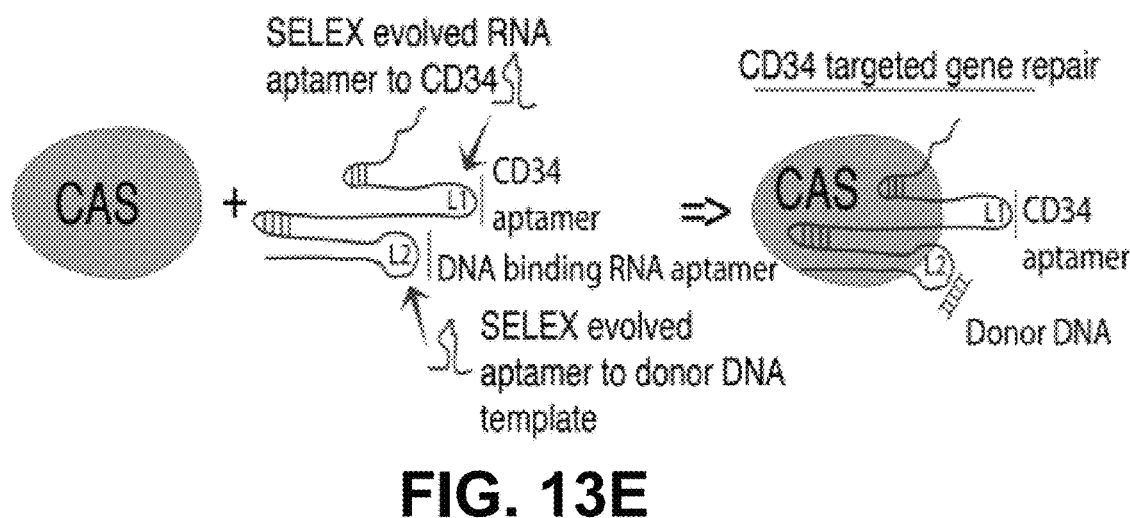
Figure 13F:
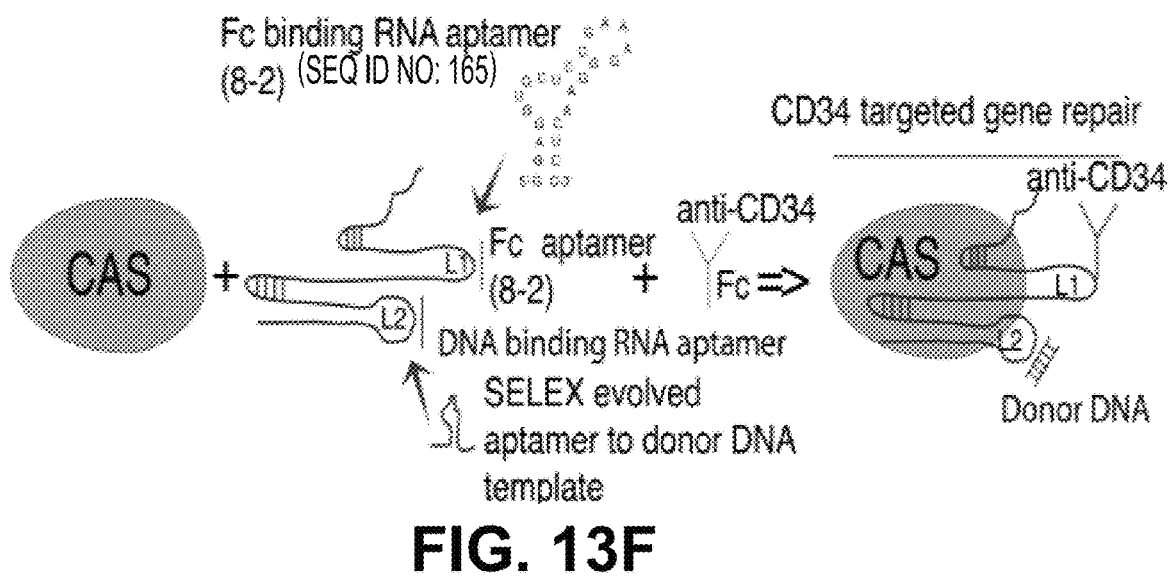
Figure 14:
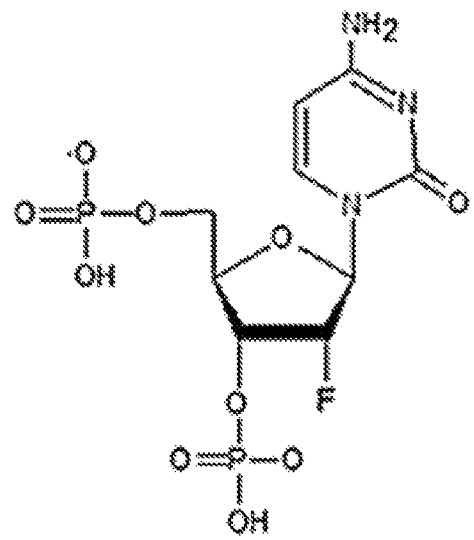
FIG. 14 shows the chemical structure of 2'-Fluoro-deoxycytosine-(2'-F-C).
Figure 15:
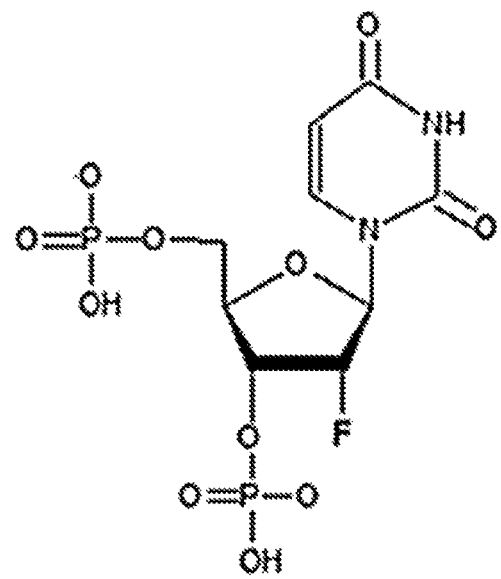
FIG. 15 shows the chemical structure of 2'-Fluoro-deoxyuridine-(2'-F-U).
Figure 16:
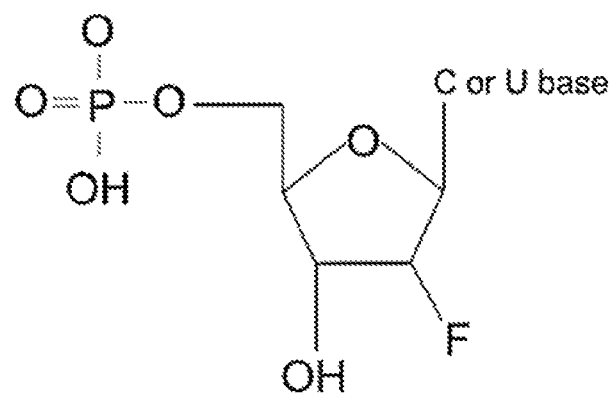
FIG. 16 shows the chemical structure of 2'F-Base.
Figure 32:
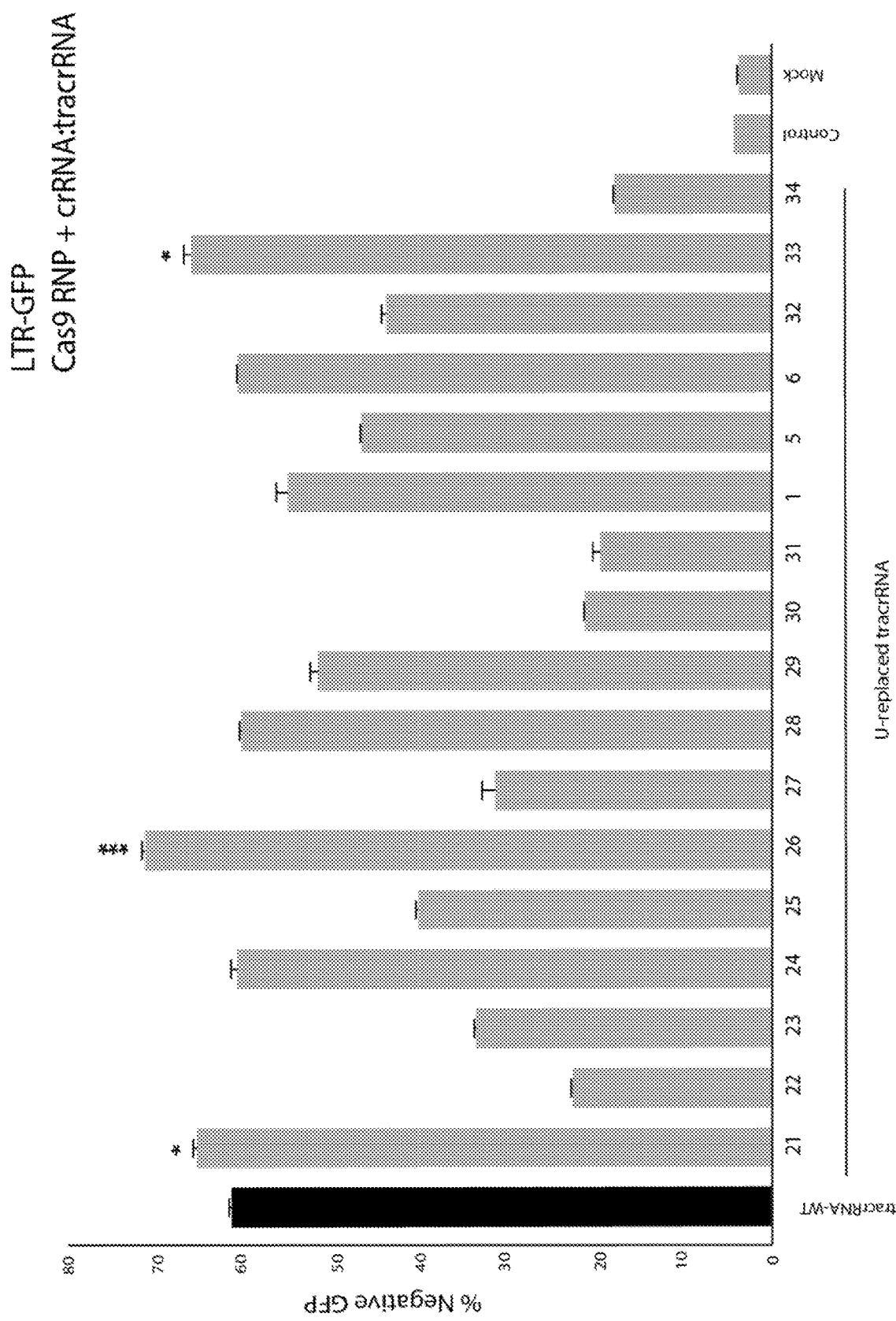
Figure 33A:
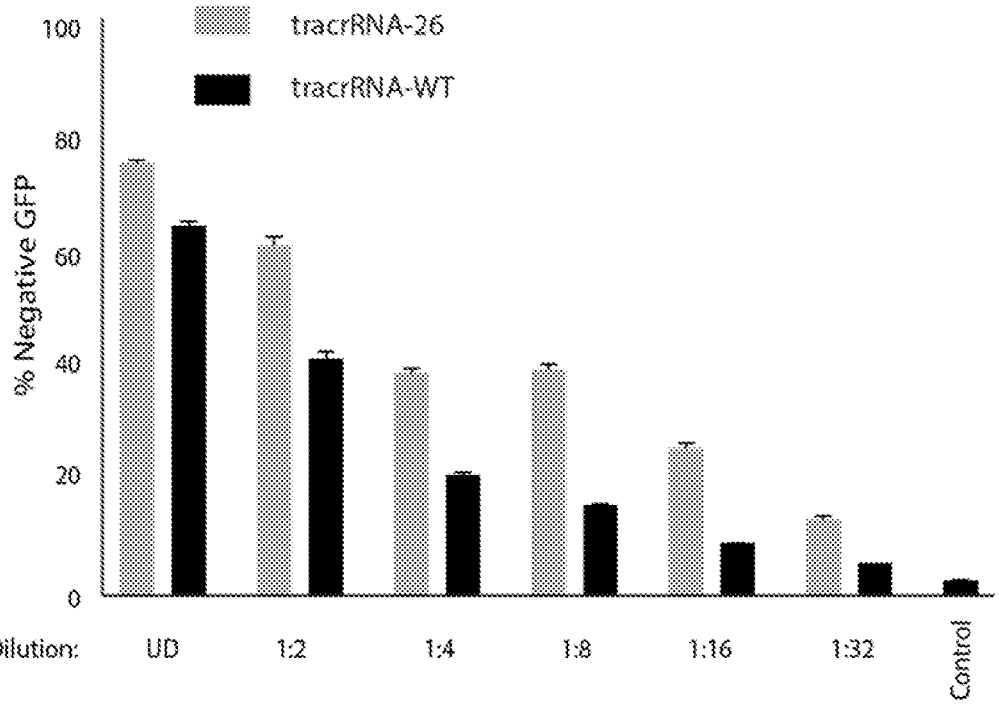
FIG. 33A) TracrRNAs were in vitro transcribed with unmodified or 2'F-CU bases. The tracrRNAs were annealed to a crRNA that targets the TAR element of HIV (TAR6) and incubated with a Cas9 RNP before electroporation into a LTR-GFP cell line. At 48-hr post-transfection the levels of GFP were determined by FACS. Errors bars were obtained by transfections performed in duplicate.
Figure 33B:
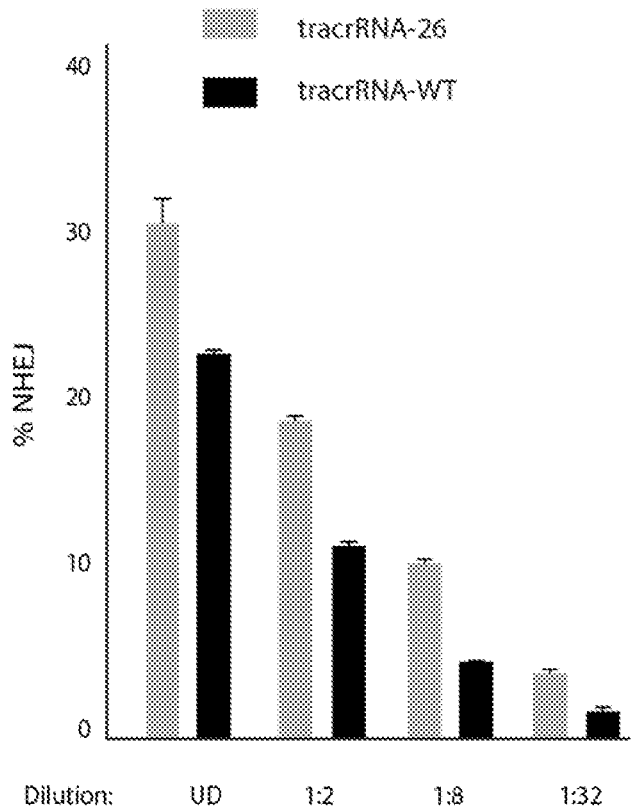
Figure 38:
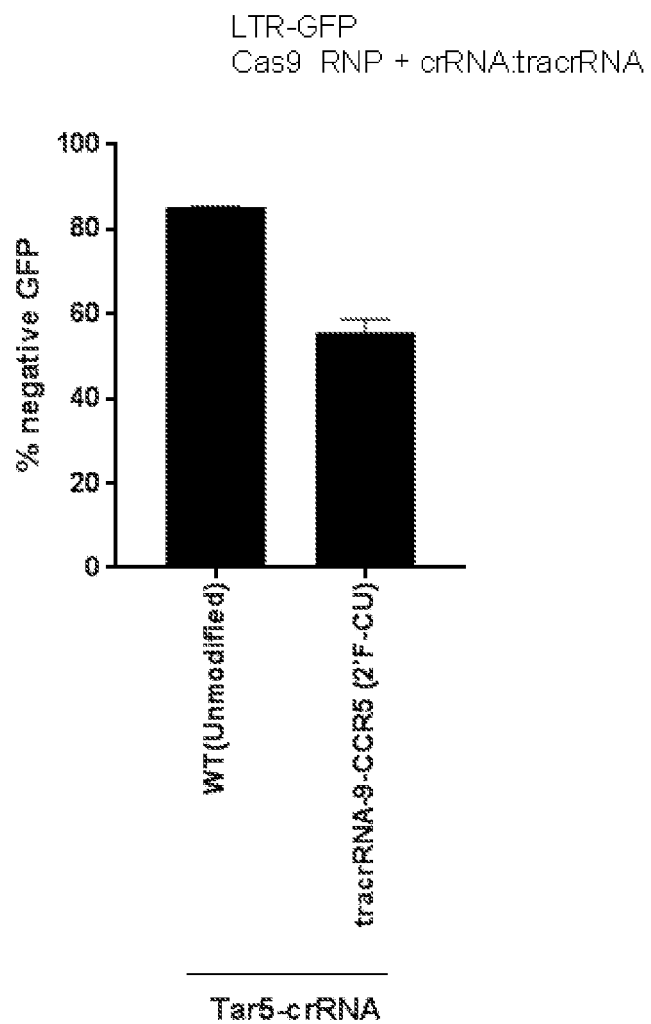
FIG. 38 is a bar graph illustrating that U-replaced tracrRNAs with a CCR5 atpamer in the stem-loop, synthesized with 2'F-pyrimidine are functional with a Cas9 RNP. A U-replaced tracrRNA with a CCR5 aptamer (tracrRNA-9-CCR5) was in vitro transcribed with 2'F-CU bases. The tracrRNAs were annealed to a crRNA that targets the TAR element of HIV (TARS) and incubated with a Cas9 RNP before electroporation into a LTR-GFP cell line. At 48-hr post-transfection the levels of GFP were determined by FACS. Errors bars were obtained by transfections performed in duplicate.

In a further experiment, the tracrRNA-9 was designed with an aptamer embedded into the stem-loop, which targets the surface receptor CCR5 (tracrRNA-9-CCR5, Table 8). The tracrRNA-9-CCR5 was synthesized with 2'F-CU and transfected as an Cas9 RNP into the LTR-HEK cell line, and showed–55% knockdown of the reporter (FIG. 38), but was lower than a WT-tracrRNA without modifications (~85%). Overall, these data demonstrate that a U-replaced tracrRNA with a CCR5 aptamer and modified bases is functional with a Cas9 RNP Example 3: Improved Functionality of U-Replaced tracrRNAs In the initial screens, it was observed that several Pol III expressed U-replaced gRNAs had a 20%-40% increase in knockdown of a HIV reporter activity when transfected with a vector expressing spCas9 (FIG. 8A). To further validate that sequences did improve CRISPR/Cas9 activity, U-replaced tracrRNAs were synthesized and annealed with an anti-HIV crRNA. When the crRNA:tracrRNA was transfected into a HIV reporter cell line stably expressing spCas9, there was a 10%-16% increase in knockdown of HIV reporter activity with U-replaced tracrRNAs compared to a wild-type tracrRNA (FIG. 8B). These data demonstrated that U-replaced tracrRNAs improved CRISPR/Cas activity. To determine if these U-replacements in the tracrRNA could improve activity of a Cas9 loaded into an RNP, a panel of tracrRNAs were generated with U-replaced sequences and annealed with a crRNA targeting the TAR element of HIV. These gRNAs were preloaded into a Cas9 RNP complex, and transfected into a LTR-GFP reporter cell line, and three of the U-replaced tracrRNAs showed a higher percentage of GFP knockdown than the WT-tracrRNA (FIG. 32). The U-replaced tracrRNA-26 had the most pronounced increase in activity. The Cas9 RNP with tracrRNA-26 was serially diluted and consistently showed higher levels of GFP knockdown (FIG. 33A). To assess whether the U-replaced tracrRNA-26 improved indel formation, the target sites within the LTR were assessed by drop-off assay, which measures indel formation using droplet-digital PCR (ddPCR) through the loss of probe binding to the edited target site (Findlay et al., 2016). The results from the drop-off assay matched the knockdown data, as the tracrRNA-26 demonstrated higher levels of indel formation compared to WT-tracrRNA (FIG. 33B).

Figure 34A:
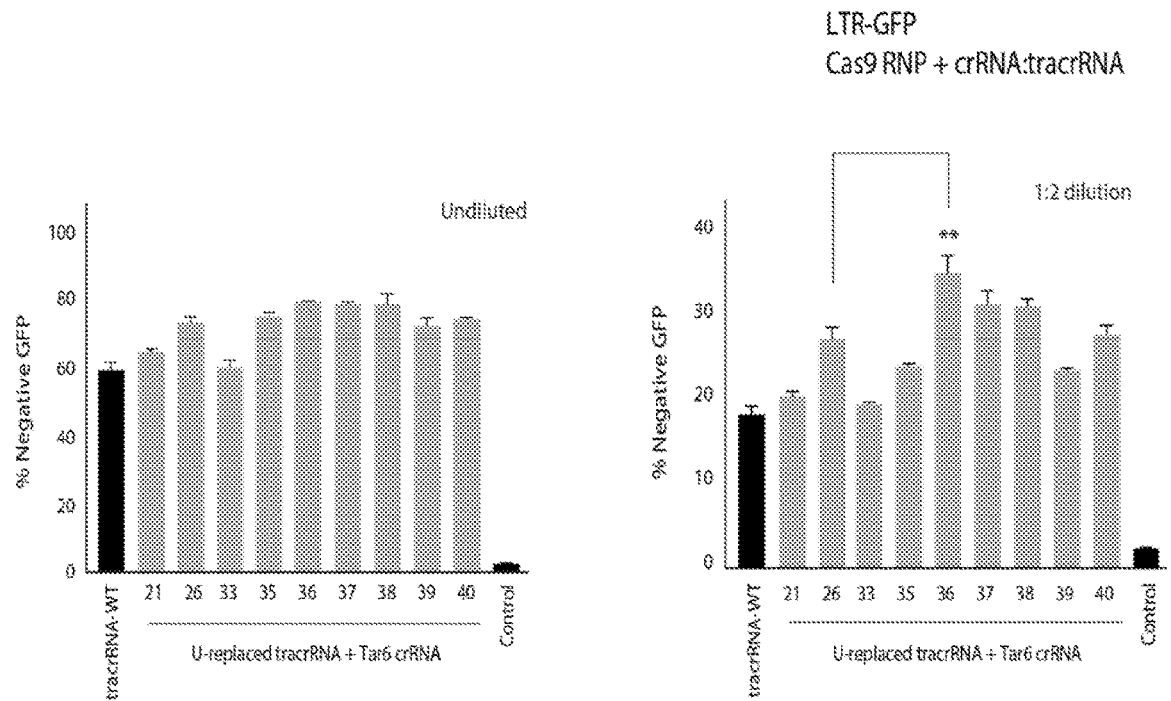
FIGS. 34A-34C are bar graphs illustrating results of a secondary screen for U-replacements that improve CRISPR/Cas9 activity. The results show that additional U-replacements within the tracrRNA may further improve the activity with Cas9 RNPs.
Figure 34B:
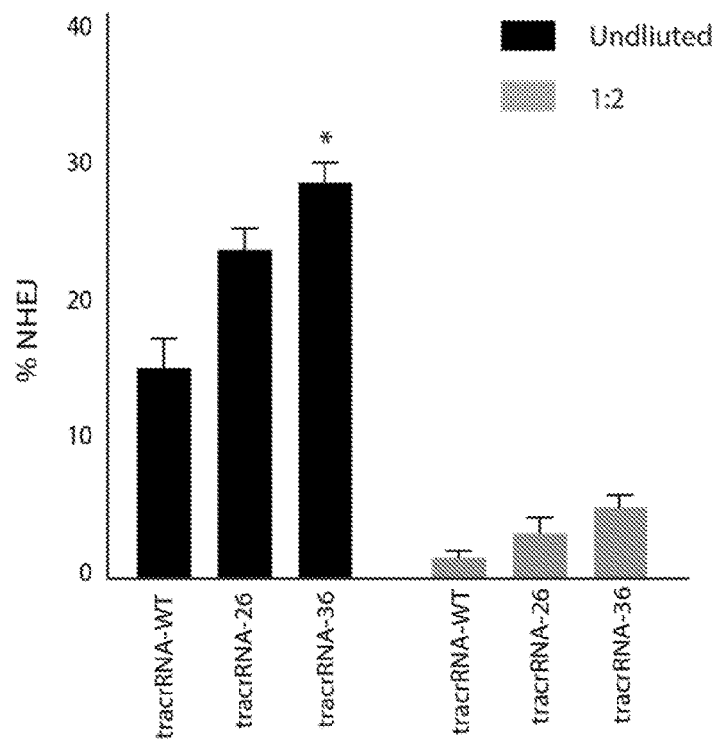
Figure 34C:
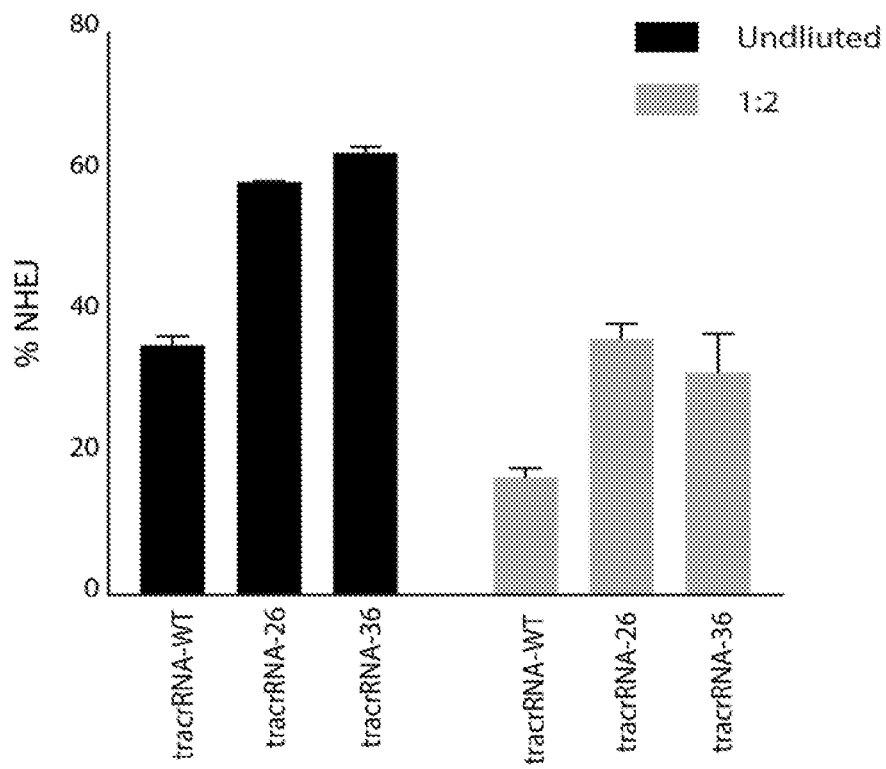
Figure 35A:
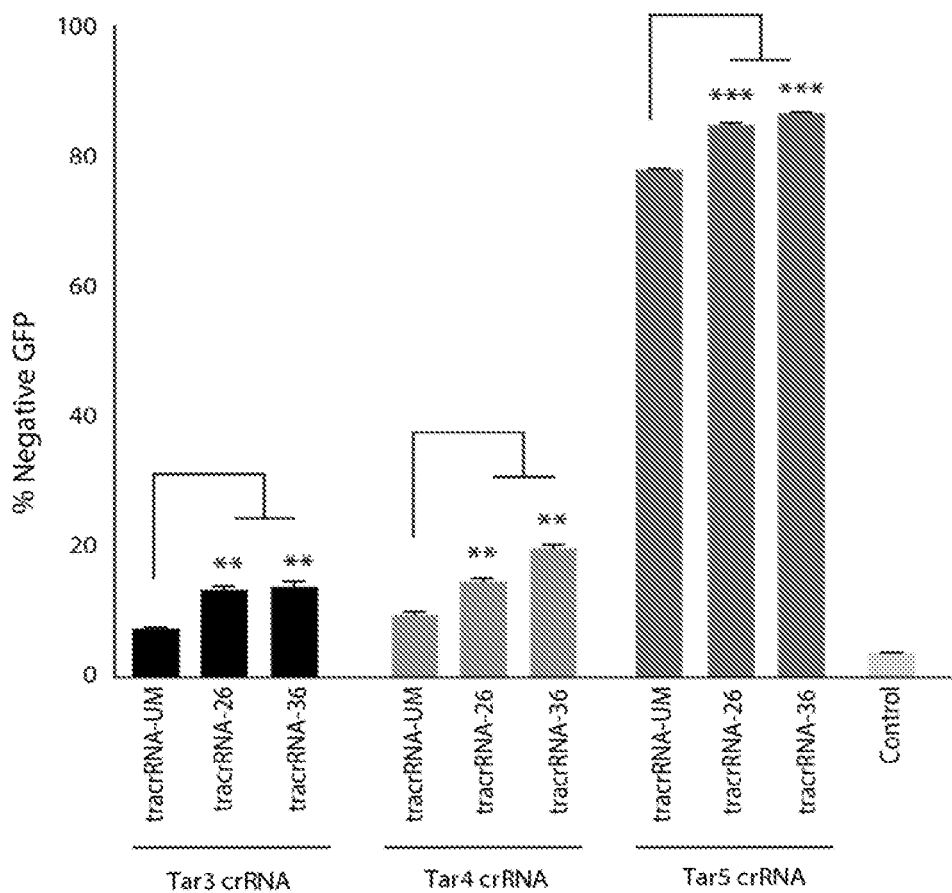
FIGS. 35A-35B are bar graphs illustrating that U-replaced tracrRNAs improve the activity with Cas9 RNP with other crRNAs targeted to the LTR of HIV.
Figure 35B:
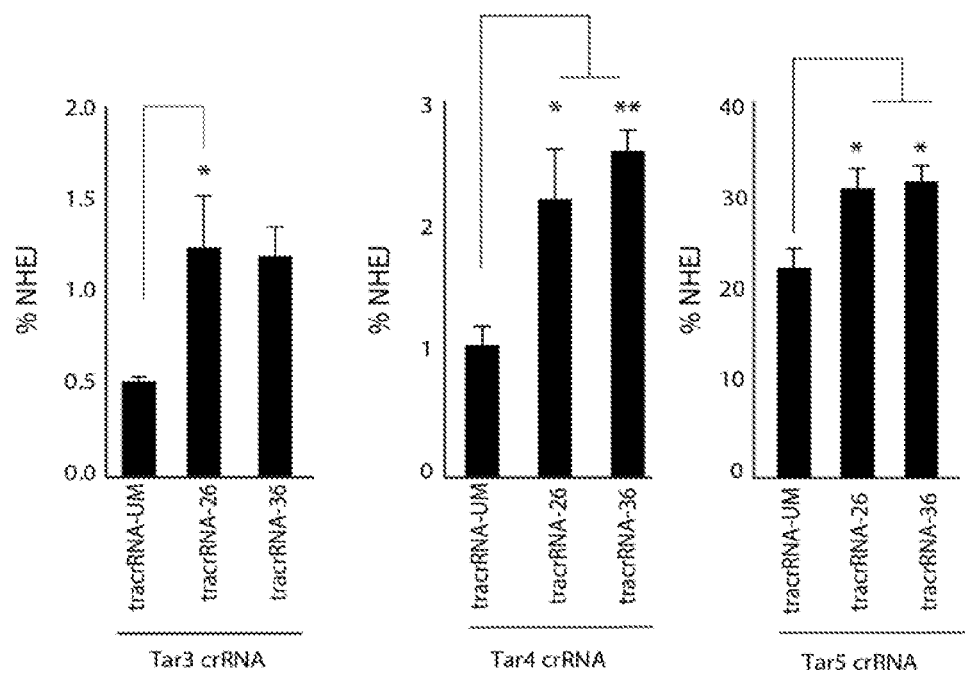

To determine if the activity levels of Cas9 RNP could be improved further through additional tracrRNA sequence changes, the tracrRNA-26 modification was combined with other sequence changes and the new U-modified tracrRNAs were transfected into LTR-GFP cells either undiluted or at a 1:2 dilution. The levels of GFP were assessed 48 hrs post-transfection. In the undiluted transfection, there were several U-replaced tracrRNAs which had slightly, but not significant, improvement of activity over the tracrRNA-26, but at 1:2 dilution tracrRNA-36 had a statistically significant increase in GFP knockdown (FIG. 34A). The analysis of indels by drop-off assay demonstrated that indels were slightly higher with tracrRNA-36 compared to tracrRNA-26 (FIG. 34B). To ensure the effects where not dependent on lipofection-mediated delivery of RNPs, Cas9 RNP gRNAs were electroporated into LTR-GFP cells, and the levels of indel formation were again higher with the U-replaced tracrRNAs than the WT-tracrRNA (FIG. 34C). To validate that this improvement in Cas9 RNP activity was not crRNA specific, three other crRNAs targeting the TAR loop (TAR3, 4 and 5) were annealed with a WT-tracrRNA, tracrRNA-26 or tracrRNA-36, and Cas9 RNPs were transfected into the LTR-GFP cells (Table 11). The levels of GFP knockdown (FIG. 35A) and indels (FIG. 35B) were increased for all three crRNAs with U-replaced tracrRNAs.

Figure 36A:
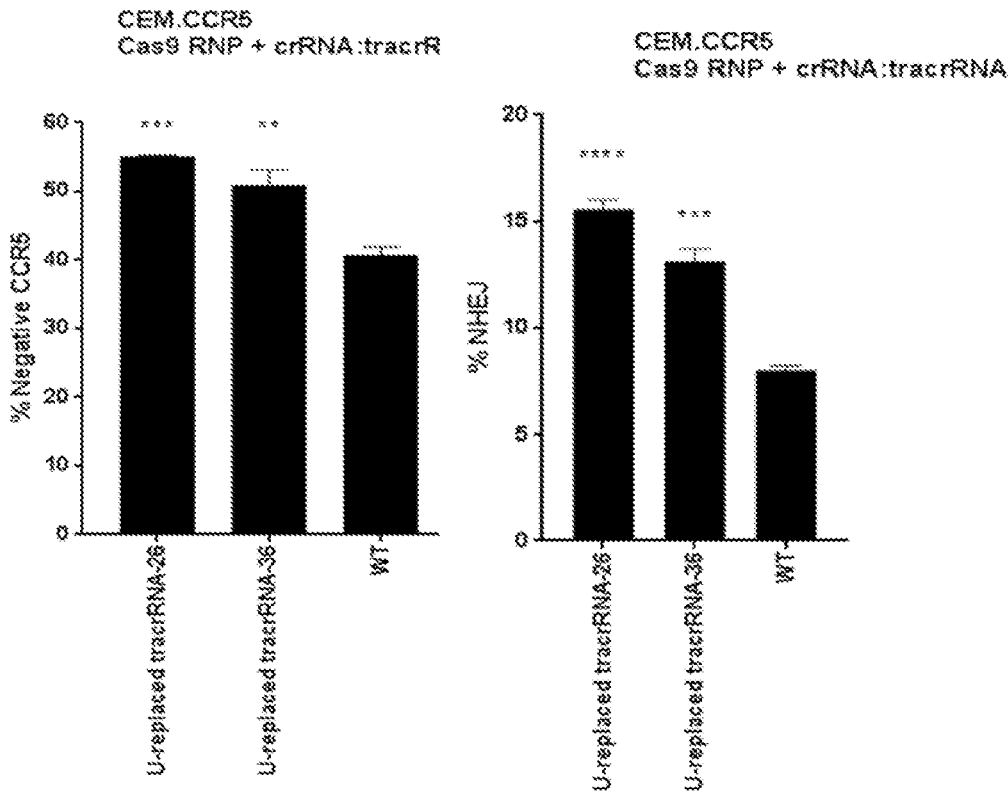
FIGS. 36A-36B are bar graphs illustrating that U-replaced tracrRNAs improve activity with Cas9 RNP targeted to CCR5.
Figure 36B:
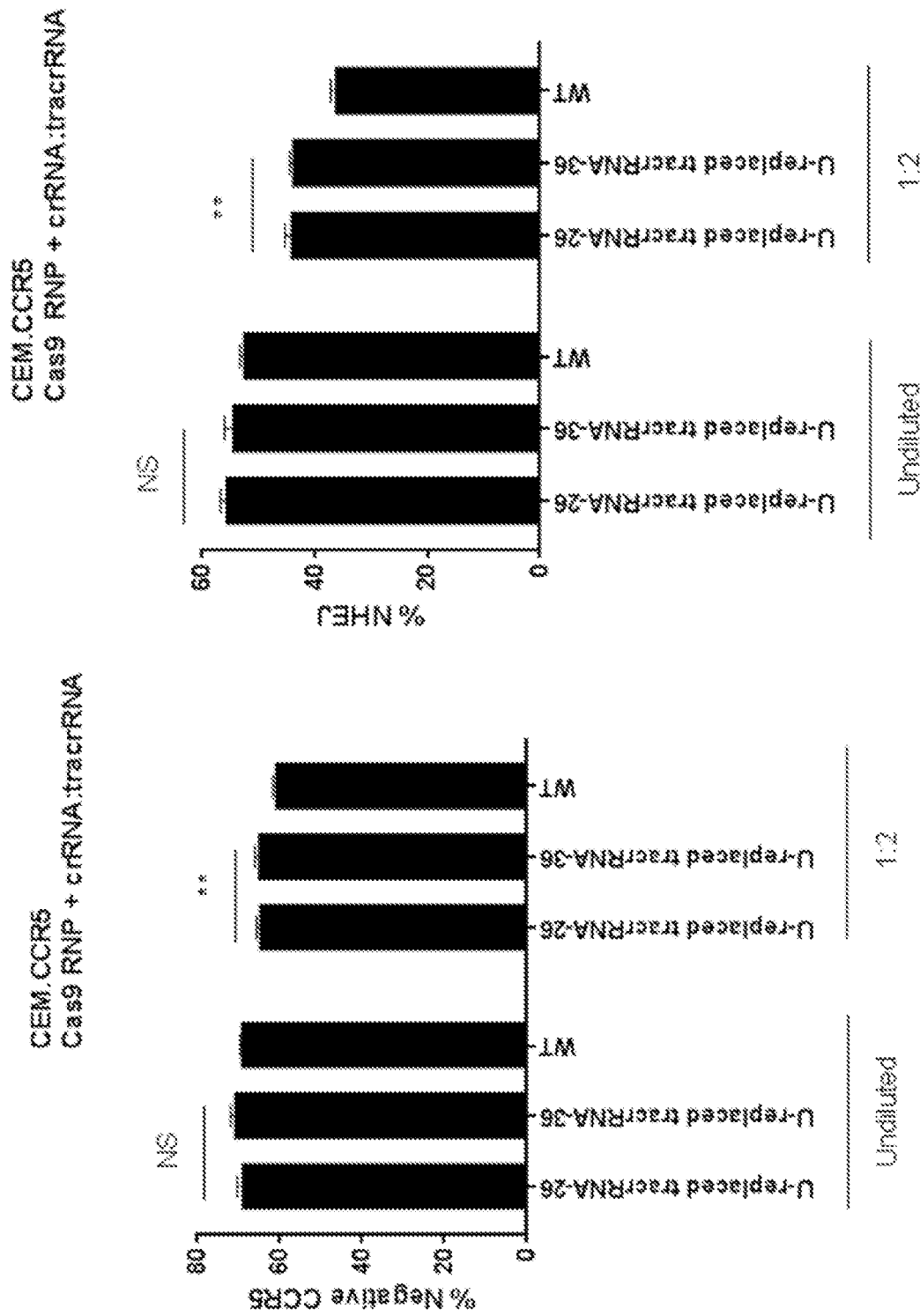
Figure 37A:
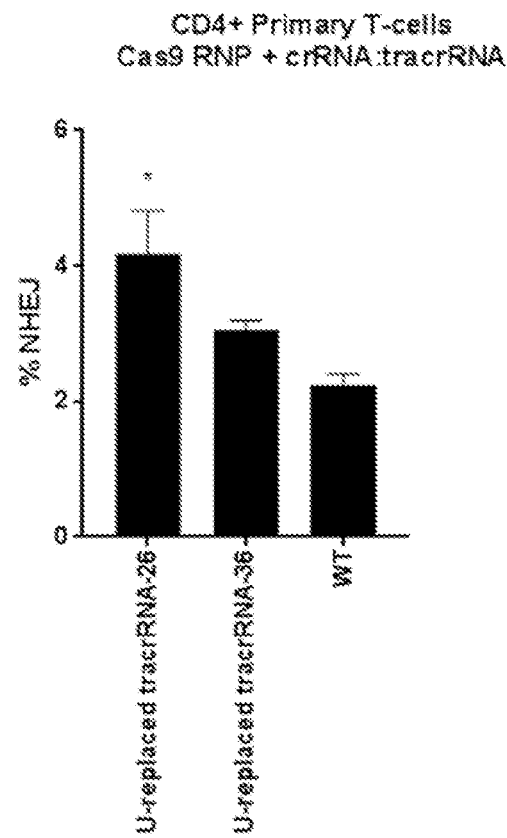
FIGS. 37A-37B are bar graphs illustrating that U-replaced tracrRNAs improve Cas9 RNP induced indels in primary CD4+ T-cells.
Figure 37B:
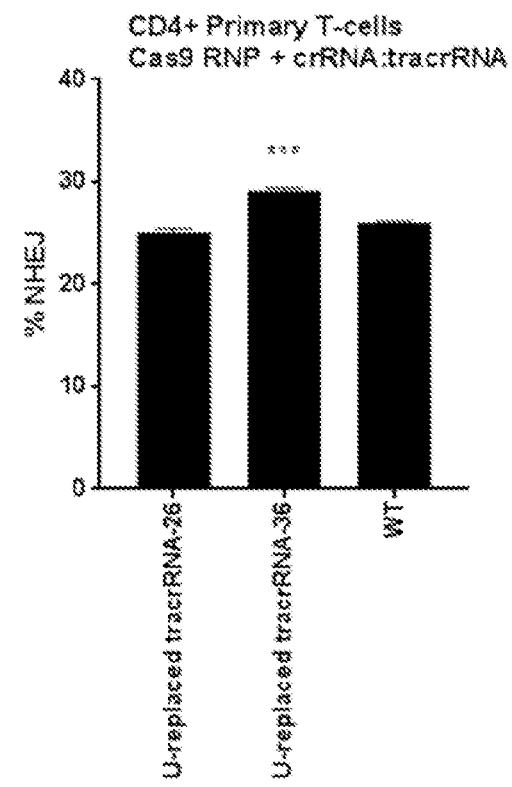

To verify that the effects were not cell line or target specific, the U-replaced tracrRNAs were annealed with two crRNAs (CCR5-1 and 2, Table 11) targeted to CCR5 and electroporated into a CEM.CCR5 cell line, and similarly resulted in improved CCR5 surface receptor knockdown as well as indel formation (FIGS. 36A-B). Lastly, to determine if the improved activity would translate into the modification of primary tissues, CD4+ T-cells were purified and electroperated with Cas9 RNP containing U-replaced tracrRNAs with the CCR5-1 and 2 crRNAs, and improved indel formation was observed with U-replaced tracrRNAs compared to a WT-tracrRNA (FIGS. 37A-B).

TABLE 11

Target sequences of sgRNAs and crRNAs

| crRNA | sequence (5'-3') |
|-------|------------------|
| Tar3  | GGUUAGACCAGAUCUGAGCC (SEQ ID NO: 233) |
| Tar4  | GGGAGCUCUCUGGCUAACU (SEQ ID NO: 234) |
| Tar5  | GUAACCAGAGAGACCCAGUAC (SEQ ID NO: 235) |
| Tar6  | AGAGCTCCCAGGCTCAGATC (SEQ ID NO: 236) |

TABLE 11-continued

Target sequences of sgRNAs and crRNAs

| crRNA | sequence (5'-3') |
|---|---|
| Tar7 | TAGTTAGCCAGAGAGCTCCC (SEQ ID NO: 237) |
| Tar8 | TTTATTGAGGCTTAAGCAGT (SEQ ID NO: 238) |
| Tar9 | ATCTGAGCCTGGGAGCTCTC (SEQ ID NO: 239) |
| Tar10 | GGGAGCTCTCTGGCTAACTA (SEQ ID NO: 240) |
| CCR5-1 crRNA-1 | ATAATTGCAGTAGCTCTAAC (SEQ ID NO: 241) |
| CCR5-2 crRNA-2 | TAGAGCTACTGCAATTATTC (SEQ ID NO: 242) |

Materials and Methods

Cell Culture

The TZM-b1 and HEK293-LTR-GFP (LTR-GFP) cells were maintained in Dulbecco's modified Eagles' medium (DMEM, ThermoScientific, MA, USA) and 10% fetal bovine serum. The HEK293-LTR-GFP-spCas9 cell line media was supplemented with 1.5 µg/ml puromycin. CEM.NKR CCR5+ cells (CEM.CCR5) were obtained from NIH AIDS Reagent Program, Division of AIDS, NIAID, NIH (Howell et al., 1985; Lyerly et al., 1987; Trkola et al., 1999) and maintained in RPMI+10% FBS. The cell lines were cultured at 37° C. with 5% $CO_2$. For the Primary CD4+ T-cells, leukapheresis products were obtained from a healthy donor under protocols approved by the City of Hope Institutional Review Board. CD4 T cells were isolated with CD4 negative selection StemCells EasySep Kit. PBMC were isolated by density gradient centrifugation over Histopaque (Sigma, MO, USA) and incubated with negative selection CD4 cocktail for 3 minutes at room temperature. Labeled cells were incubated with beads for 3 minutes at room temperature and placed on EasySep magnet for 3 minutes. CD4+ T cells were collected and activated using CD3/CD28 beads at a 1:3 ratio for 3 days prior to electroporation with Cas9 RNPs. The CD4+ T-cells were maintained in RPMI+ 10% FBS with IL-2.

Vectors

The gRNAs V1.0 harboring the U-replacements in the gRNAs were ordered as an Ultramers® (IDT, CA, USA) and amplified from a vector containing a U6 Pol-III expressed anti-HIV target sequence using HotstartTaq 2×Master Mix (NEB, MA, USA). The amplicons were cloned into a pTZ57R/T vector using the insTAclone PCR cloning kit (ThermoScientific, MA, USA) and the U-replaced clones were confirmed by sequencing.

Functional Screening of U-Replaced gRNAs

The pTZ-U6-gRNAs-V1.0 were transected with a vector expressing spCas9 (px458, addgene #48138) into TZM-b1 cells using Lipofeactiome® 3000 (Invitrogen, CA, USA). A vector expressing Tat-dsRED was included to activate the LTR, and a vector expressing Renilla luciferase as a background control (pRL-CMV; Promega, WI, USA). At 48 hrs post-transfection, a Dual-luciferase® reporter luciferase assay was performed and read on a Glomax luminometer (Promega, WI, USA).

The U-replaced gRNAs V2.0-6.0 where either purified PCR products amplified from a U6 Pol III expressed anti-HIV gRNA, or synthesized as gBlocks® (IDT, CA, USA). The PCR products or gBlocks® were diluted to 3 nM and 1.511.1 was reverse transfected into the HEK293-LTR-GFP-spCas9 cell using Lipofectamine® RNAiMAX (Invitrogen, CA, USA), and the levels of GFP were measured 48-hrs later by FACS analysis.

Activity of U-Replaced tracrRNAs

The template tracrRNAs expressed off a T7 promoter were ordered as PAGE purified oligomers (IDT, CA, USA, Table 8). The template was then used to transcribe the tracrRNA using the Durascribe® kit (Lucigen, WI, USA) according to manufacturer instructions. For tracrRNAs that lacked the 2'F-U or 2'F-C, an unmodified NTP was supplemented (NEB, MA, USA). The RNA was purified using the RNAZYMO Clean & Concentrator™ kit (ZYMO research, CA, USA) and Sodium Acetate-Ethanol precipitated as recommended by the Durascribe® protocol. The anti-HIV crRNAs were synthesized and purified by HPLC (IDT, CA, USA). The tracrRNA and crRNA were re-suspended in RNA storage buffer (Ambion, CA, USA) and diluted to 6 nM in duplex buffer (IDT, CA, USA). To determine the activity of the tracrRNAs in stable Cas9 expressing cells, the crRNAs and tracrRNAs were mixed in equal amounts to 3 nM and were then re-annealed by heating to 95° C. for 5 min and slow cooled to room temperature. Then 0.65 µL of 3 nM crRNA:tracrRNA was reverse transfected into the HEK293-LTR-GFP-spCas9 cell using Lipofectamine® RNAiMAX (Invitrogen, CA, USA), and the levels of GFP were measured 48-hrs later by FACS analysis.

To determine the activity of the tracrRNAs with RNPs, the Cas9 RNP complex was formed by mixing 0.5 µl of 3 µM Alt-R® S.p.Cas9 nuclease V3 (IDT, CA, USA) with 0.5 µl of 3 µM of gRNA or annealed crRNA:tracrRNA and made up to 55 ul in cytoplasmic-like buffer (120 mM KCl, 0.15 mM $CaCl_2$, 10 mM $KH_2PO_4$ (pH 7.6), 2 mM EGTA (pH 7.6), 5 mM $MgCl_2$,) with 100 ug/ml BSA (NEB, MA, UK) and incubated at room temperature for 15 min. Fifty-five microliters of OptiMEM with 1.5 µl RNAiMAX Reagent (Thermo Fisher Scientific, MA, USA) was added to the RNP mixture and incubated for 20 min at room temperature. A total of 50 ul was added to each well of a 48-well plate and then 200 ul of $6.4 \times 10^5$ cells/ml of LTR-GFP cells was added. For the electroporation of Cas9 RNPs, the gRNA and Cas9 were diluted to a 40 µM concentration and 0.3 µl of each was mixed with Buffer R (or Buffer T for Primary CD4+ T-cells) to a total volume of 7 ul. The reaction was incubated for 15 min at room temperature and then 5 ul was added to the cells ($1 \times 10^5$ of LTR-GFP and CEM.CCR5 cells or $3 \times 10^5$ of CD4+ T-cells per reaction). The reaction was electroporated using the 10 ul Neon® transfection system with the following settings for the LTR-GFP cells: 1700 V, 20 ms, 1 pulse, CEM.CCR5 cells: 1230 V, 40 ms, 1 pulse, and CD4+ T-cells: 1600 V, 10 ms, 3 pulse. The cells were added to 500 ul of pre-warmed media in a 48-well plate, and the LTR-GFP and CEM.CCR5/CD4+ T-cells were processed for further analysis at 48 hrs and 72 hrs post-transfection, respectively. The reaction mix was diluted in the Cytoplasmic-like buffer or Buffer R to make up the lower dilution reactions.

In order to identify the 2'F uridines involved in CRISPR/Cas9 activity, the tracrRNAs were synthesized with 2'F-Us at specific sites by the DNA/RNA Core at the City of Hope. The tracrRNAs were re-suspended, annealed and transfected as described above.

Quantification of indels: To determine the level of indel formation, DNA was extract from the cells using a QIAamp® DNA mini kit (Qiagen, Venlo, Netherlands) and a drop-off assay was performed as described elsewhere (Findlay et al., 2016). Briefly, 50 ng of total genomic DNA was mixed with ddPCR™ supermix for probes (No dUTP), and the target site was amplified with primers specific for the edited site with a FAM-conjugated target probe and HEX-conjugated reference probe (Table 12). Droplets were generated using the QX200™ AutoDG™ Droplet PCB. system. The droplets were sealed in a 96-well plate and the DNA was amplified with the following conditions: initial denaturation at 95° C. for 10 min, then 40 cycles with a 94° C. denaturation for 30 seconds, 55° C. annealing for 15 seconds and 72° C. extension for 1 min with a final incubation at 98° C. for 10 min. The droplets were analyzed on a QX200™ droplet reader using QuantaSoft™ software. The percentage of NIIEJ was determined as the number of [HEXpos-FAMneg/(HEXposFAMneg+HEXposFAMpos)]×100.

TABLE 12

Sequence of primers and probes used in the drop-off assay

| oligomer | Sequence (5'-3') | nt |
| --- | --- | --- |
| ddPCR TAR F | CGAGCCCTCAGATGCTCATA (SEQ ID NO: 243) | 21 |
| ddPCR TAR R | TTTGAGCACTCAAGGCAAGC (SEQ ID NO: 244) | 20 |
| TAR3/6 Target probe | FAM-TGGTTAGACCAGATCTGAGCCTGGGAGC-BHQ1 (SEQ ID NO: 245) | 28 |
| TAR3/5/6 Reference probe | HEX-AGGCTTAAGCAGTGGGTTCCCTAGTTAGC-BHQ1 (SEQ ID NO: 246) | 29 |
| TAR5 Target probe | FAM-TGCCTGTACTGGGTCTCTCTGGTTAGACC-BHQ1 (SEQ ID NO: 247) | 29 |
| TAR4 Target probe | FAM-TGGGTTCCCTAGTTAGCCAGAGA-BHQ1 (SEQ ID NO: 248) | 23 |
| TAR4 Reference probe | HEX-TTGCCTGTACTGGGTCTCTCTGGT-BHQ1 (SEQ ID NO: 249) | 24 |
| ddPCR CCR5 F | GGCTGTGAGGCTTATCTTCAC (SEQ ID NO: 250) | 21 |
| ddPCR CCR5 R | TCTGTCACCTGCATAGCTTG (SEQ ID NO: 251) | 21 |
| CCR5-1 Target probe | FAM-CAGTAGCTCTAACAGGTTGGACC-BHQ1 (SEQ ID NO: 252) | 20 |
| CCR5-2 Target probe | FAM-CTACTGCAATTATTCAGGCCAAAG-BHQ1 (SEQ ID NO: 253) | 24 |
| CCR5 Reference probe | HEX-TGGGCTCCCTACAACATTGTCCT-BHQ1 (SEQ ID NO: 254) | 23 |

Example 4: Materials and Methods for Examples 5-12 gRNA-apt-8-2 expression vectors. The gRNAs harboring the Apt8-2 sequence (gRNA-Apt8-2) were ordered as an Ultramer® (IDT, CA, USA) and amplified from pcDNA-H1-gRNA vector (F2, Tar6 or CCR5-D) using Hotstart Taq 2×Master Mix (NEB, MA, USA). The F2-gRNA has been described previously (Saayman et al., 2016). The pcDNA-H1-gRNA vectors for Tar6 and CCR5-D were generated by digesting a generic H1-gRNA plasmid with BsmBI and inserting the target sequence using a standard oligomer cloning protocol. The amplicons were cloned into a pTZ57R/T vector using the insTAclone PCR cloning kit (ThermoScientific, MA, USA) and the clones were confirmed by sequencing.

Cell Culture. The cell lines were maintained in Dulbecco's modified Eagle medium (DMEM, ThermoScientific, MA, USA) and 10% fetal bovine serum (FBS). The HEK293-GP160 (92UG037.8) cell line used (Chen et al., 2015) and the media was supplemented with 1.5 µg/ml puromycin. The cell lines were cultured at 37° C. with 5% $CO_2$.

Validation of the gRNA-Apt8-2 vectors. The pTZ-H1-gRNA-Apt8-2 vectors were transfected with plasmids expressing variants of spCas9: a nuclease Cas9 (px458, addgene #48138), a dead Cas9 (mutated from a nickase Cas9 (D10A), px461 addgene #48140, to generate the dCas9), a dCas9-KRAB (addgene #50919), a dCas9-VPR (addgene #63798), a dCas9-rAPOBEC1 (pCMV-BE3, addgene #73021), or pcDNA3.1 (gRNA-only) intoTZM-b1 cells or pMo-HEK293 cells using Lipofectamine® 3000 (Invitrogen, CA, USA). A vector expressing Tat-dsRED was included with the Cas9 vectors to activate the LTR, except with cells receiving the dCas9-VPR vector. At 48 hrs post-transfection, a luciferase assay was performed on the TZM-b1 cells using the Bright-Glo™ luciferase kit (Promega) and levels detected on a Glomax luminometer (Promega, WI, USA).

For the T7E1 assays, the target site of the gRNA was amplified using KAPA2G Robust Hotstart Readymix (Roche, Basel, Switzerland) from 200 ng of extracted DNA from pMO-HEK293 cells (an LTR containing HEK293 reporter). The PCR products were purified using a Qiaquick PCR purification kit (Qiagen, Hilden, Germany), and 400 ng of the purified products were subjected to the T7E1 assay as previously described (Scott et al., 2017).

In vitro transcription of 2'-Fluoro gRNAs. The gRNAs were PCR amplified with a T7 promoter sequence and the template was purified using the Qiaquick PCR purification kit (Qiagen, Hilden, Germany). The purified template was used to transcribe the gRNAs using the Durascribe® T7 transcription kit according to the manufacturer instructions (Lucigen, WI, USA). For gRNAs that lacked the 2'F-U or 2'F-C, an unmodified dNTP was supplemented into the reaction (NEB, MA, USA). The RNA was purified using the MEGAClear™ Transcription Clean-up kit (Ambion, CA, USA) and Sodium Acetate-Ethanol precipitated as recommended by the Durascribe® protocol. The RNA was resuspended in RNA storage buffer (Ambion, CA, USA) and diluted in water for downstream experiments.

In vitro cleavage assay. The target substrate for the F2gRNA assays was generated by either: 1) PCR amplification of the LTR from a pNL4-3.1uc vector, or 2) an ApaI linearised pNL4-3.1uc vector. The target substrate for the No—U, No—C or No—CU gRNAs was PCR amplified from a gBLOCK containing the gRNA target sites (IDT, CA, USA). All substrates were purified using the Qiaquick PCR purification kit (Qiagen, Hilden, Germany).

The gRNAs were mixed with a recombinant nuclease Cas9 (NEB, MA, USA) at a 1:1 molar ratio for 15 min at room temperature. For assays using a crRNA and tracrRNA, the RNAs were annealed by heating a 1:1 molar ratio mixture of crRNA:tracrRNA to 95° C. for 5 min, and then slowly cooling to room temperature prior to mixing with Cas9. The target substrate was subsequently added at a final concentration of 3 nM and incubated at 37° C. for 1 hour, and then proteinase K treated for 10 min at room temperature. The digestion products were resolved on a 6% Novex® TBE gel (Invitrogen, CA, USA) and visualized with EtBr stain.

Activity of modified gRNAs in cultured cells. The in vitro transcribed 2'F TAR-gRNAs were incubated with EnGen ° Cas9-NLS (NEB, MA, USA) and the RNP complexes transfected into a HEK293-LTR-GFP cell lines according to manufacturer instructions. At 24 hrs post-transfection, the LTR was activated with 10 ng/μ0.1 of tumor necrosis factor-α (TNF-α) (ThermoScientific, MA, USA), and the levels of GFP were determined on a Beckman Coulter FC500 flow cytometer and signal analyzed using the Flowjo® software.

The gRNA-Apt8-2 delivery assay. The F2gRNA-Apt8-2 RNA was incubated with a recombinant Cas9 fused to GFP (Genscript, China) and the 2G12 antibody (NIH AIDS Reagent Program) at an equal nanomolar ratio and incubated at room temperature for 30 min in Apt8-2 binding buffer (Miyakawa et al., 2008). The Cas9:antibody complex was added to the media of the HEK293-GP160 cell line at a 200 nM concentration. The cells were trypsin treated after 24 hrs, washed with PBS and the levels of GFP were detected by flow cytometry.

Example 5: In Vitro Cleavage Activity of Chemically Modified gRNAs

Figure 17A:
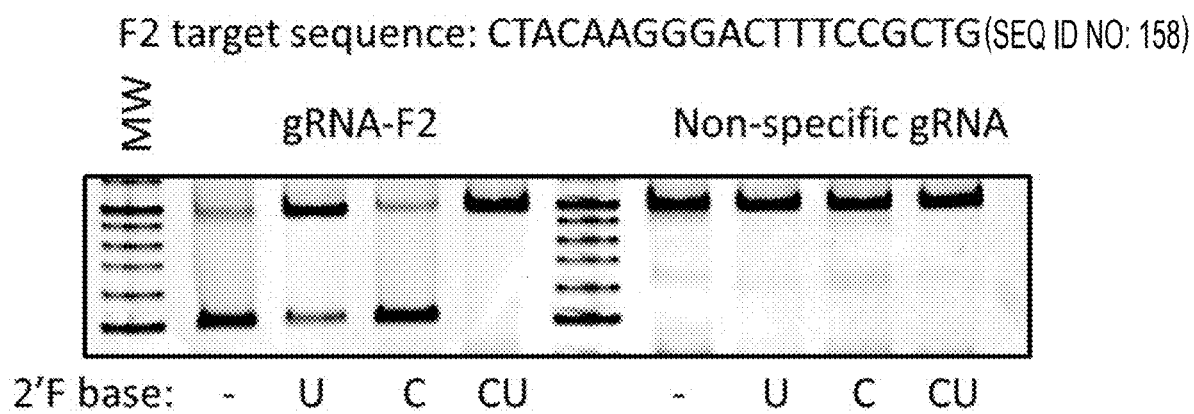

A series of gRNA that target the LTR of HIV (F2; SEQ ID NO: 158— FIG. 17A) and TAR (FIGS. 17B-17I) were synthesized by in vitro transcription with either 2'F-uridines (U), cytosines (C), or both 2'F-U and C. The modified gRNAs were incubated with Cas9 and a LTR target DNA substrate and the cleavage products were resolved using PAGE. An unmodified gRNA was included as a comparison control. A non-specific gRNA was also synthesized with the reciprocal modifications and included as a negative control.

Example 6: Tolerance of tracrRNA for 2'F-Based Modification

Figure 18:
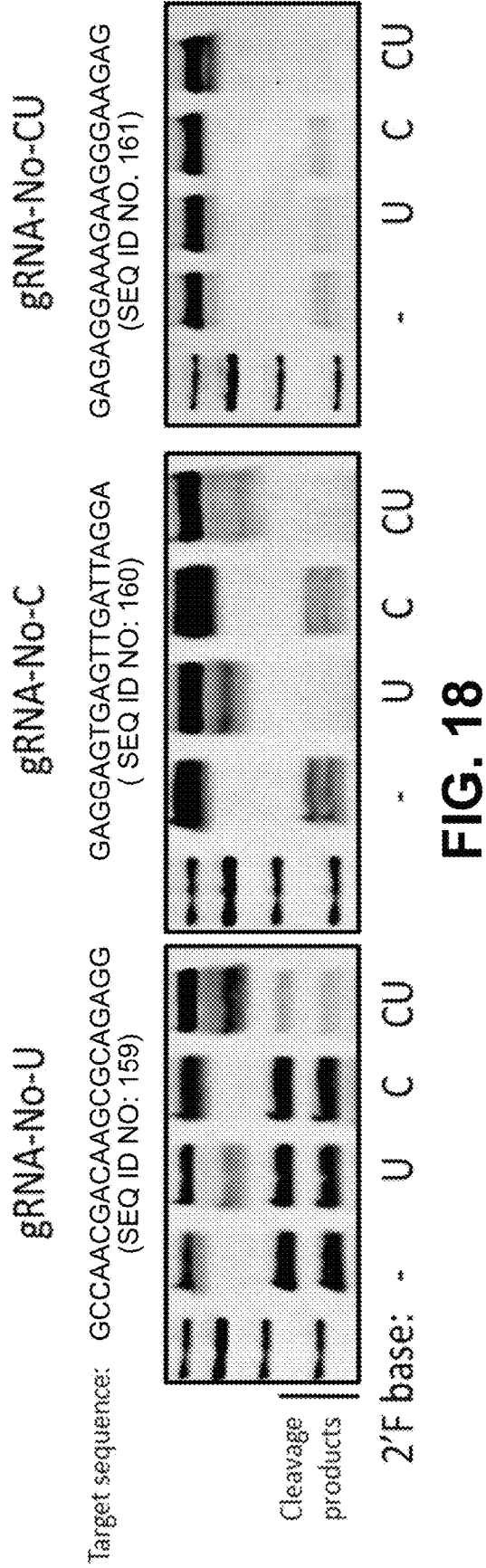
FIG. 18 presents results showing tolerance of tracrRNA for 2'F-based modifications.

Artificial gRNAs were designed that have target sequences without uridines (No—U), cytosines (No—C) or both C and U (No—CU) (See FIG. 18). The gRNAs were synthesized by in vitro transcription with either 2'F-U, 2'F-C, or both 2'F-U and C. The modified gRNA were incubated with Cas9 and a target DNA substrate and the cleavage products were resolved using PAGE. An unmodified gRNA was included as a comparison.

Example 7: Delivery of a Modified gRNA with Antibody

Figure 19A:
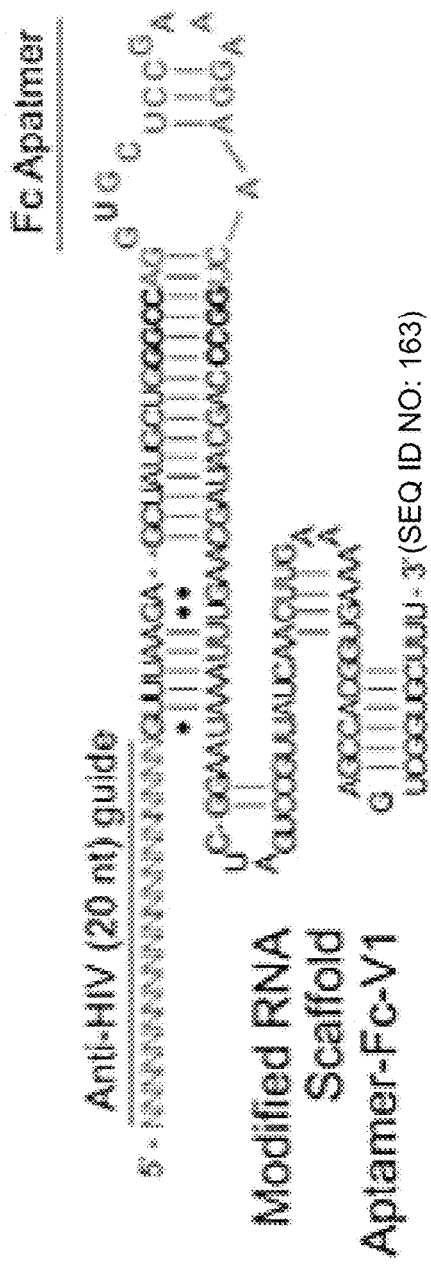
FIGS. 19A-19C present results showing delivery of a modified gRNA with antibody.
Figure 19B:
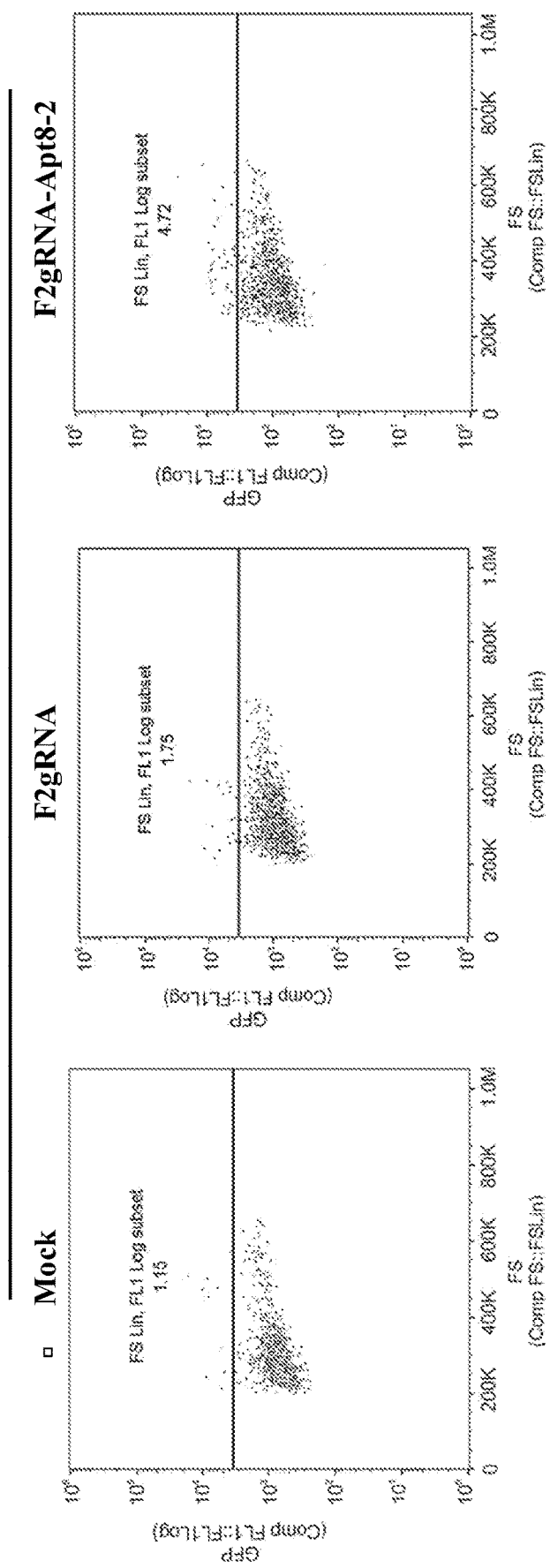
Figure 19C:
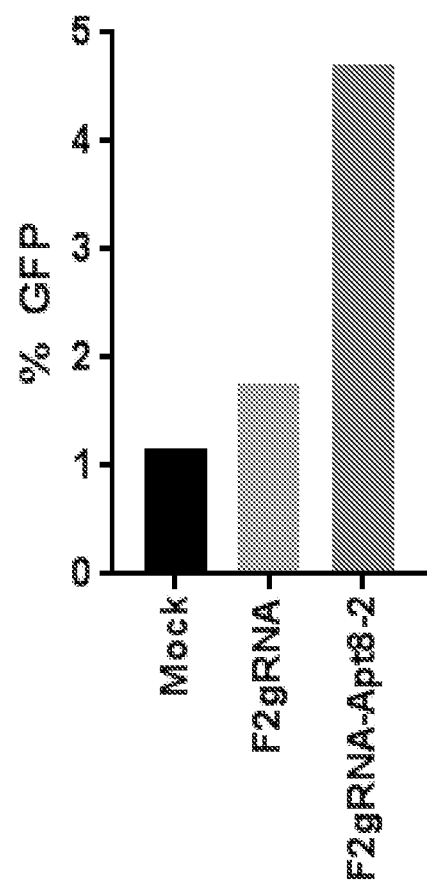

FIGS. 19A-19C present the results showing delivery of a modified gRNA with antibody. FIG. 19A shows a schematic of the F2 gRNA with the Apt8-2 aptamer embedded into the tetraloop. In FIGS. 19B and 19C, a F2-gRNA-Apt8-2 was synthesized by in vitro transcription containing 2'F-uridines and subsequently incubated with recombinant Cas9 fused to GFP (Cas9-GFP), and the 2G12 anti-GP160 antibody. The mixture was added to HEK293 cells that stably express HIV-GP160 and after 24 hrs the levels of intracellular GFP were measured by FACS. A mock (no guide RNA) or F2gRNA without the Apt8-2 aptamer were included as negative controls.

Example 8: Modified gRNAs can Leave Target Substrate

A control (gRNA-con) or anti-HIV F2 gRNA (gRNA-F2) were in vitro transcribed with 2'Flouro-U bases. The gRNAs were pre-assembled with a recombinant Cas9 and incubated with either a full length HIV pNL4-3 or 5' long terminal repeat (LTR) substrate. The presence of digestion products was indicative of target cleavage. Unmodified gRNAs were produced as a comparative cutting control.

Example 9: Modified gRNA Maintains Cas9 Activity

The aptamer modified gRNAs targeting HIV's LTR (F2 or Tar6) were transfected into TZM-b1 cells with vectors expressing either a nuclease Cas9, a catalytically dead Cas9 (dCas9), dCas9-VPR activator, dCas9-Krab repressor or mock (gRNA only) (FIGS. 22A-22G). At 48 hrs post-transfection a luciferase assay was performed to determine LTR activity. The levels were made relative to a control gRNA (gRNA-con). An unmodified gRNA-F2 was included as a positive control.

Example 10: Modified gRNA Improves Cas9-Induced Gene Modification

Figure 23A:
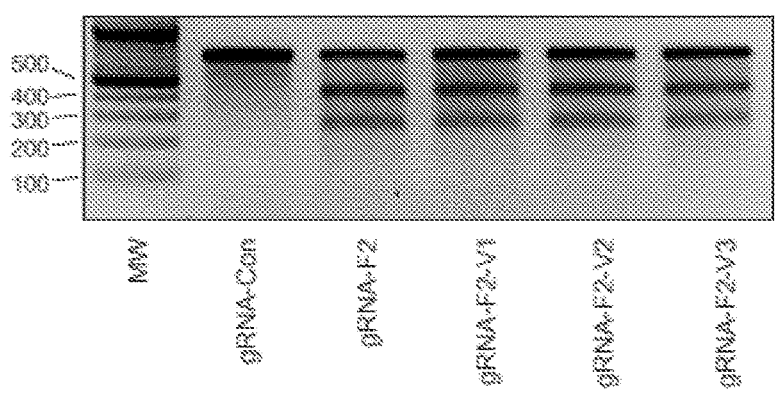
FIGS. 23A-23C present results showing that modified gRNA improves Cas9-induced gene modification.
Figure 23B:
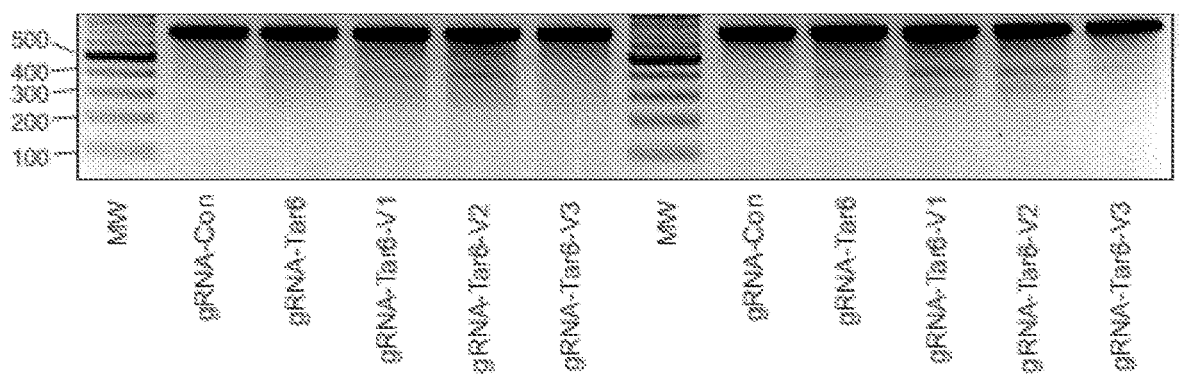
Figure 23C:
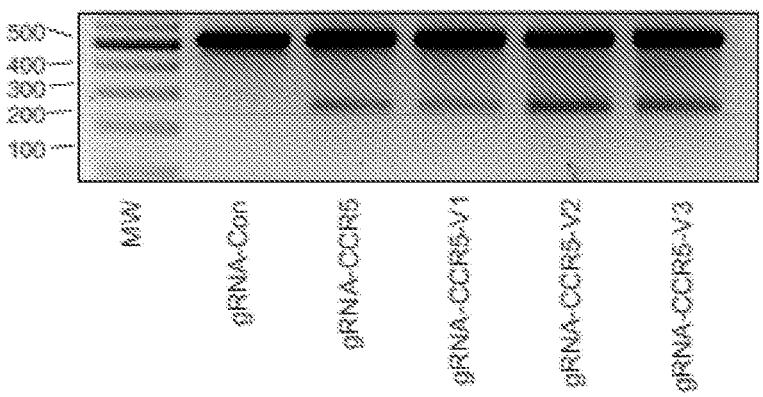

The gRNAs targeting the LTR of HIV (F2 or Tar6) or the CCR5 gene were transfected into HEK293 cells containing a HIV reporter with vectors expressing a nuclease Cas9, dCas9-APOBEC3A or dCas9-APOBEC3A with a uracil glycosylase inhibitor domain (UGI-dCas9-APOBEC3A) and at 48 hrs post-transfection, a T7E1 assay was performed on the LTR (FIG. 23). A control gRNA (gRNA-Con) was included as a negative control.

Example 11: Activity of Chemically Modified gRNAs in Cultured Cells

Figure 24:
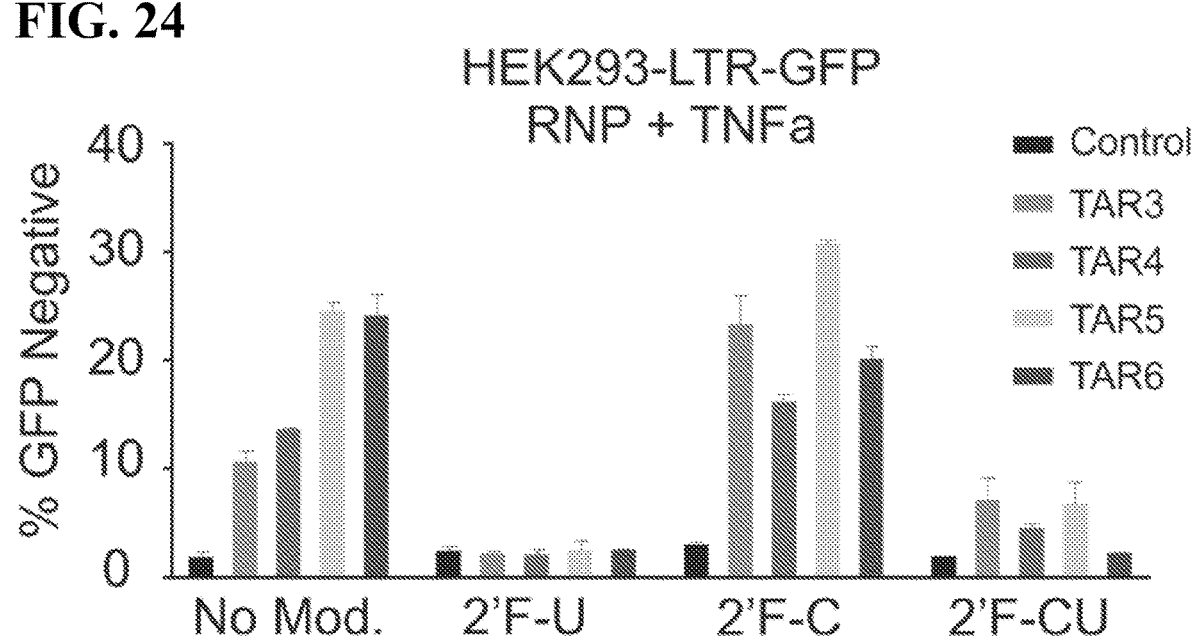
FIG. 24 presents the results showing the activity of chemically modified gRNAs in cultured cells.

The modified TAR gRNAs were incubated with Cas9-NLS and the RNP complexes were transfected into a HEK293 cell line containing a GFP flanked by the LTR's of HIV (HEK293-LTR-GFP, FIG. 24). The LTR was activated using tumor necrosis factor-α (TNF-α) and the levels of GFP were determined by FACS. Experiments were performed in duplicate and errors bars represent standard deviation. An unmodified gRNA was included as a comparison control. A non-specific gRNA (Control) was included as a negative control.

Example 12: In Vitro Cleavage Activity of Chemically Modified gRNAs

Figure 25A:
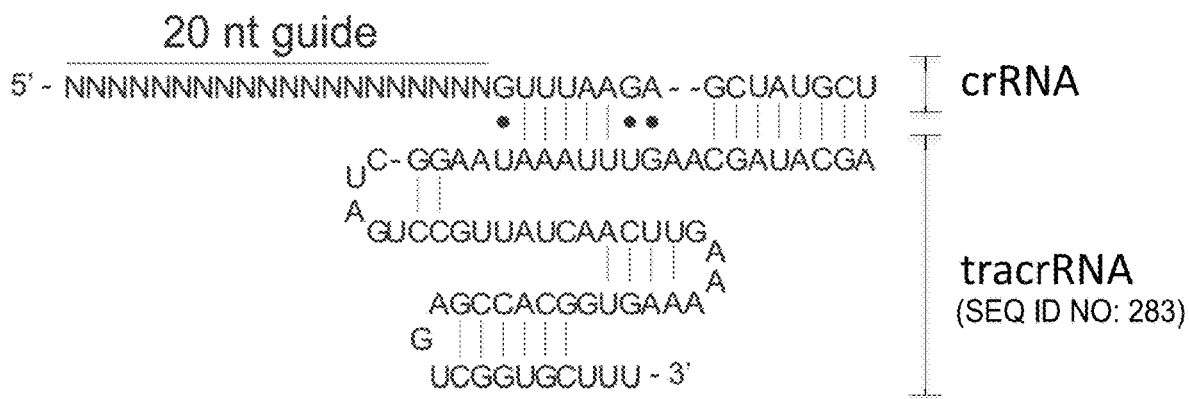
FIGS. 25A-25B present results showing the in vitro cleavage activity of chemically modification gRNAs.
Figure 25B:
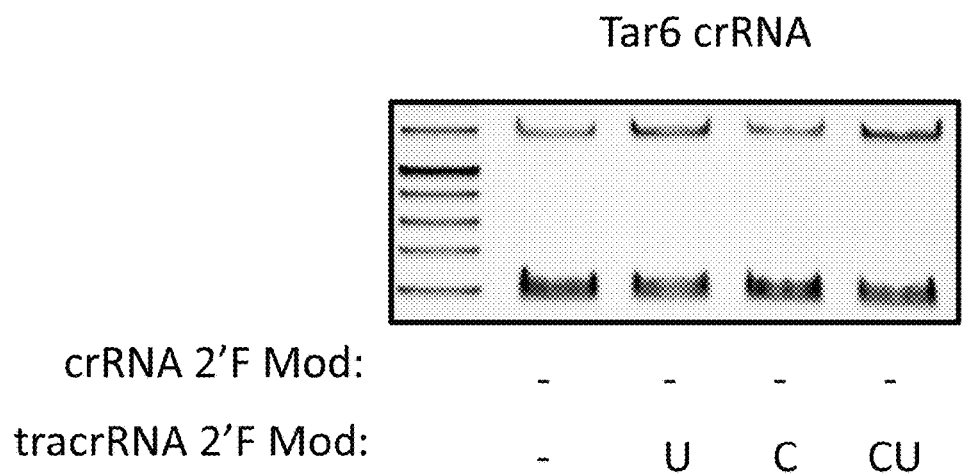

A crRNA harboring a Tar6 sequence and tracrRNA were in vitro transcribed, with the tracrRNA transcribed with either 2'F-uridines (U), cytosines (C), or both 2'F-U and C. The unmodified crRNA was annealed with the modified tracrRNA, and the RNA duplexes were incubated with Cas9 with a LTR target DNA substrate (FIGS. 25A-25B). The cleavage products were resolved using PAGE. An unmodified crRNA:tracrRNA was included as a comparison control.

A Embodiments (698P01Us)

Embodiment A1: A nucleic acid comprising a genetically modified trans-activating crRNA (tracrRNA) sequence, wherein at least one uracil nucleotide of said tracrRNA sequence is replaced with a nucleotide other than uracil.

Embodiment A2: The nucleic acid of embodiment A1, wherein said nucleotide other than uracil is guanine.

Embodiment A3: The nucleic acid of embodiment A1, wherein said nucleotide other than uracil is adenine.

Embodiment A4: The nucleic acid of embodiment A1, wherein said nucleotide other than uracil is cytosine.

Embodiment A5: The nucleic acid of embodiment A1, wherein said tracrRNA sequence further comprises one or more modified nucleotides.

Embodiment A6: The nucleic acid of embodiment A5, wherein said modified nucleotides are 2'-modified nucleotides.

Embodiment A7: The nucleic acid of embodiment A6, wherein said 2'-modified nucleotides are 2'-amine modified nucleotides, 2'-fluoro modified nucleotides, 2'-O-methyl modified nucleotides or any combination thereof.

Embodiment A8: The nucleic acid according to any one of embodiments A1 to A7, wherein said tracrRNA sequence is further modified with an insertion of an aptamer nucleic acid sequence at a loop region of said tracrRNA sequence.

Embodiment A9: The nucleic acid of embodiment A8, wherein said aptamer nucleic acid sequence is aptamer 8-2 (GGAGGUGCUCCGAAAGGAACUCC (SEQ ID NO: 2))

Embodiment A10: The nucleic acid of embodiment A8, wherein said aptamer nucleic acid sequence is capable of binding to an Fc antibody region.

Embodiment A11: The nucleic acid of embodiment A8, wherein said aptamer nucleic acid sequence is capable of binding to a cell receptor.

Embodiment A12: The nucleic acid of embodiment A11, wherein said cell receptor is CD34, CD4 or CD32a, CCR5, IL4 and VEGFA.

Embodiment A13: A vector comprising the nucleic acid of any one of embodiments A1 to A12.

Embodiment A14: A pharmaceutical composition comprising the nucleic acid of any one of embodiments A1 to A12 or the vector of embodiment A13, and a pharmaceutically acceptable excipient.

Embodiment A15: A method of altering gene expression in a cell, the method comprising introducing into said cell the nucleic acid of any one of embodiments A1 to A12, the vector of embodiment A13, or the pharmaceutical composition of embodiment A14.

Embodiment A16: The method of embodiment A15, furthering comprising introducing to said cell an RNA-guided DNA endonuclease enzyme.

Embodiment A17: The method of embodiment A16, wherein said RNA-guided DNA endonuclease enzyme is Cas9 or Cpf1 or a Class II CRISPR endonuclease or a variant thereof.

Embodiment A18: The method of embodiment A17, wherein said RNA-guided DNA endonuclease enzyme is a modified Cas endonuclease.

Embodiment A19: The method of embodiment A18, wherein said modified Cas endonuclease is deactivated Cas9 (dCas9) or mutated Cas9 nickase (D10A).

Embodiment A20: The method of embodiment A16, wherein said RNA-guided DNA endonuclease enzyme is a conjugate comprising a Cas 9 endonuclease and a transcription regulating factor.

Embodiment A21: The method of embodiment A20, wherein said conjugate comprises a dCas-APOBEC3A fusion protein, a dCas-VPR fusion protein or a dCas-KRAB fusion protein.

Embodiment A22: A method of treating a disorder in a subject in need thereof, the method comprising administering to said subject the nucleic acid of any one of embodiments A1 to A12, the vector of embodiment A13, or the pharmaceutical composition of embodiment A14, in combination with an RNA-guided DNA endonuclease enzyme.

Embodiment A23: The method of embodiment A22, wherein said disorder is HIV, cancer, COPD, Cystic Fibrosis, heart conditions/repair, and diabetes.

B Embodiments

Embodiment B1: A nucleic acid comprising a guide RNA (gRNA) sequence, wherein all cytosine nucleotides and/or all uracil nucleotides of said gRNA sequence are modified nucleotides.

Embodiment B2: The nucleic acid of embodiment B1, wherein said modified nucleotides are 2'-modified nucleotides.

Embodiment B3: The nucleic acid of embodiment B2, wherein said 2'-modified nucleotides are 2'-amine modified nucleotides, 2'-fluoro modified nucleotides, 2'-O-methyl modified nucleotides or any combination thereof.

Embodiment B4: The nucleic acid of embodiment B1, wherein all cytosine nucleotides are modified nucleotides.

Embodiment B5: The nucleic acid of embodiment B1, wherein all cytosine nucleotides are 2'-modified nucleotides.

Embodiment B6: The nucleic acid of embodiment B1, wherein all cytosine nucleotides are 2'-fluoro modified nucleotides.

Embodiment B7: The nucleic acid of embodiment B1, wherein all uracil nucleotides are modified nucleotides.

Embodiment B8: The nucleic acid of embodiment B1, wherein all uracil nucleotides are 2'-modified nucleotides.

Embodiment B9: The nucleic acid of embodiment B1, wherein all uracil nucleotides are 2'-fluoro modified nucleotides.

Embodiment B10: The nucleic acid of embodiment B1, wherein all cytosine nucleotides and all uracil nucleotides are modified nucleotides Embodiment B11: The nucleic acid according to any one of embodiments B1 to B10, wherein said gRNA sequence is further modified with an insertion of an aptamer nucleic acid sequence at a loop region of said gRNA sequence.

Embodiment B12: The nucleic acid of embodiment B11, wherein said aptamer nucleic acid sequence is aptamer 8-2 (SEQ ID NO: 2).

Embodiment B13: The nucleic acid of embodiment B11, wherein said aptamer nucleic acid sequence is capable of binding to an Fc antibody region.

Embodiment B14: The nucleic acid of embodiment B11, wherein said aptamer nucleic acid sequence is capable of binding to a cell receptor.

Embodiment B15: The nucleic acid of embodiment B14, wherein said cell receptor is CD34, CD4 or CD32a, CCR5, IL4 and VEGFA.

Embodiment B16: A nucleic acid comprising a guide RNA (gRNA) sequence, wherein all cytosine nucleotides and/or all uracil nucleotides of said gRNA sequence are modified nucleotides and wherein said gRNA sequence is further modified with an insertion of an aptamer nucleic acid sequence at a loop region of said gRNA sequence.

Embodiment B17: A nucleic acid comprising a guide RNA (gRNA) sequence, wherein all cytosine nucleotides of said gRNA sequence are modified nucleotides.

Embodiment B18: A vector comprising the nucleic acid of any one of embodiments B1 to B17.

Embodiment B19: A pharmaceutical composition comprising the nucleic acid of any one of embodiments B1 to B17 or the vector of embodiment 18, and a pharmaceutically acceptable excipient.

Embodiment B20: A method of altering gene expression in a cell, the method comprising introducing into said cell the nucleic acid of any one of embodiments B1 to B17, the vector of embodiment B18, or the pharmaceutical composition of embodiment B19.

Embodiment B21: The method of embodiment B20, furthering comprising introducing to said cell an RNA-guided DNA endonuclease enzyme.

Embodiment B22: The method of embodiment B21, wherein said RNA-guided DNA endonuclease enzyme is Cas9 or Cpf1 or a Class II CRISPR endonuclease or a variant thereof.

Embodiment B23: The method of embodiment B22, wherein said RNA-guided DNA endonuclease enzyme is a modified Cas endonuclease.

Embodiment B24: The method of embodiment B23, wherein said modified Cas endonuclease is deactivated Cas9 (dCas9) or mutated Cas9 nickase (D10A).

Embodiment B25: The method of embodiment B21, wherein said RNA-guided DNA endonuclease enzyme is a conjugate comprising a Cas9 endonuclease and a transcription regulating factor.

Embodiment B26: The method of embodiment B25, wherein said conjugate comprises a dCas-APOBEC3A fusion protein, a dCas-VPR fusion protein or a dCas-KRAB fusion protein.

Embodiment B27: A method of treating a disorder in a subject in need thereof, the method comprising administering to said subject the nucleic acid of any one of embodiments B1 to B17, the vector of embodiment B18, or the pharmaceutical composition of embodiment B19, in combination with an RNA-guided DNA endonuclease enzyme.

Embodiment B28: The method of embodiment B27, wherein said disorder is HIV, cancer, COPD, Cystic Fibrosis, heart conditions/repair, and diabetes.

C Embodiments

Embodiment C1: A nucleic acid comprising a genetically modified trans-activating crRNA (tracrRNA) sequence, wherein (a) at least one nucleotide of the modified tracrRNA sequence corresponding to a uracil of SEQ ID NO: 1 is a nucleotide other than uracil, and (b) the modified tracrRNA sequence is not a naturally occurring tracrRNA sequence.

Embodiment C2: The nucleic acid of embodiment C1, wherein the modified tracrRNA sequence is at least 80% identical to SEQ ID NO: 1 or a tracrRNA sequence selected from any of Tables 1-10.

Embodiment C3: The nucleic acid of embodiment C1 or C2, wherein the modified tracrRNA sequence increases activity of a CRISPR complex relative to SEQ ID NO: 1.

Embodiment C4: The nucleic acid of any one of embodiments C1-C3, wherein said nucleotide other than uracil is guanine.

Embodiment C5: The nucleic acid of any one of embodiments C1-C3, wherein said nucleotide other than uracil is adenine.

Embodiment C6: The nucleic acid of any one of embodiments C1-C3, wherein said nucleotide other than uracil is cytosine.

Embodiment C7: The nucleic acid of any one of embodiments C1-C6, wherein said modified tracrRNA sequence further comprises one or more modified nucleotides.

Embodiment C8: The nucleic acid of any one of embodiments C1-C7, further comprising a guide RNA (gRNA) sequence, wherein one or more cytosine nucleotides and/or one or more uracil nucleotides of said gRNA sequence are modified nucleotides.

Embodiment C9: The nucleic acid of embodiment C7 or C8, wherein all cytosine nucleotides and/or all uracil nucleotides of one or more of the modified tracrRNA sequence or the gRNA sequence are modified nucleotides.

Embodiment C10: A nucleic acid comprising a guide RNA (gRNA) sequence, wherein all cytosine nucleotides of said gRNA sequence are modified nucleotides.

Embodiment C11: The nucleic acid of any one of embodiments C7-C10, wherein said modified nucleotides are 2'-modified nucleotides.

Embodiment C12: The nucleic acid of embodiment C11, wherein said 2'-modified nucleotides are 2'-amine modified nucleotides, 2'-fluoro modified nucleotides, 2'-O-methyl modified nucleotides or any combination thereof.

Embodiment C13: The nucleic acid of embodiment C12, wherein said modified nucleotides are 2'-fluoro modified nucleotides.

Embodiment C14: The nucleic acid of any one of embodiments C1-9 or C11-C13, wherein said modified tracrRNA sequence is further modified with an insertion of an aptamer nucleic acid sequence at a loop region of said modified tracrRNA sequence.

Embodiment C15: The nucleic acid of any one of embodiments C8-C14, wherein said gRNA sequence is further modified with an insertion of an aptamer nucleic acid sequence at a loop region of said gRNA sequence.

Embodiment C16: The nucleic acid of embodiment C14 or C15, wherein said aptamer nucleic acid sequence is aptamer 8-2 (GGAGGUGCUCCGAAAGGAACUCC (SEQ ID NO: 2)).

Embodiment C17: The nucleic acid of embodiment C14 or C15, wherein said aptamer nucleic acid sequence is capable of binding to an Fc antibody region.

Embodiment C18: The nucleic acid of embodiment C14 or C15, wherein said aptamer nucleic acid sequence is capable of binding to a cell receptor.

Embodiment C19: The nucleic acid of embodiment C18, wherein said cell receptor is CD34, CD4 or CD32a, CCR5, IL4 and VEGFA.

Embodiment C20: The nucleic acid of embodiment C14 or C15, wherein said aptamer nucleic acid sequence comprises SEQ ID NO: 257.

Embodiment C21: A nucleic acid comprising a guide RNA (gRNA) sequence, wherein all cytosine nucleotides of said gRNA sequence are modified nucleotides and wherein said gRNA sequence is further modified with an insertion of an aptamer nucleic acid sequence at a loop region of said gRNA sequence.

Embodiment C22: A composition comprising: (a) a first nucleic acid comprising a genetically modified trans-activating crRNA (tracrRNA) sequence, wherein (i) at least one nucleotide of the modified tracrRNA sequence corresponding to a uracil of SEQ ID NO: 1 is a nucleotide other than uracil, and (ii) the modified tracrRNA sequence is not a naturally occurring tracrRNA sequence; and (b) a second nucleic acid comprising a guide RNA (gRNA) sequence, wherein one or more cytosine nucleotides and/or one or more uracil nucleotides of said gRNA sequence are modified nucleotides.

Embodiment C23: The composition of embodiment C22, wherein the modified tracrRNA sequence is at least 80% identical to SEQ ID NO: 1 or a tracrRNA sequence selected from any of Tables 1-10.

Embodiment C24: The composition of embodiment C22 or C23, wherein the modified tracrRNA sequence increases activity of a CRISPR complex relative to SEQ ID NO: 1.

Embodiment C25: The composition of any one of embodiments C22-C24, wherein said nucleotide other than uracil is guanine.

Embodiment C26: The composition of any one of embodiments C22-C24, wherein said nucleotide other than uracil is adenine.

Embodiment C27: The composition of any one of embodiments C22-C24, wherein said nucleotide other than uracil is cytosine.

Embodiment C28: The composition of any one of embodiments C22-C27, wherein said modified tracrRNA sequence further comprises one or more modified nucleotides.

Embodiment C29: The composition of any one of embodiments C22-C28, wherein all cytosine nucleotides and/or all uracil nucleotides of one or more of the modified tracrRNA sequence or the gRNA sequence are modified nucleotides.

Embodiment C30: The composition of any one of embodiments C22-C29, wherein said modified nucleotides are 2'-modified nucleotides.

Embodiment C31: The composition of embodiment C30, wherein said 2'-modified nucleotides are 2'-amine modified nucleotides, 2'-fluoro modified nucleotides, 2'-O-methyl modified nucleotides or any combination thereof.

Embodiment C32: The composition of embodiment C31, wherein said modified nucleotides are 2'-fluoro modified nucleotides.

Embodiment C33: The composition of any one of embodiments C22-C32, wherein said modified tracrRNA sequence is further modified with an insertion of an aptamer nucleic acid sequence at a loop region of said modified tracrRNA sequence.

Embodiment C34: The composition of embodiment C33, wherein said aptamer nucleic acid sequence is aptamer 8-2 (GGAGGUGCUCCGAAAGGAACUCC (SEQ ID NO: 2)).

Embodiment C35: The composition of embodiment C33, wherein said aptamer nucleic acid sequence is capable of binding to an Fc antibody region.

Embodiment C36: The composition of embodiment C33, wherein said aptamer nucleic acid sequence is capable of binding to a cell receptor.

Embodiment C37: The composition of embodiment C36, wherein said cell receptor is CD34, CD4 or CD32a, CCR5, IL4 and VEGFA.

Embodiment C38: The composition of embodiment C33, wherein said aptamer nucleic acid sequence comprises SEQ ID NO: 257.

Embodiment C39: The composition of any one of embodiments C22-C38, further comprising an RNA-guided DNA endonuclease enzyme.

Embodiment C40: The composition of embodiment C39, wherein said RNA-guided DNA endonuclease enzyme is Cas9 or Cpf1 or a Class II CRISPR endonuclease or a variant thereof.

Embodiment C41: The composition of embodiment C40, wherein said RNA-guided DNA endonuclease enzyme is a modified Cas endonuclease.

Embodiment C42: The composition of embodiment C41, wherein said modified Cas endonuclease is deactivated Cas9 (dCas9) or mutated Cas9 nickase (D10A).

Embodiment C43: The composition of any one of embodiments C22-C42, further comprising a pharmaceutically acceptable excipient.

Embodiment C44: A vector comprising or encoding the nucleic acid of any one of embodiments C1-C21.

Embodiment C45: A pharmaceutical composition comprising the nucleic acid of any one of embodiments C1-C21 or the vector of embodiment C44, and a pharmaceutically acceptable excipient.

Embodiment C46: A method of altering gene expression in a cell, the method comprising introducing into said cell the nucleic acid of any one of embodiments C1-C21, the composition of any one of embodiments C22-C43, the vector of embodiment C44, or the pharmaceutical composition of embodiment C45.

Embodiment C47: The method of embodiment C46, furthering comprising introducing to said cell an RNA-guided DNA endonuclease enzyme.

Embodiment C48: The method of embodiment C47, wherein said RNA-guided DNA endonuclease enzyme is Cas9 or Cpf1 or a Class II CRISPR endonuclease or a variant thereof.

Embodiment C49: The method of embodiment C48, wherein said RNA-guided DNA endonuclease enzyme is a modified Cas endonuclease.

Embodiment C50: The method of embodiment C49, wherein said modified Cas endonuclease is deactivated Cas9 (dCas9) or mutated Cas9 nickase (D10A).

Embodiment C51: The method of embodiment C47, wherein said RNA-guided DNA endonuclease enzyme is a conjugate comprising a Cas 9 endonuclease and a transcription regulating factor.

Embodiment C52: The method of embodiment C51, wherein said conjugate comprises a dCas-APOBEC3A fusion protein, a dCas-VPR fusion protein or a dCas-KRAB fusion protein.

Embodiment C53: A method of treating a disorder in a subject in need thereof, the method comprising administering to said subject the nucleic acid of any one of embodiments C1-C21, the composition of any one of embodiments C22-C43, the vector of embodiment C44, or the pharmaceutical composition of embodiment C45, in combination with an RNA-guided DNA endonuclease enzyme.

Embodiment C54: The method of embodiment C53, wherein said disorder is HIV, cancer, COPD, Cystic Fibrosis, heart conditions/repair, and diabetes.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

ADDITIONAL SEQUENCES

SEQ ID NO: 158 (F2 target sequence)
CTACAAGGGACTTTCCGCTG

SEQ ID NO: 159 (gRNA-No-U target sequence)
GCCAACGACAAGCGCAGAGG

SEQ ID NO: 160 (gRNA-No-C target sequence)
GAGGAGTGAGTTGATTAGGA

SEQ ID NO: 161 (gRNA-No-CU target sequence)
GAGAGGAAAGAAGGGAAGAG

Figure 20A:
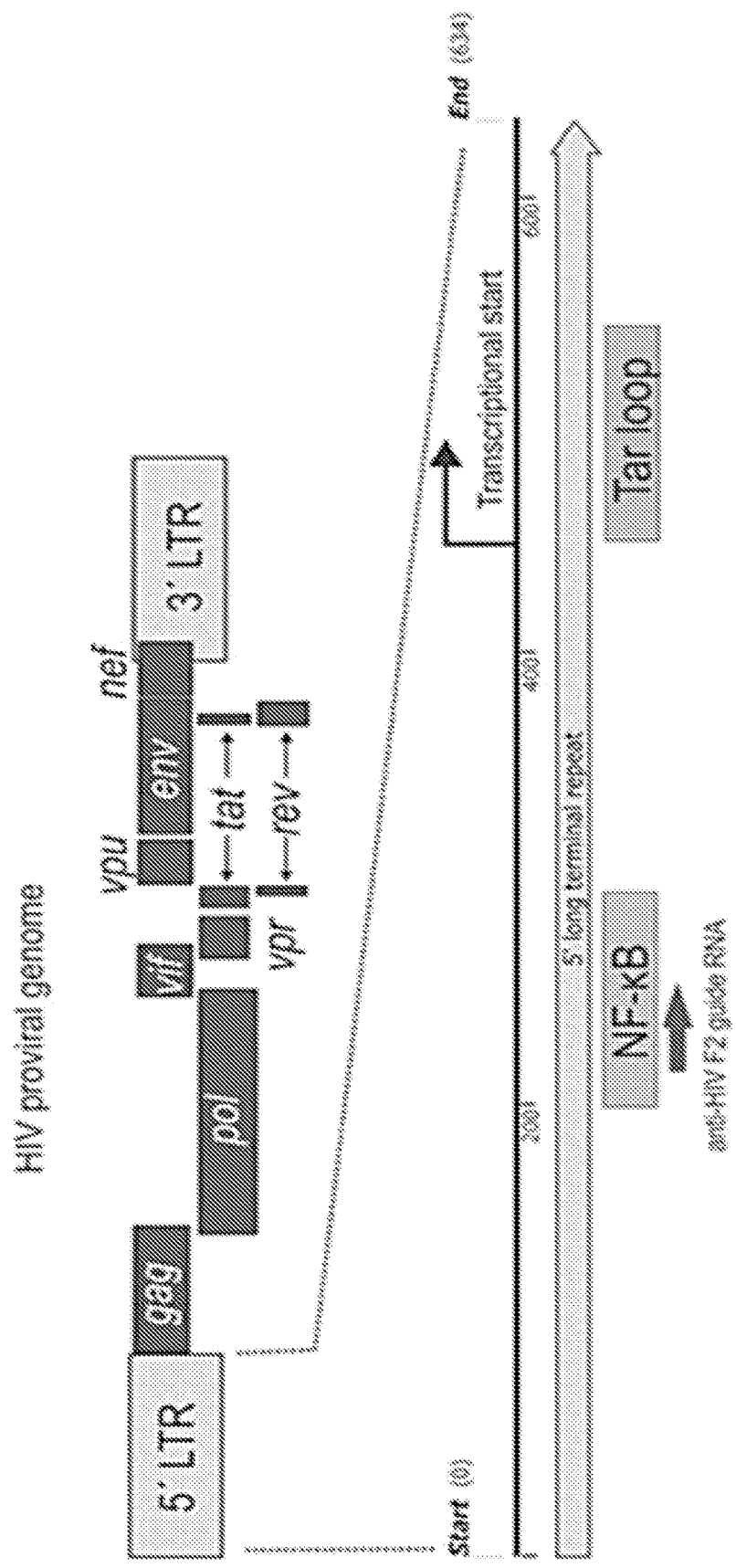
Figure 21:
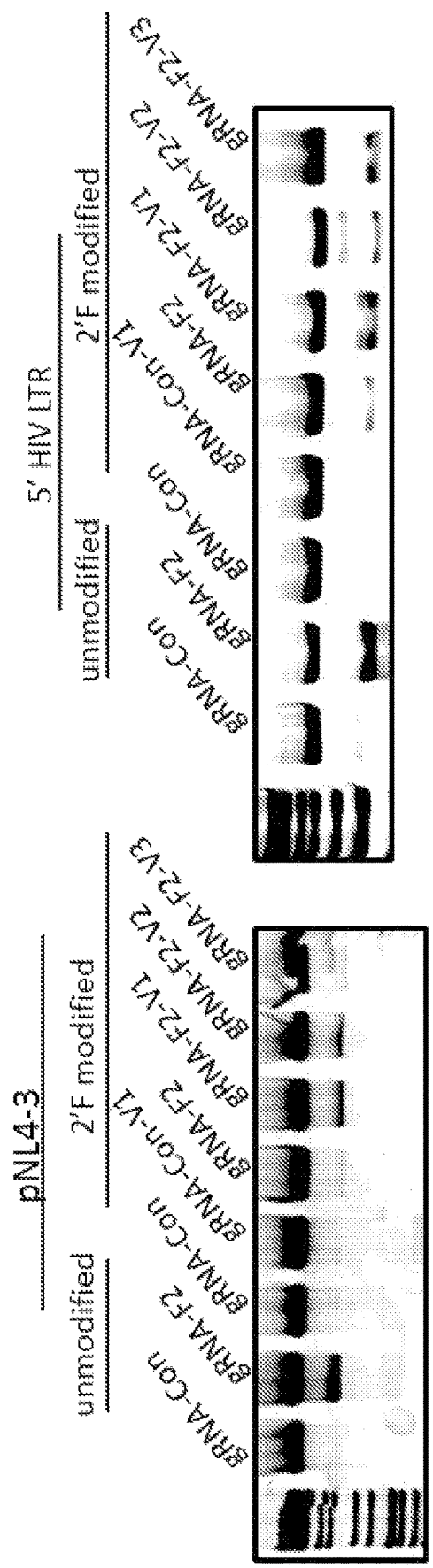
FIG. 21 presents results showing that modified gRNAs can cleave a target substrate.
Figure 22A:
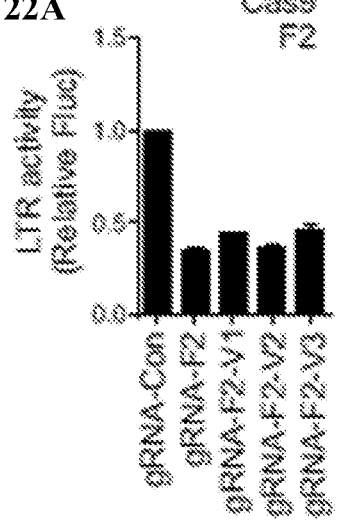
FIGS. 22A-22G present results showing that modified gRNA maintains Cas9 activity.
Figure 22B:
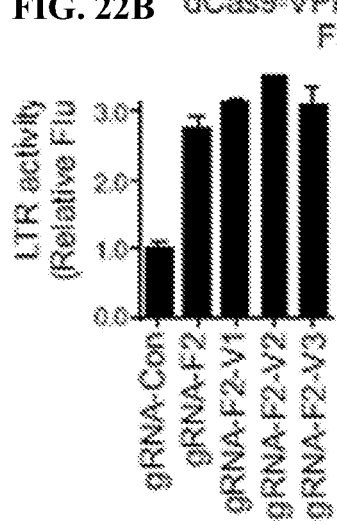
Figure 22C:
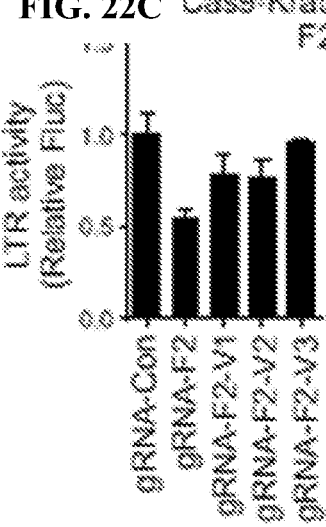
Figure 22D:
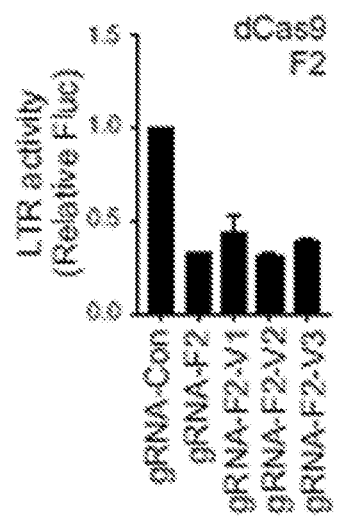
Figure 22E:
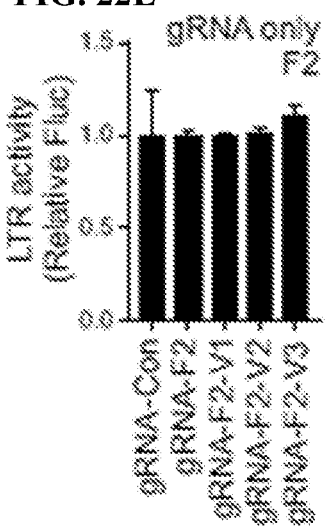
Figure 22F:
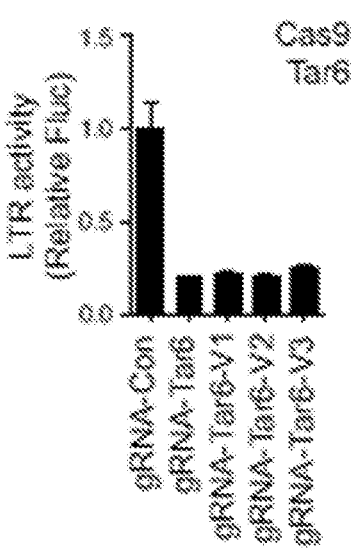
Figure 22G:
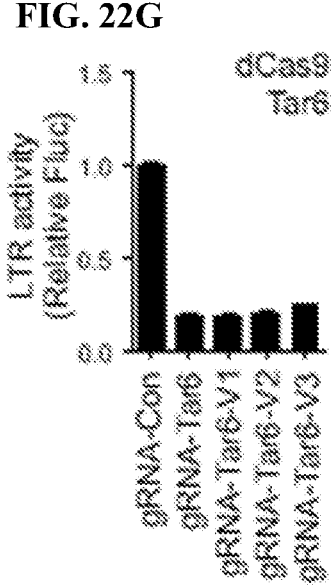
Figure 26A:
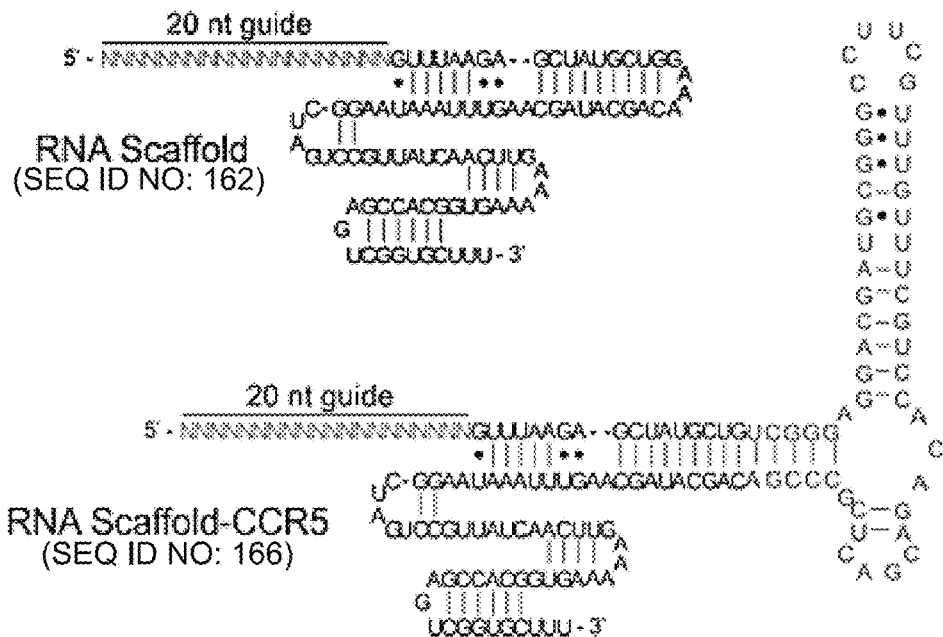
FIGS. 26A-26E present results showing that 2'F cytidine gRNAs with embedded CCR5 aptamer functionally localized Cas9 complexes to receptor bearing cells. Serum free TZMB1 cells were treated with TARS gRNA containing CCR5 RNA aptamer (2'F-C modified) in complex with CRISPR.
Figure 26B:
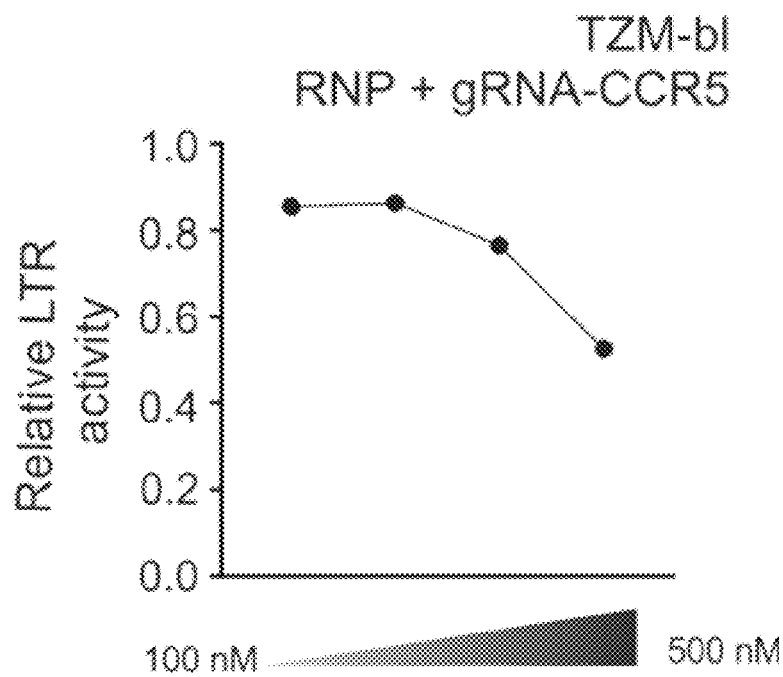
Figure 26C:
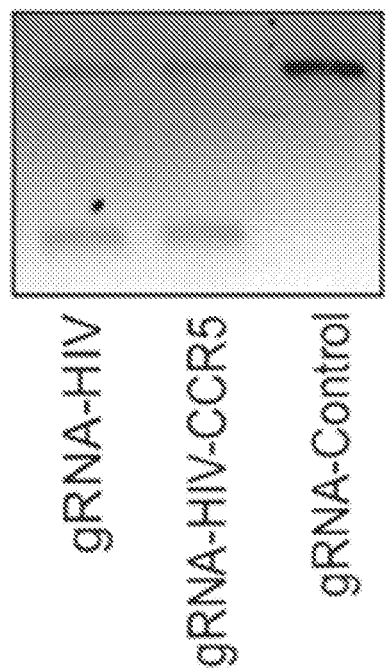
Figure 26D:
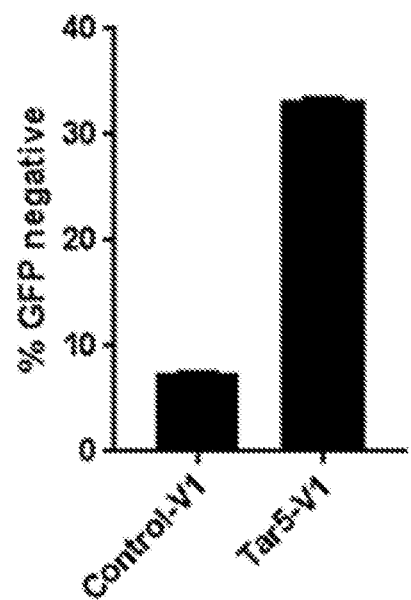
Figure 26E:
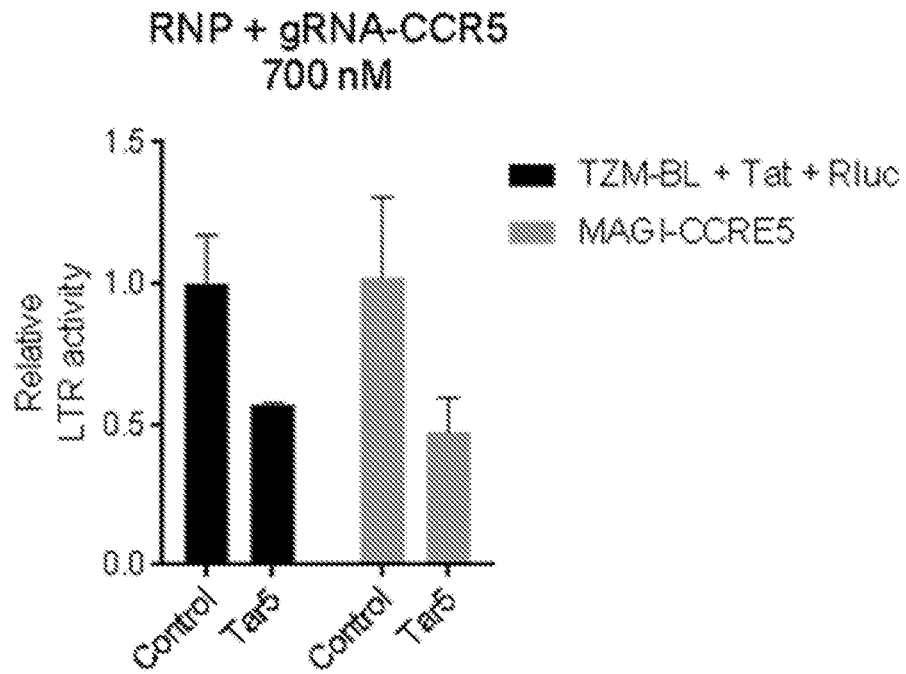

SEQ ID NO: 162 (spCas9 UracrRNA/RNA Scaffold
from FIG. 20B and FIG. 26A)
N(20)GUUUAAGAGCUAUGCUGGAAACAGCAUAGCAAGUUUAAAUAA
GGCUAGUCCGUUAUCAACUUGAAAAAGUGGCACCGAGUCGGUGCUUU
(N is any nucleotide)

SEQ ID NO: 163 (RNA Scaffold-Apt8-2-V1 from
FIGS. 19A and 20C)
N(20)GUUUAAGAGCUAUGCUGGGCCGGAGGUGCUCCGAAAGGAACU
CCGGCCCAGCAUAGCAAGUUUAAAUAAGGCUAGUCCGUUAUCAACUU
GAAAAAGUGGCACCGAGUCGGUGCUUU
(N is any nucleotide)

SEQ ID NO: 164 (RNA Scaffold-Apt8-2-V2 from
FIG. 20D)
N(20)GUUUAAGAGCUAUGCUGGAAACAGCAUAGCAAGUUUAAAUAA
GGCUAGUCCGUUAUCAACUUGGCCGGAGGUGCUCCGAAAGGAACUCC
GGCCAAGUGGCACCGAGUCGGUGCUUU
(N is any nucleotide)

SEQ ID NO: 165 (RNA Scaffold-Apt8-2-V3 from
FIG. 20E)
N(20)GUUUAAGAGCUAUGCUGGGCCGGAGGUGCUCCGAAAGGAACU
CCGGCCCAGCAUAGCAAGUUUAAAUAAGGCUAGUCCGUUAUCAACUU
GGCCGGAGGUGCUCCGAAAGGAACUCCGGCCAAGUGGCACCGAGUCG
GUGCUUU (N is any nucleotide)

SEQ ID NO: 166 (RNA Scaffold-CCR5 from
FIG. 26A)
N(20)GUUUAAGAGCUAUGCUGUCGGGAGGACGAUGCGGGCCUUCGU
UUGUUUCGUCCACAGACGACUCGCCCGACAGCAUAGCAAGUUUAAAU
AAGGCUAGUCCGUUAUCAACUUGAAAAAGUGGCACCGAGUCGGUGCU
UU (N is any nucleotide)

SEQ ID NO: 257 (aptamer targeting CCR5)
GGGAGGACGAUGCGGGCCUUCGUUUGUUUCGUCCACAGACGACUCGC
CCGA

REFERENCES

Findlay, S. D., Vincent, K. M., Berman, J. R., Postovit, L.-M., 2016. A Digital PCR-Based Method for Efficient and Highly Specific Screening of Genome Edited Cells. PLOS ONE 11, e0153901.

Howell, D. N., Andreotti, P. E., Dawson, J. R., Cresswell, P., 1985. Natural killing target antigens as inducers of interferon: studies with an immunoselected, natural killing-resistant human T lymphoblastoid cell line. The Journal of Immunology 134, 971-976.

Lyerly, H. K., Reed, D. L., Matthews, T. J., Langlois, A. J., Ahearne, P. A., Stephen R. Petteway, J., Weinhold, K. J., 1987. Anti-GP 120 Antibodies from HIV Seropositive Individuals Mediate Broadly Reactive Anti-HIV ADCC. AIDS Research and Human Retroviruses 3, 409-422.

Nishimasu, H., Ran, F. A., Hsu, Patrick D., Konermann, S., Shehata, Soraya I., Dohmae, N., Ishitani, R., Zhang, F., Nureki, O., 2014. Crystal Structure of Cas9 in Complex with Guide RNA and Target DNA. Cell 156, 935-949.

Trkola, A., Matthews, J., Gordon, C., Ketas, T., Moore, J., 1999. A cell line-based neutralization assay for primary human immunodeficiency virus type 1 isolates that use either the CCR5 or the CXCR4 coreceptor. Journal of Virology 73, 8966-8974.

Chen, J., Kovacs, J. M., Peng, H., Rits-Volloch, S., Lu, J., Park, D., Zablowsky, E., Seaman, M. S., Chen, B., 2015. Effect of the cytoplasmic domain on antigenic characteristics of HIV-1 envelope glycoprotein. Science 349, 191-195.

Miyakawa, S., Nomura, Y., Sakamoto, T., Yamaguchi, Y., Kato, K., Yamazaki, S., Nakamura, Y., 2008. Structural and molecular basis for hyperspecificity of RNA aptamer to human immunoglobulin G. RNA 14, 1154-1163.

Saayman, S. M., Lazar, D. C., Scott, T. A., Hart, J. R., Takahashi, M., Burnett, J. C., Planelles, V., Morris, K. V., Weinberg, M. S., 2016. Potent and Targeted Activation of Latent HIV-1 Using the CRISPR/dCas9 Activator Complex. Molecular Therapy 24, 488-498.

Scott, T., Moyo, B., Nicholson, S., Maepa, M. B., Watashi, K., Ely, A., Weinberg, M. S., Arbuthnot, P., 2017. ssAAVs containing cassettes encoding SaCas9 and guides targeting hepatitis B virus inactivate replication of the virus in cultured cells. Scientific Reports 7, 7401.

What is claimed is:

1. A nucleic acid comprising a trans-activating crRNA (tracrRNA) sequence, wherein the tracrRNA sequence is SEQ ID NO: 171, SEQ ID NO: 203, or SEQ ID NO: 223.

2. A composition comprising: (a) a first nucleic acid comprising a trans-activating crRNA (tracrRNA) sequence, wherein the tracrRNA sequence is SEQ ID NO: 171, SEQ ID NO: 203, or SEQ ID NO: 223; and (b) a second nucleic acid comprising a guide RNA (gRNA) sequence, wherein one or more cytosine nucleotides and/or one or more uracil nucleotides of said gRNA sequence are modified nucleotides.

3. The composition of claim 2, further comprising an RNA-guided DNA endonuclease enzyme or a pharmaceutically acceptable excipient.

4. The composition of claim 3, wherein:
(a) said RNA-guided DNA endonuclease enzyme is Cas9 or Cpf1 or a Class II CRISPR endonuclease or a variant thereof;
(b) said RNA-guided DNA endonuclease enzyme is a modified Cas endonuclease; or
(c) said RNA-guided DNA endonuclease enzyme is deactivated Cas9 (dCas9) or mutated Cas9 nickase (D10A).

5. A vector comprising or encoding the nucleic acid of claim 1.

6. A pharmaceutical composition comprising (a) the nucleic acid of claim 1, or a vector comprising or encoding the nucleic acid, and (b) a pharmaceutically acceptable excipient.

7. A method of altering gene expression in a cell, the method comprising introducing into said cell the nucleic acid of claim 1.

8. The method of claim 7, furthering comprising introducing to said cell an RNA-guided DNA endonuclease enzyme.

9. The method of claim 8, wherein:
(a) said RNA-guided DNA endonuclease enzyme is Cas9 or Cpf1 or a Class II CRISPR endonuclease or a variant thereof;
(b) said RNA-guided DNA endonuclease enzyme is a modified Cas endonuclease;
(c) said RNA-guided DNA endonuclease enzyme is deactivated Cas9 (dCas9) or mutated Cas9 nickase (D10A);
(d) said RNA-guided DNA endonuclease enzyme is a conjugate comprising a Cas 9 endonuclease and a transcription regulating factor; or
(e) said RNA-guided DNA endonuclease enzyme comprises a dCas-APOBEC3A fusion protein, a dCas-VPR fusion protein or a dCas-KRAB fusion protein.

10. A method of treating a disorder in a subject in need thereof, the method comprising administering to said subject: (a) the nucleic acid of claim 1; and (b) an RNA-guided DNA endonuclease enzyme; optionally wherein said disorder is HIV, cancer, COPD, Cystic Fibrosis, heart conditions/repair, and diabetes.

11. The nucleic acid of claim 1, wherein the tracrRNA sequence is SEQ ID NO: 171.

12. The nucleic acid of claim 1, wherein the tracrRNA sequence is SEQ ID NO: 203.

13. The nucleic acid of claim 1, wherein the tracrRNA sequence is SEQ ID NO: 223.

14. The composition of claim 2, wherein the tracrRNA sequence is SEQ ID NO: 171.

15. The composition of claim 2, wherein the tracrRNA sequence is SEQ ID NO: 203.

16. The composition of claim 2, wherein the tracrRNA sequence is SEQ ID NO: 223.

* * * * *

SEQUENCE LISTING

```
<160> NUMBER OF SEQ ID NOS: 289

<210> SEQ ID NO 1
<211> LENGTH: 68
<212> TYPE: RNA
<213> ORGANISM: Streptococcus pyogenes

<400> SEQUENCE: 1
cagcauagca aguuaaaaua aggcuagucc guuaucaacu ugaaaaagug gcaccgaguc      60
ggugcuuu                                                              68

<210> SEQ ID NO 2
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
```

-continued

<400> SEQUENCE: 2
ggaggugcuc cgaaaggaac ucc                                           23

<210> SEQ ID NO 3
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 3
nnnnnnnnnn nnnnnnnnnn gtttaagagc tatgctggaa acagcatagc aagattaaat    60
aaggctagtc cgttatcaac ttgaaaaagt ggcaccgagt cggtgcttt               109

<210> SEQ ID NO 4
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 4
nnnnnnnnnn nnnnnnnnnn gtttaagagc tatgctggaa acagcatagc aagtgtaaat    60
aaggctagtc cgttatcaac ttgaaaaagt ggcaccgagt cggtgcttt               109

<210> SEQ ID NO 5
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 5
nnnnnnnnnn nnnnnnnnnn gtttatgagc tatgctggaa acagcatagc aagtataaat    60
aaggctagtc cgttatcaac ttgaaaaagt ggcaccgagt cggtgcttt               109

<210> SEQ ID NO 6
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 6
nnnnnnnnnn nnnnnnnnnn gtttatgagc tatgctggaa acagcatagc aagtgtaaat    60
aaggctagtc cgttatcaac ttgaaaaagt ggcaccgagt cggtgcttt         109

<210> SEQ ID NO 7
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 7
nnnnnnnnnn nnnnnnnnnn gtttaagagc tatgctggaa acagcatagc aagtttaaat    60
aaggctagtc cgaaatcaac ttgaaaaagt ggcaccgagt cggtgcttt              109

<210> SEQ ID NO 8
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 8
nnnnnnnnnn nnnnnnnnnn gtttaagagc tatgctggaa acagcatagc aagtttaaat    60
aaggctagtc cgggatcaac ttgaaaaagt ggcaccgagt cggtgcttt              109

<210> SEQ ID NO 9
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 9
nnnnnnnnnn nnnnnnnnnn gtttaagagc tatgctggaa acagcatagc aagtttaaag    60
aaggctagtc cgttatcaac ttgaaaaagt ggcaccgagt cggtgcttt              109

<210> SEQ ID NO 10
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 10
nnnnnnnnnn nnnnnnnnnn gtttaagagc tatgctggaa acagcatagc aagtttaaat    60
aaggcagtcc gttatcaact tgaaaaagtg caccgagtc ggtgcttt                108

```
<210> SEQ ID NO 11
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 11
nnnnnnnnnn nnnnnnnnnn gtttaagagc tatgctggaa acagcatagc aagtttaaat      60
aaggcaagtc cgttatcaac ttgaaaaagt ggcaccgagt cggtgcttt               109

<210> SEQ ID NO 12
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 12
nnnnnnnnnn nnnnnnnnnn gtttaagagc tatgctggaa acagcatagc aagtttaaat      60
aaggcgagtc cgttatcaac ttgaaaaagt ggcaccgagt cggtgcttt               109

<210> SEQ ID NO 13
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 13
nnnnnnnnnn nnnnnnnnnn gtttaagagc tatgctggaa acagcatagc aagtttaaat      60
aaggctagac cgttatcaac ttgaaaaagt ggcaccgagt cggtgcttt               109

<210> SEQ ID NO 14
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 14
nnnnnnnnnn nnnnnnnnnn gtttatgagc tatgctggaa acagcatagc aagaataaat      60
aaggctagtc cgggatcaac ttgaaaaagt ggcaccgagt cggtgcttt               109

<210> SEQ ID NO 15
<211> LENGTH: 109
<212> TYPE: DNA
```

```
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 15
nnnnnnnnnn nnnnnnnnnn gtttatgagc tatgctggaa acagcatagc aagtataaat      60
aaggctagtc cgggatcaac ttgaaaaagt ggcaccgagt cggtgcttt                 109

<210> SEQ ID NO 16
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 16
nnnnnnnnnn nnnnnnnnnn gtttatgagc tatgctggaa acagcatagc aagagtaaat      60
aaggctagtc cgggatcaac ttgaaaaagt ggcaccgagt cggtgcttt                 109

<210> SEQ ID NO 17
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 17
nnnnnnnnnn nnnnnnnnnn gtttatgagc tatgctggaa acagcatagc aagaataaat      60
aaggctagtc cgaaatcaac ttgaaaaagt ggcaccgagt cggtgcttt                 109

<210> SEQ ID NO 18
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 18
nnnnnnnnnn nnnnnnnnnn gtttatgagc tatgctggaa acagcatagc aagagtaaat      60
aaggctagtc cgaaatcaac ttgaaaaagt ggcaccgagt cggtgcttt                 109

<210> SEQ ID NO 19
<211> LENGTH: 86
<212> TYPE: DNA
<213> ORGANISM: Artificial Sequence
<220> FEATURE:
<223> OTHER INFORMATION: Description of Artificial Sequence: Synthetic
```

-continued

```
oligonucleotide

<400> SEQUENCE: 19
taatacgact cactatagga gcatagcaag tataaataag gctagaccgg gatcaacttg    60
aaaaagtggc accgagtcgg tgcttt                                        86

<210> SEQ ID NO 20
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 20
nnnnnnnnnn nnnnnnnnnn gtttatgagc tatgctggaa acagcatagc aagtataaat    60
aaggctagtc cgggatcaac ttgaaaaagt ggcaccgagt cggtgcttt              109

<210> SEQ ID NO 21
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 21
nnnnnnnnnn nnnnnnnnnn gtttatgagc tatgctggaa acagcatagc aagtataaat    60
aaggcgagac cgggatcaac ttgaaaaagt ggcaccgagt cggtgcttt              109

<210> SEQ ID NO 22
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 22
nnnnnnnnnn nnnnnnnnnn gtttatgagc tatgctggaa acagcatagc aagtataaat    60
aaggcaagac cgggatcaac ttgaaaaagt ggcaccgagt cggtgcttt              109

<210> SEQ ID NO 23
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 23
```
nnnnnnnnnn nnnnnnnnnn gtttatgagc tatgctggaa acagcatagc aagtataaat    60
aaggcagacc gggatcaact tgaaaaagtg gcaccgagtc ggtgcttt    108

<210> SEQ ID NO 24
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 24
nnnnnnnnnn nnnnnnnnnn gtttatgagc tatgctggaa acagcatagc aagtataaag    60
aaggcgagac cgggatcaac ttgaaaaagt ggcaccgagt cggtgcttt    109

<210> SEQ ID NO 25
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 25
nnnnnnnnnn nnnnnnnnnn gtttatgagc tatgctggaa acagcatagc aagtataaag    60
aaggcaagac cgggatcaac ttgaaaaagt ggcaccgagt cggtgcttt    109

<210> SEQ ID NO 26
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 26
nnnnnnnnnn nnnnnnnnnn gtttatgagc tatgctggaa acagcatagc aagtataaag    60
aaggcagacc gggatcaact tgaaaaagtg gcaccgagtc ggtgcttt    108

<210> SEQ ID NO 27
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 27
nnnnnnnnnn nnnnnnnnnn ttttatgagc tatgctggaa acagcatagc aagtataaag    60

```
aaggcgagac cgggatcaac ttgaaaaagt ggcaccgagt cggtgcttt              109
```

<210> SEQ ID NO 28
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 28

```
nnnnnnnnnn nnnnnnnnnn ttttatgagc tatgctggaa acagcatagc aagtataaag    60
aaggcaagac cgggatcaac ttgaaaaagt ggcaccgagt cggtgcttt              109
```

<210> SEQ ID NO 29
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 29

```
nnnnnnnnnn nnnnnnnnnn ttttatgagc tatgctggaa acagcatagc aagtataaaa    60
aaggcgagac cgggatcaac ttgaaaaagt ggcaccgagt cggtgcttt              109
```

<210> SEQ ID NO 30
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 30

```
nnnnnnnnnn nnnnnnnnnn ttttatgagc tatgctggaa acagcatagc aagtataaaa    60
aaggcaagac cgggatcaac ttgaaaaagt ggcaccgagt cggtgcttt              109
```

<210> SEQ ID NO 31
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 31

```
nnnnnnnnnn nnnnnnnnnn ctttatgagc tatgctggaa acagcatagc aagtataaag    60
aaggcgagac cgggatcaac ttgaaaaagt ggcaccgagt cggtgcttt              109
```

```
<210> SEQ ID NO 32
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 32
nnnnnnnnnn nnnnnnnnnn ctttatgagc tatgctggaa acagcatagc aagtataaag     60
aaggcaagac cgggatcaac ttgaaaaagt ggcaccgagt cggtgcttt                109

<210> SEQ ID NO 33
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 33
nnnnnnnnnn nnnnnnnnnn gtttatgagc tttgctggaa acagcaaagc aagtataaat     60
aaggcaagac cgggatcaac ttgaaaaagt ggcaccgagt cggtgcttt                109

<210> SEQ ID NO 34
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 34
nnnnnnnnnn nnnnnnnnnn gtttatgagc tttgctggaa acagcaaagc aagtataaat     60
aaggcaagac cgggaacaac ttgaaaaagt ggcaccgagt cggtgcttt                109

<210> SEQ ID NO 35
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 35
nnnnnnnnnn nnnnnnnnnn gtttatgagc tttgctggaa acagcaaagc aagtataaat     60
aaggcaagac cgggaacaac ttgaaaaagt ggcaccgaga cggtgcttt                109

<210> SEQ ID NO 36
<211> LENGTH: 109
<212> TYPE: DNA
```

```
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 36
nnnnnnnnnn nnnnnnnnnn gtttatgagc tttgctggaa acagcaaagc aagtataaat      60
aaggcaagac cgggaacaac ttgaaaaagt ggcaccgaga cggagcttt               109

<210> SEQ ID NO 37
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 37
nnnnnnnnnn nnnnnnnnnn gtttatgagc tttgctggaa acagcaaagc aagtataaat      60
aaggcaagac cgggaacaac ttgaaaaagt ggcaccgagg cggtgcttt               109

<210> SEQ ID NO 38
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 38
nnnnnnnnnn nnnnnnnnnn gtttatgagc tttgctggaa acagcaaagc aagtataaat      60
aaggcaagac cgggaacaac ttgaaaaagt ggcaccgagg cggagcttt               109

<210> SEQ ID NO 39
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 39
nnnnnnnnnn nnnnnnnnnn gtttatgagc tttgctggaa acagcaaagc aagtataaat      60
aaggcaagac cgggagcaac ttgaaaaagt ggcaccgagt cggtgcttt               109

<210> SEQ ID NO 40
<211> LENGTH: 109
<212> TYPE: DNA
<213> ORGANISM: Artificial Sequence
<220> FEATURE:
<223> OTHER INFORMATION: Description of Artificial Sequence: Synthetic
```

```
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 40
nnnnnnnnnn nnnnnnnnnn gtttatgagc tttgctggaa acagcaaagc aagtataaat      60
aaggcaagac cgggagcaac ttgaaaaagt ggcaccgaga cggtgcttt                 109

<210> SEQ ID NO 41
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 41
nnnnnnnnnn nnnnnnnnnn gtttatgagc tttgctggaa acagcaaagc aagtataaat      60
aaggcaagac cgggagcaac ttgaaaaagt ggcaccgaga cggagcttt                 109

<210> SEQ ID NO 42
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 42
nnnnnnnnnn nnnnnnnnnn gtttatgagc tttgctggaa acagcaaagc aagtataaat      60
aaggcaagac cgggagcaac ttgaaaaagt ggcaccgagg cggtgcttt                 109

<210> SEQ ID NO 43
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 43
nnnnnnnnnn nnnnnnnnnn gtttatgagc tttgctggaa acagcaaagc aagtataaat      60
aaggcaagac cgggagcaac ttgaaaaagt ggcaccgagg cggagcttt                 109

<210> SEQ ID NO 44
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
```

<222> LOCATION: (1)..(20)
<223> OTHER INFORMATION: n is a, c, g, or t

<400> SEQUENCE: 44
nnnnnnnnnn nnnnnnnnnn gtttatgagc tttgctggaa acagcaaagc aagtataaat    60
aaggcaagac cgggatcaac ttgaaaaagt ggcaccgagt cggagcttt              109

<210> SEQ ID NO 45
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 45
nnnnnnnnnn nnnnnnnnnn gtttatgagc tatgctggaa acagcatagc aagtataaat    60
aaggcaagac cgggaacaac ttgaaaaagt ggcaccgagt cggtgcttt              109

<210> SEQ ID NO 46
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 46
nnnnnnnnnn nnnnnnnnnn gtttatgagc tatgctggaa acagcatagc aagtataaat    60
aaggcaagac cgggagcaac ttgaaaaagt ggcaccgagt cggtgcttt              109

<210> SEQ ID NO 47
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 47
nnnnnnnnnn nnnnnnnnnn gtttatgagc tatgctggaa acagcatagc aagtataaac    60
aaggcaagac cgggatcaac ttgaaaaagt ggcaccgagt cggtgcttt              109

<210> SEQ ID NO 48
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 48
nnnnnnnnnn nnnnnnnnnn gtttaagagc tatgctggaa acagcatagc aagtttaaac    60
aaggctagtc cgttatcaac ttgaaaaagt ggcaccgagt cggtgcttt              109

<210> SEQ ID NO 49
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 49
nnnnnnnnnn nnnnnnnnnn gtttatgagc tatgctggaa acagcatagc aagtataaat    60
aaggcaagac cgggatcaac ttgaaaaagt ggcaccgaga cggtgcttt              109

<210> SEQ ID NO 50
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 50
nnnnnnnnnn nnnnnnnnnn gtttatgagc tatgctggaa acagcatagc aagtataaat    60
aaggcaagac cgggatcaac ttgaaaaagt ggcaccgagg cggtgcttt              109

<210> SEQ ID NO 51
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 51
nnnnnnnnnn nnnnnnnnnn gtttatgagc tatgctggaa acagcatagc aagtataaat    60
aaggcaagac cgggatcaac ttgaaaaagt ggcaccgagt cggagcttt              109

<210> SEQ ID NO 52
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 52
nnnnnnnnnn nnnnnnnnnn gtttatgagc tttgctggaa acagcaaagc aagtataaat    60
aaggcaagac cgggagcaac atgaaaaagt ggcaccgagg cggtgcttt            109

<210> SEQ ID NO 53
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 53
nnnnnnnnnn nnnnnnnnnn gtttatgagc tttgctggaa acagcaaagc aagtataaat   60
aaggcaagac cgggagcaac acgaaagagt ggcaccgagg cggtgcttt            109

<210> SEQ ID NO 54
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 54
nnnnnnnnnn nnnnnnnnnn gtttatgagc tttgctggaa acagcaaagc aagtataaat   60
aaggcaagac cgggagcagc acgaaagagc ggcaccgagg cggtgcttt            109

<210> SEQ ID NO 55
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 55
nnnnnnnnnn nnnnnnnnnn gtttatgagc tttgctggaa acagcaaagc aagtataaat   60
aaggcaagac cgggagcagc acgaaagagc ggcaccgagg cggagcttt            109

<210> SEQ ID NO 56
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 56
nnnnnnnnnn nnnnnnnnnn gtttatgagc tttgctggaa acagcaaagc aagtataaat   60
aaggcaagac cgggagcacc acgaaagagg ggcaccgagg cggtgcttt            109

```
<210> SEQ ID NO 57
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 57
nnnnnnnnnn nnnnnnnnnn gtttatgagc tttgctggaa acagcaaagc aagtataaat     60
aaggcaagac cgggagcacc acgaaagagg ggcaccgagg cggagcttt              109

<210> SEQ ID NO 58
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 58
nnnnnnnnnn nnnnnnnnnn gtttatgagc tttgctggaa acagcaaagc aagtataaat     60
aaggcaagac cgggagcaac ctgaaaaggt ggcaccgagg cggtgcttt              109

<210> SEQ ID NO 59
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 59
nnnnnnnnnn nnnnnnnnnn gtttatgagc tttgctggaa acagcaaagc aagtataaat     60
aaggcaagac cgggagcaac ccgaaagggt ggcaccgagg cggtgcttt              109

<210> SEQ ID NO 60
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 60
nnnnnnnnnn nnnnnnnnnn gtttatgagc tttgctggaa acagcaaagc aagtataaat     60
aaggcaagac cgggagcagc ccgaaagggc ggcaccgagg cggtgcttt              109

<210> SEQ ID NO 61
<211> LENGTH: 109
```

```
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 61
nnnnnnnnnn nnnnnnnnnn gtttatgagc tttgctggaa acagcaaagc aagtataaat    60
aaggcaagac cgggagcagc ccgaaagggc ggcaccgagg cggagcttt              109

<210> SEQ ID NO 62
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 62
nnnnnnnnnn nnnnnnnnnn gtttatgagc tttgctggaa acagcaaagc aagtataaat    60
aaggcaagac cgggagcacc ccgaaagggg ggcaccgagg cggtgcttt              109

<210> SEQ ID NO 63
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 63
nnnnnnnnnn nnnnnnnnnn gtttatgagc tttgctggaa acagcaaagc aagtataaat    60
aaggcaagac cgggagcacc ccgaaagggg ggcaccgagg cggagcttt              109

<210> SEQ ID NO 64
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 64
nnnnnnnnnn nnnnnnnnnn gtttaagagc tatgctggaa acagcatagc aagtttaaat    60
aaggctagtc cgttatcaac ttgaaaaagt ggcaccgagt cggtgcaaa              109

<210> SEQ ID NO 65
<211> LENGTH: 109
<212> TYPE: DNA
<213> ORGANISM: Artificial Sequence
<220> FEATURE:
```

```
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 65
nnnnnnnnnn nnnnnnnnnn gtttaagagc tatgctggaa acagcatagc aagtttaaat    60
aaggctagtc cgttatcaac ttgaaaaagt ggcaccgagt cggtgcatt              109

<210> SEQ ID NO 66
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 66
nnnnnnnnnn nnnnnnnnnn gtttaagagc tatgctggaa acagcatagc aagtttaaat    60
aaggctagtc cgttatcaac ttgaaaaagt ggcaccgagt cggtgcaat              109

<210> SEQ ID NO 67
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 67
nnnnnnnnnn nnnnnnnnnn gtttaagagc tatgctggaa acagcatagc aagtttaaat    60
aaggctagtc cgttatcaac ttgaaaaagt ggcaccgagt cggtgcata              109

<210> SEQ ID NO 68
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 68
nnnnnnnnnn nnnnnnnnnn gtttaagagc tatgctggaa acagcatagc aagtttaaat    60
aaggctagtc cgttatcaac ttgaaaaagt ggcaccgagt cggtgctat              109

<210> SEQ ID NO 69
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
```

```
<221> NAME/KEY: misc_feature
<222> LOCATION: (1)..(20)
<223> OTHER INFORMATION: n is a, c, g, or t

<400> SEQUENCE: 69
nnnnnnnnnn nnnnnnnnnn gtttaagagc tatgctggaa acagcatagc aagtttaaat      60
aaggctagtc cgttatcaac ttgaaaaagt ggcaccgagt cggtgctaa                 109

<210> SEQ ID NO 70
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 70
nnnnnnnnnn nnnnnnnnnn gtttaagagc tatgctggaa acagcatagc aagtttaaat      60
aaggctagtc cgttatcaac ttgaaaaagt ggcaccgagt cggtgctta                 109

<210> SEQ ID NO 71
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 71
nnnnnnnnnn nnnnnnnnnn gtttaagagc tatgctggaa acagcatagc aagtttaaat      60
aaggctagtc cgttatcaac ttgaaaaagt ggcaccgagt cggtgcggg                 109

<210> SEQ ID NO 72
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 72
nnnnnnnnnn nnnnnnnnnn gtttaagagc tatgctggaa acagcatagc aagtttaaat      60
aaggctagtc cgttatcaac ttgaaaaagt ggcaccgagt cggtgcggt                 109

<210> SEQ ID NO 73
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t
```

<400> SEQUENCE: 73
nnnnnnnnnn nnnnnnnnnn gtttaagagc tatgctggaa acagcatagc aagtttaaat    60
aaggctagtc cgttatcaac ttgaaaaagt ggcaccgagt cggtgcgtg                109

<210> SEQ ID NO 74
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 74
nnnnnnnnnn nnnnnnnnnn gtttaagagc tatgctggaa acagcatagc aagtttaaat    60
aaggctagtc cgttatcaac ttgaaaaagt ggcaccgagt cggtgcgtt                109

<210> SEQ ID NO 75
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 75
nnnnnnnnnn nnnnnnnnnn gtttaagagc tatgctggaa acagcatagc aagtttaaat    60
aaggctagtc cgttatcaac ttgaaaaagt ggcaccgagt cggtgctgt                109

<210> SEQ ID NO 76
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 76
nnnnnnnnnn nnnnnnnnnn gtttaagagc tatgctggaa acagcatagc aagtttaaat    60
aaggctagtc cgttatcaac ttgaaaaagt ggcaccgagt cggtgctgg                109

<210> SEQ ID NO 77
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 77

-continued nnnnnnnnnn nnnnnnnnnn gtttaagagc tatgctggaa acagcatagc aagtttaaat    60
aaggctagtc cgttatcaac ttgaaaaagt ggcaccgagt cggtgcttg                109

<210> SEQ ID NO 78
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 78
nnnnnnnnnn nnnnnnnnnn gtttaagagc tatgctggaa acagcatagc aagtttaaat    60
aaggctagtc cgttatcaac ttgaaaaagt ggcaccgagt cggtgcccc                109

<210> SEQ ID NO 79
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 79
nnnnnnnnnn nnnnnnnnnn gtttatgagc tttgctggaa acagcaaagc aagtataaat    60
aaggcaagac cgggaacaac ttgaaaaagt ggcaccgaga cggtgcaaa                109

<210> SEQ ID NO 80
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 80
nnnnnnnnnn nnnnnnnnnn gtttatgagc tttgctggaa acagcaaagc aagtataaat    60
aaggcaagac cgggaacaac ttgaaaaagt ggcaccgagg cggtgcttt                109

<210> SEQ ID NO 81
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 81
nnnnnnnnnn nnnnnnnnnn gtttatgagc tttgctggaa acagcaaagc aagtataaat    60
aaggcaagac cgggaacaac ttgaaaaagt ggcaccgagg cggtgcaaa                109

```
<210> SEQ ID NO 82
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 82
nnnnnnnnnn nnnnnnnnnn gtttatgagc tttgctggaa acagcaaagc aagaataaat      60
aaggcaagac cgggaacaac ttgaaaaagt ggcaccgaga cggtgctttt                109

<210> SEQ ID NO 83
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 83
nnnnnnnnnn nnnnnnnnnn gtttatgagc tttgctggaa acagcaaagc aagaataaat      60
aaggcaagac cgggaacaac ttgaaaaagt ggcaccgaga cggtgcaaa                 109

<210> SEQ ID NO 84
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 84
nnnnnnnnnn nnnnnnnnnn gtttatgagc tttgctggaa acagcaaagc aagaataaat      60
aaggcaagac cgggaacaac ttgaaaaagt ggcaccgagg cggtgcaaa                 109

<210> SEQ ID NO 85
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 85
nnnnnnnnnn nnnnnnnnnn gtttatgagc tttgctggaa acagcaaagc aagaataaat      60
aaggcaagac cgggaacaac ccgaaagggt ggcaccgaga cggtgcttt                 109

<210> SEQ ID NO 86
```

```
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 86
nnnnnnnnnn nnnnnnnnnn gtttatgagc tttgctggaa acagcaaagc aagaataaat      60
aaggcaagac cgggaacaac ccgaaagggt ggcaccgagg cggtgctttt                109

<210> SEQ ID NO 87
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 87
nnnnnnnnnn nnnnnnnnnn gtttatgagc tttgctggaa acagcaaagc aagaataaat      60
aaggcaagac cgggaacaac ccgaaagggt ggcaccgaga cggtgcaaa                 109

<210> SEQ ID NO 88
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 88
nnnnnnnnnn nnnnnnnnnn gtttatgagc tttgctggaa acagcaaagc aagaataaat      60
aaggcaagac cgggaacaac ccgaaagggt ggcaccgagg cggtgcaaa                 109

<210> SEQ ID NO 89
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 89
nnnnnnnnnn nnnnnnnnnn gtttatgagc tttgctggaa acagcaaagc aagtataaat      60
aaggcaagac cgggaacaac ccgaaagggt ggcaccgaga cggtgcttt                 109

<210> SEQ ID NO 90
<211> LENGTH: 109
<212> TYPE: DNA
<213> ORGANISM: Artificial Sequence
```

```
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 90
nnnnnnnnnn nnnnnnnnnn gtttatgagc tttgctggaa acagcaaagc aagtataaat    60
aaggcaagac cgggaacaac ccgaaagggt ggcaccgagg cggtgcttt               109

<210> SEQ ID NO 91
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 91
nnnnnnnnnn nnnnnnnnnn gtttatgagc tttgctggaa acagcaaagc aagtataaat    60
aaggcaagac cgggaacagc ccgaaagggc ggcaccgaga cggtgcttt               109

<210> SEQ ID NO 92
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 92
nnnnnnnnnn nnnnnnnnnn gtttatgagc tttgctggaa acagcaaagc aagtataaat    60
aaggcaagac cgggaacagc ccgaaagggc ggcaccgagg cggtgcttt               109

<210> SEQ ID NO 93
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 93
nnnnnnnnnn nnnnnnnnnn gtttatgagc tttgctggaa acagcaaagc aagtataaat    60
aaggcaagac cgggaacagc ccgaaagggc ggccccgaga cggggcttt               109

<210> SEQ ID NO 94
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
```

```
<220> FEATURE:
<221> NAME/KEY: misc_feature
<222> LOCATION: (1)..(20)
<223> OTHER INFORMATION: n is a, c, g, or t

<400> SEQUENCE: 94
nnnnnnnnnn nnnnnnnnnn gtttatgagc tttgctggaa acagcaaagc aagtataaat      60
aaggcaagac cgggaacagc ccgaaagggc ggccccgagg cggggcttt                 109

<210> SEQ ID NO 95
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 95
nnnnnnnnnn nnnnnnnnnn gtttatgagc tttgctggaa acagcaaagc aagtataaat      60
aaggcaagac cgggaacagc ccgaaagggc ggcgccgaga cggcgcttt                 109

<210> SEQ ID NO 96
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 96
nnnnnnnnnn nnnnnnnnnn gtttatgagc tttgctggaa acagcaaagc aagtataaat      60
aaggcaagac cgggaacagc ccgaaagggc ggcgccgagg cggcgcttt                 109

<210> SEQ ID NO 97
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 97
nnnnnnnnnn nnnnnnnnnn gtttatgagc tttgctggaa acagcaaagc aagtataaat      60
aaggcaagac cgggaacacc ccgaaagggg ggcaccgaga cggtgcttt                 109

<210> SEQ ID NO 98
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
```

<223> OTHER INFORMATION: n is a, c, g, or t

<400> SEQUENCE: 98
nnnnnnnnnn nnnnnnnnnn gtttatgagc tttgctggaa acagcaaagc aagtataaat    60
aaggcaagac cgggaacacc ccgaaagggg ggccccgaga cggggcttt               109

<210> SEQ ID NO 99
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 99
nnnnnnnnnn nnnnnnnnnn gtttatgagc tttgctggaa acagcaaagc aagtataaat    60
aaggcaagac cgggaacacc ccgaaagggg ggccccgagg cggggcttt               109

<210> SEQ ID NO 100
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 100
nnnnnnnnnn nnnnnnnnnn gtttatgagc tttgctggaa acagcaaagc aagtataaat    60
aaggcaagac cgggaacacc ccgaaagggg ggcgccgaga cggcgcttt               109

<210> SEQ ID NO 101
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 101
nnnnnnnnnn nnnnnnnnnn gtttatgagc tttgctggaa acagcaaagc aagtataaat    60
aaggcaagac cgggaacacc ccgaaagggg ggcgccgagg cggcgcttt               109

<210> SEQ ID NO 102
<211> LENGTH: 109
<212> TYPE: DNA
<213> ORGANISM: Artificial Sequence
<220> FEATURE:
<223> OTHER INFORMATION: description of artificial sequence: synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 102
nnnnnnnnnn nnnnnnnnnn gtttatgagc tttgctggaa acagcaaagc aagtataaat    60
aaggcaagac cgggaacagc ccgaaagggc ggcgccgaga cggcgcccc               109

<210> SEQ ID NO 103
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 103
nnnnnnnnnn nnnnnnnnnn gtttctgagc tttgctggaa acagcaaagc aagtagaaat    60
aaggcaagac cgggaacagc ccgaaagggc ggcgccgaga cggcgcttt               109

<210> SEQ ID NO 104
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 104
nnnnnnnnnn nnnnnnnnnn gtttctgagc tttgctggaa acagcaaagc aagtagaaat    60
aaggcaagac cgggaacagc ccgaaagggc ggcgccgaga cggcgcccc               109

<210> SEQ ID NO 105
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 105
nnnnnnnnnn nnnnnnnnnn gtttctgagc tatgctggaa acagcatagc aagtagaaat    60
aaggcaagac cgggatcaac ttgaaaaagt ggcaccgagt cggtgcttt               109

<210> SEQ ID NO 106
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 106
nnnnnnnnnn nnnnnnnnnn gtttctgagc tttgctggaa acagcaaagc aagtagaaat    60
aaggcaagac cgggatcaac ttgaaaaagt ggcaccgagt cggtgctttt    109

<210> SEQ ID NO 107
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 107
nnnnnnnnnn nnnnnnnnnn gtttctgagc tttgctggaa acagcaaagc aagtagaaat    60
aaggcaagac cgggaacaac ttgaaaaagt ggcaccgagg cggtgcttt    109

<210> SEQ ID NO 108
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 108
nnnnnnnnnn nnnnnnnnnn gtttctgagc tttgctggaa acagcaaagc aagtagaaat    60
aaggcaagac cgggaacaac ttgaaaaagt ggcaccgaga cggtgcttt    109

<210> SEQ ID NO 109
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 109
nnnnnnnnnn nnnnnnnnnn gttttgagc tttgctggaa acagcaaagc aagtaaaaat    60
aaggcaagac cgggaacagc ccgaaagggc ggcgccgaga cggcgcttt    109

<210> SEQ ID NO 110
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 110
nnnnnnnnnn nnnnnnnnnn gttttgagc tttgctggaa acagcaaagc aagtaaaaat    60
aaggcaagac cgggaacagc ccgaaagggc ggcgccgaga cggcgcccc    109

```
<210> SEQ ID NO 111
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 111
nnnnnnnnnn nnnnnnnnnn gttttttgagc tatgctggaa acagcatagc aagtaaaaat       60
aaggcaagac cgggatcaac ttgaaaaagt ggcaccgagt cggtgcttt                   109

<210> SEQ ID NO 112
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 112
nnnnnnnnnn nnnnnnnnnn gttttttgagc tttgctggaa acagcaaagc aagtaaaaat       60
aaggcaagac cgggatcaac ttgaaaaagt ggcaccgagt cggtgcttt                   109

<210> SEQ ID NO 113
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 113
nnnnnnnnnn nnnnnnnnnn gttttttgagc tttgctggaa acagcaaagc aagtaaaaat       60
aaggcaagac cgggaacaac ttgaaaaagt ggcaccgagg cggtgcttt                   109

<210> SEQ ID NO 114
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 114
nnnnnnnnnn nnnnnnnnnn gttttttgagc tttgctggaa acagcaaagc aagtaaaaat       60
aaggcaagac cgggaacaac ttgaaaaagt ggcaccgaga cggtgcttt                   109

<210> SEQ ID NO 115
<211> LENGTH: 109
<212> TYPE: DNA
```

```
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 115
nnnnnnnnnn nnnnnnnnnn gtttttgagc tatgctggaa acagcatagc aagtaaaaat      60
aaggctagtc cgggatcaac ttgaaaaagt ggcaccgagt cggtgcttt                 109

<210> SEQ ID NO 116
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 116
nnnnnnnnnn nnnnnnnnnn gtttcagagc tatgctgaaa agcatagcaa gttgaaataa     60
ggctagtccg ttatcaactt gaaaagtgg caccgagtcg gtgctttt                   109

<210> SEQ ID NO 117
<211> LENGTH: 107
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 117
nnnnnnnnnn nnnnnnnnnn gtttctgagc tttgctgaaa agcaaagcaa gtagaaataa     60
ggcaagaccg ggaacagccc gaaagggcgg cgccgagacg gcgcttt                   107

<210> SEQ ID NO 118
<211> LENGTH: 107
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 118
nnnnnnnnnn nnnnnnnnnn gtttctgagc tttgctgaaa agcaaagcaa gtagaaataa     60
ggcaagaccg ggaacagccc gaaagggcgg cgccgagacg gcgcccc                   107

<210> SEQ ID NO 119
<211> LENGTH: 107
<212> TYPE: DNA
<213> ORGANISM: Artificial Sequence
<220> FEATURE:
<223> OTHER INFORMATION: Description of Artificial Sequence: Synthetic
``` polynucleotide
<220> FEATURE:
<221> NAME/KEY: misc_feature
<222> LOCATION: (1)..(20)
<223> OTHER INFORMATION: n is a, c, g, or t

<400> SEQUENCE: 119
nnnnnnnnnn nnnnnnnnnn gtttctgagc tatgctgaaa agcatagcaa gtagaaataa      60
ggcaagaccg ggatcaactt gaaaaagtgg caccgagtcg gtgcttt                    107

<210> SEQ ID NO 120
<211> LENGTH: 107
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 120
nnnnnnnnnn nnnnnnnnnn gtttctgagc tttgctgaaa agcaaagcaa gtagaaataa      60
ggcaagaccg ggatcaactt gaaaaagtgg caccgagtcg gtgcttt                    107

<210> SEQ ID NO 121
<211> LENGTH: 107
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 121
nnnnnnnnnn nnnnnnnnnn gtttctgagc tttgctgaaa agcaaagcaa gtagaaataa      60
ggcaagaccg ggaacaactt gaaaaagtgg caccgaggcg gtgcttt                    107

<210> SEQ ID NO 122
<211> LENGTH: 107
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 122
nnnnnnnnnn nnnnnnnnnn gtttctgagc tttgctgaaa agcaaagcaa gtagaaataa      60
ggcaagaccg ggaacaactt gaaaaagtgg caccgagacg gtgcttt                    107

<210> SEQ ID NO 123
<211> LENGTH: 107
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 123
nnnnnnnnnn nnnnnnnnnn gtttttgagc tttgctgaaa agcaaagcaa gtaaaaataa    60
ggcaagaccg ggaacagccc gaaagggcgg cgccgagacg gcgcttt               107

<210> SEQ ID NO 124
<211> LENGTH: 107
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 124
nnnnnnnnnn nnnnnnnnnn gttttgagc tttgctgaaa agcaaagcaa gtaaaaataa    60
ggcaagaccg ggaacagccc gaaagggcgg cgccgagacg gcgcccc               107

<210> SEQ ID NO 125
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 125
agcauagcaa guuuaaauaa ggcuaguccg uuaucaacuu gaaaaagugg caccgagucg    60
gugcuuu                                                            67

<210> SEQ ID NO 126
<211> LENGTH: 36
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or u

<400> SEQUENCE: 126
nnnnnnnnnn nnnnnnnnnn guuuaagagc uaugcu                             36

<210> SEQ ID NO 127
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 127
agcauagcaa guauaaauaa ggcuaguccg ggaucaacuu gaaaaagugg caccgagucg    60
gugcuuu                                                            67

<210> SEQ ID NO 128
<211> LENGTH: 36
<212> TYPE: RNA

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(20)
<223> OTHER INFORMATION: n is a, c, g, or u

<400> SEQUENCE: 128
nnnnnnnnnn nnnnnnnnnn guuuaugagc uaugcu                                 36

<210> SEQ ID NO 129
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 129
agcaaagcaa guagaaauaa ggcaagaccg ggaacaacuu gaaaaagugg caccgaggcg       60
gugcuuu                                                                 67

<210> SEQ ID NO 130
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(20)
<223> OTHER INFORMATION: n is a, c, g, or u

<400> SEQUENCE: 130
nnnnnnnnnn nnnnnnnnnn guuucugagc uuugcu                                 36

<210> SEQ ID NO 131
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 131
agcaaagcaa guagaaauaa ggcaagaccg ggaacaaccc gaaagggugg caccgaggcg       60
gugcuuu                                                                 67

<210> SEQ ID NO 132
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(20)
<223> OTHER INFORMATION: n is a, c, g, or u

<400> SEQUENCE: 132
nnnnnnnnnn nnnnnnnnnn guuucugagc uuugcu                                 36

<210> SEQ ID NO 133
```

```
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 133
agcaaagcaa guagaaauaa ggcaagaccg ggaacagccc gaaagggcgg cgccgaggcg      60
gcgcaaa                                                               67

<210> SEQ ID NO 134
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(20)
<223> OTHER INFORMATION: n is a, c, g, or u

<400> SEQUENCE: 134
nnnnnnnnnn nnnnnnnnnn guuucugagc uuugcu                                36

<210> SEQ ID NO 135
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 135
agcauagcaa guauaaauaa ggcuagaccg ggaucaacuu gaaaaagugg caccgagucg      60
gugcuuu                                                               67

<210> SEQ ID NO 136
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(20)
<223> OTHER INFORMATION: n is a, c, g, or u

<400> SEQUENCE: 136
nnnnnnnnnn nnnnnnnnnn guuuaugagc uaugcu                                36

<210> SEQ ID NO 137
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 137
agcauagcaa guuuaaauaa ggcuagaccg uuaucaacuu gaaaaagugg caccgagucg      60
gugcuuu                                                               67

<210> SEQ ID NO 138
```

```
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(20)
<223> OTHER INFORMATION: n is a, c, g, or u

<400> SEQUENCE: 138
nnnnnnnnnn nnnnnnnnnn guuuaagagc uaugcu                                  36

<210> SEQ ID NO 139
<211> LENGTH: 112
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(23)
<223> OTHER INFORMATION: a, c, u, g, unknown or other. This region may
      encompass 20-23 nucleotides

<400> SEQUENCE: 139
nnnnnnnnnn nnnnnnnnnn nnnguuuuag agcuaugcug gaaacagcau agcaaguuaa        60
aauaaggcua guccguuauc aacuugaaaa aguggcaccg agucggugcu uu               112

<210> SEQ ID NO 140
<211> LENGTH: 144
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(23)
<223> OTHER INFORMATION: a, c, u, g, unknown or other. This region may
      encompass 20-23 nucleotides

<400> SEQUENCE: 140
nnnnnnnnnn nnnnnnnnnn nnnguuguag cucccuuucu cauuucggaa acgaaaugag        60
aaccguugcu acaauaaggc cgucugaaaa gaugugccgc aacgcucugc cccuuaaagc       120
uucugcuuua aggggcaucg uuua                                              144

<210> SEQ ID NO 141
<211> LENGTH: 114
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(23)
<223> OTHER INFORMATION: a, c, u, g, unknown or other. This region may
      encompass 20-23 nucleotides

<400> SEQUENCE: 141
nnnnnnnnnn nnnnnnnnnn nnnguuuuag uacucuguaa uuugaaaaaa uuacagaauc        60
uacuaaaaca aggcaaaaug ccguguuuau cucgucaacu uguuggcgag auuu             114

<210> SEQ ID NO 142
```

```
<211> LENGTH: 119
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(23)
<223> OTHER INFORMATION: a, c, u, g, unknown or other. This region may
      encompass 20-23 nucleotides

<400> SEQUENCE: 142
nnnnnnnnnn nnnnnnnnnn nnnguuuuug uacucucaag auucaauaau cuugcagaag    60
cuacaaagau aaggcuucau gccgaaauca acacccuguc auuuauggc agguguuu      119

<210> SEQ ID NO 143
<211> LENGTH: 118
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(23)
<223> OTHER INFORMATION: a, c, u, g, unknown or other. This region may
      encompass 20-23 nucleotides

<400> SEQUENCE: 143
nnnnnnnnnn nnnnnnnnnn nnnguuuuag agcuguguug uuugttaaaa caacacagcg    60
aguuaaaaua aggcuuaguc cguacucaac uugaaaaggu ggcaccgauu cgguguuu     118

<210> SEQ ID NO 144
<211> LENGTH: 99
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(23)
<223> OTHER INFORMATION: a, c, u, g, unknown or other. This region may
      encompass 20-23 nucleotides

<400> SEQUENCE: 144
nnnnnnnnnn nnnnnnnnnn nnnguuuuag ucccugaaaa gggacuaaaa uaaagaguuu    60
gcgggacucu gcggggguuac aaucccuaa aaccgcuuu                           99

<210> SEQ ID NO 145
<211> LENGTH: 141
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(23)
<223> OTHER INFORMATION: a, c, u, g, unknown or other. This region may
      encompass 20-23 nucleotides

<400> SEQUENCE: 145
nnnnnnnnnn nnnnnnnnnn nnngucauag uuccccugag aaaucagggu uacuaugaua    60
agggcuuucu gccuaaggca gacugacccg cggcguuggg gaucgccugu cgcccgcuuu   120
uggcgggcau uccccauccu u                                             141
```

<210> SEQ ID NO 146
<211> LENGTH: 96
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: misc_feature
<222> LOCATION: (1)..(23)
<223> OTHER INFORMATION: a, c, u, g, unknown or other. This region may
encompass 20-23 nucleotides

<400> SEQUENCE: 146
nnnnnnnnnn nnnnnnnnnn nnnguuucag uugcgccgaa aggcgcucug uaaucauuua    60
aaaguauuuu gaacggaccu cuguuugaca cgucug                              96

<210> SEQ ID NO 147
<211> LENGTH: 43
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: misc_feature
<222> LOCATION: (21)..(43)
<223> OTHER INFORMATION: a, c, u, g, unknown or other. This region may
encompass 20-23 nucleotides

<400> SEQUENCE: 147
uaauuucuac uguuguagau nnnnnnnnnn nnnnnnnnnn nnn                      43

<210> SEQ ID NO 148
<211> LENGTH: 43
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: misc_feature
<222> LOCATION: (21)..(43)
<223> OTHER INFORMATION: a, c, u, g, unknown or other. This region may
encompass 20-23 nucleotides

<400> SEQUENCE: 148
uaauuucuac ucuuguagau nnnnnnnnnn nnnnnnnnnn nnn                      43

<210> SEQ ID NO 149
<211> LENGTH: 43
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: misc_feature
<222> LOCATION: (21)..(43)
<223> OTHER INFORMATION: a, c, u, g, unknown or other. This region may
encompass 20-23 nucleotides

<400> SEQUENCE: 149
uaauuucuac uauuguagau nnnnnnnnnn nnnnnnnnnn nnn                      43

<210> SEQ ID NO 150
<211> LENGTH: 44
<212> TYPE: RNA

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (22)..(44)
<223> OTHER INFORMATION: a, c, u, g, unknown or other. This region may
      encompass 20-23 nucleotides

<400> SEQUENCE: 150
uaauuucuac ucuuuguaga unnnnnnnnn nnnnnnnnnn nnnn                    44

<210> SEQ ID NO 151
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (20)..(42)
<223> OTHER INFORMATION: a, c, u, g, unknown or other. This region may
      encompass 20-23 nucleotides

<400> SEQUENCE: 151
uaauuucuac uuuguagaun nnnnnnnnnn nnnnnnnnnn nn                      42

<210> SEQ ID NO 152
<211> LENGTH: 44
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (22)..(44)
<223> OTHER INFORMATION: a, c, u, g, unknown or other. This region may
      encompass 20-23 nucleotides

<400> SEQUENCE: 152
uaauuucuac uguuuguaga unnnnnnnnn nnnnnnnnnn nnnn                    44

<210> SEQ ID NO 153
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (21)..(43)
<223> OTHER INFORMATION: a, c, u, g, unknown or other. This region may
      encompass 20-23 nucleotides

<400> SEQUENCE: 153
uaauuucuac uucgguagau nnnnnnnnnn nnnnnnnnnn nnn                     43

<210> SEQ ID NO 154
<211> LENGTH: 65
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 154
```

```
cauagcaagu uuaaauaagg cuaguccguu aucaacuuga aaaaguggca ccgagucggu    60
gcuuu                                                                65

<210> SEQ ID NO 155
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 155
agcauagcaa guuuaaauaa ggcuaguccg uuaucaacuu gaaaaagugg caccgagucg    60
gugcuuu                                                              67

<210> SEQ ID NO 156
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 156
agcauagcaa guuuaaauaa ggcuaguccg uuaucaacuu gaaaaagugg caccgagucg    60
gugcuuu                                                              67

<210> SEQ ID NO 157
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 157
agcauagcaa guuuaaauaa ggcuaguccg uuaucaacuu gaaaaagugg caccgagucg    60
gugcuuu                                                              67

<210> SEQ ID NO 158
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
ctacaaggga ctttccgctg                                                20

<210> SEQ ID NO 159
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 159
gccaacgaca agcgcagagg                                                20

<210> SEQ ID NO 160
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 160
gaggagtgag ttgattagga                                                   20

<210> SEQ ID NO 161
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 161
gagaggaaag aagggaagag                                                   20

<210> SEQ ID NO 162
<211> LENGTH: 109
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or u

<400> SEQUENCE: 162
nnnnnnnnnn nnnnnnnnnn guuuaagagc uaugcuggaa acagcauagc aaguuuaaau       60
aaggcuaguc cguuaucaac uugaaaaagu ggcaccgagu cggugcuuu                  109

<210> SEQ ID NO 163
<211> LENGTH: 136
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or u

<400> SEQUENCE: 163
nnnnnnnnnn nnnnnnnnnn guuuaagagc uaugcugggc cggaggugcu ccgaaaggaa       60
cuccggccca gcauagcaag uuuaaauaag gcuaguccgu uaucaacuug aaaaaguggc      120
accgagucgg ugcuuu                                                     136

<210> SEQ ID NO 164
<211> LENGTH: 136
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or u

<400> SEQUENCE: 164
nnnnnnnnnn nnnnnnnnnn guuuaagagc uaugcuggaa acagcauagc aaguuuaaau       60
```

```
aaggcuaguc cguuaucaac uuggccggag gugcuccgaa aggaacuccg gccaagugge    120 accgagucgg ugcuuu                                                  136
```

<210> SEQ ID NO 165
<211> LENGTH: 163
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or u

<400> SEQUENCE: 165

```
nnnnnnnnnn nnnnnnnnnn guuuaagagc uaugcugggc cggaggugcu ccgaaaggaa    60
cuccggccca gcauagcaag uuuaaauaag gcuagccgu uaucaacuug gccggaggug    120
cuccgaaagg aacuccggcc aaguggcacc gagucggugc uuu                    163
```

<210> SEQ ID NO 166
<211> LENGTH: 158
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or u

<400> SEQUENCE: 166

```
nnnnnnnnnn nnnnnnnnnn guuuaagagc uaugcugucg ggaggacgau gcgggccuuc    60
guuuguuucg uccacagacg acucgcccga cagcauagca aguuuaaaua aggcuagucc    120
guuaucaacu ugaaaaagug gcaccgaguc ggugcuuu                          158
```

<210> SEQ ID NO 167
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 167

```
agcauagcaa guauaaauaa ggcaagaccg ggaucaacuu gaaaaagugg caccgagucg    60
gugcuuu                                                            67
```

<210> SEQ ID NO 168
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(20)
<223> OTHER INFORMATION: n is a, c, g, or u

<400> SEQUENCE: 168

```
nnnnnnnnnn nnnnnnnnnn guuuaugagc uaugcu                             36
```

```
<210> SEQ ID NO 169
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 169
agcauagcaa guauaaauaa ggcaagaccg ggaacaacuu gaaaaagugg caccgaggcg      60
gugcuuu                                                               67

<210> SEQ ID NO 170
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(20)
<223> OTHER INFORMATION: n is a, c, g, or u

<400> SEQUENCE: 170
nnnnnnnnnn nnnnnnnnnn guuuaugagc uaugcu                               36

<210> SEQ ID NO 171
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 171
agcauagcaa guauaaauaa ggcaagaccg ggaacagccc gaaagggcgg cgccgaggcg      60
gcgcccc                                                               67

<210> SEQ ID NO 172
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(20)
<223> OTHER INFORMATION: n is a, c, g, or u

<400> SEQUENCE: 172
nnnnnnnnnn nnnnnnnnnn guuuaugagc uaugcu                               36

<210> SEQ ID NO 173
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 173
agcauagcaa guauaaauaa ggcuaguccg ggaucagccc gaaagggcgg cgccgagucg      60
gcgcccc                                                               67
```

```
<210> SEQ ID NO 174
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(20)
<223> OTHER INFORMATION: n is a, c, g, or u

<400> SEQUENCE: 174
nnnnnnnnnn nnnnnnnnnn guuuaugagc uaugcu                                 36

<210> SEQ ID NO 175
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 175
agcauagcaa guauaaauaa ggcaaguccg ggaacagccc gaaagggcgg cgccgaggcg        60
gcgcccc                                                                  67

<210> SEQ ID NO 176
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(20)
<223> OTHER INFORMATION: n is a, c, g, or u

<400> SEQUENCE: 176
nnnnnnnnnn nnnnnnnnnn guuuaugagc uaugcu                                 36

<210> SEQ ID NO 177
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 177
agcauagcaa guauaaauaa ggcuagaccg ggaacagccc gaaagggcgg cgccgaggcg        60
gcgcccc                                                                  67

<210> SEQ ID NO 178
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(20)
<223> OTHER INFORMATION: n is a, c, g, or u

<400> SEQUENCE: 178
nnnnnnnnnn nnnnnnnnnn guuuaugagc uaugcu                                 36
```

<210> SEQ ID NO 179
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 179
agcauagcaa guauaaauaa ggcaagaccg ggaucagccc gaaagggcgg cgccgaggcg     60
gcgcccc                                                               67

<210> SEQ ID NO 180
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(20)
<223> OTHER INFORMATION: n is a, c, g, or u

<400> SEQUENCE: 180
nnnnnnnnnn nnnnnnnnnn guuuaugagc uaugcu                               36

<210> SEQ ID NO 181
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 181
agcauagcaa guauaaauaa ggcaagaccg ggaacagccc gaaagggcgg cgccgagucg     60
gcgcccc                                                               67

<210> SEQ ID NO 182
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(20)
<223> OTHER INFORMATION: n is a, c, g, or u

<400> SEQUENCE: 182
nnnnnnnnnn nnnnnnnnnn guuuaugagc uaugcu                               36

<210> SEQ ID NO 183
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 183
agcauagcaa guauaaauaa ggcuaguccg ggaacagccc gaaagggcgg cgccgaggcg     60
gcgcccc                                                               67

<210> SEQ ID NO 184
<211> LENGTH: 36
<212> TYPE: RNA
<213> ORGANISM: Artificial Sequence
<220> FEATURE:
<223> OTHER INFORMATION: Description of Artificial Sequence: Synthetic
     oligonucleotide
<220> FEATURE:
<221> NAME/KEY: misc_feature
<222> LOCATION: (1)..(20)
<223> OTHER INFORMATION: n is a, c, g, or u

<400> SEQUENCE: 184
nnnnnnnnnn nnnnnnnnnn guuuaugagc uaugcu                               36

<210> SEQ ID NO 185
<211> LENGTH: 67
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 185
agcauagcaa guauaaauaa ggcaaguccg ggaacagccc gaaagggcgg cgccgagucg     60
gcgcccc                                                               67

<210> SEQ ID NO 186
<211> LENGTH: 36
<212> TYPE: RNA
<213> ORGANISM: Artificial Sequence
<220> FEATURE:
<223> OTHER INFORMATION: Description of Artificial Sequence: Synthetic
     oligonucleotide
<220> FEATURE:
<221> NAME/KEY: misc_feature
<222> LOCATION: (1)..(20)
<223> OTHER INFORMATION: n is a, c, g, or u

<400> SEQUENCE: 186
nnnnnnnnnn nnnnnnnnnn guuuaugagc uaugcu                               36

<210> SEQ ID NO 187
<211> LENGTH: 67
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 187
agcauagcaa guauaaauaa ggcuaguccg ggaacagccc gaaagggcgg cgccgagucg     60
gcgcccc                                                               67

<210> SEQ ID NO 188
<211> LENGTH: 36
<212> TYPE: RNA
<213> ORGANISM: Artificial Sequence
<220> FEATURE:
<223> OTHER INFORMATION: Description of Artificial Sequence: Synthetic
     oligonucleotide
<220> FEATURE:
<221> NAME/KEY: misc_feature
<222> LOCATION: (1)..(20)
<223> OTHER INFORMATION: n is a, c, g, or u

<400> SEQUENCE: 188
nnnnnnnnnn nnnnnnnnnn guuuaugagc uaugcu                                    36

<210> SEQ ID NO 189
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 189
agcauagcaa guauaaauaa ggcaagaccg ggaacagccc gaaagggcgg caccgagucg      60
gugcccc                                                                67

<210> SEQ ID NO 190
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(20)
<223> OTHER INFORMATION: n is a, c, g, or u

<400> SEQUENCE: 190
nnnnnnnnnn nnnnnnnnnn guuuaugagc uaugcu                                    36

<210> SEQ ID NO 191
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 191
agcauagcaa guauaaauaa ggcaagaccg ggaacagccc gaaagggcgg caccgagucg      60
gugcuuu                                                                67

<210> SEQ ID NO 192
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(20)
<223> OTHER INFORMATION: n is a, c, g, or u

<400> SEQUENCE: 192
nnnnnnnnnn nnnnnnnnnn guuuaugagc uaugcu                                    36

<210> SEQ ID NO 193
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 193
agcauagcaa guauaaauaa ggcuaguccg uuaucaacuu gaaaagugg caccgagucg       60 gugcuuu 67

<210> SEQ ID NO 194
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(20)
<223> OTHER INFORMATION: n is a, c, g, or u

<400> SEQUENCE: 194
nnnnnnnnnn nnnnnnnnnn guuuaugagc uaugcu                                36

<210> SEQ ID NO 195
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 195
agcaaagcaa guauaaauaa ggcaagaccg ggaucaacuu gaaaaagugg caccgagucg       60
gugcuuu                                                                67

<210> SEQ ID NO 196
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(20)
<223> OTHER INFORMATION: n is a, c, g, or u

<400> SEQUENCE: 196
nnnnnnnnnn nnnnnnnnnn guuuaugagc uuugcu                                36

<210> SEQ ID NO 197
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 197
agcaaagcaa guauaaauaa ggcaagaccg ggaacaacuu gaaaaagugg caccgagucg       60
gugcuuu                                                                67

<210> SEQ ID NO 198
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(20)
<223> OTHER INFORMATION: n is a, c, g, or u

```
<400> SEQUENCE: 198
nnnnnnnnnn nnnnnnnnnn guuuaugagc uuugcu                                36

<210> SEQ ID NO 199
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 199
agcaaagcaa guuuaaauaa ggcuaguccg uuaucaacuu gaaaaagugg caccgagucg       60
gugcuuu                                                                67

<210> SEQ ID NO 200
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(20)
<223> OTHER INFORMATION: n is a, c, g, or u

<400> SEQUENCE: 200
nnnnnnnnnn nnnnnnnnnn guuuagagc uuugcu                                 36

<210> SEQ ID NO 201
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 201
agcauagcaa guauaaauaa ggcaagaccg ggaacaacuu gaaaaagugg caccgagucg       60
gugcuuu                                                                67

<210> SEQ ID NO 202
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(20)
<223> OTHER INFORMATION: n is a, c, g, or u

<400> SEQUENCE: 202
nnnnnnnnnn nnnnnnnnnn guuuaugagc uaugcu                                36

<210> SEQ ID NO 203
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 203
```
agcauagcaa guuuaaauaa ggcuaguccg uuaacaacuu gaaaaagugg caccgagucg    60
gugcuuu                                                              67

<210> SEQ ID NO 204
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(20)
<223> OTHER INFORMATION: n is a, c, g, or u

<400> SEQUENCE: 204
nnnnnnnnnn nnnnnnnnnn guuuaagagc uaugcu                              36

<210> SEQ ID NO 205
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 205
agcauagcaa guauaaauaa ggcaagaccg ggaucaacuu gaaaaagugg caccgagucg    60
gugcuuu                                                              67

<210> SEQ ID NO 206
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(20)
<223> OTHER INFORMATION: n is a, c, g, or u

<400> SEQUENCE: 206
nnnnnnnnnn nnnnnnnnnn guuuaugagc uaugcu                              36

<210> SEQ ID NO 207
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 207
agcauagcaa guuuaaauaa ggcaaguccg uuaucaacuu gaaaaagugg caccgagucg    60
gugcuuu                                                              67

<210> SEQ ID NO 208
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature

```
<222> LOCATION: (1)..(20)
<223> OTHER INFORMATION: n is a, c, g, or u

<400> SEQUENCE: 208
nnnnnnnnnn nnnnnnnnnn guuuaagagc uaugcu                                    36

<210> SEQ ID NO 209
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 209
agcauagcaa guuuaaauaa ggcuaguccg ggaucaacuu gaaaaagugg caccgagucg          60
gugcuuu                                                                   67

<210> SEQ ID NO 210
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(20)
<223> OTHER INFORMATION: n is a, c, g, or u

<400> SEQUENCE: 210
nnnnnnnnnn nnnnnnnnnn guuuaagagc uaugcu                                    36

<210> SEQ ID NO 211
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 211
agcauagcaa guauaaauaa ggcaagaccg ggaucaacuu gaaaaagugg caccgagacg          60
gugcuuu                                                                   67

<210> SEQ ID NO 212
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(20)
<223> OTHER INFORMATION: n is a, c, g, or u

<400> SEQUENCE: 212
nnnnnnnnnn nnnnnnnnnn guuuaugagc uaugcu                                    36

<210> SEQ ID NO 213
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide
```

<400> SEQUENCE: 213
agcauagcaa guauaaauaa ggcaagaccg ggaucaacuu gaaaaagugg caccgaggcg    60
gugcuuu                                                              67

<210> SEQ ID NO 214
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(20)
<223> OTHER INFORMATION: n is a, c, g, or u

<400> SEQUENCE: 214
nnnnnnnnnn nnnnnnnnnn guuuaugagc uaugcu                              36

<210> SEQ ID NO 215
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 215
agcauagcaa guuuaaauaa ggcuaguccg guaucaacuu gaaaaagugg caccgagucg    60
gugcuuu                                                              67

<210> SEQ ID NO 216
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(20)
<223> OTHER INFORMATION: n is a, c, g, or u

<400> SEQUENCE: 216
nnnnnnnnnn nnnnnnnnnn guuuaagagc uaugcu                              36

<210> SEQ ID NO 217
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 217
agcauagcaa guuuaaauaa ggcuaguccg ugaucaacuu gaaaaagugg caccgagucg    60
gugcuuu                                                              67

<210> SEQ ID NO 218
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

```
<220> FEATURE:
<221> NAME/KEY: misc_feature
<222> LOCATION: (1)..(20)
<223> OTHER INFORMATION: n is a, c, g, or u

<400> SEQUENCE: 218
nnnnnnnnnn nnnnnnnnnn guuuaagagc uaugcu                              36

<210> SEQ ID NO 219
<211> LENGTH: 66
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 219
agcauagcaa guuuaaauaa ggcaguccgu uaucaacuug aaaaaguggc accgagucgg     60
ugcuuu                                                               66

<210> SEQ ID NO 220
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(20)
<223> OTHER INFORMATION: n is a, c, g, or u

<400> SEQUENCE: 220
nnnnnnnnnn nnnnnnnnnn guuuaagagc uaugcu                              36

<210> SEQ ID NO 221
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 221
agcauagcaa guauaaauaa ggcuaguccg uuaacaacuu gaaaaagugg caccgagucg     60
gugcuuu                                                              67

<210> SEQ ID NO 222
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(20)
<223> OTHER INFORMATION: n is a, c, g, or u

<400> SEQUENCE: 222
nnnnnnnnnn nnnnnnnnnn guuuaugagc uaugcu                              36

<210> SEQ ID NO 223
<211> LENGTH: 67
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 223
agcauagcaa guuuaaauaa ggcuaguccg uuaacaacgg gaaaccgugg caccgagucg      60
gugcuuu                                                                67

<210> SEQ ID NO 224
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(20)
<223> OTHER INFORMATION: n is a, c, g, or u

<400> SEQUENCE: 224
nnnnnnnnnn nnnnnnnnnn guuuaagagc uaugcu                                36

<210> SEQ ID NO 225
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 225
agcauagcaa guauaaauaa ggcuaguccg ugaacaccgg gaaaccgggg caccgagucg      60
gugcuuu                                                                67

<210> SEQ ID NO 226
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(20)
<223> OTHER INFORMATION: n is a, c, g, or u

<400> SEQUENCE: 226
nnnnnnnnnn nnnnnnnnnn guuuaugagc uaugcu                                36

<210> SEQ ID NO 227
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 227
agcauagcaa guuuaaauaa ggcuaguccg ugaacaccgg gaaaccgggg caccgagucg      60
gugcuuu                                                                67

<210> SEQ ID NO 228
<211> LENGTH: 36
<212> TYPE: RNA
<213> ORGANISM: Artificial Sequence
<220> FEATURE:
```

```
<223> OTHER INFORMATION: Description of Artificial Sequence: Synthetic
      oligonucleotide
<220> FEATURE:
<221> NAME/KEY: misc_feature
<222> LOCATION: (1)..(20)
<223> OTHER INFORMATION: n is a, c, g, or u

<400> SEQUENCE: 228
nnnnnnnnnn nnnnnnnnnn guuuaagagc uaugcu                                 36

<210> SEQ ID NO 229
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 229
agcauagcaa guuuaaauaa ggcuaguccg uuaacaccgg gaaaccgggg caccgagucg       60
gugcuuu                                                                 67

<210> SEQ ID NO 230
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(20)
<223> OTHER INFORMATION: n is a, c, g, or u

<400> SEQUENCE: 230
nnnnnnnnnn nnnnnnnnnn guuuaagagc uaugcu                                 36

<210> SEQ ID NO 231
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 231
agcauagcaa guuuaaauaa ggcuaguccg ugaacaacuu gaaaaagugg caccgagucg       60
gugcuuu                                                                 67

<210> SEQ ID NO 232
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(20)
<223> OTHER INFORMATION: n is a, c, g, or u

<400> SEQUENCE: 232
nnnnnnnnnn nnnnnnnnnn guuuaagagc uaugcu                                 36

<210> SEQ ID NO 233
<211> LENGTH: 20
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 233
gguuagacca gaucugagcc                                                    20

<210> SEQ ID NO 234
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 234
gggagcucuc uggcuaacu                                                     19

<210> SEQ ID NO 235
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 235
guaaccagag agacccagua c                                                  21

<210> SEQ ID NO 236
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 236
agagctccca ggctcagatc                                                    20

<210> SEQ ID NO 237
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 237
tagttagcca gagagctccc                                                    20

<210> SEQ ID NO 238
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 238
tttattgagg cttaagcagt                                                    20

<210> SEQ ID NO 239
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 239
atctgagcct gggagctctc                                                   20

<210> SEQ ID NO 240
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 240
gggagctctc tggctaacta                                                   20

<210> SEQ ID NO 241
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 241
ataattgcag tagctctaac                                                   20

<210> SEQ ID NO 242
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 242
tagagctact gcaattattc                                                   20

<210> SEQ ID NO 243
<211> LENGTH: 21
<212> TYPE: DNA
<213> ORGANISM: Artificial Sequence
<220> FEATURE:
<223> OTHER INFORMATION: description of artificial sequence: synthetic
      oligonucleotide

<400> SEQUENCE: 243
cgagccctca gatgctacat a                                                 21

<210> SEQ ID NO 244
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 244
tttgagcact caaggcaagc                                                   20

<210> SEQ ID NO 245
<211> LENGTH: 28
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 245
tggttagacc agatctgagc ctgggagc                                            28

<210> SEQ ID NO 246
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 246
aggcttaagc agtgggttcc ctagttagc                                           29

<210> SEQ ID NO 247
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 247
tgcctgtact gggtctctct ggttagacc                                           29

<210> SEQ ID NO 248
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 248
tgggttccct agttagccag aga                                                 23

<210> SEQ ID NO 249
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 249
ttgcctgtac tgggtctctc tggt                                                24

<210> SEQ ID NO 250
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 250
ggctgtgagg cttatcttca c                                                   21

<210> SEQ ID NO 251
<211> LENGTH: 20
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 251
tctgtcacct gcatagcttg                                              20

<210> SEQ ID NO 252
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 252
cagtagctct aacaggttgg acc                                          23

<210> SEQ ID NO 253
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 253
ctactgcaat tattcaggcc aaag                                         24

<210> SEQ ID NO 254
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 254
tgggctccct acaacattgt cct                                          23

<210> SEQ ID NO 255
<211> LENGTH: 116
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 255
agcauagcaa guauaaauaa ggcaagaccg ggaacagccc ucgggaggac gaugcgggcc    60
uucguuuguu ucguccacag acgacucgcc cgagggcggc gccgaggcgg cgcccc       116

<210> SEQ ID NO 256
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(20)
<223> OTHER INFORMATION: n is a, c, g, or u

<400> SEQUENCE: 256
nnnnnnnnnn nnnnnnnnnn guuuaugagc uaugcu                            36

<210> SEQ ID NO 257

```
<211> LENGTH: 51
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 257
gggaggacga ugcgggccuu cguuuguuuc guccacagac gacucgcccg a            51

<210> SEQ ID NO 258
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 258
nnnnnnnnnn nnnnnnnnnn gtttatgagc tttgctggaa acagcaaagc aagaataaat    60
aaggcaagac cgggaacaac ttgaaaaagt ggcaccgagg cggtgcttt               109

<210> SEQ ID NO 259
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, or t

<400> SEQUENCE: 259
nnnnnnnnnn nnnnnnnnnn gtttatgagc tttgctggaa acagcaaagc aagtataaat    60
aaggcaagac cgggaacacc ccgaaagggg ggcaccgagg cggtgcttt               109

<210> SEQ ID NO 260
<211> LENGTH: 115
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (93)..(115)
<223> OTHER INFORMATION: a, c, u, g, unknown or other. This region may
      encompass 20-23 nucleotides

<400> SEQUENCE: 260
ggucuagagg acagaauuuu ucaacgggug ugccaauggc cacuuuccag guggcaaagc    60
ccguugagcu ucucaaaucu gagaaguggc acnnnnnnnn nnnnnnnnnn nnnn         115

<210> SEQ ID NO 261
<211> LENGTH: 53
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
```

```
<222> LOCATION: (31)..(53)
<223> OTHER INFORMATION: a, c, u, g, unknown or other. This region may
      encompass 20-23 nucleotides

<400> SEQUENCE: 261
ggccacccca auaucgaagg ggacuaaaac nnnnnnnnnn nnnnnnnnnn nnn          53

<210> SEQ ID NO 262
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (19)..(41)
<223> OTHER INFORMATION: a, c, u, g, unknown or other. This region may
      encompass 20-23 nucleotides

<400> SEQUENCE: 262
aauucuacuc uuguagaunn nnnnnnnnnn nnnnnnnnn n                        41

<210> SEQ ID NO 263
<211> LENGTH: 59
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(23)
<223> OTHER INFORMATION: a, c, u, g, unknown or other. This region may
      encompass 20-23 nucleotides

<400> SEQUENCE: 263
nnnnnnnnnn nnnnnnnnnn nnnguugugg aagguccagu uuuggggcu auuacaaca     59

<210> SEQ ID NO 264
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 264
ctacaaggga ctttccgctg                                               20

<210> SEQ ID NO 265
<211> LENGTH: 37
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(20)
<223> OTHER INFORMATION: n is a, c, g, or u

<400> SEQUENCE: 265
nnnnnnnnnn nnnnnnnnnn guuuaagagc uaugcug                            37

<210> SEQ ID NO 266
<211> LENGTH: 36
<212> TYPE: RNA
<213> ORGANISM: Artificial Sequence
```

```
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(20)
<223> OTHER INFORMATION: n is a, c, g, or u

<400> SEQUENCE: 266
nnnnnnnnnn nnnnnnnnnn guuuaagagc uaugcu                                  36

<210> SEQ ID NO 267
<211> LENGTH: 89
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 267
guuuuagagc uaugcuggaa acagcauagc aaguuaaaau aaggcuaguc cguuaucaac        60
uugaaaaagu ggcaccgagu cggugcuuu                                          89

<210> SEQ ID NO 268
<211> LENGTH: 89
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 268
uuuuaugagc uuugcuggaa acagcaaagc aagaauaaaa aaggcaagac cgaaaacacc        60
gggaaaccgg ggccccgagg cggggcaaa                                          89

<210> SEQ ID NO 269
<211> LENGTH: 89
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 269
cuuuccgagc ucugcuggaa acagcagagc aagcggaaag aaggcgaggc cgggagcagc        60
ccgaaagggc ggcgccgaga cggcgcggg                                          89

<210> SEQ ID NO 270
<211> LENGTH: 89
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 270
guuuuagagc uaugcuggaa acagcauagc aaguuaaaac aaggcuaguc cguuaccaac        60
uugaaaaagu ggcaccgagc cggugccccc                                         89

<210> SEQ ID NO 271
<211> LENGTH: 89
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 271
buuumygagc uyugcuggaa acagcaragc aagmrkaaav aaggcragrc cgrravcasc    60
ssgaaassgs ggcsccgagv cggsgcvvv                                     89

<210> SEQ ID NO 272
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 272
ggaggugcuc cgaaagggaa cucc                                          24

<210> SEQ ID NO 273
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 273
uaguuagcca gagagcuccc                                               20

<210> SEQ ID NO 274
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 274
gggagcucuc uggcuaac                                                 18

<210> SEQ ID NO 275
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 275
uuuauugagg cuuaagcagu                                               20

<210> SEQ ID NO 276
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 276
uaaccagaga gacccaguac                                               20

<210> SEQ ID NO 277
<211> LENGTH: 20
<212> TYPE: RNA
<213> ORGANISM: Artificial Sequence
<220> FEATURE:

```
<223> OTHER INFORMATION: Description of Artificial Sequence: Synthetic
      oligonucleotide

<400> SEQUENCE: 277
aucugagccu gggagcucuc                                                   20

<210> SEQ ID NO 278
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 278
agagcuccca ggcucagauc                                                   20

<210> SEQ ID NO 279
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 279
gggagcucuc uggcuaacua                                                   20

<210> SEQ ID NO 280
<211> LENGTH: 132
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(20)
<223> OTHER INFORMATION: n is a, c, g, or u

<400> SEQUENCE: 280
nnnnnnnnnn nnnnnnnnnn guuuaagagc uaugcugggc caggugcucc gaaaggaacu       60
ggcccagcau agcaaguuua aauaaggcua guccguuauc aacuugaaaa aguggcaccg      120
agucggugcu uu                                                          132

<210> SEQ ID NO 281
<211> LENGTH: 132
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(20)
<223> OTHER INFORMATION: n is a, c, g, or u

<400> SEQUENCE: 281
nnnnnnnnnn nnnnnnnnnn guuuaagagc uaugcuggaa acagcauagc aaguuuaaau       60
aaggcuaguc cguuaucaac uuggccaggu gcuccgaaag gaacuggcca aguggcaccg      120
agucggugcu uu                                                          132

<210> SEQ ID NO 282
<211> LENGTH: 155
<212> TYPE: RNA
```

<213> ORGANISM: Artificial Sequence
<220> FEATURE:
<223> OTHER INFORMATION: Description of Artificial Sequence: Synthetic
       oligonucleotide
<220> FEATURE:
<221> NAME/KEY: misc_feature
<222> LOCATION: (1)..(20)
<223> OTHER INFORMATION: n is a, c, g, or u

<400> SEQUENCE: 282
nnnnnnnnnn nnnnnnnnnn guuuaagagc uaugcugggc caggugcucc gaaaggaacu      60
ggcccagcau agcaaguuua aauaaggcua guccguuauc aacuuggcca ggugcuccga     120
aaggaacugg ccaaguggca ccgagucggu gcuuu                                155

<210> SEQ ID NO 283
<211> LENGTH: 103
<212> TYPE: RNA
<213> ORGANISM: Artificial Sequence
<220> FEATURE:
<223> OTHER INFORMATION: Description of Artificial Sequence: Synthetic
       polynucleotide
<220> FEATURE:
<221> NAME/KEY: misc_feature
<222> LOCATION: (1)..(20)
<223> OTHER INFORMATION: n is a, c, g, or u

<400> SEQUENCE: 283
nnnnnnnnnn nnnnnnnnnn guuuaagagc uaugcuagca uagcaaguuu aaauaaggcu      60
aguccguuau caacuugaaa aguggcacc gagucggugc uuu                        103

<210> SEQ ID NO 284
<211> LENGTH: 20
<212> TYPE: RNA
<213> ORGANISM: Artificial Sequence
<220> FEATURE:
<223> OTHER INFORMATION: Description of Artificial Sequence: Synthetic
       oligonucleotide

<400> SEQUENCE: 284
uaguuagcca gagagcuccc                                                  20

<210> SEQ ID NO 285
<211> LENGTH: 20
<212> TYPE: RNA
<213> ORGANISM: Artificial Sequence
<220> FEATURE:
<223> OTHER INFORMATION: Description of Artificial Sequence: Synthetic
       oligonucleotide

<400> SEQUENCE: 285
uuuauugagg cuuaagcagu                                                  20

<210> SEQ ID NO 286
<211> LENGTH: 20
<212> TYPE: RNA
<213> ORGANISM: Artificial Sequence
<220> FEATURE:
<223> OTHER INFORMATION: Description of Artificial Sequence: Synthetic
       oligonucleotide

<400> SEQUENCE: 286
uaaccagaga gacccaguac                                                  20

<210> SEQ ID NO 287
<211> LENGTH: 20
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 287
aucugagccu gggagcucuc                                                    20

<210> SEQ ID NO 288
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 288
agagcuccca ggcucagauc                                                    20

<210> SEQ ID NO 289
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 289
gggagcucuc uggcuaacua                                                    20
```